US011116831B2

(12) United States Patent
Kong et al.

(10) Patent No.: US 11,116,831 B2
(45) Date of Patent: Sep. 14, 2021

(54) CHIMERIC NOROVIRUS P PARTICLE AND PREPARATION AND USE THEREOF

(71) Applicants: Changchun BCHT Biotechnology Co., Changchun (CN); Jilin University, Changchun (CN)

(72) Inventors: Wei Kong, Changchun (CN); Hui Wu, Changchun (CN); Chunlai Jiang, Changchun (CN); Xianghui Yu, Changchun (CN); Lu Fu, Changchun (CN); Yingnan Li, Changchun (CN)

(73) Assignees: Changchun BCHT Biotechnology Co., Changchun (CN); Jilin University, Changchun (CN)

(*) Notice: Subject to any disclaimer, the term of this patent is extended or adjusted under 35 U.S.C. 154(b) by 206 days.

(21) Appl. No.: 15/744,585

(22) PCT Filed: Jun. 29, 2016

(86) PCT No.: PCT/CN2016/087643

§ 371 (c)(1),
(2) Date: Jan. 12, 2018

(87) PCT Pub. No.: WO2017/008638

PCT Pub. Date: Jan. 19, 2017

(65) Prior Publication Data

US 2019/0247486 A1 Aug. 15, 2019

(30) Foreign Application Priority Data

Jul. 15, 2015 (CN) ......................... 201510415556.1

(51) Int. Cl.
*C12N 7/00* (2006.01)
*A61K 39/12* (2006.01)
(Continued)

(52) U.S. Cl.
CPC ............ *A61K 39/12* (2013.01); *A61K 9/0019* (2013.01); *A61K 9/0043* (2013.01); *A61K 39/00* (2013.01);
(Continued)

(58) Field of Classification Search
None
See application file for complete search history.

(56) References Cited

U.S. PATENT DOCUMENTS

2004/0141984 A1* 7/2004 Bachmann ......... A61K 39/0007 424/184.1
2010/0322962 A1* 12/2010 Jiang ...................... A61K 39/12 424/196.11
(Continued)

FOREIGN PATENT DOCUMENTS

CN 1504240 A 6/2004
CN 101278043 A 10/2008
(Continued)

OTHER PUBLICATIONS

Konietzko, "Gains and losses on the road to understanding Alzheimer's disease," Swiss Med Weekly 145: w14333 (Year: 2015).*
(Continued)

*Primary Examiner* — M Franco G Salvoza
(74) *Attorney, Agent, or Firm* — Leydig, Voit & Mayer, Ltd.

(57) ABSTRACT

Provided is a recombinant P particle formed from a norovirus capsid P protein of a chimeric Aβ1-m peptide (m being an integer ranging from 6 to 15), wherein the recombinant P particles form an ordered and repetitive antigen array. Also provided are a nucleotide sequence encoding the recombinant P particle, a pharmaceutical composition comprising same and a use thereof for preparing a medicament for
(Continued)

treating or preventing Alzheimer's disease. Also provided is a method for preparing the recombinant P particle.

9 Claims, 34 Drawing Sheets

Specification includes a Sequence Listing.

(51) Int. Cl.

| | |
|---|---|
| *A61K 39/385* | (2006.01) |
| *C12N 15/62* | (2006.01) |
| *C12N 15/70* | (2006.01) |
| *C07K 19/00* | (2006.01) |
| *A61K 39/00* | (2006.01) |
| *C12N 7/04* | (2006.01) |
| *A61P 25/28* | (2006.01) |
| *A61K 9/00* | (2006.01) |
| *A61K 39/39* | (2006.01) |

(52) U.S. Cl.

CPC ............ *A61K 39/385* (2013.01); *A61K 39/39* (2013.01); *A61P 25/28* (2018.01); *C07K 19/00* (2013.01); *C12N 7/00* (2013.01); *C12N 7/04* (2013.01); *C12N 15/62* (2013.01); *C12N 15/70* (2013.01); *A61K 2039/55505* (2013.01); *A61K 2039/55561* (2013.01)

(56) References Cited

U.S. PATENT DOCUMENTS

| | | | | |
|---|---|---|---|---|
| 2012/0087940 A1 | 4/2012 | Inoue et al. | | |
| 2014/0017269 A1* | 1/2014 | Tan | A61K 39/12 424/186.1 | |
| 2014/0271712 A1* | 9/2014 | Baric | C07K 14/005 424/216.1 | |

FOREIGN PATENT DOCUMENTS

| | | | | |
|---|---|---|---|---|
| CN | 101538558 A | 9/2009 | | |
| CN | 102272301 A | 12/2011 | | |
| CN | 103154242 A | 6/2013 | | |
| CN | 104583393 A | 4/2015 | | |
| WO | WO 2006/112553 A2 | 10/2006 | | |
| WO | WO-2013192604 A1 * | 12/2013 | C07K 14/005 | |

OTHER PUBLICATIONS

Sarkar et al., "Alzheimer's disease: the silver tsunami of the 21(st) century," Neural Regen Res 11(5): 693-7 (Year: 2016).*

Robinson et al., "Optimizing the stability of single-chain proteins by linker length and composition mutagenesis," PNAS, vol. 95: 5929-5934 (Year: 1998).*

Feng et al. (Jan. 2012) "Prokaryotic expression and immunogenicity of the chimeric HBcAg containing Aβ1-15," Journal of Central South University (Med Sci). 37(3):290-295.—English Abstract Only.

Fu et al. (Sep. 5, 2015) "Norovirus P particle: An excellent vaccine platform for antibody production against Alzheimer's disease," Immunology Letters. 168(1):22-30.

Tan et al. (2011) "Norovirus P Particle, a Novel Platform for Vaccine Development and Antibody Production," Journal of Virology. 85(2):753-764.

European Extended Search Report, dated Feb. 4, 2019, corresponding to European Application No. 16823785.7, a related application, 9 pp.

Fu et al. (Dec. 1, 2017) "Norovirus P Particle-Based Active A[beta] Immunotherapy Elicits Sufficient Immunogenicity and Improves Cognitive Capacity in a Mouse Model of Alzheimer's Disease," Scientific Reports, 7(1), 14 pp.

Li et al. (2016) "Establishment of a Novel Method Without Sequence Modification for Developing NoV P Particle-Based Chimeric Vaccines," Protein Expression and Purification 121:73-80.

Tan et al. (Jun. 1, 2012) "Norovirus P Particle: a Subviral Nanoparticle for Vaccine Development Against Norovirus, Rotavirus and Influenza Virus," Nanomedicine, 7(6):889-897.

Wiessner et al. (Jun. 22, 2011) "The Second-Generation Active A Immunotherapy CAD106 Reduces Amyloid Accumulation in APP Transgenic Mice While Minimizing Potential Side Effects," The Journal of Neuroscience 31(25):9323-9331.

Chinese First Office Action and Search Report, dated Mar. 23, 2020, corresponding to Chinese Application No. 201510415556.1, a corresponding application, 8 pp.

Brody et al. (2008) "Active and Passive Immunotherapy for Neurodegenerative Disorders," Annu. Rev. Neurosci. 31: 175-193.

Panza et al. (2019) "Amyloid-β Immunotherapy for Alzheimer Disease: Is It Now Long Shot?," Ann. Neurol. 85:303-315.

Rosenberg et al. (2020) "Active Immunotherapy to Prevent Alzheimer Disease—A DNA Amyloid β 1-42 Trimer Vaccine," JAMA Neurology 77(3) 289-290.

Indian Examination Report, dated Sep. 2, 2020, corresponding to Indian Patent Application No. 201827004047, 8 pp.

European Office Action, dated Apr. 9, 2020, corresponding to European Patent Application No. 16823785.7, 7 pp.

* cited by examiner

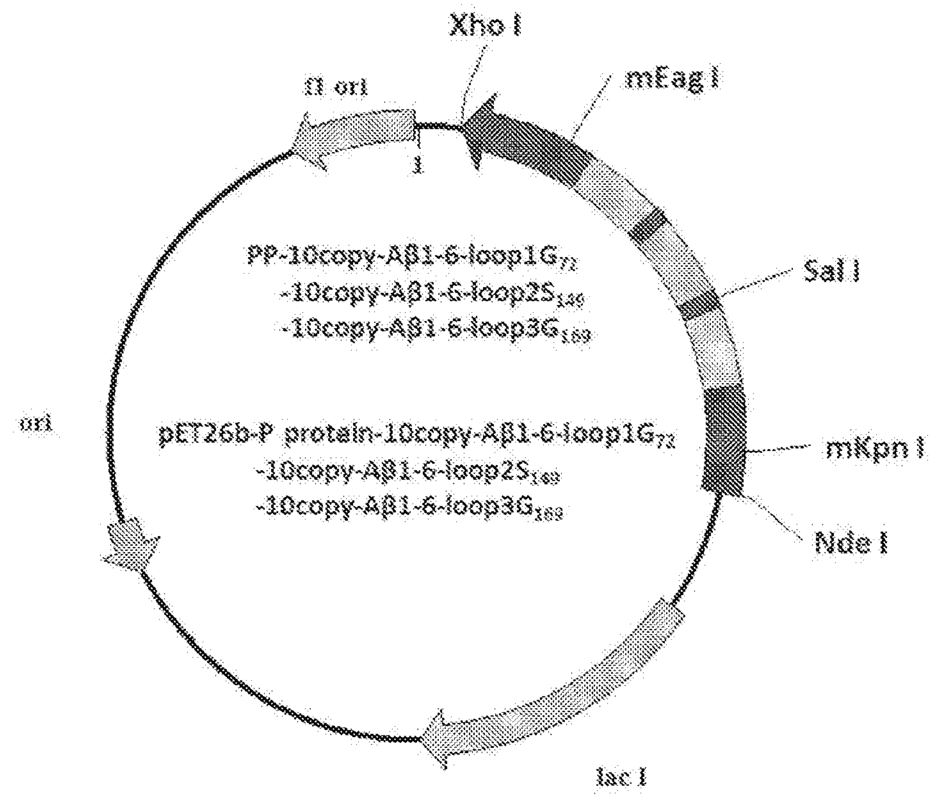
Figure 1M
Figure 1
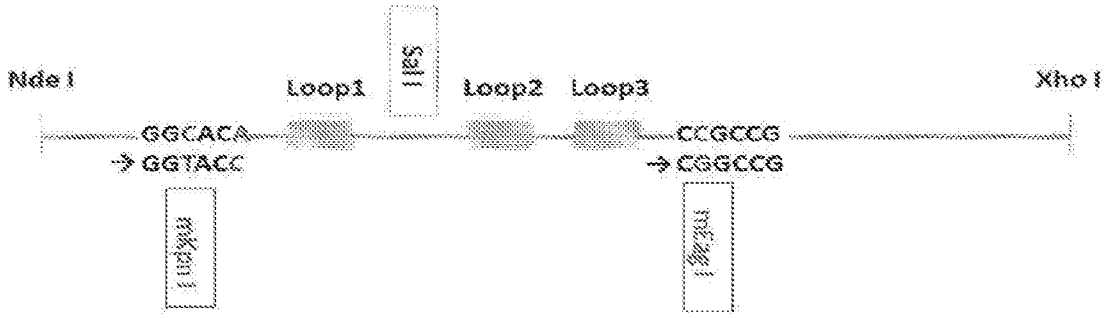
Figure 2A

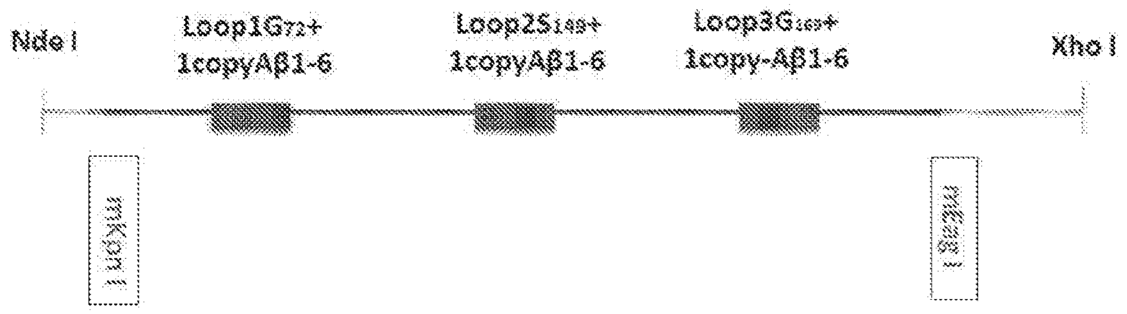
Figure 2I
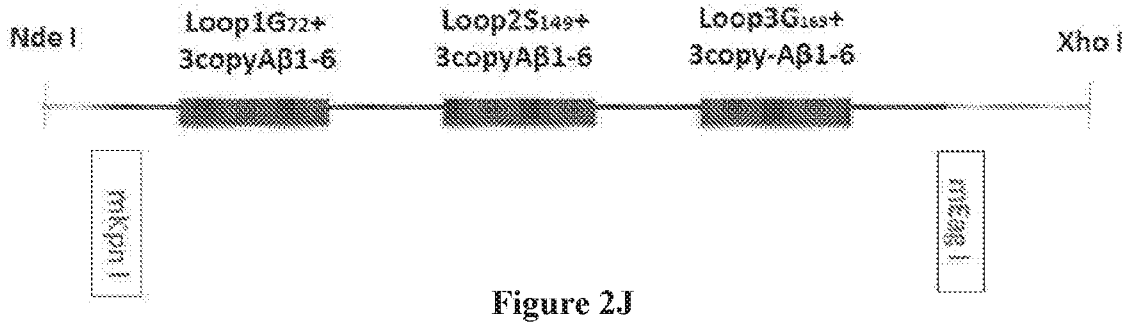
Figure 2J
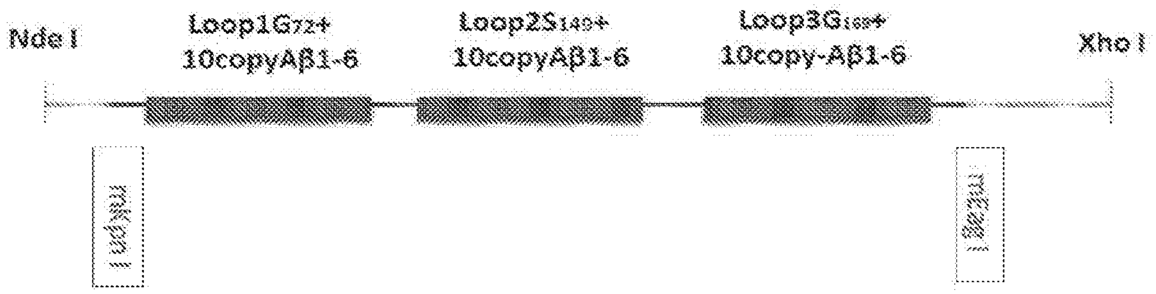
Figure 2K
Figure 2

(SEQ ID NO: 148)

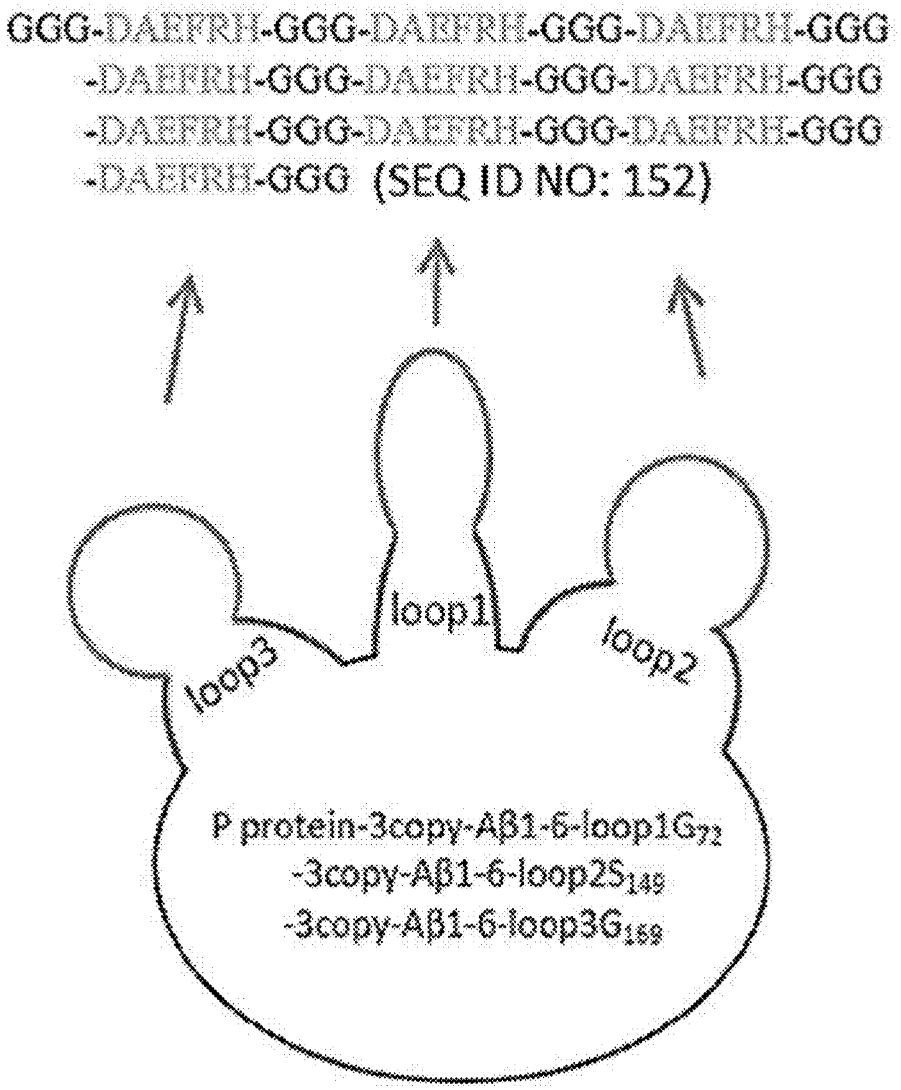
Figure 3J
Figure 3
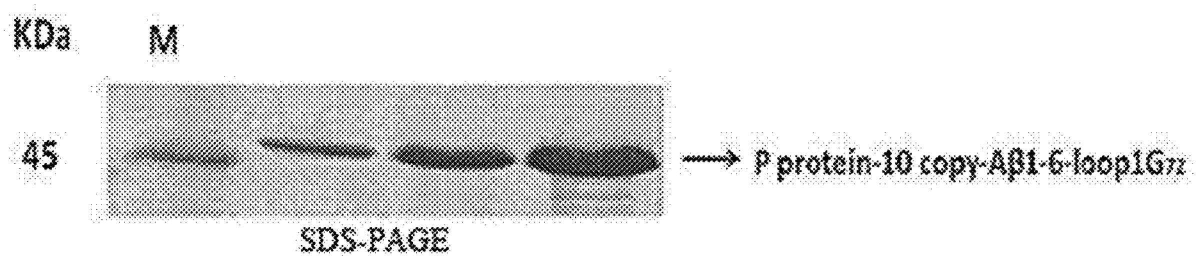
Figure 4A.1

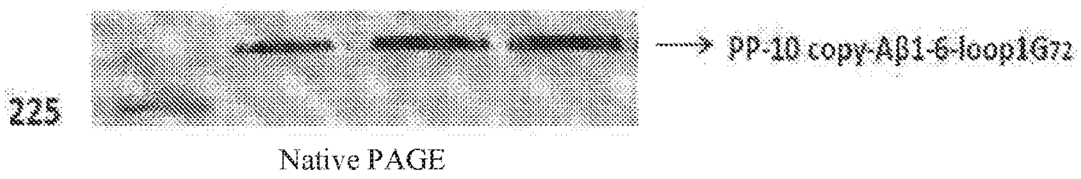
Figure 4A.2
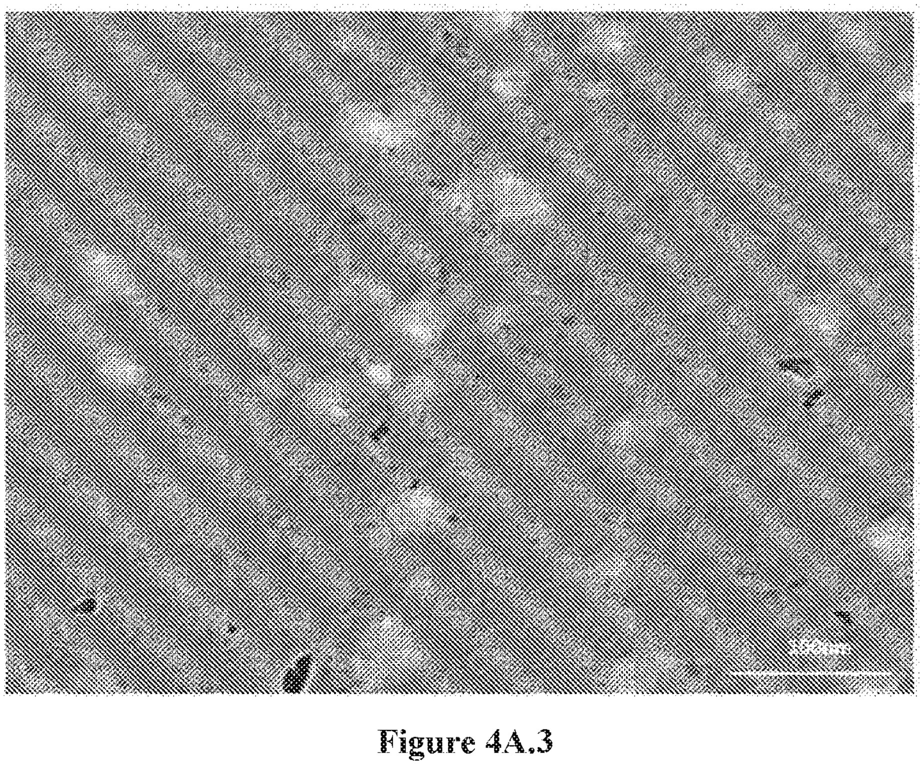
Figure 4A.3
Figure 4A
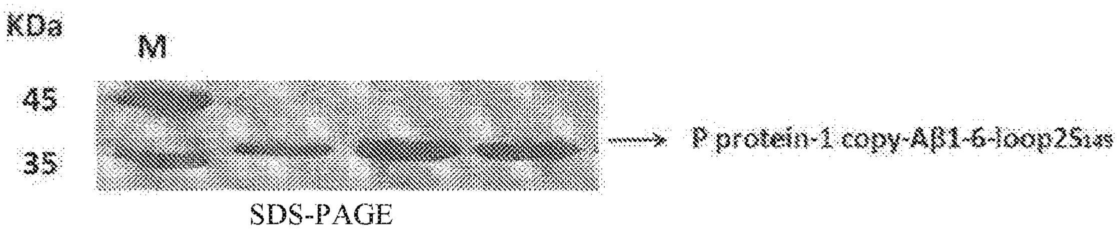
Figure 4B.1

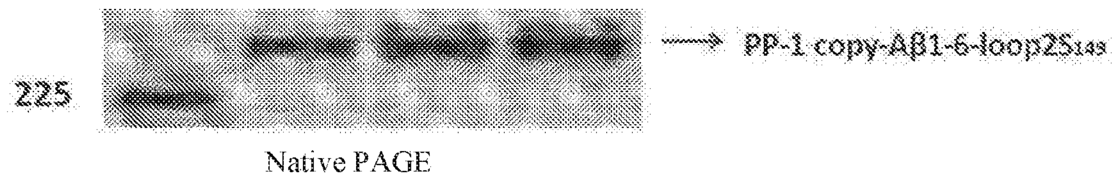
Figure 4B.2
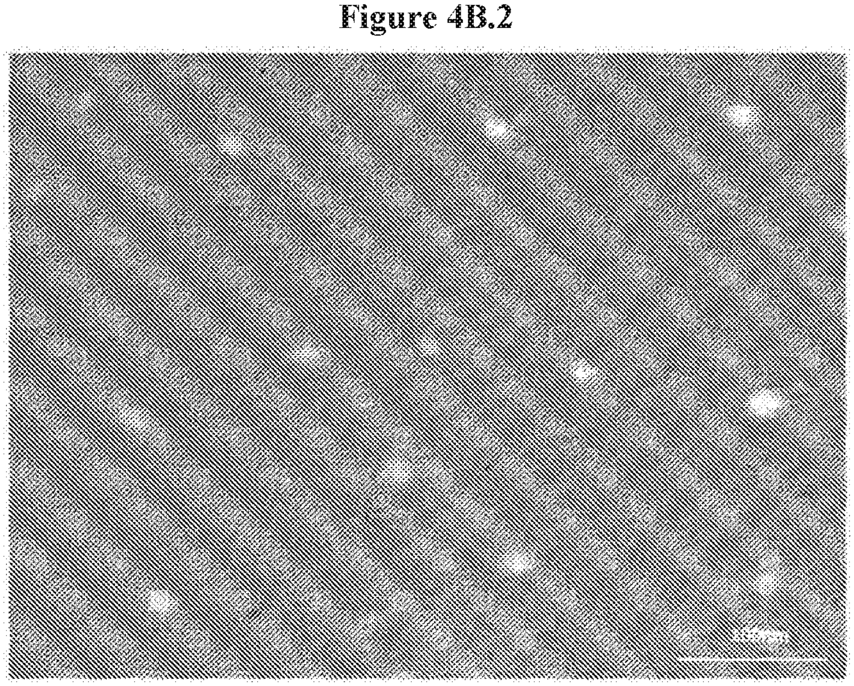
Figure 4B.3
Figure 4B
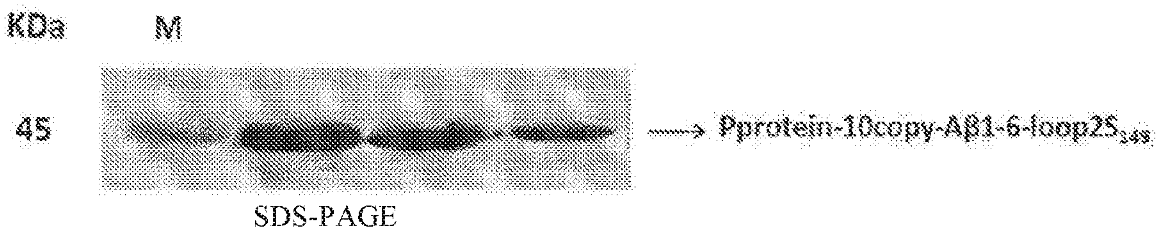
Figure 4C.1
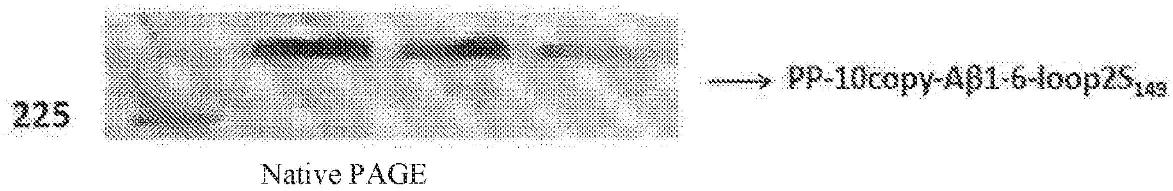
Figure 4C.2

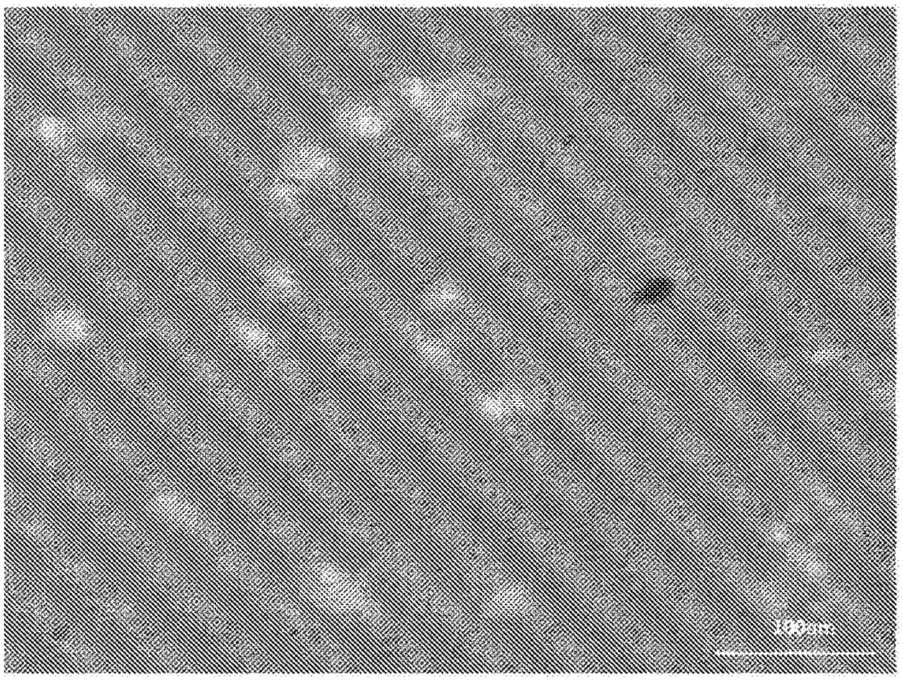
Figure 4C.3
Figure 4C
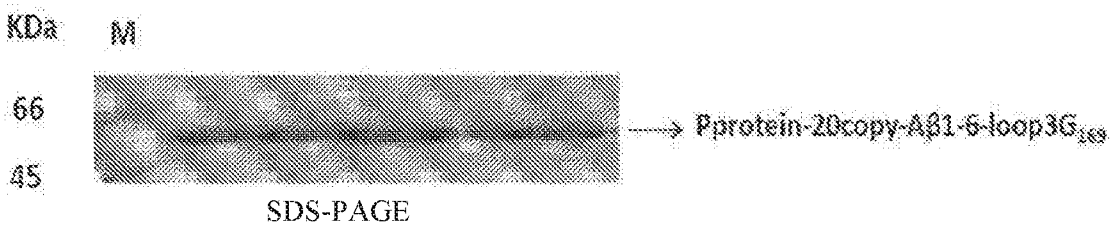
Figure 4D.1
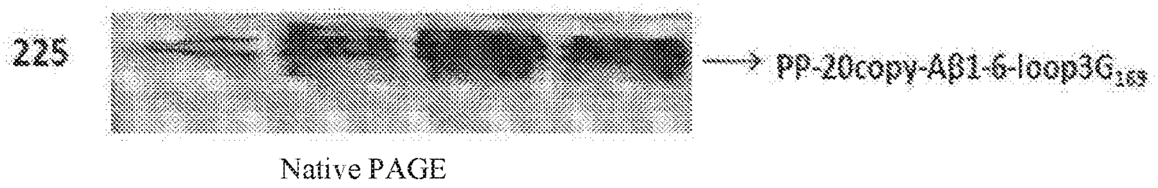
Figure 4D.2

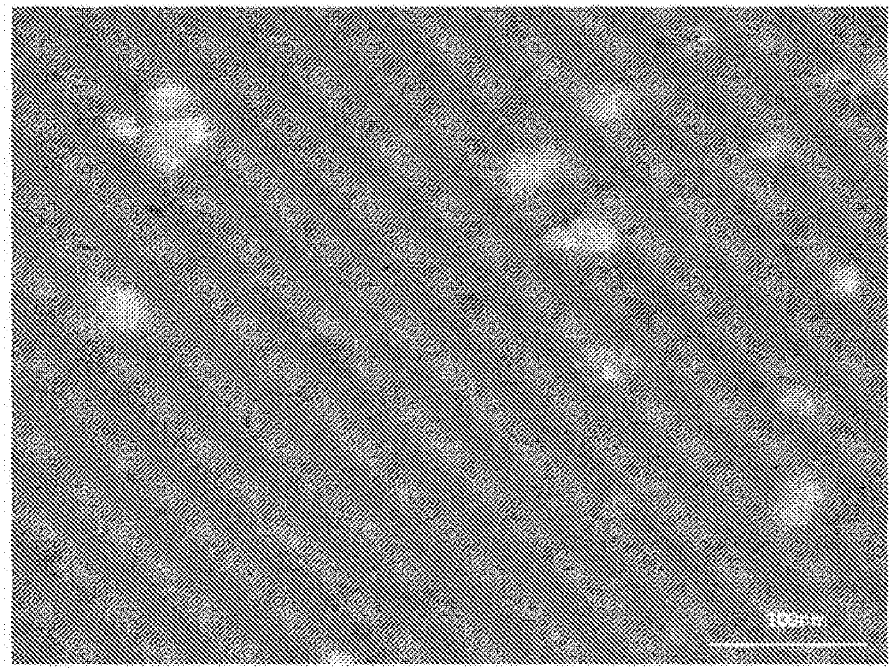
Figure 4D.3
Figure 4D
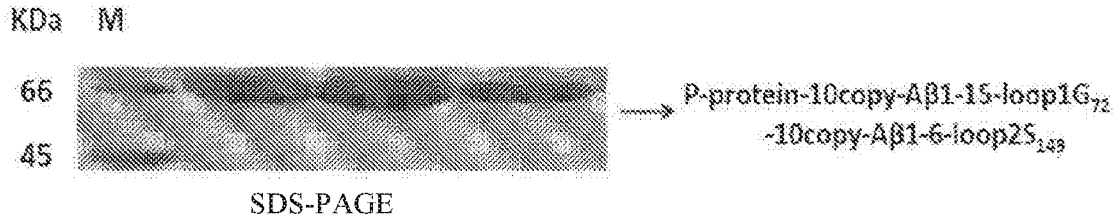
Figure 4E.1
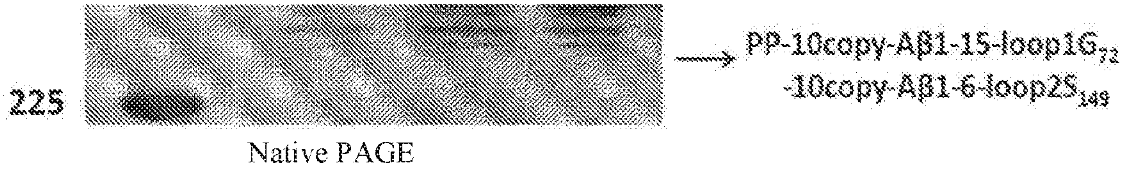
Figure 4E.2

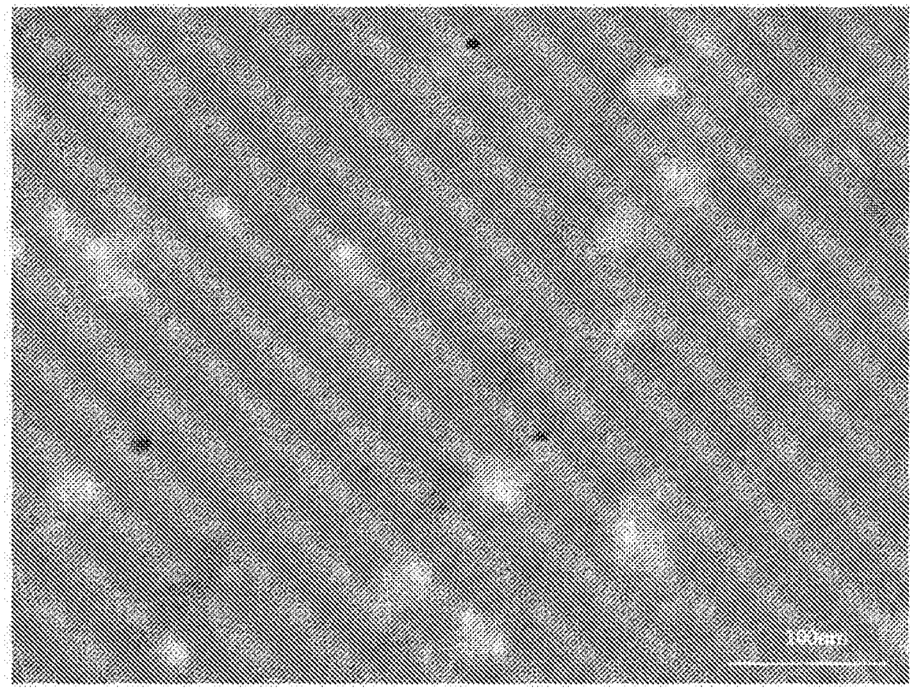
Figure 4E.3
Figure 4E
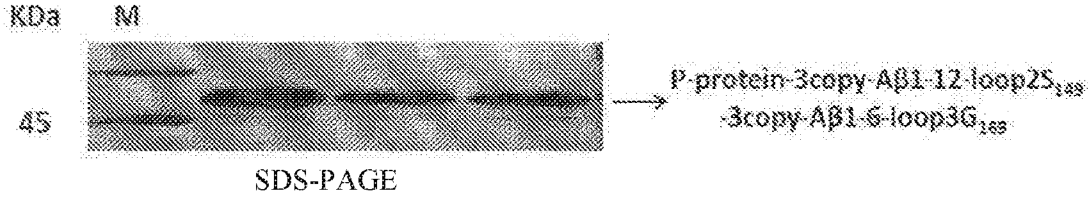
Figure 4F.1
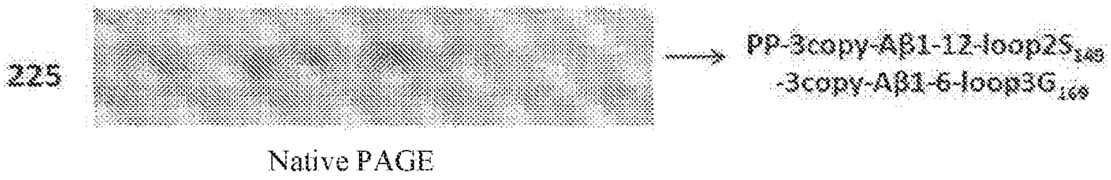
Figure 4F.2

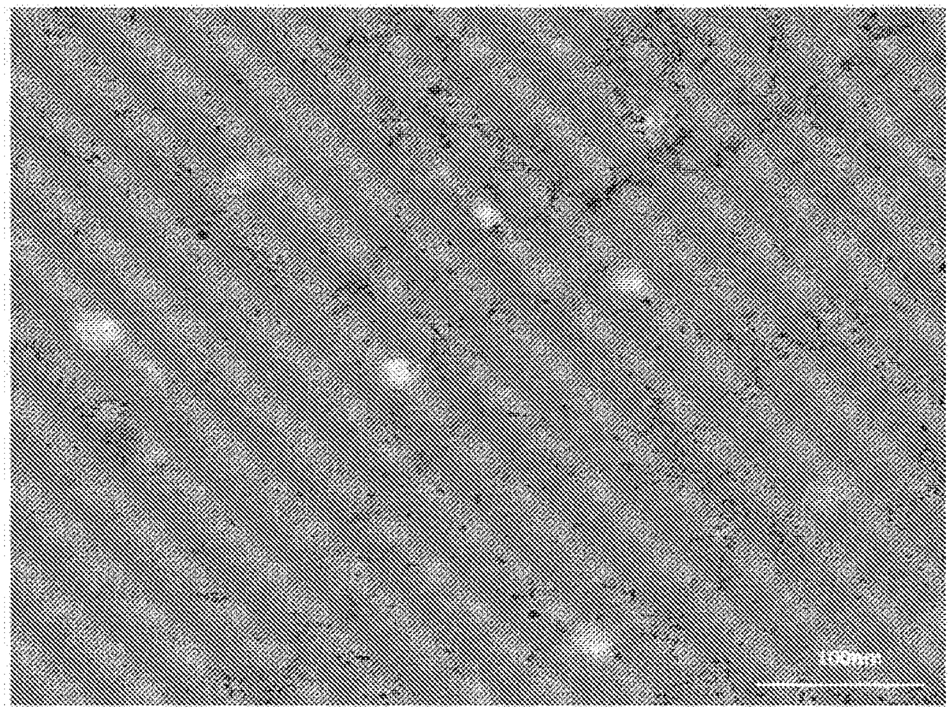
Figure 4F.3
Figure 4F
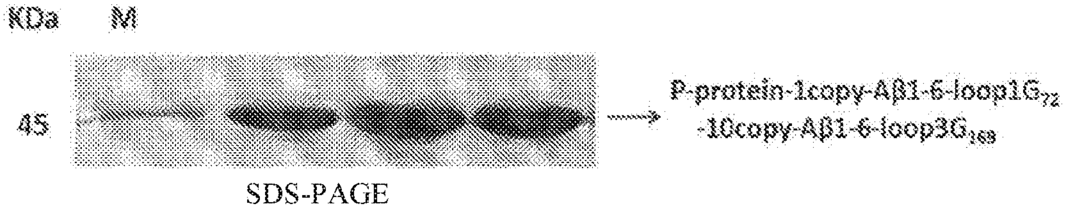
Figure 4G.1
Figure 4G.2

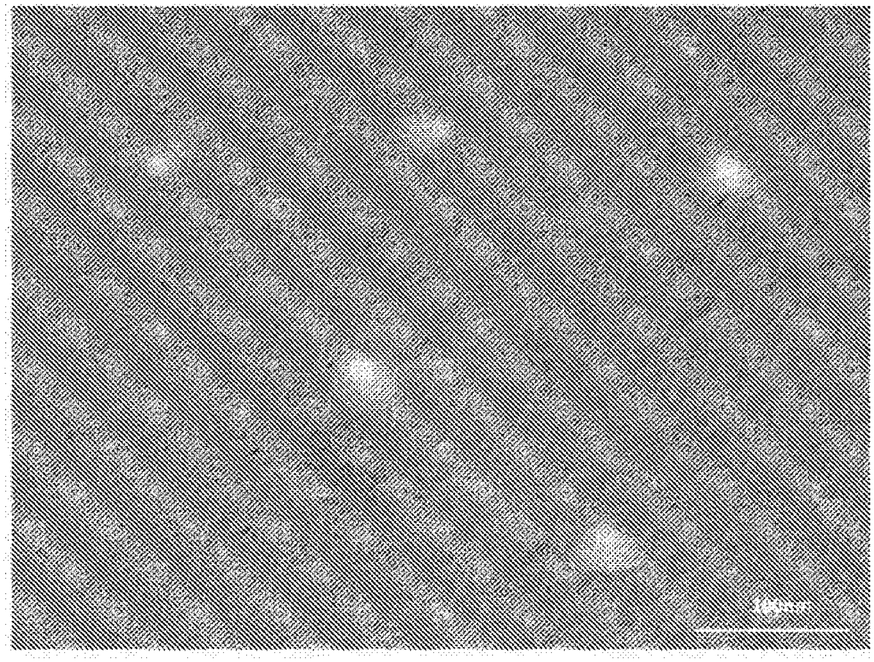
Figure 4G.3
Figure 4G
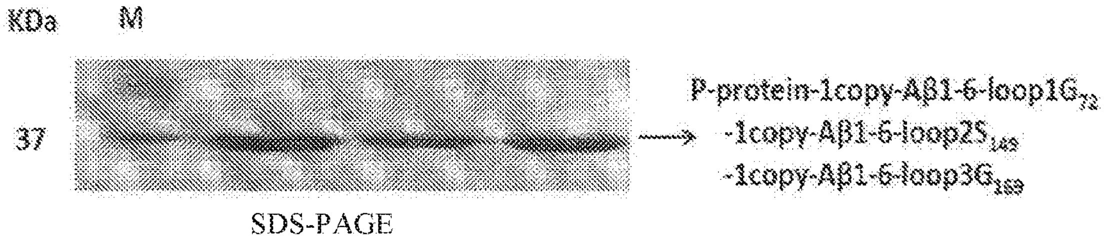
Figure 4H.1
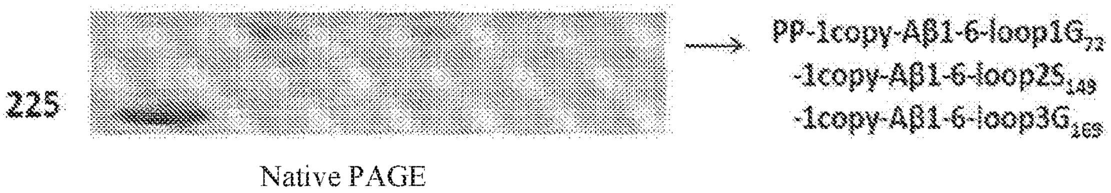
Figure 4H.2

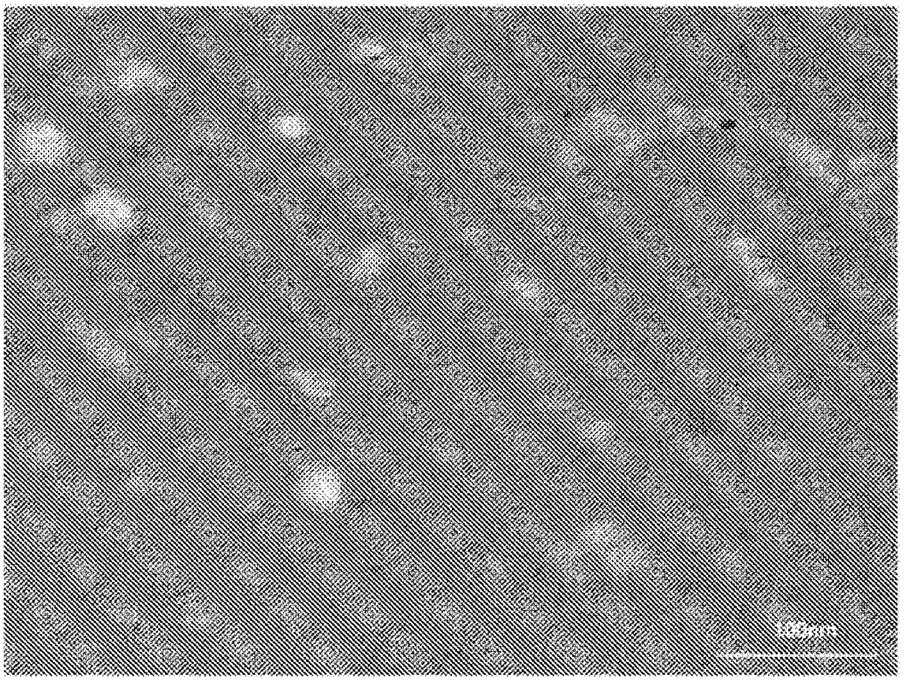
Figure 4H.3
Figure 4H
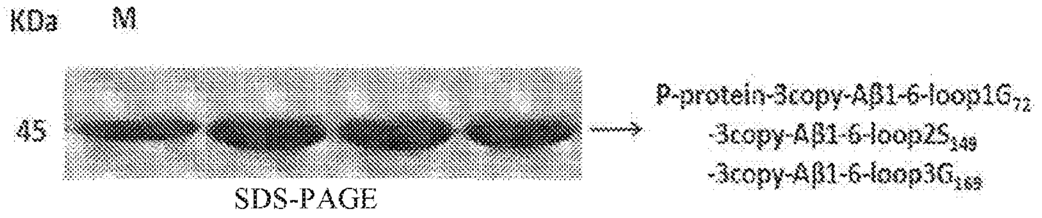
Figure 4I.1
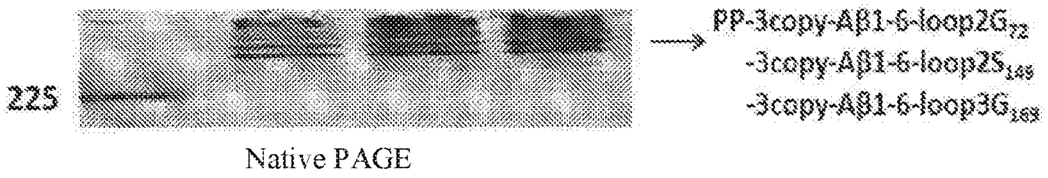
Figure 4I.2

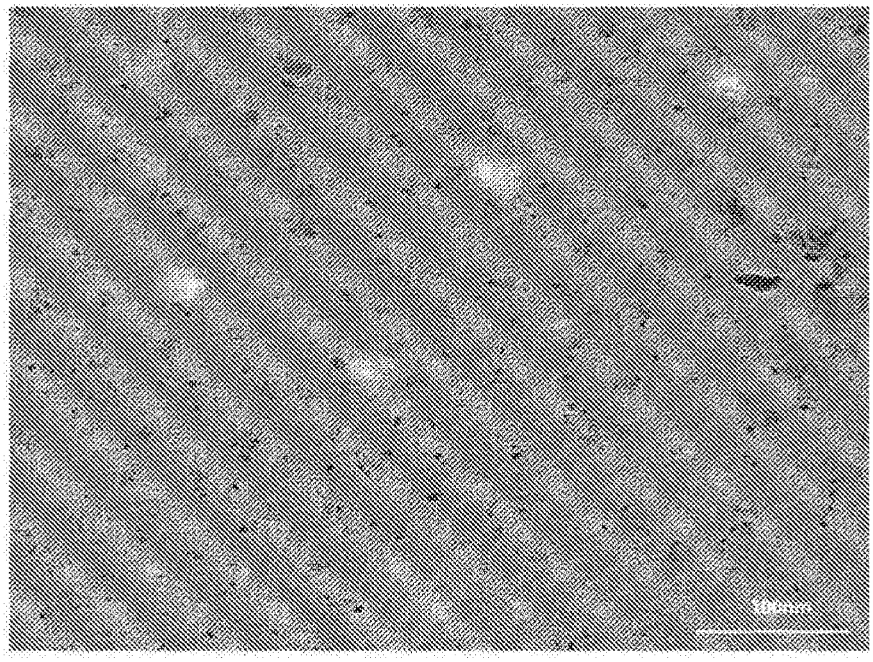
Figure 4I.3
Figure 4I
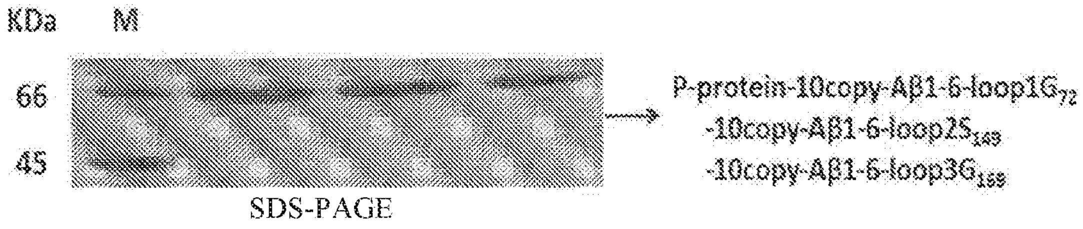
Figure 4J.1
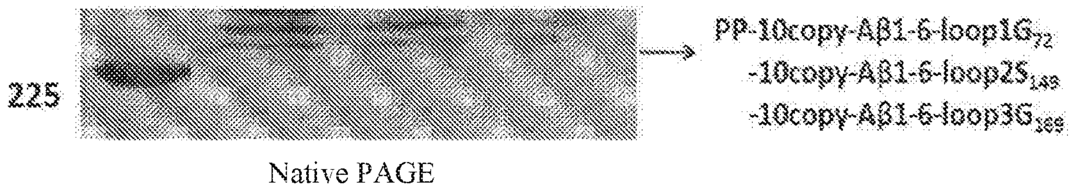
Figure 4J.2

Figure 4J.3

ELISPOT experiment for groping for the immune dosage of PP-10copy-Aβ1-6-loop2S149

PP-10copy-Aβ 1-6-loop2$S_{149}$+ CpG subcutaneous

PP-10copy-Aβ 1-6-loop2$S_{149}$+ CpG nasal

CHIMERIC NOROVIRUS P PARTICLE AND PREPARATION AND USE THEREOF

CROSS-REFERENCE TO RELATED APPLICATIONS

This application is a U.S. National Stage Application filed under 35 U.S.C. § 371 of International Application No. PCT/CN2016/087643, filed Jun. 29, 2016, which claims the benefit of Chinese Application No. 201510415556.1, filed Jul. 15, 2015. Both of these applications are hereby incorporated by reference in their entireties.

TECHNICAL FIELD

The present invention relates to the fields of molecular biology and immunology. In particular, the present invention relates to a recombinant P particle formed from a norovirus capsid P protein of a chimeric Aβ1-m peptide, wherein the recombinant P particles form an ordered and repetitive antigen array, and wherein m is an integer ranging from 6 to 15.

BACKGROUND ART

Alzheimer's disease (AD), also named senile dementia, is a progressive neurodegenerative disease. Its main clinical characteristics include gradual occurrences of memory deterioration, cognitive function disorders and abnormal behaviors, and ending up with a loss of the ability to live independently. AD leads to death from the complications 10-20 years after the onset thereof. Currently, this most common neurodegenerative disease cannot be cured or effectively delayed, and severely jeopardizes the physical and mental health and life quality of the elderly.

Researchers generally believe that the amyloid-β protein (Aβ) in the brain tissue is a primary pathogenic cause of neuronal damage and cognitive function disorders. Aβ is derived from its precursor β-amyloid precursor protein (abbreviated as βAPP). βAPP, as a transmembrane protein, is ubiquitously present in various tissues of the body and expressed most highly in the brain tissue. In the amyloid cleaving pathway, βAPP can be cleaved into Aβ proteins which are 38-43 amino acids in length, wherein Aβ1-42 protein is the main type that forms amyloid deposits.

Aβ active immune vaccine, which is intended to stimulate the body to produce Aβ antibodies and thus clear up Aβ1-42 deposits in the brain, is an important method for treating Alzheimer's disease. As a pioneer of AD vaccines, Aβ1-42 polypeptide vaccine shows a good therapeutic effect of delaying memory decline in the AD transgenic mouse model. Nevertheless, in the clinical trials of Aβ1-42 polypeptide vaccine, 6% of the AD patients showed the side effect of cephalomeningitis, and they had a low level of Aβ1-42 antibody. The research showed that although Aβ1-42 polypeptide vaccine could elicit antibody reactions, it may promote vaccinated patients to produce autoimmune T cell reactions in the brain and thus induce meningoencephalitis as it carries a large number of T cell epitopes. In comparison with Aβ1-42, polypeptide Aβ1-15 comprising only the first 15 amino acids at the N-terminal of Aβ polypeptide, comprises only B cell epitopes instead of T cell epitopes, and this polypeptide vaccine could stimulate the human body to produce specific immunological reactions against Aβ1-42 protein and show good safety in human trials. Therefore, Aβ1-15 has become an antigenic peptide with great research potentials. However, as a hapten, Aβ1-15 does not have a good immunological effect and sustainability of inducing the production of antibodies. Therefore, there are urgent needs for a vaccine against Alzheimer's disease with high safety and good immunological effect.

In the prior art, it is often preferred to synthesize the virus-like particle and Aβ polypeptide respectively, and then couple them in order to obtain vaccines with high immunogenicity. However, as to the vaccines obtained by methods such as coupling, it is difficult to control the number of the inserted epitopes, and to purify the vaccines effectively.

SUMMARY OF THE INVENTION

The inventors found that the capsid P protein of norovirus is a very ideal antigen exhibition platform for an Aβ1-m (m is an integer ranging from 6 to 15) peptide. When different copies of Aβ1-m (m is an integer ranging from 6 to 15) peptide encoding sequences with various lengths are inserted into the loop of the DNA sequence encoding the capsid P protein of norovirus, Aβ1-m can be exhibited on the utmost surface of the recombinant P particle formed from the recombinant P protein, thereby helping to stimulate the body to the greatest extent to produce specific immunological reactions against Aβ1-42 proteins. The recombinant P particle of the present application can be prepared easily, and are controllable in terms of the number of the inserted epitopes; they can be purified easily and manufactured with a low cost; they have good safety and high immunogenicity, and can induce the production of high-titer antibodies.

In the present invention, multiple copies of DNA encoding antigen peptide Aβ1-m (m is an integer ranging from 6 to 15) are inserted into the DNA encoding loop1, loop2 and/or loop3 of the P protein by means of genetic engineering. By in vitro expression and self-assembly of recombinant proteins, a recombinant P particle capable of sufficiently exhibiting the antigen epitopes of Aβ1-m (m is an integer ranging from 6 to 15) is formed, thereby helping to enhance the efficacy, sustainability and safety of vaccination.

In a first aspect, the present invention provides a recombinant P particle formed from a norovirus capsid P protein of a chimeric Aβ1-m peptide, wherein m is an integer ranging from 6 to 15. In an embodiment of the invention, m may be 6, 7, 8, 9, 10, 11, 12, 13, 14 or 15. Said recombinant P particles form an ordered and repetitive antigen array, wherein the amino acid sequence of at least one of the Aβ1-m peptides is embedded into loop1, loop2 and/or loop3 of the norovirus capsid P protein.

In a preferred embodiment of the present invention, the amino acid sequence of a norovirus capsid P protein is shown as SEQ ID NO: 1. In the recombinant P particle, N1 Aβ1-m peptide sequences are embedded behind one or more amino acid sites selected from the group consisting of amino acids 70-74 of SEQ ID NO:1, i.e. I70, A71, G72, T73 and Q74; N2 Aβ1-m peptide sequences are embedded after one or more amino acid sites selected from the group consisting of amino acids 148-151 of SEQ ID NO:1, i.e. T148, S149, N150 and D151; and N3 Aβ1-m peptide sequences are embedded after one or more amino acid sites selected from the group consisting of amino acids 168-171 of SEQ ID NO:1, i.e. D168, G169, S170 and T171; wherein N1, N2 and N3 each are independently selected from an integer ranging from 0 to 40, and N1+N2+N3≥1. In particular, N1, N2 and N3 each are independently selected from 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and 40, and N1+N2+N3≥1.

That "Aβ1-m peptide sequences are embedded after one amino acid site" means that the N terminal of the Aβ1-m peptide sequences is directly linked to the C terminal of the amino acid residue via a peptide bond or is linked to the amino acid via an amino acid linker. In a preferred embodiment, the amino acid linker is $(Gly)_n$, wherein preferably n is 1-10, and more preferably n=3.

The multiple consecutive Aβ1-m peptide sequences inserted into SEQ ID NO:1 can be directly linked or linked via an amino acid linker. In a preferred embodiment, the amino acid linker is $(Gly)_n$, wherein preferably n is 1-10, and more preferably n=3.

In the present invention, an Aβ1-m peptide sequence means the polypeptide consisting of the first m amino acids at the N terminal of the entire Aβ1-42 protein, wherein m is an integer ranging from 6 to 15. For example, the Aβ1-m peptide according to the present invention can be a polypeptide consisting of amino acids 1-6, 1-7, 1-8, 1-9, 1-10, 1-11, 1-12, 1-13, 1-14 or 1-15 at the N terminal of the entire Aβ1-42 protein.

The Aβ1-m peptide sequence according to the present invention can be an Aβ1-m peptide from human, mouse, primate, rabbit, African clawed frog (*Xenopuslaevis*), rat and guinea pig. The amino acid sequences of Aβ1-15 peptides from human, mouse, primate, rabbit, African clawed frog, rat and guinea pig are shown as SEQ ID NO:2 to SEQ ID NO:8, respectively. According to these sequences, those skilled in the art could easily determine the Aβ1-m peptide (m is an integer ranging from 6 to 15) of the present invention. Preferably, the Aβ1-m peptide is a human Aβ1-m peptide.

In a second aspect, the present invention further provides a nucleotide sequence encoding a norovirus capsid P protein of a chimeric Aβ1-m peptide from which the recombinant P particle of the first aspect is formed, wherein m is an integer ranging from 6 to 15. In an embodiment of the invention, m may be 6, 7, 8, 9, 10, 11, 12, 13, 14 or 15. The nucleotide sequence comprises a nucleotide sequence encoding a norovirus capsid P protein and at least one copy of a nucleotide sequence encoding a Aβ1-m peptide, wherein the at least one copy of a nucleotide sequence encoding a Aβ1-m peptide is inserted into the nucleotide sequence encoding a loop of a norovirus capsid P protein, and wherein the inserted nucleotide sequence encoding a Aβ1-m peptide would not result in a frameshift mutation of the norovirus capsid P protein.

In a specific embodiment, the at least one copy of a nucleotide sequence encoding a Aβ1-m peptide can be inserted into the nucleotide sequence encoding the same loop of a norovirus capsid P protein, or into the nucleotide sequences encoding different loops of a norovirus capsid P protein. For example, where the nucleotide sequence encoding a norovirus capsid P protein is SEQ ID NO: 9, loop1 corresponds to nucleotides 208-222, loop2 corresponds to nucleotides 442-453, and loop3 corresponds to nucleotides 502-513.

In a specific embodiment of the invention, the numbers of the Aβ1-m peptide-encoding nucleotide sequences inserted into loop1, loop2 and loop3 are N1, N2 and N3, respectively; N1, N2 and N3 each are independently selected from 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and 40, and $N1+N2+N3 \geq 1$.

In a specific embodiment of the invention, the 5' end nucleotide of the nucleotide sequence encoding a Aβ1-m peptide is linked directly to the nucleotide sequence encoding a loop of a norovirus capsid P protein via 3',5'-phosphodiester bond or via a DNA linker. The insertion would not result in frame shift during translation of the nucleotide sequence, whether it is a direct insertion or an insertion via a DNA linker.

In a preferred embodiment, the DNA linker is (GGA)n, (GGG)n or (GGC)n, wherein preferably n is 1-10, and more preferably n is 3.

In a specific embodiment of the invention, the multiple consecutive Aβ1-m peptide-encoding nucleotide sequences inserted into the nucleotide sequence encoding a norovirus capsid P protein are linked directly to each other by 3',5'-phosphodiester bond or by a DNA linker. The insertion would not result in frame shift during translation of the nucleotide sequence, whether it is a direct insertion or an insertion by a DNA linker. In a preferred embodiment, the DNA linker is (GGA)n, (GGG)n or (GGC)n, wherein preferably n is 1-10, and more preferably n is 3.

Preferably, the Aβ1-m peptide nucleotide sequence is a nucleotide sequence encoding an Aβ1-m peptide from human, mouse, primate, rabbit, African clawed frog (*Xenopuslaevis*), rat and guinea pig. More preferably, the Aβ1-m peptide nucleotide sequence is a nucleotide sequence encoding an Aβ1-m peptide from human.

In a preferred embodiment of the invention, the nucleotide sequences encoding norovirus capsid P proteins of chimeric Aβ1-m peptides are SEQ ID NOs: 15-141. More preferably, the nucleotide sequence encoding a norovirus capsid P protein of a chimeric Aβ1-m peptide is selected from SEQ ID NO:24, SEQ ID NO:39, SEQ ID NO:40, SEQ ID NO:57, SEQ ID NO:73, SEQ ID NO:92, SEQ ID NO:117, SEQ ID NO:132, SEQ ID NO:133 and SEQ ID NO:134.

In a third aspect, the present invention also provides a pharmaceutical composition used for preventing or treating Alzheimer's disease, comprising the recombinant P particle in the first aspect of the invention and a pharmaceutically acceptable carrier. The pharmaceutical composition is preferably used in mammals, and more preferably used in human. Preferably, the pharmaceutical composition is a vaccine composition, and more preferably, the vaccine composition also comprises an adjuvant. In a specific embodiment of the invention, the adjuvant is CpG. In another specific embodiment of the invention, the adjuvant is an aluminum adjuvant. The vaccine composition is preferably administered subcutaneously or nasally, and more preferably administered subcutaneously.

In a fourth aspect, the present invention also provides use of the recombinant P particle in the first aspect of the invention in the manufacture of a medicament for treating or preventing Alzheimer's disease. Preferably, the medicament is a vaccine. The medicament is preferably used in mammals, and more preferably used in human.

In a fifth aspect, the present invention also provides a method for preparing the recombinant P particle in the first aspect of the invention, comprising the following steps:

i) obtaining an expression vector comprising a nucleic acid encoding a norovirus capsid P protein of a chimeric Aβ1-m peptide, wherein m is an integer ranging from 6 to 15;

ii) transferring the expression vector into a receptor cell;

iii) expressing the norovirus capsid P protein of a chimeric Aβ1-m peptide, and allowing it to self-assemble into a recombinant P particle;

and preferably, the method also comprises isolation and purification steps.

In a specific embodiment, cation exchange chromatography and/or hydrophobic chromatography can be used for purification.

Figure 1A:
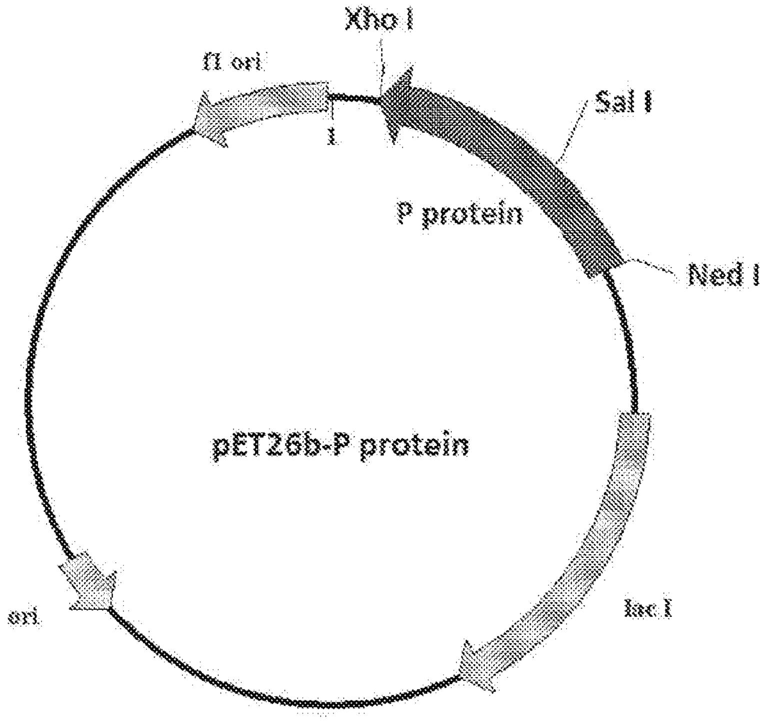
FIG. 1 shows the maps of the various recombinant pET26b plasmid constructs.

A is the schematic diagram of pET26b-P protein plasmid that has been constructed.

B is the schematic diagram of pET26b-P protein-mEagI plasmid with a mEagI restriction enzyme site obtained by mutation.

C is the schematic diagram of pET26b-P protein-mEagI&mKpnI plasmid with a mEagI restriction enzyme site and a mKpnI restriction enzyme site obtained by mutation.

D is the schematic diagram of pET26b-P protein-10copy-Aβ1-6-loop1$G_{72}$ plasmid with the gene fragment of interest P protein-10copy-Aβ1-6-loop1$G_{72}$ loaded between a mKpnI restriction enzyme site and a SalI restriction enzyme site.

E is the schematic diagram of pET26b-P protein-1copy-Aβ1-6-loop2$S_{149}$ plasmid with the gene fragment of interest P protein-1copy-Aβ1-6-loop2$S_{149}$ loaded between a mEagI restriction enzyme site and a SalI restriction enzyme site.

F is a schematic diagram of pET26b-Pprotein-10copy-Aβ1-6-loop2$S_{149}$ plasmid with the gene fragment of interest P protein-10copy-Aβ1-6-loop2$S_{149}$ loaded between a mEagI restriction enzyme site and a SalI restriction enzyme site.

G is the schematic diagram of pET26b-P protein-20copy-Aβ1-6-loop3$G_{169}$ plasmid with the gene fragment of interest P protein-20copy-Aβ1-6-loop3$G_{169}$ loaded between a mEagI restriction enzyme site and a SalI restriction enzyme site.

H is the schematic diagram of pET26b-Pprotein-10copy-Aβ1-15-loop1$G_{72}$-10copy-Aβ1-6-loop2$S_{149}$ plasmid with the gene fragment of interest Pprotein-10copy-Aβ1-15-loop1$G_{72}$-10copy-Aβ1-6-loop2$S_{149}$ loaded between a mEagI restriction enzyme site and a mKpnI restriction enzyme site.

I is the schematic diagram of pET26b-P protein-3copy-Aβ1-12-loop2$S_{149}$-3copy-Aβ1-6-loop3$G_{169}$ plasmid with the gene fragment of interest Pprotein-3copy-Aβ1-12-loop2$S_{149}$-3copy-Aβ1-6-loop3$G_{169}$ loaded between a mEagI restriction enzyme site and a mKpnI restriction enzyme site.

J is the schematic diagram of pET26b-P protein-1copy-Aβ1-6-loop1$G_{72}$-10copy-Aβ1-6-loop3$G_{169}$ plasmid with the gene fragment of interest P protein-1copy-Aβ1-6-loop1$G_{72}$-10copy-Aβ1-6-loop3$G_{169}$ loaded between a mEagI restriction enzyme site and a mKpnI restriction enzyme site.

K is the schematic diagram of pET26b-P protein-1copy-Aβ1-6-loop1$G_{72}$-1copy-Aβ1-6-loop2$S_{149}$-1copy-Aβ1-6-loop3$G_{169}$ plasmid with the gene fragment of interest Pprotein-1copy-Aβ1-6-loop1$G_{72}$-1copy-Aβ1-6-loop2$S_{149}$-1copy-Aβ1-6-loop3$G_{169}$ loaded between a mEagI restriction enzyme site and a mKpnI restriction enzyme site.

L is the schematic diagram of pET26b-P protein-3 copy-Aβ1-6-loop1$G_{72}$-3copy-Aβ1-6-loop2$S_{149}$-3copy-Aβ1-6-loop3$G_{169}$ plasmid with the gene fragment of interest P protein-3 copy-Aβ1-6-loop1$G_{72}$-3copy-Aβ1-6-loop2$S_{149}$-3copy-Aβ1-6-loop3$G_{169}$ loaded between a mEagI restriction enzyme site and a mKpnI restriction enzyme site.

M is the schematic diagram of pET26b-P protein-10copy-Aβ1-6-loop1$G_{72}$-10copy-Aβ1-6-loop2$S_{149}$-10copy-Aβ1-6-loop3$G_{169}$ plasmid with the gene fragment of interest Pprotein-10copy-Aβ1-6-loop1$G_{72}$-10copy-Aβ1-6-loop2$S_{149}$-10copy-Aβ1-6-loop3$G_{169}$ loaded between a mEagI restriction enzyme site and a mKpnI restriction enzyme site.

FIG. 2 shows the schematic diagrams of the structures of gene fragments of interest.

A is the schematic diagram of the locations of three loops of P protein (loop1, loop2 and loop3), together with site-directed mutation sites and restriction enzyme sites carried by P protein gene;

B is the schematic diagram of a P particle gene fragment of interest with 10 copies of Aβ1-6 gene embedded behind site $G_{72}$ into loop1, abbreviated as P protein-10copy-Aβ1-6-loop1$G_{72}$;

C is the schematic diagram of a P particle gene fragment of interest with one copy of Aβ1-6 gene embedded behind site $S_{149}$ into loop2, abbreviated as P protein-1copy-Aβ1-6-loop2$S_{149}$;

D is the schematic diagram of a P particle gene fragment of interest with 10 copies of Aβ1-6 gene embedded behind site $S_{149}$ into loop2, abbreviated as P protein-10copy-Aβ1-6-loop2$S_{149}$;

E is the schematic diagram of a P particle gene fragment of interest with 20 copies of Aβ1-6 gene embedded behind site $G_{169}$ into loop3, abbreviated as P protein-20copy-Aβ1-6-loop3$G_{169}$;

F is the schematic diagram of a P particle gene fragment of interest with 10 copies of Aβ1-15 gene embedded behind site $G_{72}$ into loop1 and 10 copies of Aβ1-6 gene embedded behind site $S_{149}$ into loop2, abbreviated as P protein-10copy-Aβ1-15-loop1$G_{72}$-10copy-Aβ1-6-loop2$S_{149}$;

G is the schematic diagram of a P particle gene fragment of interest with 3 copies of Aβ1-12 gene embedded behind site $S_{149}$ into loop2 and 3 copies of Aβ1-6 gene embedded behind site $G_{169}$ into loop3, abbreviated as P protein-3copy-Aβ1-12-loop2$S_{149}$-3copy-Aβ1-6-loop3$G_{169}$;

H is the schematic diagram of a P particle gene fragment of interest with one copy of Aβ1-6 gene embedded behind site $G_{72}$ into loop1 and 10 copies of Aβ1-6 gene embedded behind site $G_{169}$ into loop3, abbreviated as P protein-1copy-Aβ1-6-loop1$G_{72}$-10copy-Aβ1-6-loop3$G_{169}$;

I is the schematic diagram of a P particle gene fragment of interest with one copy of Aβ1-6 gene embedded behind site $G_{72}$ into loop1, one copy of Aβ1-6 gene embedded behind site $S_{149}$ into loop2 and one copy of Aβ1-6 gene embedded behind site $G_{169}$ into loop3, abbreviated as P protein-1copy-Aβ1-6-loop1$G_{72}$-1copy-Aβ1-6-loop2$S_{149}$-1copy-Aβ1-6-loop3$G_{169}$;

J is the schematic diagram of a P particle gene fragment of interest with 3 copies of Aβ1-6 gene embedded behind site $G_{72}$ into loop1, 3 copies of Aβ1-6 gene embedded behind site $S_{149}$ into loop2 and 3 copies of Aβ1-6 gene embedded behind site $G_{169}$ into loop3, abbreviated as P protein-3copy-Aβ1-6-loop1$G_{72}$-3copy-Aβ1-6-loop2$S_{149}$-3copy-Aβ1-6-loop3$G_{169}$; and K is the schematic diagram of a P particle gene fragment of interest with 10 copies of Aβ1-6 gene embedded behind site $G_{72}$ into loop1, 10 copies of Aβ1-6 gene embedded behind site $S_{149}$ into loop2 and 10 copies of Aβ1-6 gene embedded behind site $G_{169}$ into loop3, abbreviated as P protein-10copy-Aβ1-6-loop1$G_{72}$-10copy-Aβ1-6-loop2$S_{149}$-10copy-Aβ1-6-loop3$G_{169}$.

FIG. 3 shows the schematic diagram of 10 recombinant P particles. A is the schematic diagram of P protein-10copy-Aβ1-6-loop1$G_{72}$; B is the schematic diagram of Pprotein-1copy-Aβ1-6-loop2$S_{149}$; C is the schematic diagram of P protein-10copy-Aβ1-6-loop2$S_{149}$; D is the schematic diagram of P protein-20copy-Aβ1-6-loop3$G_{169}$; E is the schematic diagram of P protein-10copy-Aβ1-15-loop1$G_{72}$-10copy-Aβ1-6-loop2$S_{149}$; F is the schematic diagram of P protein-3copy-Aβ1-12-loop2$S_{149}$-3copy-Aβ1-6-loop3$G_{169}$; G is the schematic diagram of P protein-1copy-Aβ1-6-loop1$G_{72}$-10copy-Aβ1-6-loop3$G_{169}$; H is the schematic diagram of P protein-1copy-Aβ1-6-loop1$G_{72}$-1copy-Aβ1-6-loop2$S_{149}$-1copy-Aβ1-6-loop3$G_{169}$; I is the schematic diagram of P protein-3copy-Aβ1-6-loop1$G_{72}$-3copy-Aβ1-6-loop2$S_{149}$-3copy-Aβ1-6-loop3$G_{169}$; and J is the schematic diagram of P protein-10copy-Aβ1-6-loop1$G_{72}$-10copy-Aβ1-6-loop2$S_{149}$-10copy-Aβ1-6-loop3$G_{169}$.

Figures 4, 4J:
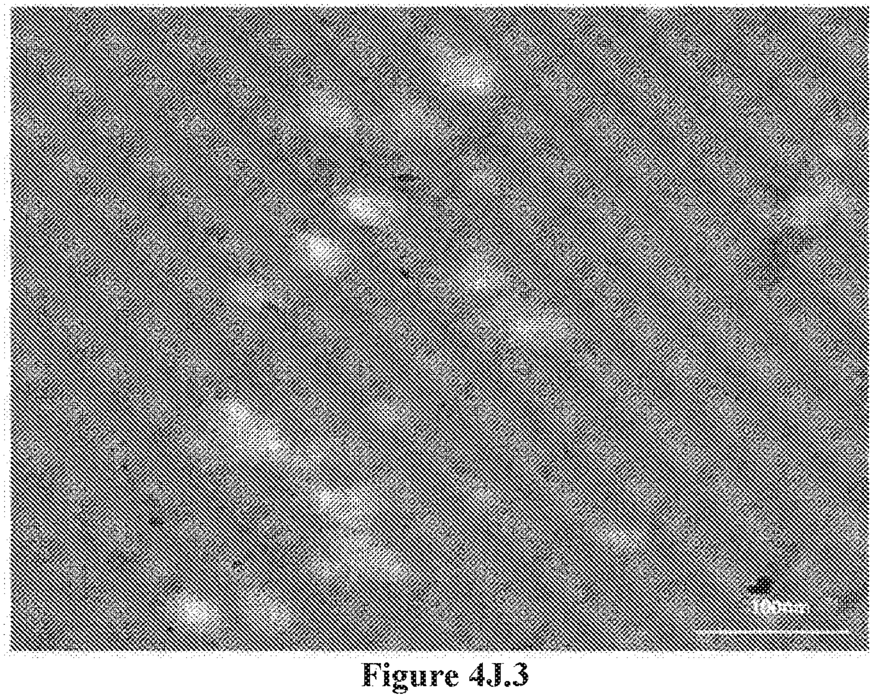

FIG. 4 shows the purification and characterization of recombinant P particles. A is the SDS-PAGE and Native-PAGE graphs, as well as the electron microscope image of PP-10copy-Aβ1-6-loop1$G_{72}$ protein; B is the SDS-PAGE and Native-PAGE graphs, as well as the electron microscope image of PP-1copy-Aβ1-6-loop2$S_{149}$ protein; C is the SDS-PAGE and Native-PAGE graphs, as well as the electron microscope image of PP-10copy-Aβ1-6-loop2$S_{149}$ protein; D is the SDS-PAGE and Native-PAGE graphs, as well as the electron microscope image of PP-20copy-Aβ1-6-loop3$G_{169}$ protein; E is the SDS-PAGE and Native-PAGE graphs, as well as the electron microscope image of PP-10copy-Aβ1-15-loop1$G_{72}$-10copy-Aβ1-6-loop2$S_{149}$ protein; F is the SDS-PAGE and Native-PAGE graphs, as well as the electron microscope image of PP-3copy-Aβ1-12-loop2$S_{149}$-3copy-Aβ1-6-loop3$G_{169}$ protein; G is the SDS-PAGE and Native-PAGE graphs, as well as the electron microscope image of PP-1copy-Aβ1-6-loop1$G_{72}$-10copy-Aβ1-6-loop3$G_{169}$ protein; H is the SDS-PAGE and Native-PAGE graphs, as well as the electron microscope image of PP-1copy-Aβ1-6-loop1$G_{72}$-1copy-Aβ1-6-loop2$S_{149}$-1copy-Aβ1-6-loop3$G_{169}$ protein; I is the SDS-PAGE and Native-PAGE graphs, as well as the electron microscope image of PP-3copy-Aβ1-6-loop1$G_{72}$-3copy-Aβ1-6-loop2$S_{149}$-3copy-Aβ1-6-loop3$G_{169}$ protein; J is the SDS-PAGE and Native-PAGEgraphs, as well as the electron microscope image of PP-10copy-Aβ1-6-loop1$G_{72}$-10copy-Aβ1-6-loop2$S_{149}$-10copy-Aβ1-6-loop3$G_{169}$ protein.

Figure 5A:
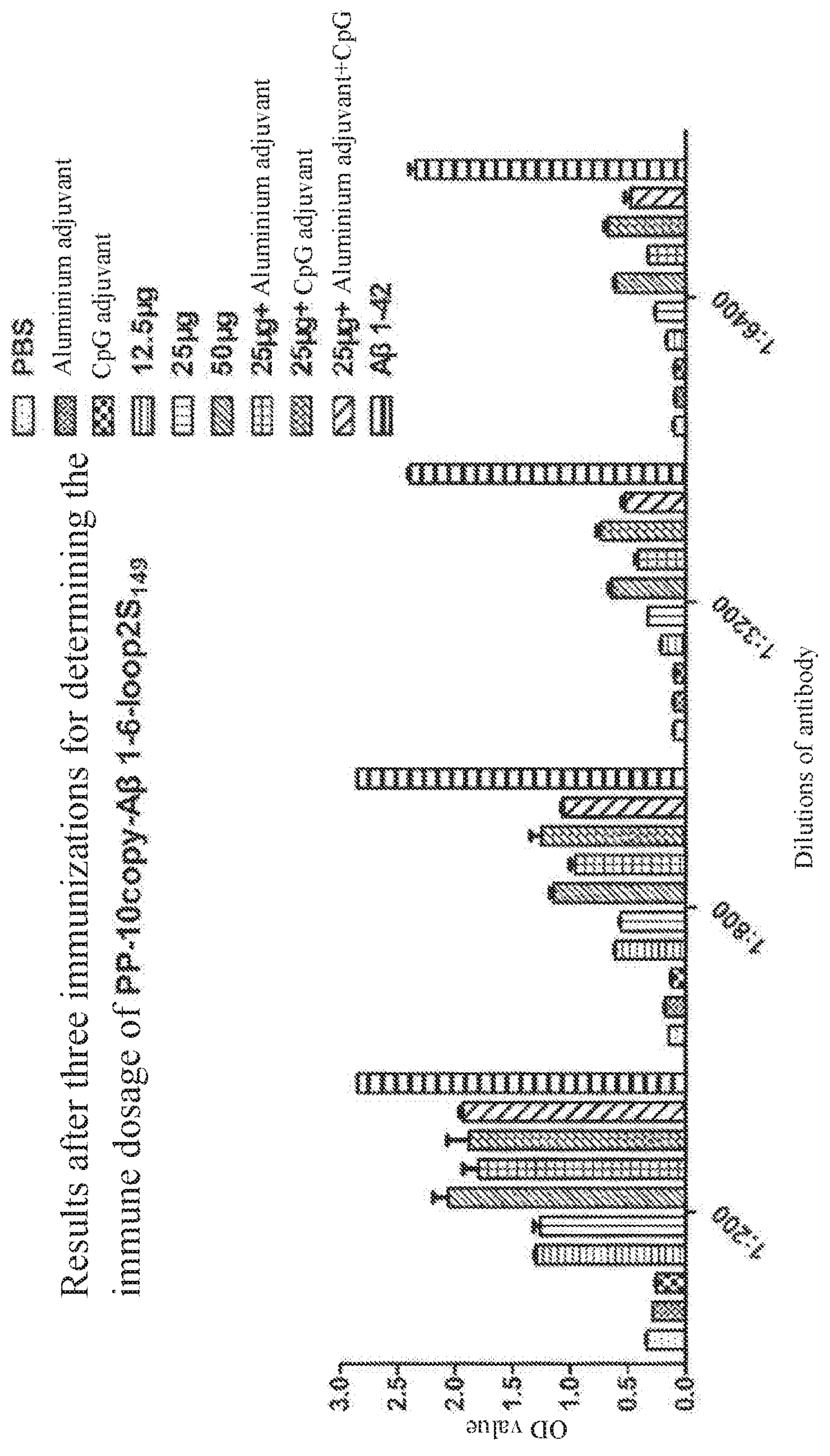
Figures 5, 5B:
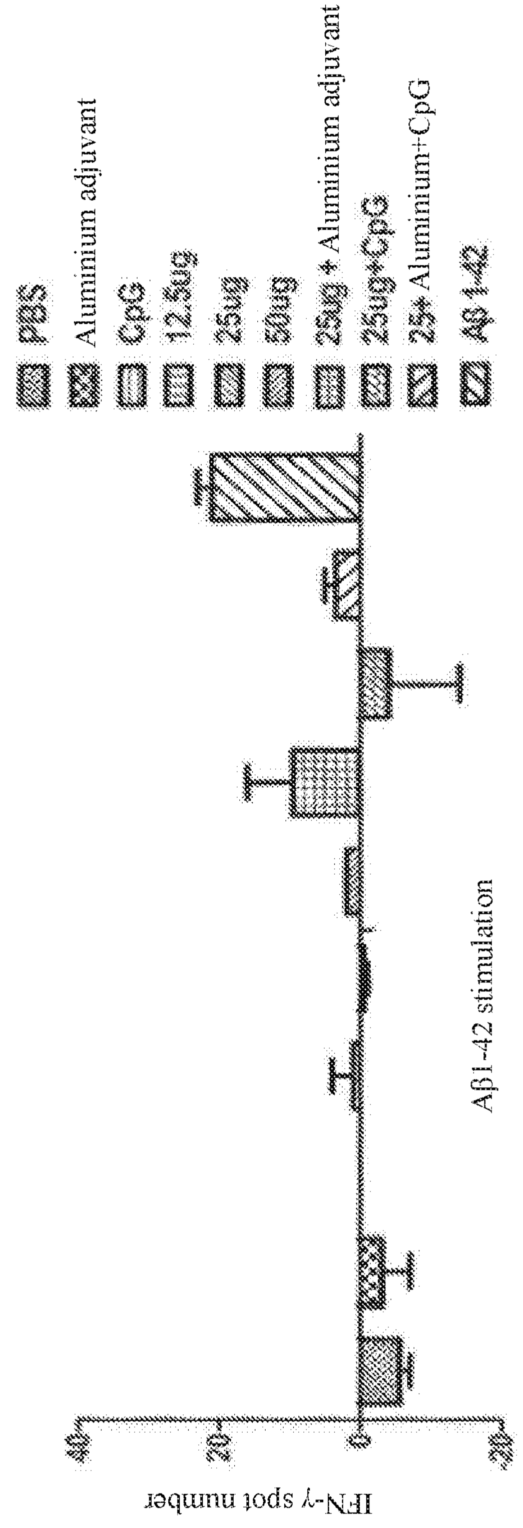

FIG. 5 shows the determination of optimal immune dosage and optimal immune adjuvant of PP-10copy-Aβ1-6-loop2$S_{149}$ protein vaccine in a C57BL/6J mouse model.

A is the detection of anti-Aβ42 antibody in mouse immune serum after immunization with different dosages of PP-10copy-Aβ1-6-loop2$S_{149}$ protein vaccine stimulated by different immune adjuvants. B is the detection of T cell responses produced by mouse spleen lymphocytes after immunization with different forms of PP-10copy-Aβ1-6-loop2$S_{149}$ protein vaccine.

Figure 6A:
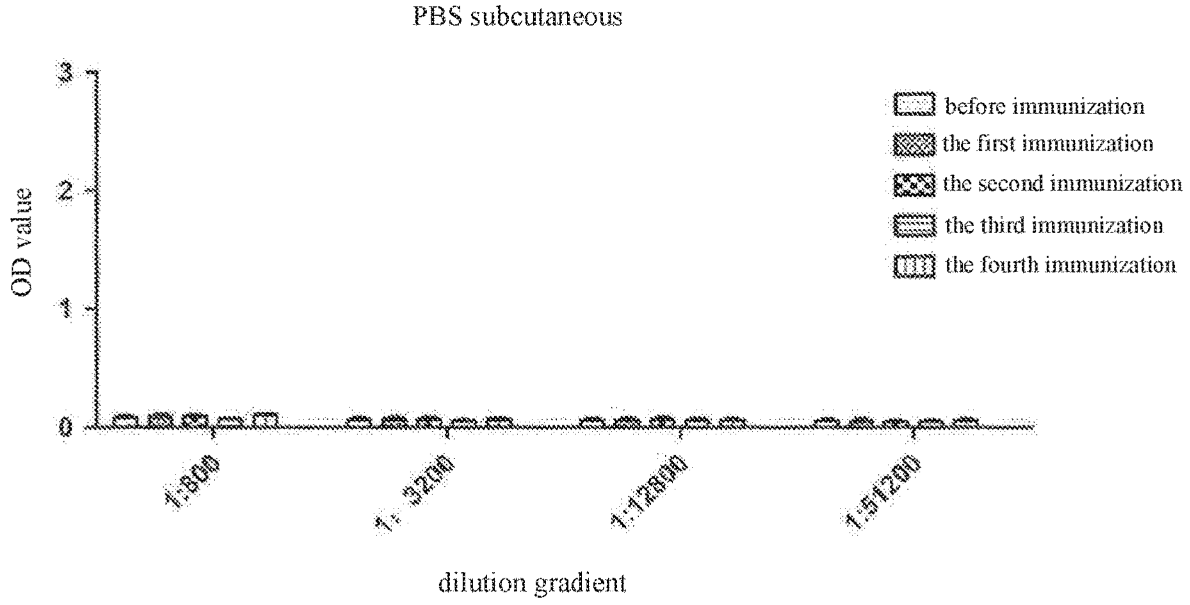
Figure 6B:
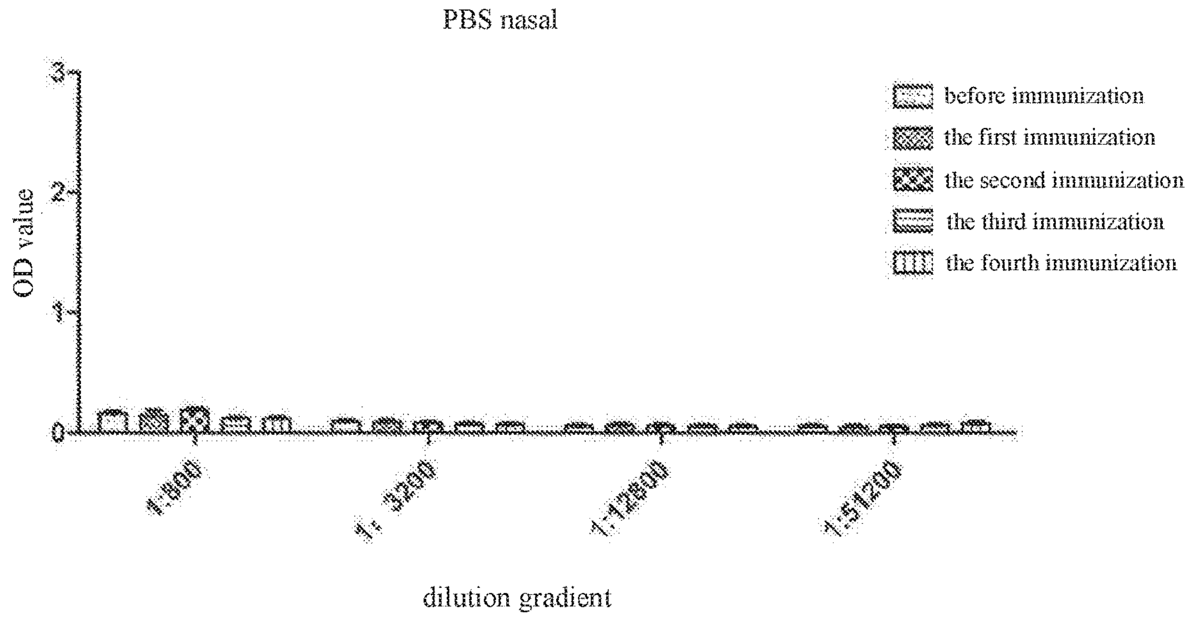
Figure 6C:
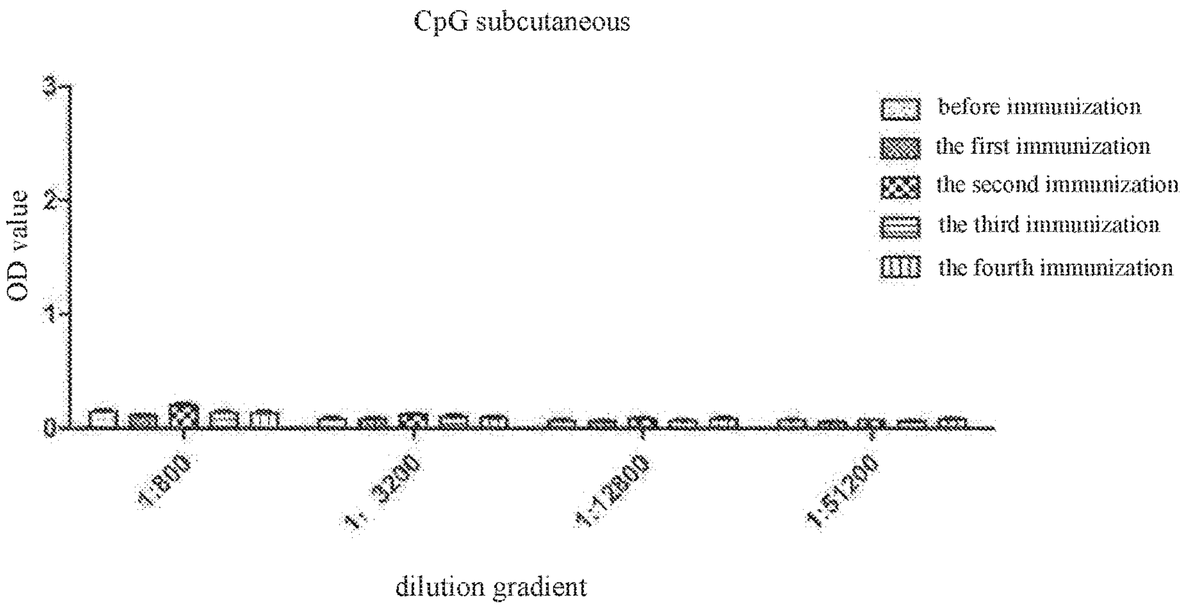
Figure 6D:
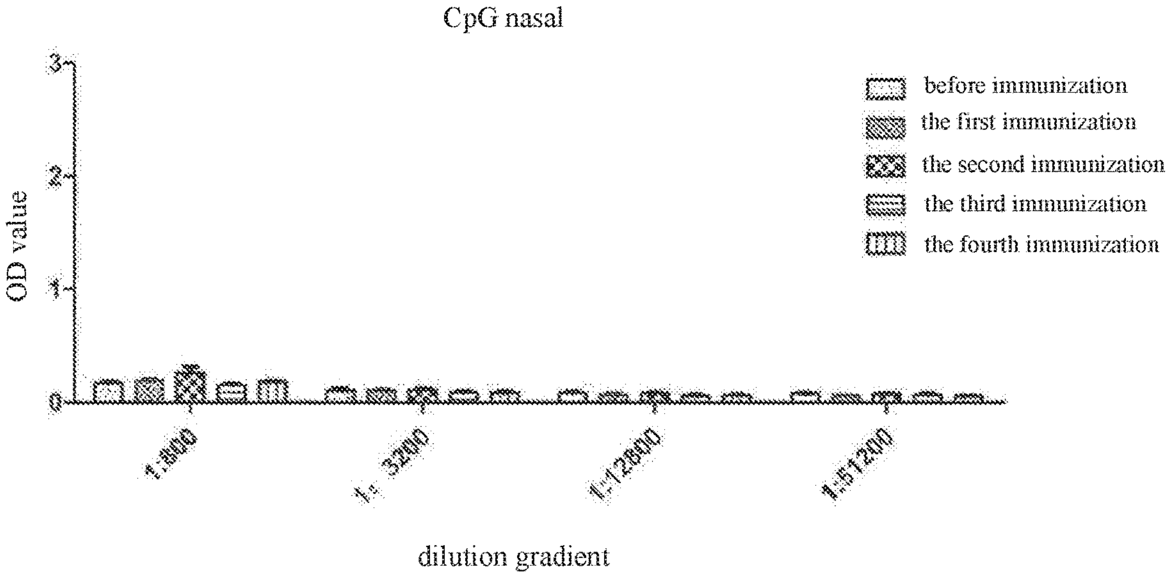
Figure 6E:
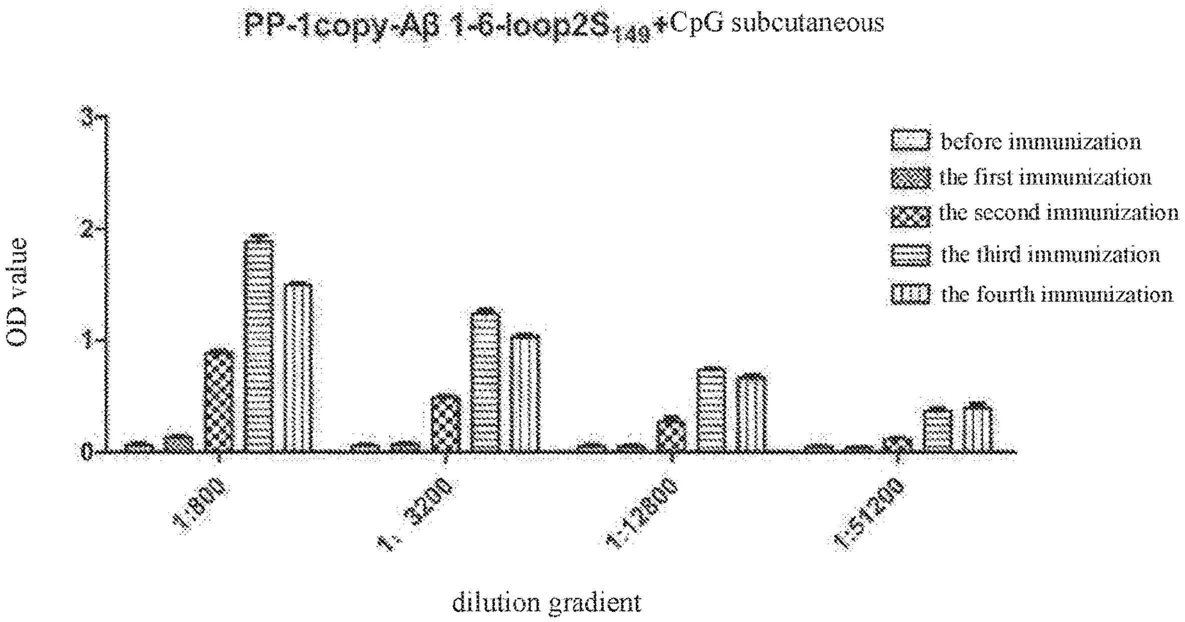
Figure 6F:
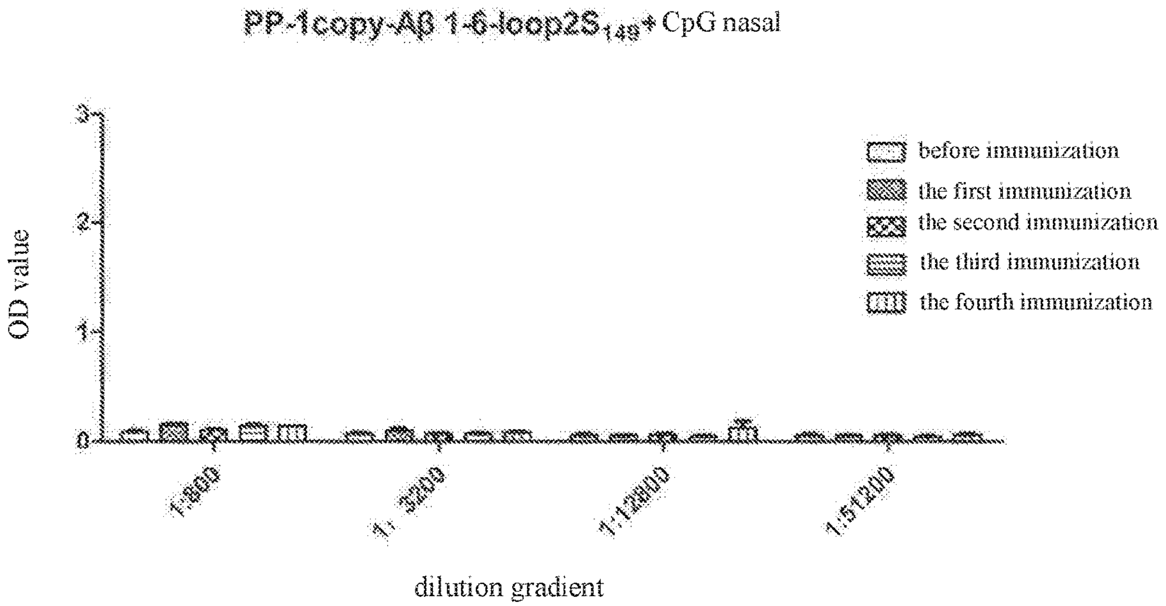
Figure 6G:
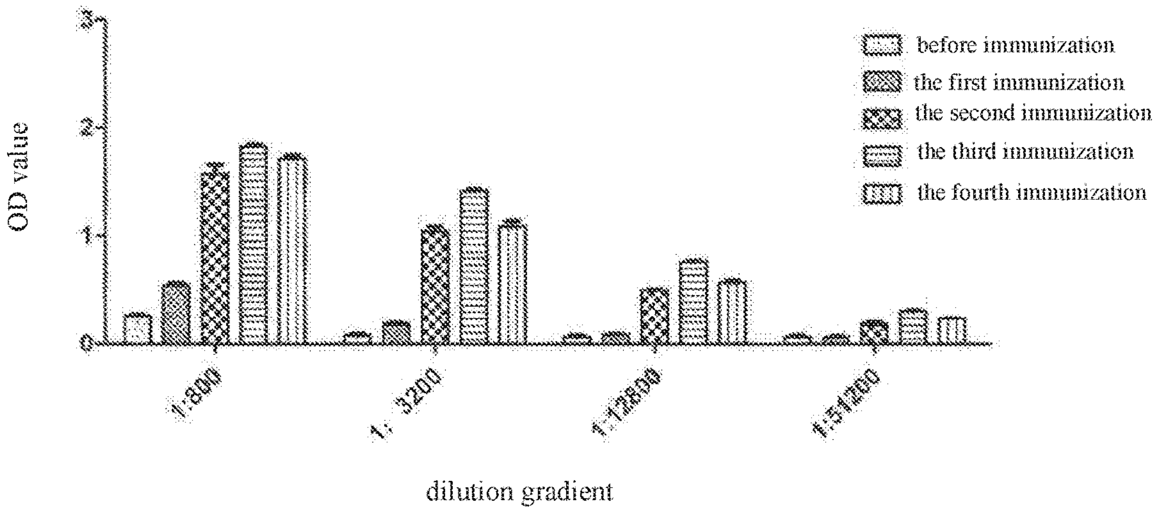
Figure 6H:
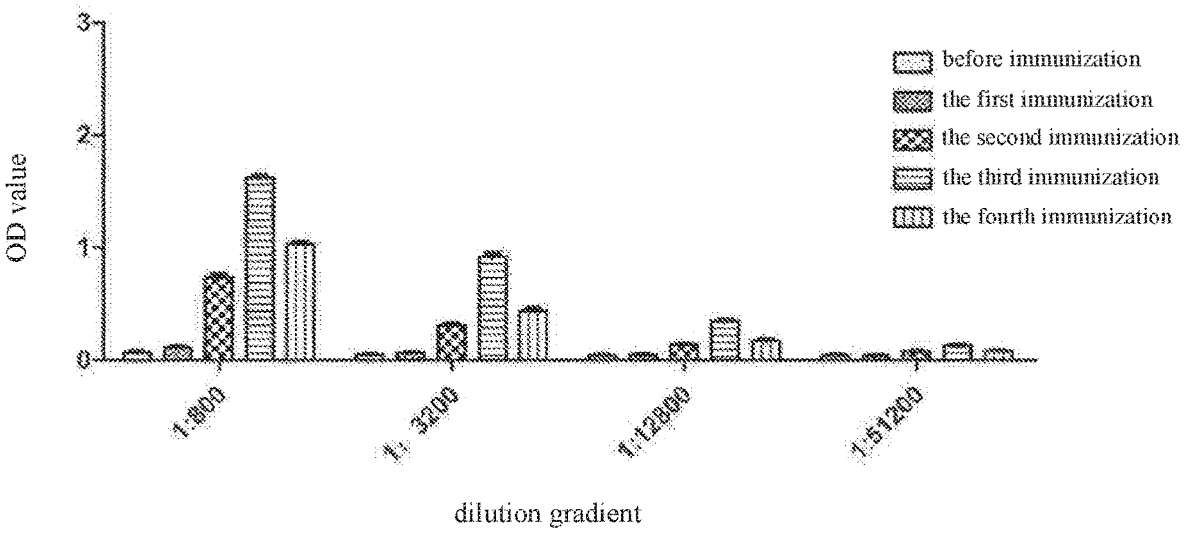
Figure 6I:
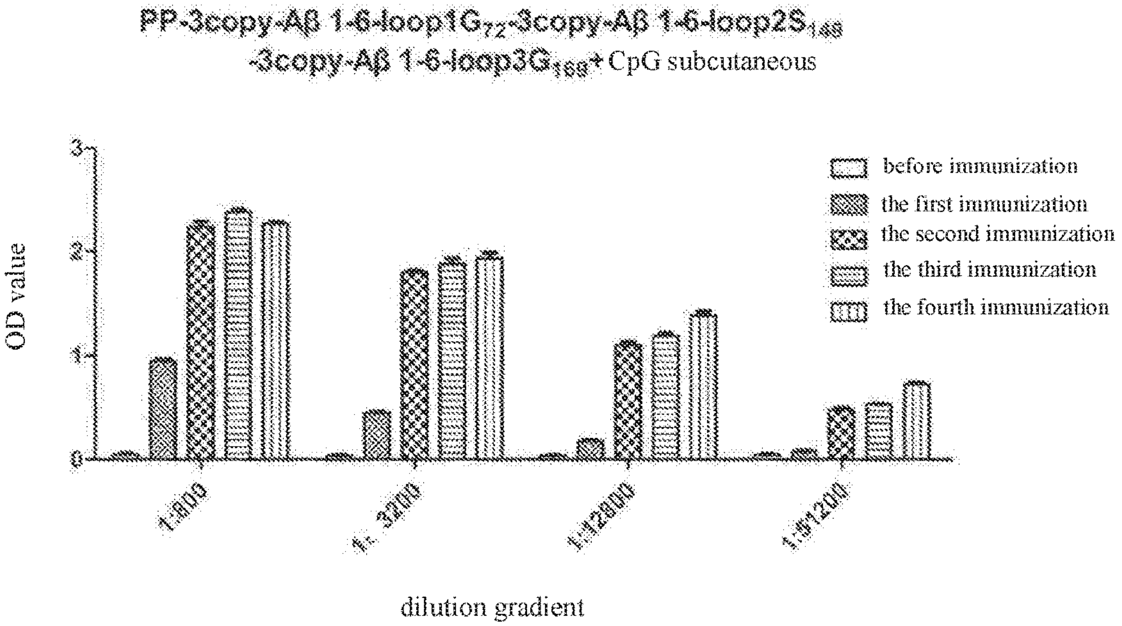
Figure 6J:
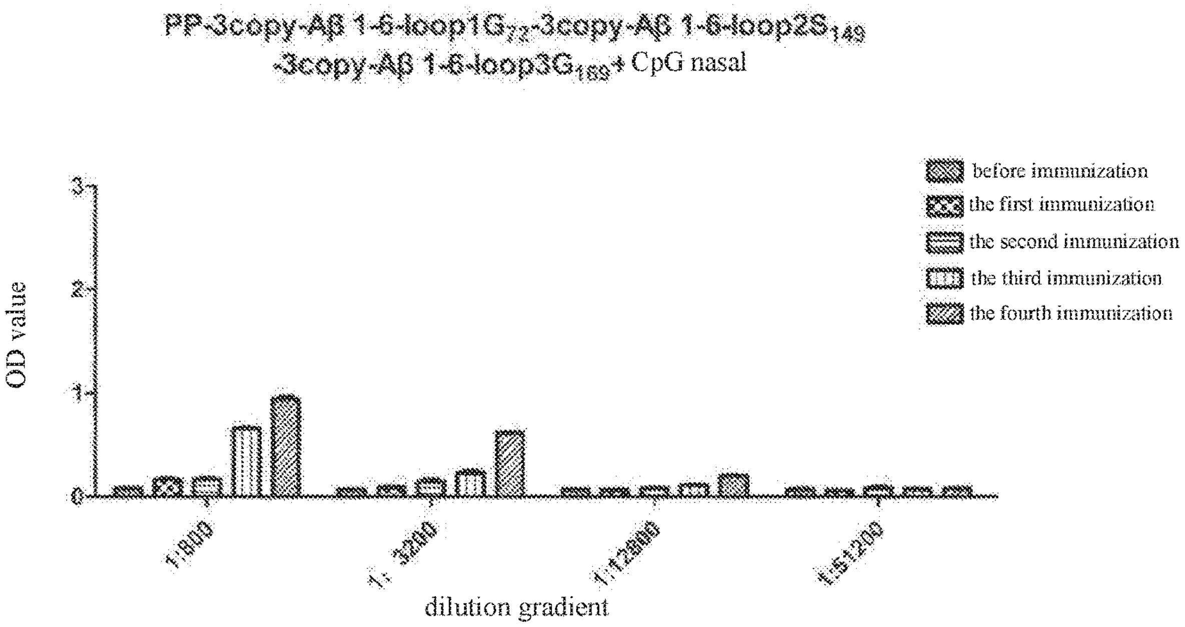
Figures 6, 6K:
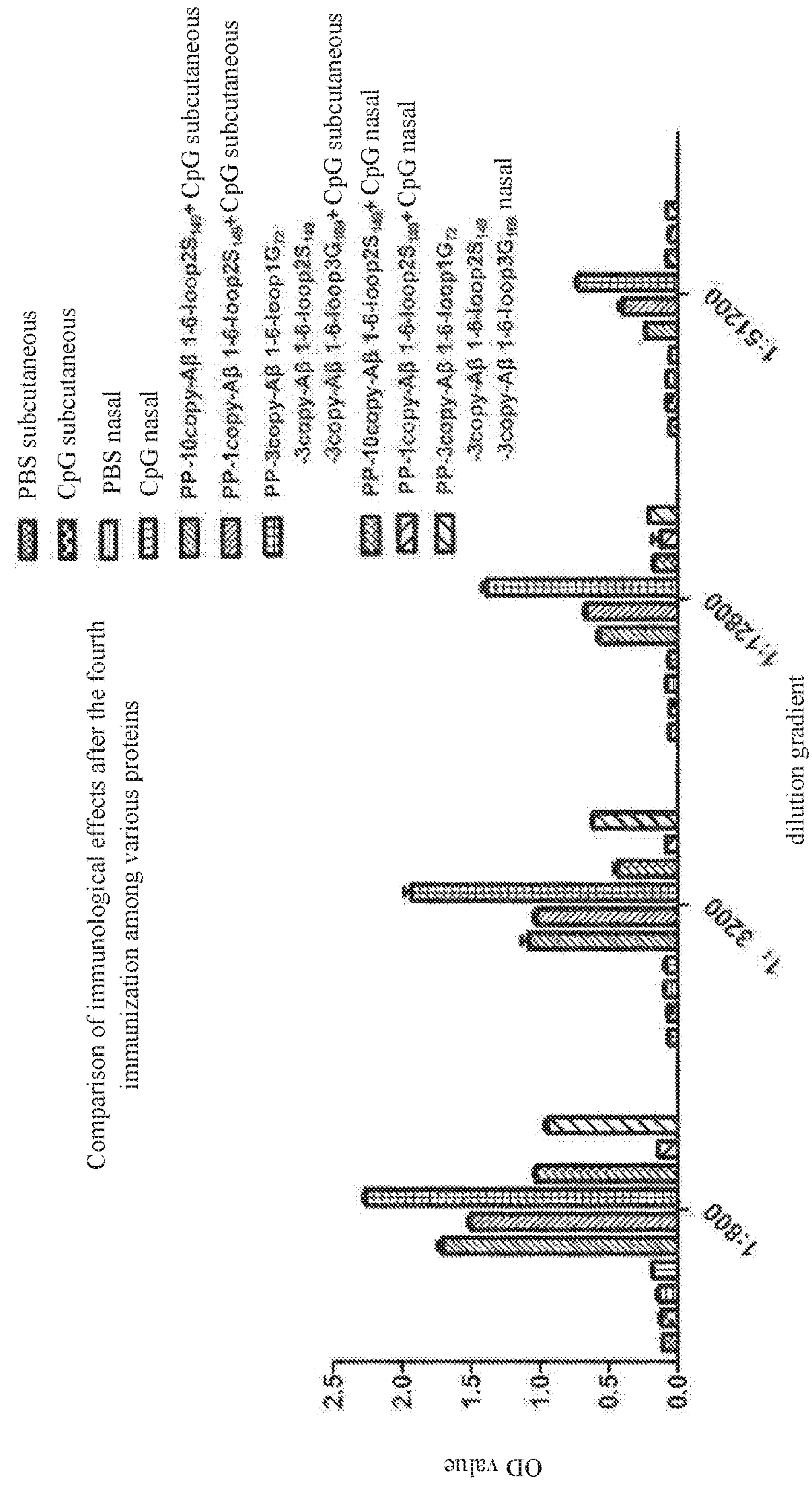

FIG. 6 shows the ELISA detection of anti-Aβ42 antibody in mouse immune serum and the comparison of Aβ42 antibody levels from different immune groups after the mice are immunized with three different forms of protein vaccine. A is the statistical graph of four immunization results for the group of subcutaneous immunization with PBS. B is the statistical graph of four immunization results for the group of nasal immunization with PBS. C is the statistical graph of four immunization results for the group of subcutaneous immunization with CpG. D is the statistical graph of four immunization results for the group of nasal immunization with CpG. E is the statistical graph of four immunization results for the group of subcutaneous immunization with PP-1copy-Aβ1-6-loop2$S_{149}$ and the adjuvant CpG. F is the statistical graph of four immunization results for the group of nasal immunization with PP-1copy-Aβ1-6-loop2$S_{149}$ and the adjuvant CpG. G is the statistical graph of four immunization results for the group of subcutaneous immunization with PP-10copy-Aβ1-6-loop2$S_{149}$ and the adjuvant CpG. H is the statistical graph of four immunization results for the group of nasal immunization with PP-10copy-Aβ1-6-loop2$S_{149}$ and the adjuvant CpG. I is the statistical graph of four immunization results for the group of subcutaneous immunization with PP-3copy-Aβ1-6-loop1$G_{72}$-3copy-Aβ1-6-loop2$S_{149}$-3copy-Aβ1-6-loop3$G_{169}$ and the adjuvant CpG. J is the statistical graph of four immunization results for the group of nasal immunization with PP-3copy-Aβ1-6-loop1$G_{72}$-3copy-Aβ1-6-loop2$S_{149}$-3copy-Aβ1-6-loop3$G_{169}$ and the adjuvant CpG. K is the comparison of results after the fourth immunization for each group, wherein the best immunological effect is observed in the group of subcutaneous immunization with PP-3copy-Aβ1-6-loop1$G_{72}$-3copy-Aβ1-6-loop2$S_{149}$-3copy-Aβ1-6-loop3$G_{169}$ and the adjuvant CpG.

SEQUENCE LISTING

SEQ ID NO: 1 is the amino acid sequence of a norovirus capsid P protein.

SEQ ID NOs: 2-8 are amino acid sequences of Aβ1-15 peptides from human, mouse, primate, rabbit, African clawed frog (*Xenopuslaevis*), rat and guinea pig.

SEQ ID NO: 9 is the nucleotide sequence encoding a norovirus P protein.

SEQ ID NO: 10 is the nucleotide sequence encoding an A1-15 peptide from human.

SEQ ID NO: 11 is a site-directed mutation forward primer used in the process of obtaining pET26b-P protein-mEagI plasmid.

SEQ ID NO:12 is a site-directed mutation reverse primer used in the process of obtaining pET26b-P protein-mEagI plasmid.

SEQ ID NO: 13 is a site-directed mutation forward primer used in the process of obtaining pET26b-P protein-mEagI&mKpnI plasmid.

SEQ ID NO: 14 is a site-directed mutation reverse primer used in the process of obtaining pET26b-Pprotein-mEagI&mKpnI plasmid.

SEQ ID NO: 15-SEQ ID NO: 141 are nucleotide sequences encoding norovirus capsid P proteins of chimeric Aβ1-m peptides prepared in the examples of the invention.

SEQ ID NO: 143-SEQ ID NO: 152 are nucleotide sequences of DNA fragments of interest synthesized in the process of constructing recombinant plasmids expressing preferred 10 recombinant P proteins, corresponding to 10copy-Aβ1-6-loop1$G_{72}$, 1copy-Aβ1-6-loop2$S_{149}$, 10copy-Aβ1-6-loop2$S_{149}$, 20copy-Aβ1-6-loop3$G_{169}$, 3copy-Aβ1-12-loop2$S_{149}$-3copy-Aβ1-6-loop3$G_{169}$, 10copy-Aβ1-15-loop1$G_{72}$-10copy-Aβ1-6-loop2$S_{149}$, 1copy-Aβ1-6-loop1-$G_{72}$-10copy-Aβ1-6-loop3$G_{169}$, 1copy-Aβ1-6-loop1$G_{72}$-1copy-Aβ1-6-loop2$S_{149}$-1copy-Aβ1-6-loop3$G_{169}$, 3copy-Aβ1-6-loop1$G_{72}$-3copy-Aβ1-6-loop2$S_{149}$-3copy-Aβ1-6-loop3$G_{169}$, and 10copy-Aβ1-6-loop1$G_{72}$-10copy-Aβ1-6-loop2$S_{149}$-10copy-Aβ1-6-loop3$G_{169}$, respectively.

DETAILED DESCRIPTION OF THE INVENTION

Definition

All the technical terms used in the present invention have the same meanings as those skilled in the art commonly understand, unless otherwise indicated.

An ordered and repetitive antigen array refers to multiple Aβ1-m peptides (m is an integer ranging from 6 to 15) repetitively and orderly arranged on the surface of a norovirus recombinant P particle.

P protein refers to the P protein in the norovirus capsid P proteins, which can self-assemble in vitro into a P particle. When used herein, P protein used at the gene level means a gene fragment, nucleotide sequence, plasmid, etc. encoding a P protein; P protein used at the protein level means a P protein monomer or dimer. In the accompanying figures, all schematic diagrams of protein show P protein, such as the plasmids encoding P proteins shown in FIGS. 1, 2 and 3, and the P protein monomer shown in the denatured electrophoresis of FIG. 4.

P particle (abbreviated as PP) refers to a protein particle formed by the in vitro self-assembly of P protein in norovirus. The most common form of P particle is a tetracosamer. When used herein, P particle (PP) only used at the protein level means the form of polymer (such as a tetracosamer), including various proteins used for property detection and immunization, such as the polymer form shown in the denatured electrophoresis of FIG. 4.

Pprotein-N1copy-Aβ1-m-loop1Ak1-N2copy-Aβ1-m-loop2Ak2-N3copy-Aβ1-m-loop 3Ak3 means that N1 copies of Aβ1-m are embedded behind the amino acid at position K2 into loop1 of P protein, N2 copies of Aβ1-m are embedded behind the amino acid at position K2 into loop2 of P protein, and N3 copies of Aβ1-m are embedded behind the amino acid at position K3 into loop3 of P protein, wherein m is an integer ranging from 6 to 15. Unless otherwise indicated, Aβ1-m is linked to P protein via a polypeptide linker having three glycines. For example, P protein-1copy-Aβ1-6-loop2$T_{148}$-1copy-Aβ1-6-loop2$S_{149}$-1copy-Aβ1-6-loop2$N_{150}$ means a P protein in which one copy of Aβ1-6 is respectively embedded behind the amino acid at position 148, behind the amino acid at position 149, and behind the amino acid at position 150 into loop2, and each Aβ1-6 is linked to P protein via an amino acid linker having three glycines encoded by GGA.

P protein-10copy-Aβ1-6-loop2$S_{149}$(GGA)o means that 10 copies of Aβ1-6 are embedded behind the amino acid at position 149 into loop2 of P protein, and there is no linker between Aβ1-6 and P protein, and no amino acid linker between each Aβ1-6, i.e. Aβ1-6 is directly linked to P protein or another Aβ1-6 via a peptide bond.

P protein-10copy-Aβ1-6-loop2$S_{149}$$(GGC)_3$ means that 10 copies of Aβ1-6 are embedded behind the amino acid at position 149 into loop2 of P protein, Aβ1-6 is linked to P protein via an amino acid linker having three glycines encoded by GGC, and each Aβ1-6 is linked to each other via an amino acid linker having three glycines encoded by GGC.

The technical solutions of the invention are further illustrated by the following examples; however, the present invention is not limited to these examples. Unless otherwise indicated, the formulations and devices used herein are all commercially available.

The present invention provides 127 recombinant P particles in which multiple copies of Aβ1-m peptides (m is an integer ranging from 6 to 15) are embedded into loop1, loop2 and/or loop3 of P protein. The P proteins from which said 127 recombinant P particles are formed are shown in Table 1.

TABLE 1

The amino acid sequences of the recombinant P proteins from which said 127 recombinant P particles of the present invention are formed and the nucleotide sequences encoding the recombinant P proteins.

| NO. | Recombinant P Protein | Nucleotide Sequences encoding the Recombinant P proteins |
|---|---|---|
| 1 | P protein-1copy-Aβ1-6-loop1$I_{70}$ | SEQ ID NO: 15 |
| 2 | P protein-10copy-Aβ1-9-loop1$I_{70}$ | SEQ ID NO: 16 |
| 3 | P protein-20copy-Aβ1-12-loop1$I_{70}$ | SEQ ID NO: 17 |
| 4 | P protein-40copy-Aβ1-15-loop1$I_{70}$ | SEQ ID NO: 17 |
| 5 | P protein-1copy-Aβ1-9-loop1$A_{71}$ | SEQ ID NO: 19 |
| 6 | P protein-10copy-Aβ1-12-loop1$A_{71}$ | SEQ ID NO: 20 |
| 7 | P protein-20copy-Aβ1-15-loop1$A_{71}$ | SEQ ID NO: 21 |
| 8 | P protein-40copy-Aβ1-6-loop1$A_{71}$ | SEQ ID NO: 22 |
| 9 | P protein-1copy-Aβ1-6-loop1$G_{72}$ | SEQ ID NO: 23 |
| 10 | P protein-10copy-Aβ1-6-loop1$G_{72}$ | SEQ ID NO: 24 |
| 11 | P protein-20copy-Aβ1-6-loop1$G_{72}$ | SEQ ID NO: 25 |
| 12 | P protein-40copy-Aβ1-6-loop1$G_{72}$ | SEQ ID NO: 26 |
| 13 | P protein-1copy-Aβ1-12-loop1$T_{73}$ | SEQ ID NO: 27 |
| 14 | P protein-10copy-Aβ1-15-loop1$T_{73}$ | SEQ ID NO: 28 |
| 15 | P protein-20copy-Aβ1-6-loop1$T_{73}$ | SEQ ID NO: 29 |
| 16 | P protein-40copy-Aβ1-9-loop1$T_{73}$ | SEQ ID NO: 30 |
| 17 | P protein-1copy-Aβ1-15-loop1$Q_{74}$ | SEQ ID NO: 31 |
| 28 | P protein-10copy-Aβ1-6-loop1$Q_{74}$ | SEQ ID NO: 32 |
| 19 | P protein-20copy-Aβ1-9-loop1$Q_{74}$ | SEQ ID NO: 33 |
| 20 | P protein-40copy-Aβ1-12-loop1$Q_{74}$ | SEQ ID NO: 34 |
| 21 | P protein-1copy-Aβ1-9-loop2$T_{148}$ | SEQ ID NO: 35 |
| 22 | P protein-10copy-Aβ1-9-loop2$T_{148}$ | SEQ ID NO: 36 |
| 23 | P protein-20copy-Aβ1-9-loop2$T_{148}$ | SEQ ID NO: 37 |
| 24 | P protein-40copy-Aβ1-9-loop2$T_{148}$ | SEQ ID NO: 38 |
| 25 | P protein-1copy-Aβ1-6-loop2$S_{149}$ | SEQ ID NO: 39 |
| 26 | P protein-10copy-Aβ1-6-loop2$S_{149}$ | SEQ ID NO: 40 |
| 27 | P protein-20copy-Aβ1-6-loop2$S_{149}$ | SEQ ID NO: 41 |
| 28 | P protein-40copy-Aβ1-6-loop2$S_{149}$ | SEQ ID NO: 42 |
| 29 | P protein-1copy-Aβ1-12-loop2$N_{150}$ | SEQ ID NO: 43 |
| 30 | P protein-10copy-Aβ1-12-loop2$N_{150}$ | SEQ ID NO: 44 |
| 31 | P protein-20copy-Aβ1-12-loop2$N_{150}$ | SEQ ID NO: 45 |
| 32 | P protein-40copy-Aβ1-12-loop2$N_{150}$ | SEQ ID NO: 46 |

TABLE 1-continued

The amino acid sequences of the recombinant P proteins from which said 127 recombinant P particles of the present invention are formed and the nucleotide sequences encoding the recombinant P proteins.

| NO. | Recombinant P Protein | Nucleotide Sequences encoding the Recombinant P proteins |
|---|---|---|
| 33 | P protein-1copy-Aβ1-15-loop2D$_{151}$ | SEQ ID NO: 47 |
| 34 | P protein-10copy-Aβ1-15-loop2D$_{151}$ | SEQ ID NO: 48 |
| 35 | P protein-10copy-Aβ1-15-loop2D$_{151}$ | SEQ ID NO: 49 |
| 36 | P protein-40copy-Aβ1-15-loop2D$_{151}$ | SEQ ID NO: 50 |
| 37 | P protein-1copy-Aβ1-12-loop3D$_{168}$ | SEQ ID NO: 51 |
| 38 | P protein-10copy-Aβ1-12-loop3D$_{168}$ | SEQ ID NO: 52 |
| 39 | P protein-20copy-Aβ1-12-loop3D$_{168}$ | SEQ ID NO: 53 |
| 40 | P protein-40copy-Aβ1-12-loop3D$_{168}$ | SEQ ID NO: 54 |
| 41 | P protein-1copy-Aβ1-6-loop3G$_{169}$ | SEQ ID NO: 55 |
| 42 | P protein-10copy-Aβ1-6-loop3G$_{169}$ | SEQ ID NO: 56 |
| 43 | P protein-20copy-Aβ1-6-loop3G$_{169}$ | SEQ ID NO: 57 |
| 44 | P protein-40copy-Aβ1-6-loop3G$_{169}$ | SEQ ID NO: 58 |
| 45 | P protein-1copy-Aβ1-15-loop3S$_{170}$ | SEQ ID NO: 59 |
| 46 | P protein-10copy-Aβ1-15-loop3S$_{170}$ | SEQ ID NO: 60 |
| 47 | P protein-20copy-Aβ1-15-loop3S$_{170}$ | SEQ ID NO: 61 |
| 48 | P protein-40copy-Aβ1-15-loop3S$_{170}$ | SEQ ID NO: 62 |
| 49 | P protein-1copy-Aβ1-9-loop3T$_{171}$ | SEQ ID NO: 63 |
| 50 | P protein-10copy-Aβ1-9-loop3T$_{171}$ | SEQ ID NO: 64 |
| 51 | P protein-20copy-Aβ1-9-loop3T$_{171}$ | SEQ ID NO: 65 |
| 52 | P protein-40copy-Aβ1-9-loop3T$_{171}$ | SEQ ID NO: 66 |
| 53 | P protein-3copy-Aβ1-6-loop1G$_{72}$-3copy-Aβ1-6-loop2S$_{149}$ | SEQ ID NO: 67 |
| 54 | P protein-10copy-Aβ1-9-loop1G$_{72}$-10copy-Aβ1-9-loop2S$_{149}$ | SEQ ID NO: 68 |
| 55 | P protein-20copy-Aβ1-12-loop1G$_{72}$-20copy-Aβ1-12-loop2S$_{149}$ | SEQ ID NO: 69 |
| 56 | P protein-40copy-Aβ1-15-loop1G$_{72}$-40copy-Aβ1-15-loop2S$_{149}$ | SEQ ID NO: 70 |
| 57 | P protein-1copy-Aβ1-6-loop1I$_{70}$-1copy-Aβ1-12-loop2T$_{148}$ | SEQ ID NO: 71 |
| 58 | P protein-3copy-Aβ1-9-loop1A$_{71}$-3copy-Aβ1-6-loop2S$_{149}$ | SEQ ID NO: 72 |
| 59 | P protein-10copy-Aβ1-15-loop1G$_{72}$-10copy-Aβ1-6-loop2S$_{149}$ | SEQ ID NO: 73 |
| 60 | P protein-20copy-Aβ1-9-loop1G$_{72}$-20copy-Aβ1-15-loop2N$_{150}$ | SEQ ID NO: 74 |
| 61 | P protein-30copy-Aβ1-15-loop1T$_{73}$-30copy-Aβ1-12-loop2D$_{151}$ | SEQ ID NO: 75 |
| 62 | P protein-40copy-Aβ1-12-loop1Q$_{74}$-40copy-Aβ1-9-loop2S$_{149}$ | SEQ ID NO: 76 |
| 63 | P protein-1copy-Aβ1-6-loop1G$_{72}$-10copy-Aβ1-6-loop2S$_{149}$ | SEQ ID NO: 77 |
| 64 | P protein-10copy-Aβ1-9-loop1G$_{72}$-20copy-Aβ1-9-loop2S$_{149}$ | SEQ ID NO: 78 |
| 65 | P protein-20copy-Aβ1-12-loop1G$_{72}$-40copy-Aβ1-12-loop2S$_{149}$ | SEQ ID NO: 79 |
| 66 | P protein-40copy-Aβ1-15-loop1G$_{72}$-10copy-Aβ1-15-loop2S$_{149}$ | SEQ ID NO: 80 |
| 67 | P protein-1copy-Aβ1-6-loop1I$_{70}$-10copy-Aβ1-12-loop2T$_{148}$ | SEQ ID NO: 81 |
| 68 | P protein-10copy-Aβ1-9-loop1A$_{71}$-20copy-Aβ1-6-loop2S$_{149}$ | SEQ ID NO: 82 |
| 69 | P protein-20copy-Aβ1-15-loop1G$_{72}$-40copy-Aβ1-6-loop2S$_{149}$ | SEQ ID NO: 83 |
| 70 | P protein-40copy-Aβ1-9-loop1G$_{72}$-20copy-Aβ1-15-loop2N$_{150}$ | SEQ ID NO: 84 |
| 71 | P protein-20copy-Aβ1-15-loop1T$_{73}$-10copy-Aβ1-12-loop2D$_{151}$ | SEQ ID NO: 85 |
| 72 | P protein-10copy-Aβ1-12-loop1Q$_{74}$-1copy-Aβ1-9-loop2S$_{149}$ | SEQ ID NO: 86 |
| 73 | P protein-1copy-Aβ1-15-loop2S$_{149}$-1copy-Aβ1-15-loop3G$_{169}$ | SEQ ID NO: 87 |
| 74 | P protein-10copy-Aβ1-12-loop2S$_{149}$-10copy-Aβ1-12-loop3G$_{169}$ | SEQ ID NO: 88 |
| 75 | P protein-20copy-Aβ1-6-loop2S$_{149}$-20copy-Aβ1-6-loop3G$_{169}$ | SEQ ID NO: 89 |
| 76 | P protein-40copy-Aβ1-9-loop2S$_{149}$-40copy-Aβ1-9-loop3G$_{169}$ | SEQ ID NO: 90 |
| 77 | P protein-1copy-Aβ1-6-loop2T$_{148}$-1copy-Aβ1-9-loop3D$_{168}$ | SEQ ID NO: 91 |
| 78 | P protein-3copy-Aβ1-12-loop2S$_{149}$-3copy-Aβ1-6-loop3G$_{169}$ | SEQ ID NO: 92 |
| 79 | P protein-10copy-Aβ1-9-loop2S$_{149}$-10copy-Aβ1-15-loop3G$_{169}$ | SEQ ID NO: 93 |
| 80 | P protein-20copy-Aβ1-15-loop2S$_{149}$-20copy-Aβ1-6-loop3G$_{169}$ | SEQ ID NO: 94 |
| 81 | P protein-30copy-Aβ1-9-loop2N$_{150}$-30copy-Aβ1-12-loop3S$_{170}$ | SEQ ID NO: 95 |
| 82 | P protein-40copy-Aβ1-15-loop2D$_{151}$-40copy-Aβ1-12-loop3T$_{171}$ | SEQ ID NO: 96 |
| 83 | P protein-1copy-Aβ1-6-loop2S$_{149}$-10copy-Aβ1-6-loop3G$_{169}$ | SEQ ID NO: 97 |
| 84 | P protein-10copy-Aβ1-9-loop2S$_{149}$-20copy-Aβ1-9-loop3G$_{169}$ | SEQ ID NO: 98 |
| 85 | P protein-20copy-Aβ1-12-loop2S$_{149}$-40copy-Aβ1-12-loop3G$_{169}$ | SEQ ID NO: 99 |
| 86 | P protein-40copy-Aβ1-15-loop2S$_{149}$-10copy-Aβ1-15-loop2G$_{169}$ | SEQ ID NO: 100 |
| 87 | P protein-1copy-Aβ1-6-loop2T$_{148}$-10copy-Aβ1-9-loop3D$_{168}$ | SEQ ID NO: 101 |
| 88 | P protein-10copy-Aβ1-15-loop2N$_{150}$-20copy-Aβ1-6-loop3S$_{170}$ | SEQ ID NO: 102 |
| 89 | P protein-20copy-Aβ1-l2-loop2S$_{149}$-40copy-Aβ1-15-loop3G$_{169}$ | SEQ ID NO: 103 |
| 90 | P protein-40copy-Aβ1-15-loop2D$_{151}$-20copy-Aβ1-12-loop3T$_{171}$ | SEQ ID NO: 104 |
| 91 | P protein-20copy-Aβ1-12-loop2S$_{149}$-10copy-Aβ1-6-loop3G$_{169}$ | SEQ ID NO: 105 |
| 92 | P protein-10copy-Aβ1-9-loop2S$_{149}$-1copy-Aβ1-15-loop3G$_{169}$ | SEQ ID NO: 106 |
| 93 | P protein-1copy-Aβ1-15-loop1G$_{72}$-1copy-Aβ1-15-loop3G$_{169}$ | SEQ ID NO: 107 |
| 94 | P protein-10copy-Aβ1-9-loop1G$_{72}$-10copy-Aβ1-9-loop3G$_{169}$ | SEQ ID NO: 108 |
| 95 | P protein-20copy-Aβ1-6-loop1G$_{72}$-20copy-Aβ1-6-loop3G$_{169}$ | SEQ ID NO: 109 |
| 96 | P protein-40copy-Aβ1-12-loop1G$_{72}$-40copy-Aβ1-12-loop3G$_{169}$ | SEQ ID NO: 110 |
| 97 | P protein-1copy-Aβ1-6-loop1$_{170}$-1copy-Aβ1-9-loop3D$_{168}$ | SEQ ID NO: 111 |
| 98 | P protein-3copy-Aβ1-6-loop1G$_{72}$-3copy-Aβ1-12-loop3G$_{169}$ | SEQ ID NO: 112 |
| 99 | P protein-10copy-Aβ1-9-loop1A$_{71}$-10copy-Aβ1-15-loop3G$_{169}$ | SEQ ID NO: 113 |
| 100 | P protein-20copy-Aβ1-12-loop1G$_{72}$-20copy-Aβ1-9-loop3S$_{170}$ | SEQ ID NO: 114 |
| 101 | P protein-30copy-Aβ1-12-loop1Q$_{74}$-30copy-Aβ1-15-loop3T$_{171}$ | SEQ ID NO: 115 |
| 102 | P protein-40copy-Aβ1-15-loop1T$_{73}$-40copy-Aβ1-6-loop3G$_{169}$ | SEQ ID NO: 116 |
| 103 | P protein-1copy-Aβ1-6-loop1G$_{72}$-10copy-Aβ1-6-loop3G$_{169}$ | SEQ ID NO: 117 |
| 104 | P protein-10copy-Aβ1-9-loop1G$_{72}$-20copy-Aβ1-9-loop3G$_{169}$ | SEQ ID NO: 118 |

TABLE 1-continued

The amino acid sequences of the recombinant P proteins from which said 127 recombinant P particles of the present invention are formed and the nucleotide sequences encoding the recombinant P proteins.

| NO. | Recombinant P Protein | Nucleotide Sequences encoding the Recombinant P proteins |
|---|---|---|
| 105 | P protein-20copy-Aβ1-12-loop1$G_{72}$-40copy-Aβ1-12-loop3$G_{169}$ | SEQ ID NO: 119 |
| 106 | P protein-40copy-Aβ1-15-loop1$G_{72}$-10copy-Aβ1-15-loop3$G_{169}$ | SEQ ID NO: 120 |
| 107 | P protein-1copy-Aβ1-6-loop1$I_{70}$-10copy-Aβ1-9-loop3$D_{168}$ | SEQ ID NO: 121 |
| 108 | P protein-3copy-Aβ1-6-loop1$G_{72}$-10copy-Aβ1-12-loop3$G_{169}$ | SEQ ID NO: 122 |
| 109 | P protein-10copy-Aβ1-12-loop1$G_{72}$-1copy-Aβ1-15-loop3$S_{170}$ | SEQ ID NO: 123 |
| 110 | P protein-20copy-Aβ1-9-loop1$A_{71}$-40copy-Aβ1-15-loop3$G_{169}$ | SEQ ID NO: 124 |
| 111 | P protein-40copy-Aβ1-9-loop1$Q_{74}$-20copy-Aβ1-12-loop3$T_{171}$ | SEQ ID NO: 125 |
| 112 | P protein-30copy-Aβ1-15-loop1$T_{73}$-15copy-Aβ1-6-loop3$G_{169}$ | SEQ ID NO: 126 |
| 113 | P protein-1copy-Aβ1-6-loop1$I_{70}$-10copy-Aβ1-9-loop2$T_{148}$-20copy-Aβ1-12-loop3$D_{168}$ | SEQ ID NO: 127 |
| 114 | P protein-10copy-Aβ1-15-loop1$A_{71}$-20copy-Aβ1-12-loop2$S_{149}$-40copy-Aβ1-9-loop3$G_{169}$ | SEQ ID NO: 128 |
| 115 | P protein-1copy-Aβ1-6-loop1$G_{72}$-3copy-Aβ1-9-loop2$N_{150}$-10copy-Aβ1-15-loop3$S_{170}$ | SEQ ID NO: 129 |
| 116 | P protein-10copy-Aβ1-6-loop1$Q_{74}$-30copy-Aβ1-12-loop2$D_{151}$-20copy-Aβ1-15-loop3$T_{173}$ | SEQ ID NO: 130 |
| 117 | P protein-10copy-Aβ1-6-loop1$T_{73}$-10copy-Aβ1-6-loop2$S_{149}$-10copy-Aβ1-6-loop3$G_{169}$ | SEQ ID NO: 131 |
| 118 | P protein-1copy-Aβ1-6-loop1$G_{72}$-1copy-Aβ1-6-loop2$S_{149}$-1copy-Aβ1-6-loop3$G_{169}$ | SEQ ID NO: 132 |
| 119 | P protein-3copy-Aβ1-6-loop1$G_{72}$-3copy-Aβ1-6-loop2$S_{149}$-3copy-Aβ1-6-loop3$G_{169}$ | SEQ ID NO: 133 |
| 120 | P protein-10copy-Aβ1-6-loop1$G_{72}$-10copy-Aβ1-6-loop2$S_{149}$-10copy-Aβ1-6-loop3$G_{169}$ | SEQ ID NO: 134 |
| 121 | P protein-40copy-Aβ1-6-loop1$G_{72}$-40copy-Aβ1-6-loop2$S_{149}$-40copy-Aβ1-6-loop3$G_{169}$ | SEQ ID NO: 135 |
| 122 | P protein-10copy-Aβ1-6-loop2$S_{149}$$(GGA)_0$ | SEQ ID NO: 136 |
| 123 | P protein-10copy-Aβ1-6-loop2$S_{149}$$(GGA)_1$ | SEQ ID NO: 137 |
| 124 | P protein-10copy-Aβ1-6-loop2$S_{149}$$(GGA)_5$ | SEQ ID NO: 138 |
| 125 | P protein-10copy-Aβ1-6-loop2$S_{149}$$(GGA)_{10}$ | SEQ ID NO: 139 |
| 126 | P protein-10copy-Aβ1-6-loop2$S_{149}$$(GGC)_3$ | SEQ ID NO: 140 |
| 127 | P protein-1copy-Aβ1-6-loop2$T_{148}$-1copy-Aβ1-6-loop2$S_{149}$-1copy-Aβ1-6-loop2$N_{150}$ | SEQ ID NO: 141 |

The number of the recombinant P protein or recombinant P particle in the following tables respectively corresponds to the corresponding number of recombinant P protein in Table 1.

Figure 1B:
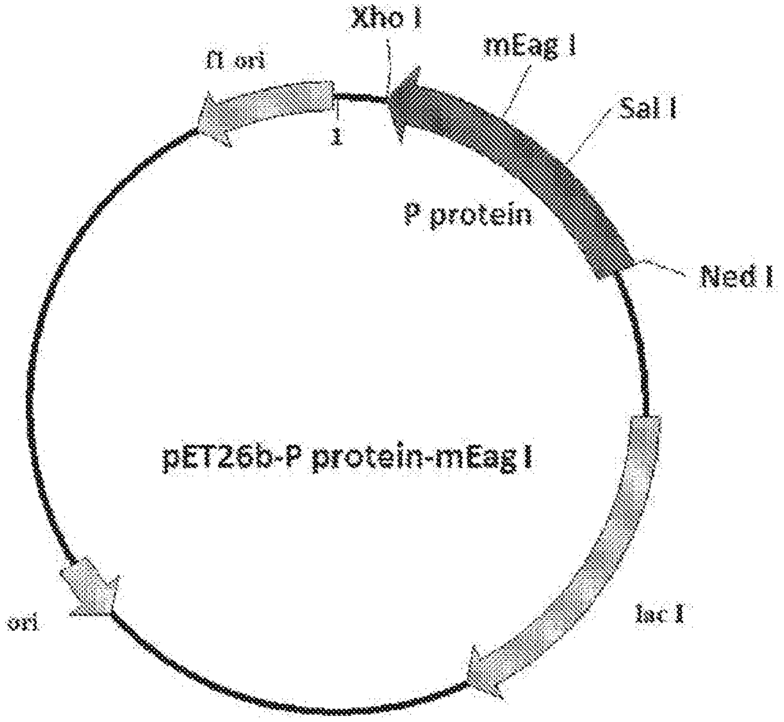
Figure 1C:
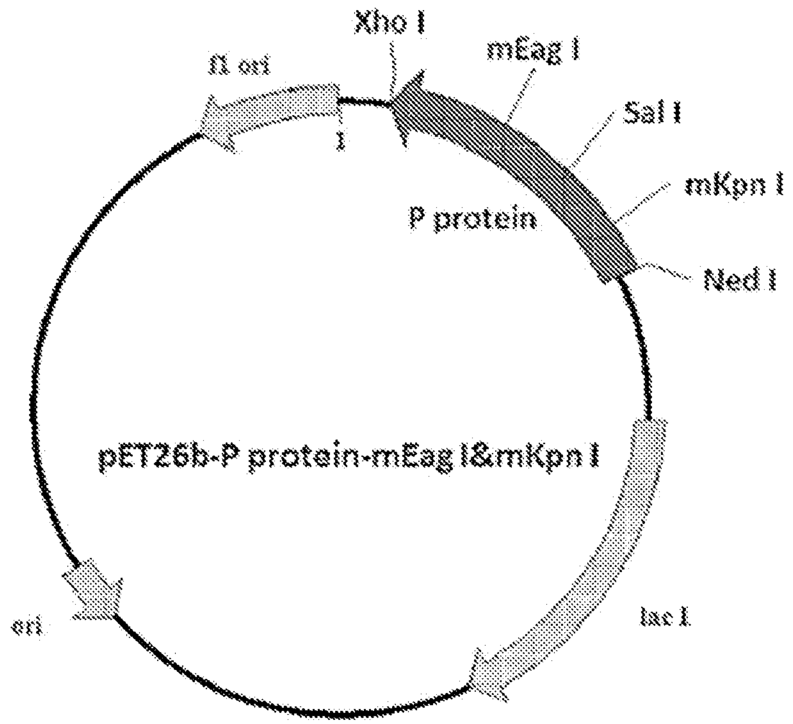

The present invention also provides a method for preparing said recombinant P protein particles, comprising the following steps:

1. Synthesizing artificially a DNA fragment comprising a DNA fragment encoding loop1, loop2 and/or loop3 domain(s) of a P protein embedded with multiple copies of Aβ1-m peptide;

2. Constructing pET26b-P protein plasmid (as shown in FIG. 1A);

3. Carrying out site-directed mutation at the position before loop1 and behind loop3 of P protein by a point mutation method on condition that the amino acid sequence remains unchanged, to obtain the new restriction enzyme sites mKpnI and mEagI (as shown in FIG. 1B);

4. According to various construction requirements, replacing multiple wild-type circular DNA in its entirety with the synthetic DNA fragment encoding loop1, loop2 and/or loop3 domain(s) of a P protein embedded with multiple copies of Aβ1-m peptide obtained in step 1 by using the restriction enzyme site SalI in the nucleic acid encoding P protein and the obtained enzyme sites mKpnI and mEagI in order to construct various recombinant P protein expression plasmids carrying multiple copies of Aβ1-m peptide respectively (as shown in FIG. 1D-1M);

5. Transferring the expression plasmids obtained in step 4 into *Escherichia coli*, where the P protein embedded with an Aβ1-m immunogen is stably expressed and self-assembles into a P particle in the form of a tetracosamer.

Furthermore, according to the present invention, the following analysis and verification experiments were carried out:

1. Ten preferred protein vaccines were characterized by particle diameter determination and electron microscope analysis (as shown in FIG. 4).

2. Experiments were carried out with different immune dosages and different immune adjuvants in a C57BL/6J mouse model, using PP-10copy-Aβ1-6-loop2$S_{149}$ protein vaccine. Results show that when CpG is used as the immune adjuvant, 25 μg protein vaccine could stimulate the mouse to produce the highest titer of a specific antibody against Aβ1-42, and meanwhile would not induce the mouse to produce T cell responses against Aβ1-42 (as shown in FIG. 5).

3. Using PP-1copy-Aβ1-6-loop2$S_{149}$, PP-10copy-Aβ1-6-loop2$S_{149}$ and PP-3copy-Aβ1-6-loop1$G_{72}$-3copy-Aβ1-6-loop2$S_{149}$-3copy-Aβ1-6-loop3$G_{169}$ as the immunogens, and CpG as the immune adjuvant, the immunological effects of the three protein vaccines were compared in mouse models, and the effects of both subcutaneous and nasal immunization on the immunological effects of the protein vaccines were analyzed (as shown in FIG. 6). Experimental results show that compared with nasal immunization, subcutaneous immunization is more beneficial for the protein vaccines to induce antibodies.

4. Immunization was carried out with 127 candidate proteins. Various proteins were compared for their immunological effects, and the optimal candidate vaccine was screened. Results show that various vaccines can stimulate the mouse to produce a specific antibody against Aβ1-42 compared with the PBS control group; wherein the ten proteins, PP-10copy-Aβ1-6-loop$G_{72}$, PP-1copy-Aβ1-6-loop2$S_{149}$, PP-10copy-Aβ1-6-loop2$S_{149}$, PP-20copy-Aβ1-6-loop3$G_{169}$, PP-10copy-Aβ1-15-loop1$G_{72}$-10copy-Aβ1-6-loop2$S_{149}$, PP-3copy-Aβ1-12-loop2$S_{149}$-3copy-Aβ1-6-loop3$G_{169}$, PP-1copy-Aβ1-6-loop1$G_{72}$-10copy-Aβ1-6-loop3$G_{169}$, PP-1copy-Aβ1-6-loop1$G_{72}$-1copy-Aβ1-6-loop2$S_{149}$-1copy-Aβ1-6-loop3$G_{169}$, PP-3 copy-Aβ1-6-loop1$G_{72}$-3copy-Aβ1-6-loop2$S_{149}$-3copy-Aβ1-6-loop3$G_{169}$, PP-10copy-Aβ1-6-loop1$G_{72}$-10copy-Aβ1-6-loop2$S_{149}$-10copy-Aβ1-6-loop3$G_{169}$, have the optimal immunological effects and can stimulate the production of a high concentration of Aβ1-42.

Example 1. Construction of pET26b-P Protein Plasmid

1 μL of Nde I enzyme and 1 μL of Xho I enzyme (purchased from Takara Corporation), and 5 μL of enzyme cleavage buffer (purchased from Takara Corporation) were respectively added to 4 μg of pET26b vector plasmid (purchased from Novagen Corporation), and finally sterile water was added to the system to reach a final volume of 50 μL. Digestion was carried out at 37° C. for 5 hours. Then the products were subjected to agarose gel electrophoresis, and recovered using a recovery column (purchased from Invitrogen) to obtain a plasmid vector having double enzyme-digested sticky ends.

A P protein nucleotide sequence as shown in SEQ ID NO: 9 was synthesized by gene synthetic method. The synthetic gene fragment was subjected to Nde I/Xho I double-enzyme digestion using the same method as mentioned above. The products were subjected to agarose gel electrophoresis, and recovered using a recovery column to obtain a gene fragment having double enzyme-digested sticky ends.

The above double enzyme-digested vector fragment and fragment of interest (with a molar ratio of 1:3, and a total volume of 15 μL) were mixed, and 0.75 μL of T4 ligase (purchased from Takara Corporation) and 1.5 μL of ligase buffer (purchased from Takara Corporation) were added. The ligation was carried out at 16° C. overnight to obtain a pET26b-P protein plasmid that can express a P protein particle, as shown in FIG. 1A.

Example 2. Construction of pET26b-P Protein Plasmid with Restriction Enzyme Sites mKpnI and mEagI The site-directed mutation method was as follows:

1. 5'CCGCCG3' was mutated to 5'CGGCCG3' by site-directed mutation method using the pET26b-P protein plasmid constructed in Example 1 to obtain pET26b-P protein-mEagI plasmid containing a mEagI restriction enzyme site without altering the amino acid sequence. The specific method was as follows: a pair of perfectly complementary bidirectional primers containing the mutation site was used:

```
(forward):
                                   SEQ ID NO: 11
5'CGTTCACTTGGCTCCGGCCGTGGCTCCAACC3',
and
```

-continued

```
(reverse):
                                   SEQ ID NO: 12
5'GGTTGGAGCCACGGCCGGAGCCAAGTGAACG3';
``` the entire plasmid was subjected to PCR reaction, wherein the PCR reaction system was a KOD-Plus DNA polymerase system (purchased from TOYOBO Corporation), and the total volume of the reaction system was 50 μL (5 μL buffer, 0.2 mM dNTP, 1 mM magnesium sulfate, 0.3 μM upstream primer and 0.3 NM downstream primer, 50 ng template DNA, 1 μL KOD enzyme, and water which was added to a final volume of 50 μL). PCR was carried out in accordance with the reaction system instructions to obtain 20 μL of PCR products. 1 μL of DpnI enzyme (purchased from NEB Corporation) was added to the PCR products. Digestion was carried out at 37° C. for 1 h. 10 μL of the digested products were added to Trant-Blue competent cells (purchased from Peking TransGen Biotech, Ltd.), and placed on ice for 30 min. After that, the cells were subjected to heat shock at 42° C. for 45 s, placed on ice for 2 min. and then were added to 600 μL of fluid LB medium without resistance, and recovered at 200 rpm at 37° C. for 1 h. The culture broth was plated on a LB solid culture plate containing kanamycin (15 μg/mL), and were placed upside down at 37° C. overnight. The obtained mutant plasmid clones were verified by sequencing. pET26b-P protein-mEagI plasmid is shown as FIG. 1B.

2. 5'GGCACA3' was mutated to 5'GGTACC3' using the pET26b-P protein-mEagI recombinant plasmid (as shown in FIG. 1B) constructed in the previous step to obtain pET26b-P protein-mEagI&mKpnI plasmid containing both a mEagI restriction enzyme site and a mKpnI restriction enzyme site without altering the amino acid sequence. The specific method was as follows:

a pair of perfectly complementary bidirectional primers containing the mutation site was used:

```
(forward):
                                   SEQ ID NO: 13
5'GGTGTCCTGCTCGGTACCACCCAGCTCTCACC3',
and (reverse):
                                   SEQ ID NO: 14
5'GGTGAGAGCTGGGTGGTACCGAGCAGGACACC3';
``` and pET26b-P protein-mEagI&mKpnI plasmid was obtained by the same construction method as mentioned above and verified by sequencing. pET26b-P protein-mEagI&mKpnI plasmid is shown as in FIG. 1C.

Example 3. Synthesis of P Particle Loop Gene Fragments of Interest Embedded with Human Aβ1-m Genes This step involves three different synthesis schemes in total:

The first is a P particle loop gene fragment of interest embedded with a human Aβ1-m gene located between a mKpnI restriction enzyme site and a SalI restriction enzyme site. That is, N1 copies of Aβ1-m gene are merely embedded into loop1. The P protein prepared by this method is abbreviated as P protein-N 1copy-Aβ1-m-loop1.

The second is a P particle loop gene fragment of interest embedded with a human Aβ1-m gene located between a SalI restriction enzyme site and a mEagI restriction enzyme site. That is, (1) N2 copies of Aβ1-m gene are merely embedded into loop2, and the P protein prepared by this method is abbreviated as P protein-N2copy-Aβ1-m-loop2; (2) N3 copies of Aβ1-m gene are merely embedded into loop3, and the P protein prepared by this method is abbreviated as P protein-N3copy-Aβ1-m-loop3; and (3) N2 copies of Aβ1-m gene are embedded into loop2 and N3 copies of Aβ1-m gene are embedded into loop3, and the P protein prepared by this method is abbreviated as P protein-N2copy-Aβ1-m-loop2-N3copy-Aβ1-m-loop3, wherein each m is independently selected from an integer ranging from 1 to 40.

The third is a P particle loop gene fragment of interest embedded with a human Aβ1-m gene located between a mKpnI restriction enzyme site and a mEagI restriction enzyme site. That is, (1) N1 copies of Aβ1-m gene are embedded into loop1 and N2 copies of Aβ1-m gene are embedded into loop2, and the P protein prepared by this method is abbreviated as protein-N1copy-Aβ1-m-loop1-N2copy-Aβ1-m-loop2; (2) N1 copies of Aβ1-m gene are embedded into loop1 and N3 copies of Aβ1-m gene are embedded into loop3, and the P protein prepared by this method is abbreviated as P protein-N1copy-Aβ1-m-loop1-N3copy-Aβ1-m-loop3; and (3) N1 copies of Aβ1-m gene are embedded into loop1, N2 copies of Aβ1-m gene are embedded into loop2 and N3 copies of Aβ1-m gene are embedded into loop3, and the P protein prepared by this method is abbreviated as P protein-N1copy-Aβ1-m-loop1-N2copy-Aβ1-m-loop2-N3 copy-Aβ1-m-loop3, wherein each m is independently selected from an integer ranging from 1 to 40.

The above three synthesis schemes are illustrated as follows:

3.1 Scheme I:

3.1.1

Figure 2B:
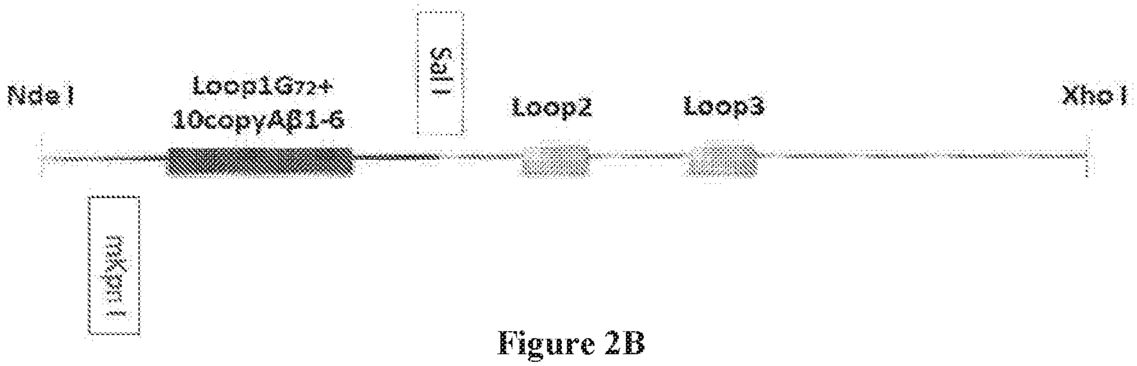

The loop1 gene fragment embedded with DNA encoding 10 copies of Aβ1-6 peptide of P protein-10copy-Aβ1-6-loop1 $G_{72}$ (as shown in FIG. 2B) was synthesized. The sequence of the synthetic gene fragment is shown as SEQ ID NO: 143.

3.2 Scheme II 3.2.1

Figure 2C:
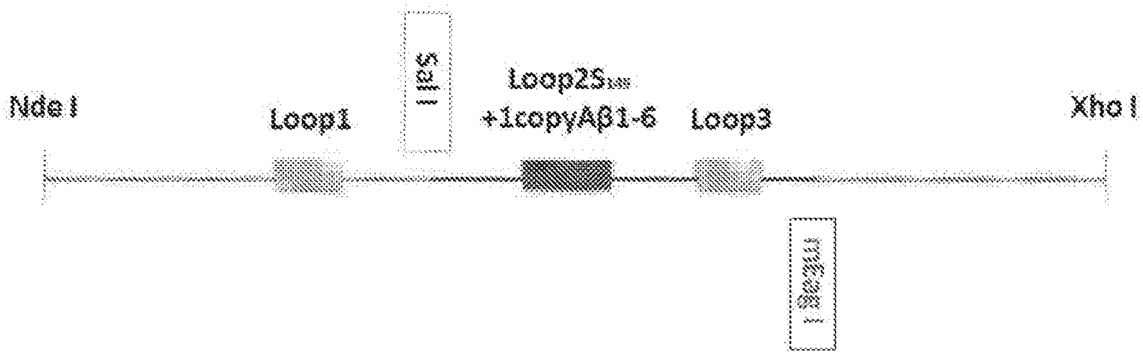

The loop2 gene fragment embedded with DNA encoding one copy of Aβ1-6 peptide of P protein-1copy-Aβ1-6-loop2$S_{149}$ (as shown in FIG. 2C) was synthesized. The sequence of the synthetic gene fragment is shown as SEQ ID NO: 144.

3.2.2

Figure 2D:
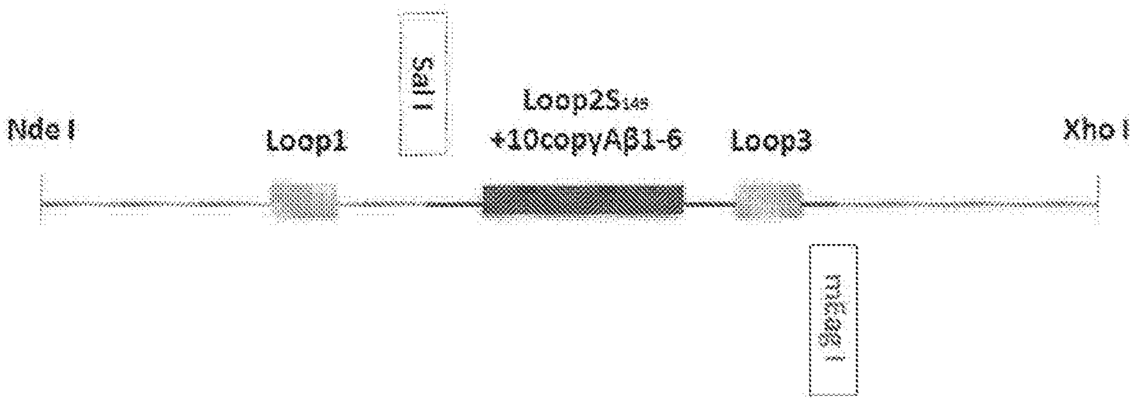

The loop2 gene fragment embedded with DNA encoding 10 copies of Aβ1-6 peptide of P protein-10copy-Aβ1-6-loop2$S_{149}$ (as shown in FIG. 2D) was synthesized. The sequence of the synthetic gene fragment is shown as SEQ ID NO: 145.

3.2.3

Figure 2E:
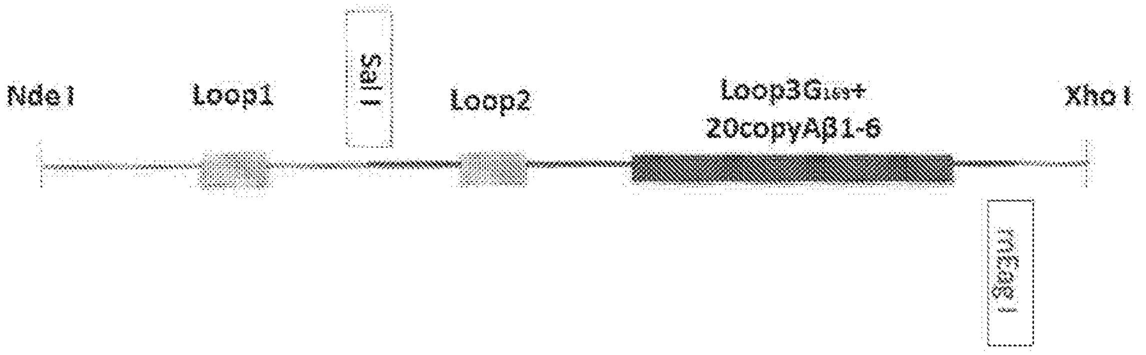

The loop3 gene fragment embedded with DNA encoding 20 copies of Aβ1-6 peptide of P protein-20copy-Aβ1-6-loop3$G_{169}$ (as shown in FIG. 2E) was synthesized. The sequence of the synthetic gene fragment is shown as SEQ ID NO: 146.

3.2.4

Figure 2F:
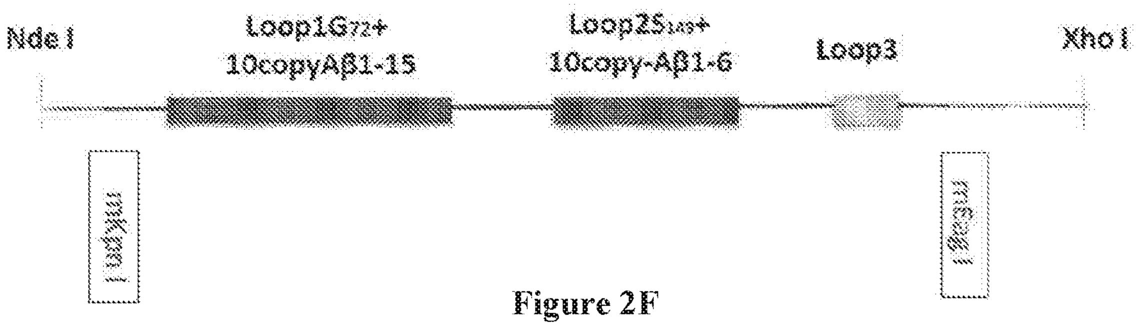
Figure 2G:
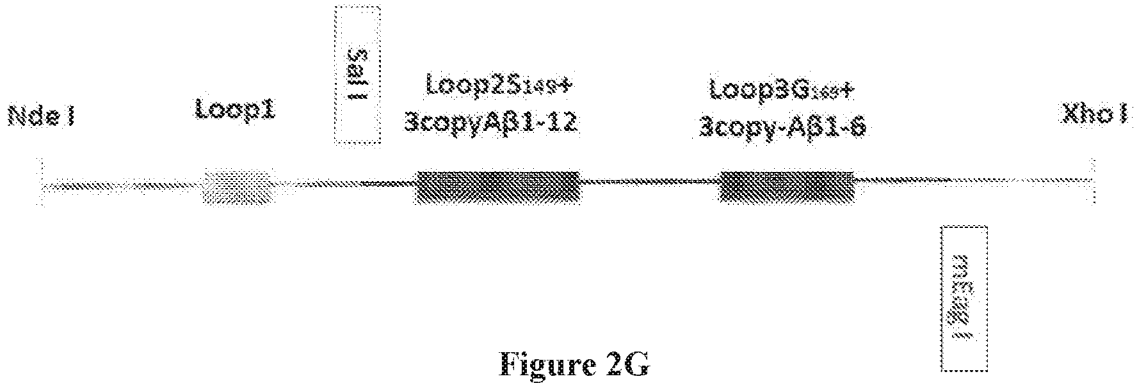

The loop2 gene fragment embedded with DNA encoding 3 copies of Aβ1-12 peptide and loop3 gene fragment embedded with DNA encoding 3 copies of Aβ1-6 peptide of P protein-3copy-Aβ1-12-loop2$S_{149}$-3copy-Aβ1-6-loop3$G_{169}$ (as shown in FIG. 2G) were synthesized. The sequence of the synthetic gene fragments is shown as SEQ ID NO: 147.

3.3 Scheme III 3.3.1

The loop1 gene fragment embedded with DNA encoding 10 copies of Aβ1-15 peptide and loop2 gene fragment embedded with DNA encoding 10 copies of Aβ1-6 peptide of P protein-10copy-Aβ1-15-loop1$G_{72}$-10copy-Aβ1-6-loop2$S_{149}$ (as shown in FIG. 2F) were synthesized. The sequence of the synthetic gene fragments is shown as SEQ ID NO: 148.

3.3.2

Figure 2H:
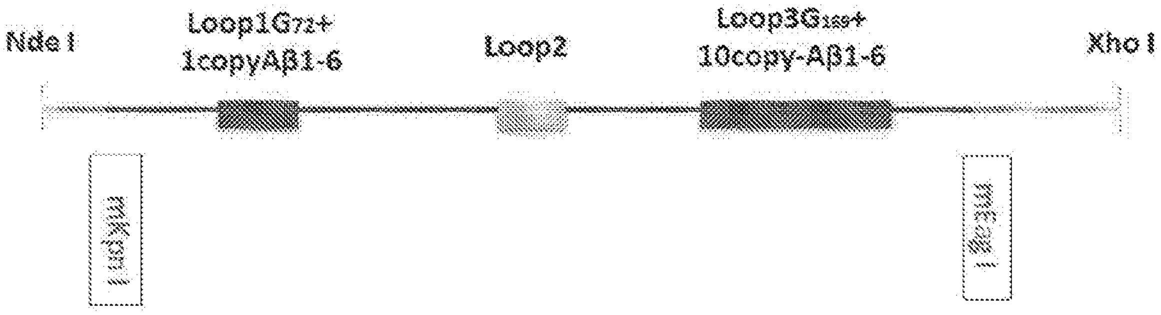
Figure 3A:
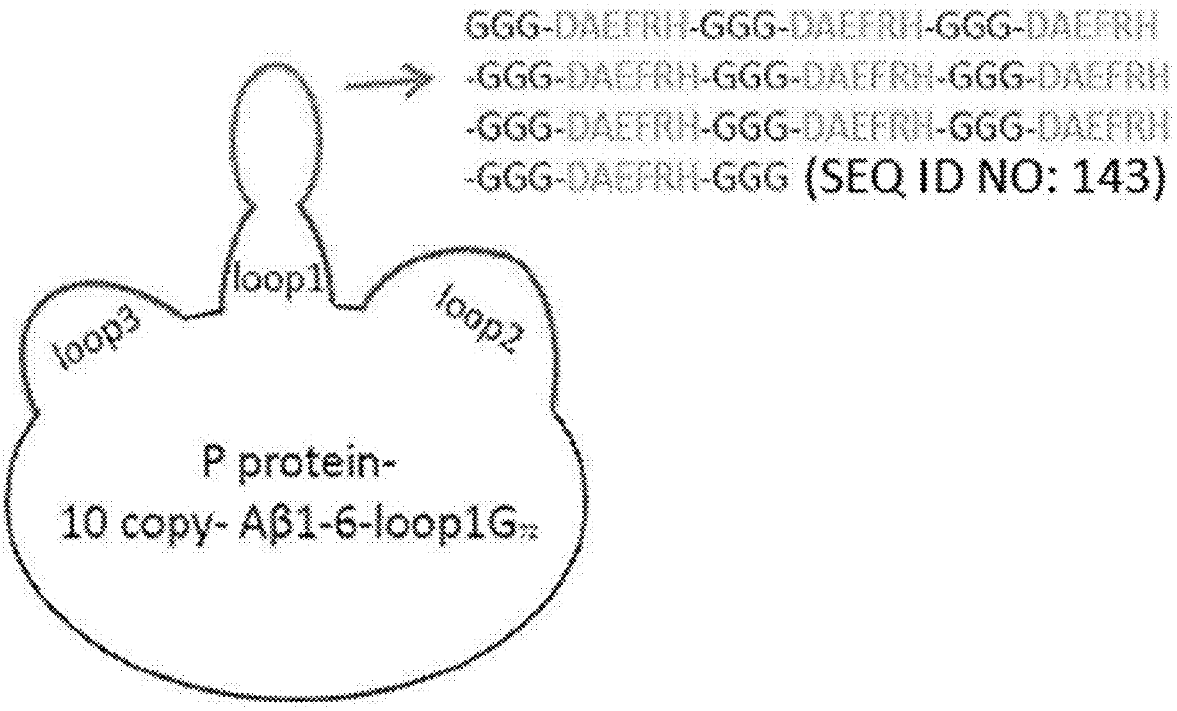
Figure 3B:
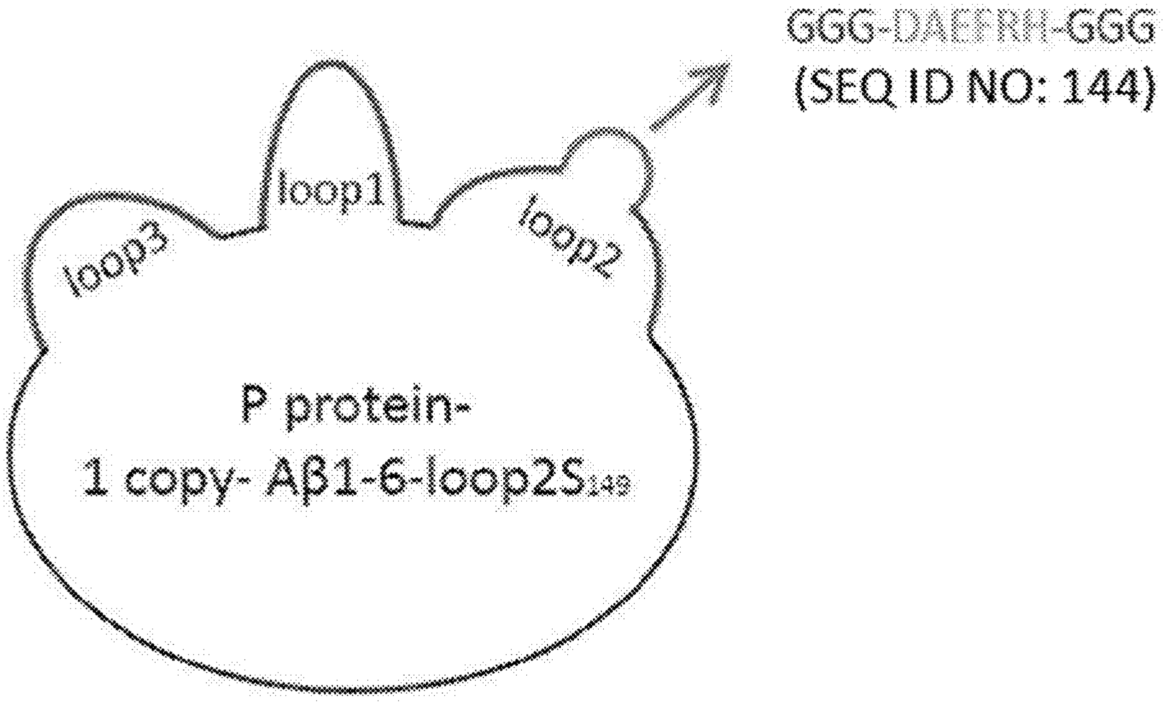
Figure 3C:
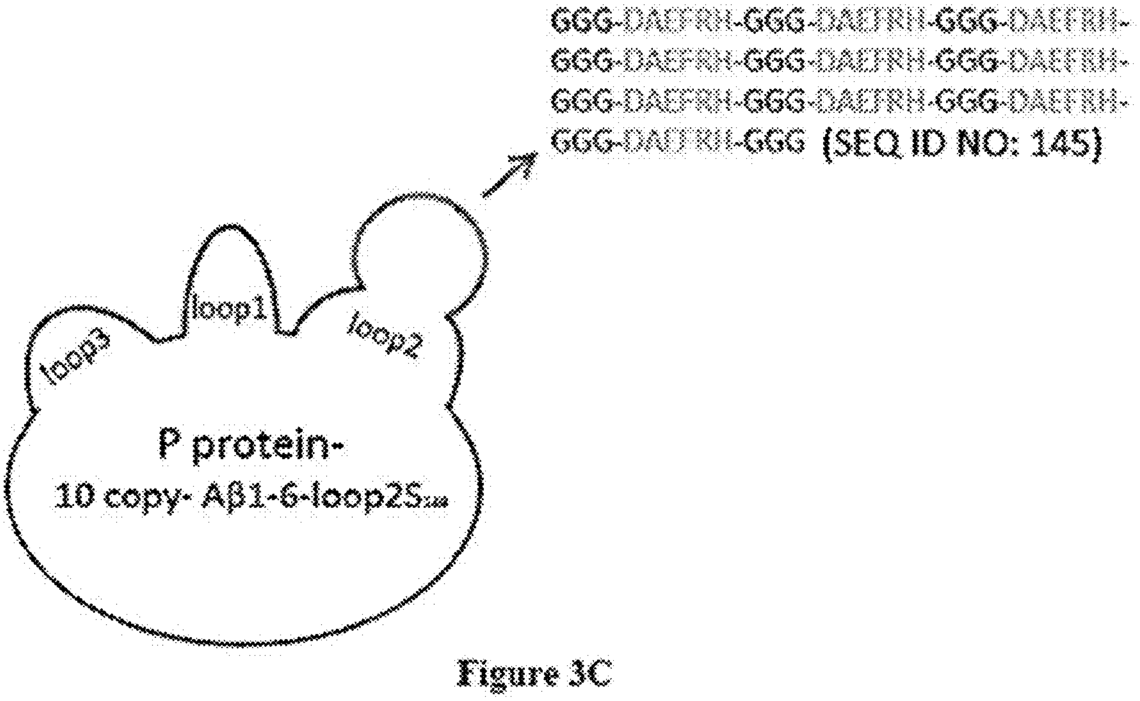
Figure 3D:
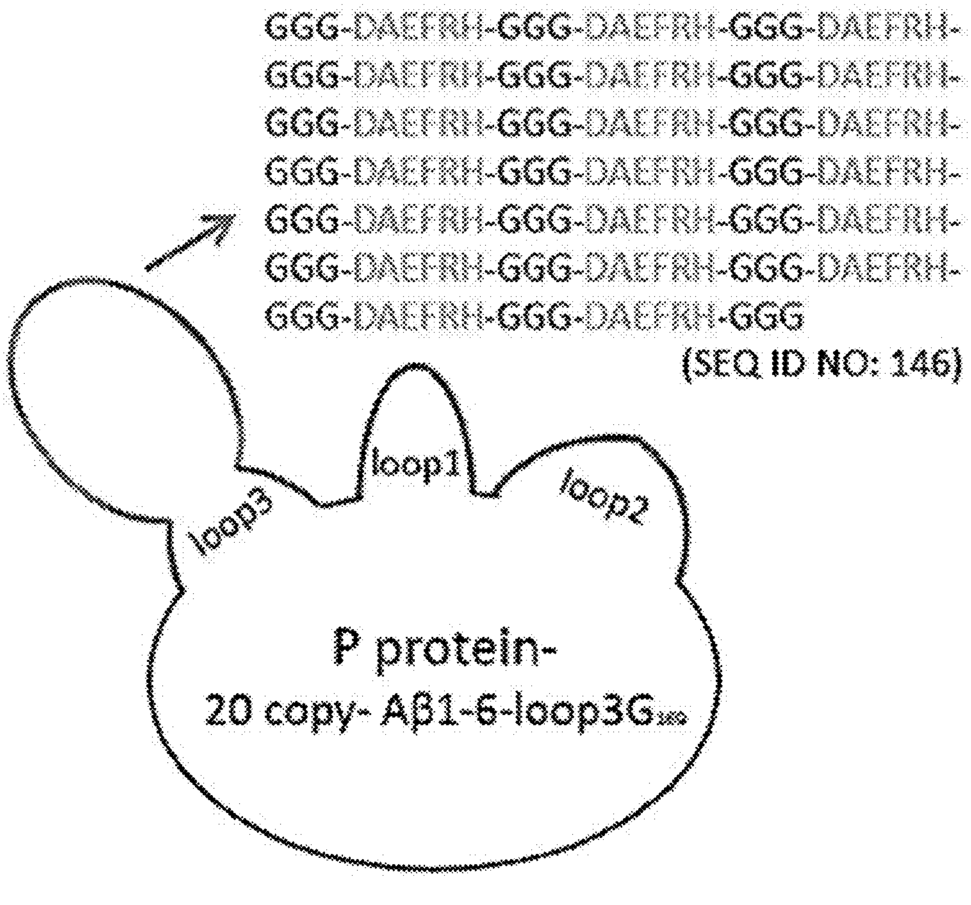
Figure 3E:
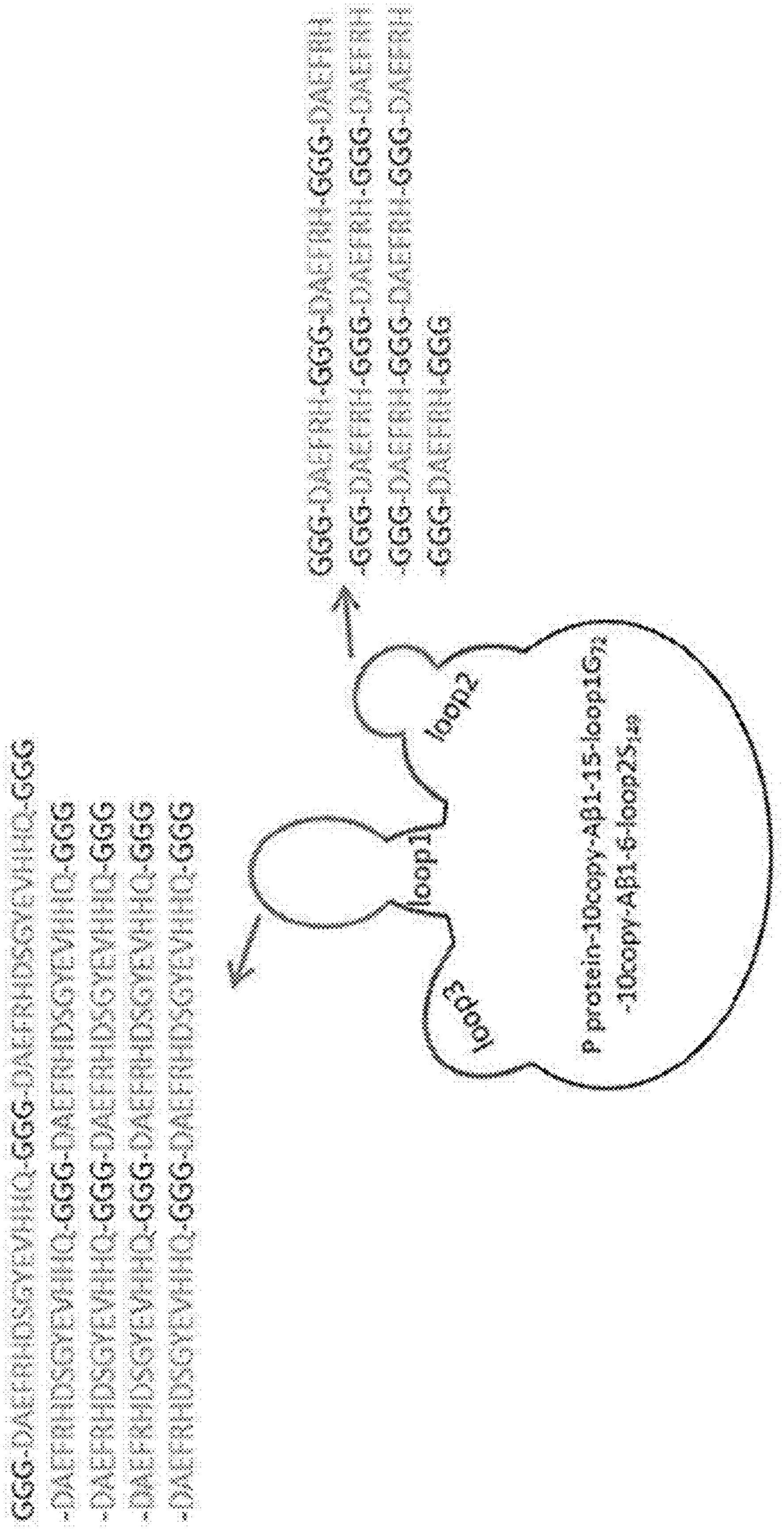
Figure 3F:
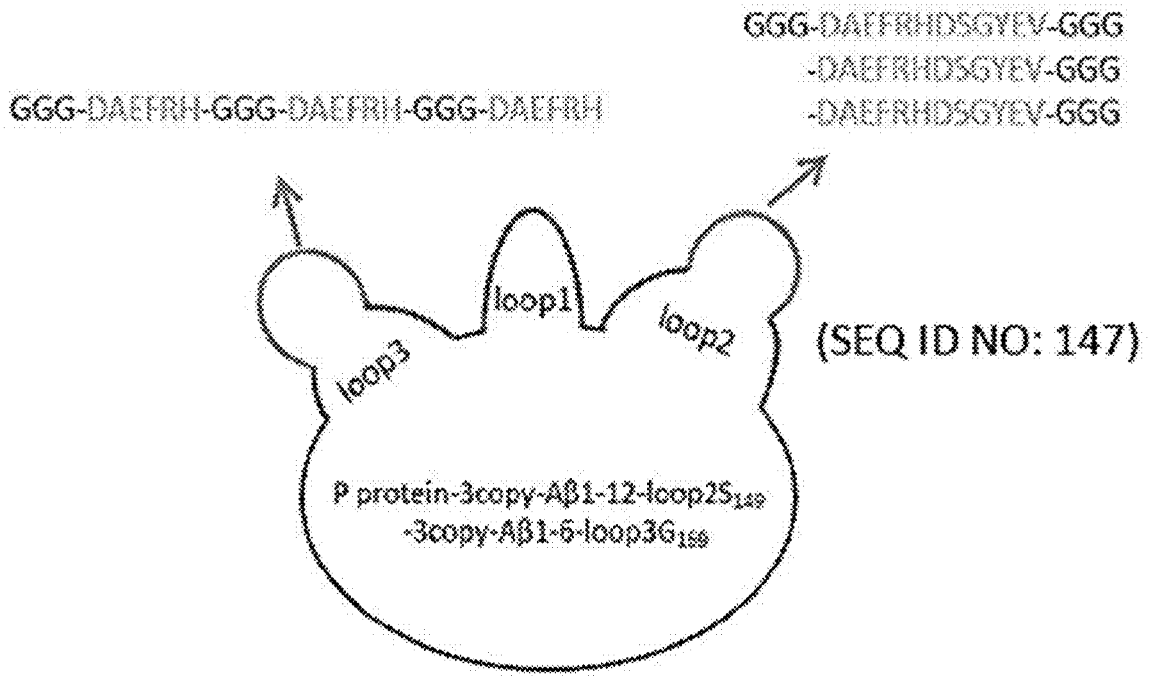
Figure 3G:
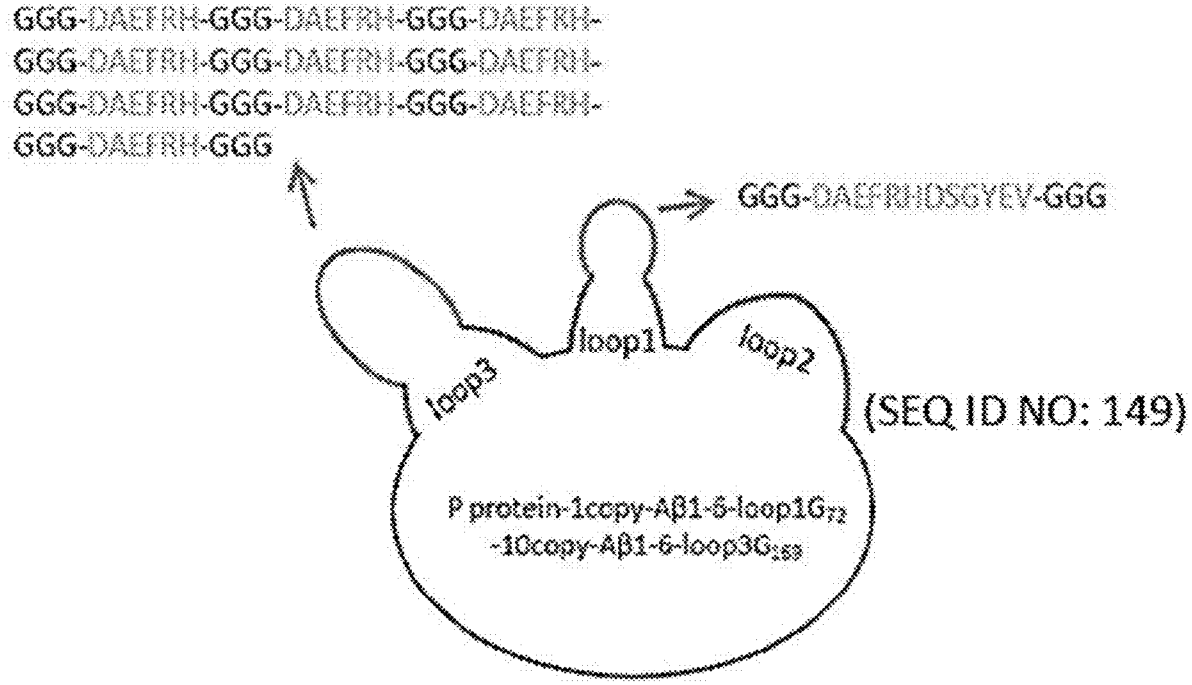
Figure 3H:
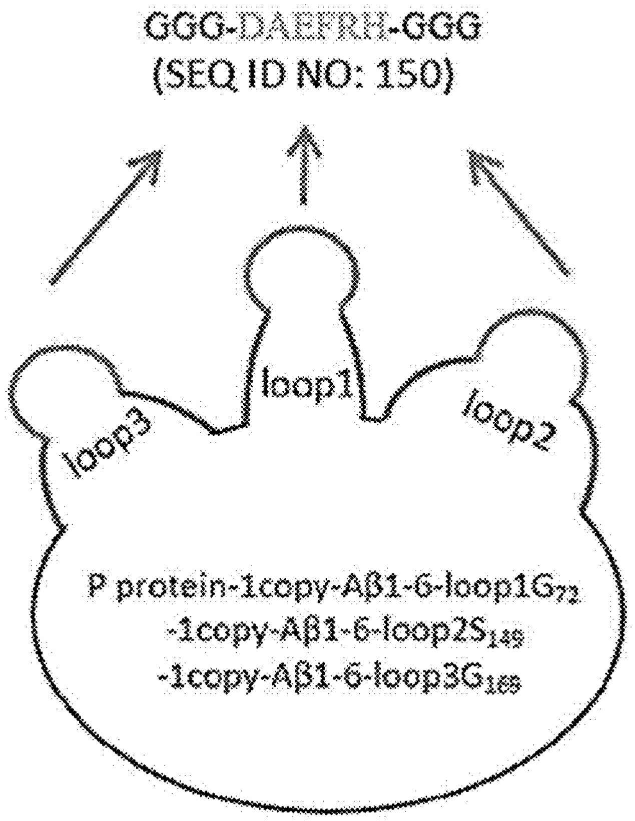
Figure 3I:
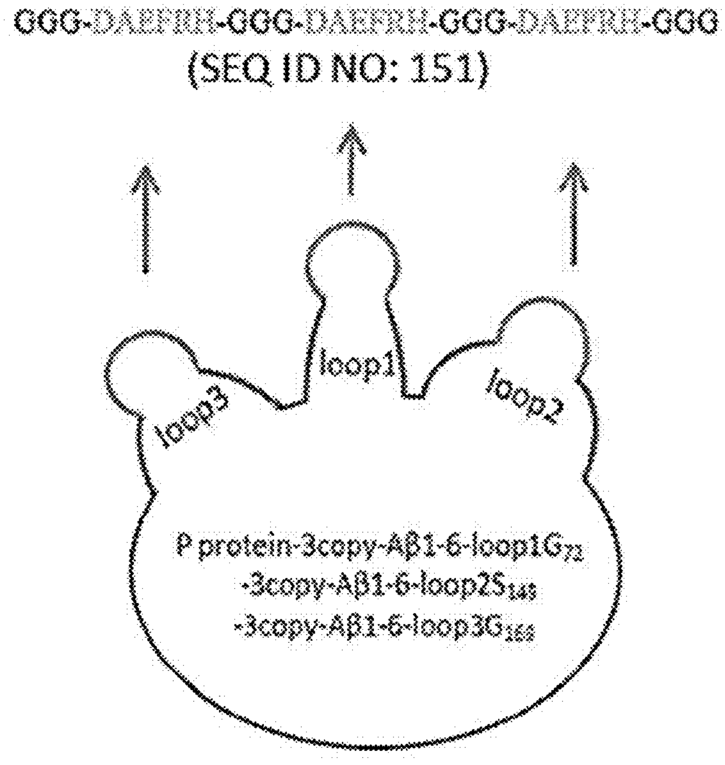

The loop1 gene fragment embedded with DNA encoding 1 copy of Aβ1-6 peptide and loop3 gene fragment embedded with DNA encoding 10 copies of Aβ1-6 peptide of P protein-1copy-A61-6-loop1 $G_{72}$-10copy-Aβ1-6-loop3$S_{169}$ (as shown in FIG. 2H) were synthesized. The sequence of the synthetic gene fragments is shown as SEQ ID NO: 149.

3.3.3

The loop123 gene fragment embedded respectively with DNA encoding 1 copy of Aβ1-6 peptide of P protein-1copy-Aβ1-6-loop1$G_{72}$-1copy-Aβ1-6-loop2$S_{149}$-1copy-Aβ1-6-loop3$G_{169}$ (as shown in FIG. 2I) was synthesized. The sequence of the synthetic gene fragment is shown as SEQ ID NO: 150.

3.3.4

The loop1, loop2, loop3 gene fragments embedded respectively with DNA encoding 3 copies of Aβ1-6 peptide of P protein-3copy-Aβ1-6-loop1$G_{72}$-3copy-Aβ1-6-loop2$S_{149}$-3copy-Aβ1-6-loop3$G_{169}$ (as shown in FIG. 2J) were synthesized. The sequence of the synthetic gene fragments is shown as SEQ ID NO: 151.

3.3.5

The loop1, loop2, loop3 gene fragments embedded respectively with DNA encoding 10 copies of Aβ1-6 peptide of Pprotein-10copy-Aβ1-6-loop1$G_{72}$-10copy-Aβ1-6-loop2$S_{149}$-10copy-Aβ1-6-loop3$G_{169}$ (as shown in FIG. 2K) were synthesized. The sequence of the synthetic gene fragments is shown as SEQ ID NO: 152.

Furthermore, in addition to the above 10 recombinant P proteins, synthetic methods of other 117 recombinant P proteins respectively involved the above three schemes, as specifically shown in Table 2.

TABLE 2

Synthetic methods of 127 recombinant P proteins and construction methods of 127 plasmids expressing the recombinant P proteins according to the invention

| | Synthetic methods of recombinant P proteins | | Construction methods of plasmids expressing recombinant P proteins | |
|---|---|---|---|---|
| NO. | Scheme | Similar Scheme | Scheme | Similar Scheme |
| 1 | 1 | 3.1.1 | 1 | 4.1.1 |
| 2 | 1 | 3.1.1 | 1 | 4.1.1 |
| 3 | 1 | 3.1.1 | 1 | 4.1.1 |
| 4 | 1 | 3.1.1 | 1 | 4.1.1 |
| 5 | 1 | 3.1.1 | 1 | 4.1.1 |
| 6 | 1 | 3.1.1 | 1 | 4.1.1 |
| 7 | 1 | 3.1.1 | 1 | 4.1.1 |
| 8 | 1 | 3.1.1 | 1 | 4.1.1 |
| 9 | 1 | 3.1.1 | 1 | 4.1.1 |
| 10 | 1 | 3.1.1 | 1 | 4.1.1 |
| 11 | 1 | 3.1.1 | 1 | 4.1.1 |
| 12 | 1 | 3.1.1 | 1 | 4.1.1 |
| 13 | 1 | 3.1.1 | 1 | 4.1.1 |
| 14 | 1 | 3.1.1 | 1 | 4.1.1 |
| 15 | 1 | 3.1.1 | 1 | 4.1.1 |
| 16 | 1 | 3.1.1 | 1 | 4.1.1 |
| 17 | 1 | 3.1.1 | 1 | 4.1.1 |
| 28 | 1 | 3.1.1 | 1 | 4.1.1 |
| 19 | 1 | 3.1.1 | 1 | 4.1.1 |
| 20 | 1 | 3.1.1 | 1 | 4.1.1 |
| 21 | 2 | 3.2.1 | 2 | 4.2.1 |

TABLE 2-continued

Synthetic methods of 127 recombinant P proteins and construction methods of 127 plasmids expressing the recombinant P proteins according to the invention

| | Synthetic methods of recombinant P proteins | | Construction methods of plasmids expressing recombinant P proteins | |
|---|---|---|---|---|
| NO. | Scheme | Similar Scheme | Scheme | Similar Scheme |
| 22 | 2 | 3.2.1 | 2 | 4.2.1 |
| 23 | 2 | 3.2.1 | 2 | 4.2.1 |
| 24 | 2 | 3.2.1 | 2 | 4.2.1 |
| 25 | 2 | 3.2.1 | 2 | 4.2.1 |
| 26 | 2 | 3.2.1 | 2 | 4.2.1 |
| 27 | 2 | 3.2.1 | 2 | 4.2.1 |
| 28 | 2 | 3.2.1 | 2 | 4.2.1 |
| 29 | 2 | 3.2.1 | 2 | 4.2.1 |
| 30 | 2 | 3.2.1 | 2 | 4.2.1 |
| 31 | 2 | 3.2.1 | 2 | 4.2.1 |
| 32 | 2 | 3.2.1 | 2 | 4.2.1 |
| 33 | 2 | 3.2.1 | 2 | 4.2.1 |
| 34 | 2 | 3.2.1 | 2 | 4.2.1 |
| 35 | 2 | 3.2.1 | 2 | 4.2.1 |
| 36 | 2 | 3.2.1 | 2 | 4.2.1 |
| 37 | 2 | 3.2.3 | 2 | 4.2.3 |
| 38 | 2 | 3.2.3 | 2 | 4.2.3 |
| 39 | 2 | 3.2.3 | 2 | 4.2.3 |
| 40 | 2 | 3.2.3 | 2 | 4.2.3 |
| 41 | 2 | 3.2.3 | 2 | 4.2.3 |
| 42 | 2 | 3.2.3 | 2 | 4.2.3 |
| 43 | 2 | 3.2.3 | 2 | 4.2.3 |
| 44 | 2 | 3.2.3 | 2 | 4.2.3 |
| 45 | 2 | 3.2.3 | 2 | 4.2.3 |
| 46 | 2 | 3.2.3 | 2 | 4.2.3 |
| 47 | 2 | 3.2.3 | 2 | 4.2.3 |
| 48 | 2 | 3.2.3 | 2 | 4.2.3 |
| 49 | 2 | 3.2.3 | 2 | 4.2.3 |
| 50 | 2 | 3.2.3 | 2 | 4.2.3 |
| 51 | 2 | 3.2.3 | 2 | 4.2.3 |
| 52 | 2 | 3.2.3 | 2 | 4.2.3 |
| 53 | 3 | 3.3.1 | 3 | 4.3.1 |
| 54 | 3 | 3.3.1 | 3 | 4.3.1 |
| 55 | 3 | 3.3.1 | 3 | 4.3.1 |
| 56 | 3 | 3.3.1 | 3 | 4.3.1 |
| 57 | 3 | 3.3.1 | 3 | 4.3.1 |
| 58 | 3 | 3.3.1 | 3 | 4.3.1 |
| 59 | 3 | 3.3.1 | 3 | 4.3.1 |
| 60 | 3 | 3.3.1 | 3 | 4.3.1 |
| 61 | 3 | 3.3.1 | 3 | 4.3.1 |
| 62 | 3 | 3.3.1 | 3 | 4.3.1 |
| 63 | 3 | 3.3.1 | 3 | 4.3.1 |
| 64 | 3 | 3.3.1 | 3 | 4.3.1 |
| 65 | 3 | 3.3.1 | 3 | 4.3.1 |
| 66 | 3 | 3.3.1 | 3 | 4.3.1 |
| 67 | 3 | 3.3.1 | 3 | 4.3.1 |
| 68 | 3 | 3.3.1 | 3 | 4.3.1 |
| 69 | 3 | 3.3.1 | 3 | 4.3.1 |
| 70 | 3 | 3.3.1 | 3 | 4.3.1 |
| 71 | 3 | 3.3.1 | 3 | 4.3.1 |
| 72 | 3 | 3.3.1 | 3 | 4.3.1 |
| 73 | 2 | 3.2.4 | 2 | 4.3.1 |
| 74 | 2 | 3.2.4 | 2 | 4.3.1 |
| 75 | 2 | 3.2.4 | 2 | 4.3.1 |
| 76 | 2 | 3.2.4 | 2 | 4.3.1 |
| 77 | 2 | 3.2.4 | 2 | 4.3.1 |
| 78 | 2 | 3.2.4 | 2 | 4.3.1 |
| 79 | 2 | 3.2.4 | 2 | 4.3.1 |
| 80 | 2 | 3.2.4 | 2 | 4.3.1 |
| 81 | 2 | 3.2.4 | 2 | 4.3.1 |
| 82 | 2 | 3.2.4 | 2 | 4.3.1 |
| 83 | 2 | 3.2.4 | 2 | 4.3.1 |
| 84 | 2 | 3.2.4 | 2 | 4.3.1 |
| 85 | 2 | 3.2.4 | 2 | 4.3.1 |
| 86 | 2 | 3.2.4 | 2 | 4.3.1 |
| 87 | 2 | 3.2.4 | 2 | 4.3.1 |
| 88 | 2 | 3.2.4 | 2 | 4.3.1 |
| 89 | 2 | 3.2.4 | 2 | 4.3.1 |
| 90 | 2 | 3.2.4 | 2 | 4.3.1 |
| 91 | 2 | 3.2.4 | 2 | 4.3.1 |
| 92 | 2 | 3.2.4 | 2 | 4.3.1 |
| 93 | 3 | 3.3.2 | 3 | 4.3.1 |
| 94 | 3 | 3.3.2 | 3 | 4.3.1 |
| 95 | 3 | 3.3.2 | 3 | 4.3.1 |
| 96 | 3 | 3.3.2 | 3 | 4.3.1 |
| 97 | 3 | 3.3.2 | 3 | 4.3.1 |
| 98 | 3 | 3.3.2 | 3 | 4.3.1 |
| 99 | 3 | 3.3.2 | 3 | 4.3.1 |
| 100 | 3 | 3.3.2 | 3 | 4.3.1 |
| 101 | 3 | 3.3.2 | 3 | 4.3.1 |
| 102 | 3 | 3.3.2 | 3 | 4.3.1 |
| 103 | 3 | 3.3.2 | 3 | 4.3.1 |
| 104 | 3 | 3.3.2 | 3 | 4.3.1 |
| 105 | 3 | 3.3.2 | 3 | 4.3.1 |
| 106 | 3 | 3.3.2 | 3 | 4.3.1 |
| 107 | 3 | 3.3.2 | 3 | 4.3.1 |
| 108 | 3 | 3.3.2 | 3 | 4.3.1 |
| 109 | 3 | 3.3.2 | 3 | 4.3.1 |
| 110 | 3 | 3.3.2 | 3 | 4.3.1 |
| 111 | 3 | 3.3.2 | 3 | 4.3.1 |
| 112 | 3 | 3.3.2 | 3 | 4.3.1 |
| 113 | 3 | 3.3.3 | 3 | 4.3.1 |
| 114 | 3 | 3.3.3 | 3 | 4.3.1 |
| 115 | 3 | 3.3.3 | 3 | 4.3.1 |
| 116 | 3 | 3.3.3 | 3 | 4.3.1 |
| 117 | 3 | 3.3.3 | 3 | 4.3.1 |
| 118 | 3 | 3.3.3 | 3 | 4.3.1 |
| 119 | 3 | 3.3.3 | 3 | 4.3.1 |
| 120 | 3 | 3.3.3 | 3 | 4.3.1 |
| 121 | 3 | 3.3.3 | 3 | 4.3.1 |
| 122 | 2 | 3.2.1 | 2 | 4.2.1 |
| 123 | 2 | 3.2.1 | 2 | 4.2.1 |
| 124 | 2 | 3.2.1 | 2 | 4.2.1 |
| 125 | 2 | 3.2.1 | 2 | 4.2.1 |
| 126 | 2 | 3.2.1 | 2 | 4.2.1 |
| 127 | 2 | 3.2.1 | 2 | 4.2.1 |

Example 4. Construction of a pET26b Vector Stably Expressing a P Protein Embedded with an Aβ1-m Immunogen Corresponding to Example 3, this step involves three different synthesis schemes in total:

The first, directed at Scheme I of Example 3, is a P particle loop gene fragment of interest embedded with a human Aβ1-m gene located between a mKpnI restriction enzyme site and a SalI restriction enzyme site. That is, N1 copies of API-m gene are merely embedded into loop1. The P protein prepared by this method is abbreviated as P protein-N1copy-Aβ1-m-loop1.

The second, directed at Scheme II of Example 3, is a P particle loop gene fragment of interest embedded with a human API-m gene located between a SalI restriction enzyme site and a mEagI restriction enzyme site. That is, (1) N2 copies of Aβ1-m gene are merely embedded into loop2, and the P protein prepared by this method is abbreviated as P protein-N2copy-Aβ1-m-loop2; (2) N3 copies of Aβ1-m gene are merely embedded into loop3, and the P protein prepared by this method is abbreviated as P protein-N3copy-Aβ1-m-loop3; and (3) N2 copies of Aβ1-m gene are embedded into loop2 and N3 copies of Aβ1-m gene are embedded into loop3, and the P protein prepared by this method is abbreviated as P protein-N2copy-Aβ1-m-loop2-N3copy-Aβ1-m-loop3.

The third, directed at Scheme III of synthesizing a P protein embedded with an API-m immunogen in Example 3, is a P particle loop gene fragment of interest embedded with a human API-m gene located between a mKpnI restriction enzyme site and a mEagI restriction enzyme site. That is, (1) N1 copies of Aβ1-m gene are embedded into loop1 and N2 copies of Aβ1-m gene are embedded into loop2, and the P protein prepared by this method is abbreviated as P protein-N1copy-Aβ1-m-loop1-N2copy-Aβ1-m-loop2; (2) N1 copies of Aβ1-m gene are embedded into loop1 and N3 copies of Aβ1-m gene are embedded into loop3, and the P protein prepared by this method is abbreviated as P protein-N1copy-Aβ1-m-loop1-N3copy-Aβ1-m-loop3; and (3) N1 copies of Aβ1-m gene are embedded into loop1, N2 copies of Aβ1-m gene are embedded into loop2 and N3 copies of Aβ1-m gene are embedded into loop3, and the P protein prepared by this method is abbreviated as P protein-N1copy-Aβ1-m-loop1-N2copy-Aβ1-m-loop2-N3copy-Aβ1-m-loop3.

The above three synthesis schemes are illustrated as follows:

4.1 Scheme I:

The pET26b-P protein-mEagI-mKpnI plasmid vector obtained in Example 2 was subjected to SalI/KpnI double-enzyme digestion, using the mKpnI restriction enzyme site obtained by mutation and the SalI restriction enzyme site carried by the sequence itself, in order to excise the original loop1 region. The plasmid was recovered as the vector.

Meanwhile, the recombinant loop1 DNA fragment comprising multiple copies of the human Aβ1-m sequence synthesized in Example 3 was subjected to SalI/KpnI double-enzyme digestion in order to obtain the DNA fragment of interest.

The digested DNA fragment of interest was ligated to the digested vector in order to obtain a pET26b plasmid that can express a recombinant P protein embedded with an Aβ1-m immunogen. Finally, the plasmid was verified by sequencing, and thus a correct plasmid was obtained.

4.1.1 Construction of a plasmid vector expressing PP-10copy-Aβ1-6-loop1$G_{72}$ Protein 1 μL of Sal I enzyme and 1 μL of Kpn I enzyme (purchased from Takara Corporation) and 5 μL of digestion buffer (purchased from Takara Corporation) were added respectively to 4 μg of pET26b-P protein-mEagI-mKpnI vector plasmid obtained in Example 2, and finally sterile water was added to the system to reach a final volume of 50 μL. Digestion was carried out at 37° C. for 5 hours. The digested products were subjected to agarose gel electrophoresis, and recovered using gel recovery kit (purchased from Tiangen Biotech Co., Ltd.) to obtain a plasmid vector having sticky ends.

Meanwhile, the DNA fragment 10copy-Aβ1-6-loop1$G_{72}$ synthesized in Example 3 was subjected to SalI/KpnI double-enzyme digestion by the same method to obtain the gene fragment of interest.

Figure 1D:
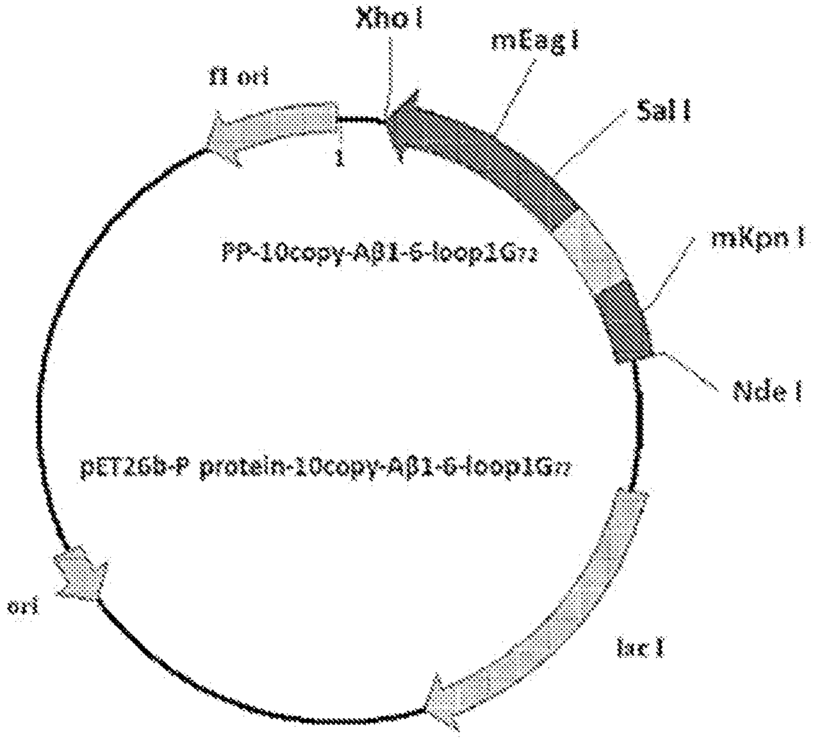

The digested vector was mixed with the digested gene fragment of interest. 0.75 μL of T4 ligase (purchased from Takara Corporation) and 1.5 μL of ligase buffer (purchased from Takara Corporation) were added to the mixture. The ligation was carried out at 16° C. overnight to obtain a plasmid vector expressing PP-10copy-Aβ1-6-loop1$G_{72}$ protein. The plasmid was verified by sequencing, as shown in FIG. 1D.

4.2 Scheme II

The pET26b-P protein-mEagI-mKpnI plasmid vector obtained in Example 2 was subjected to SalI/EagI double-enzyme digestion, using the mKpnI restriction enzyme site obtained by mutation and the SalI restriction enzyme site carried by the sequence itself, in order to excise the original loop2 and loop3 regions. The plasmid was recovered as the vector.

Meanwhile, the recombinant loop2 and loop3 DNA fragments comprising multiple copies of the human Aβ1-m sequence synthesized in Example 3 was subjected to SalI/EagI double-enzyme digestion to obtain the DNA fragment of interest.

The digested DNA fragment of interest was ligated to the digested vector to obtain a pET26b plasmid that can express a recombinant P protein embedded with an Aβ1-m immunogen. Finally, the plasmid was verified by sequencing, and thus a correct plasmid was obtained.

4.2.1 Construction of a Plasmid Vector Expressing PP-1Copy-Aβ1-6-loop2$S_{149}$ Protein 1 μL of SalI enzyme and 1 μL of EagI enzyme (purchased from Takara Corporation) and an appropriate amount of digestion buffer (purchased from Takara Corporation) were respectively added to 4 μg of the pET26b-P protein-mEagI-mKpnI plasmid vector obtained in Example 2, and finally sterile water was added to reach a final volume of 50 μL. Digestion was carried out at 37° C. for 5 hours. The digested products were subjected to agarose gel electrophoresis, and recovered using gel recovery kit (purchased from Tiangen Biotech Co., Ltd.) to obtain a plasmid vector having sticky ends.

Meanwhile, the DNA fragment 1copy-Aβ1-6-loop2$S_{149}$ synthesized in Example 3 was subjected to SalI/KpnI double-enzyme digestion by the same method to obtain the gene fragment of interest.

Figure 1E:
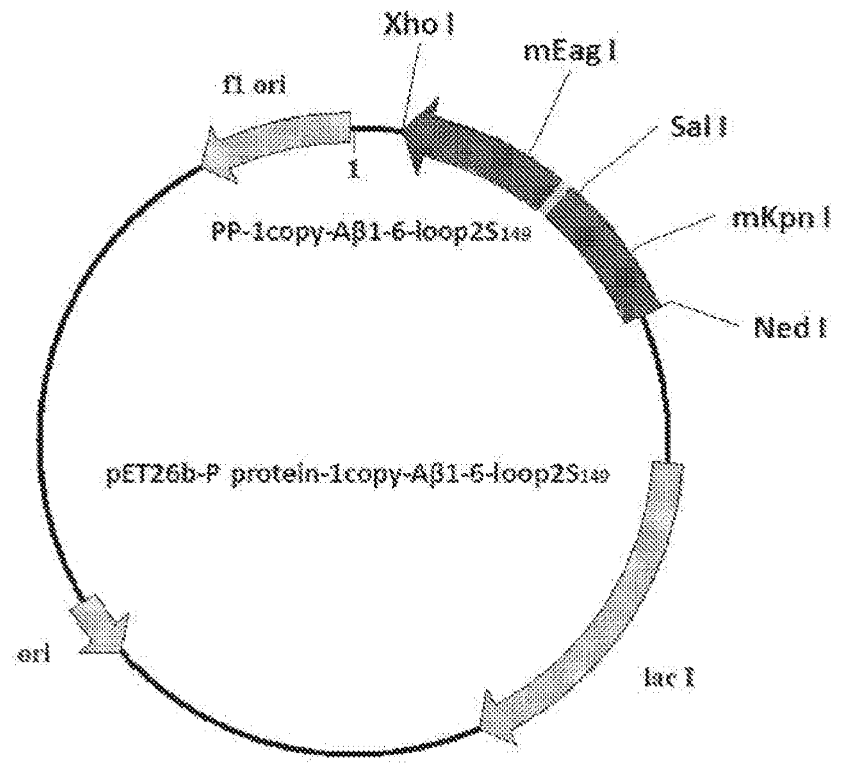

The digested vector was mixed with the digested gene fragment of interest. 0.75 μL of T4 ligase (purchased from Takara Corporation) and 1.5 μL of ligase buffer (purchased from Takara Corporation) were added to the mixture. The ligation was carried out at 16° C. overnight to obtain a plasmid vector expressing PP-1copy-Aβ1-6-loop2$S_{149}$ protein. The plasmid was verified by sequencing, as shown in FIG. 1E.

Figure 1F:
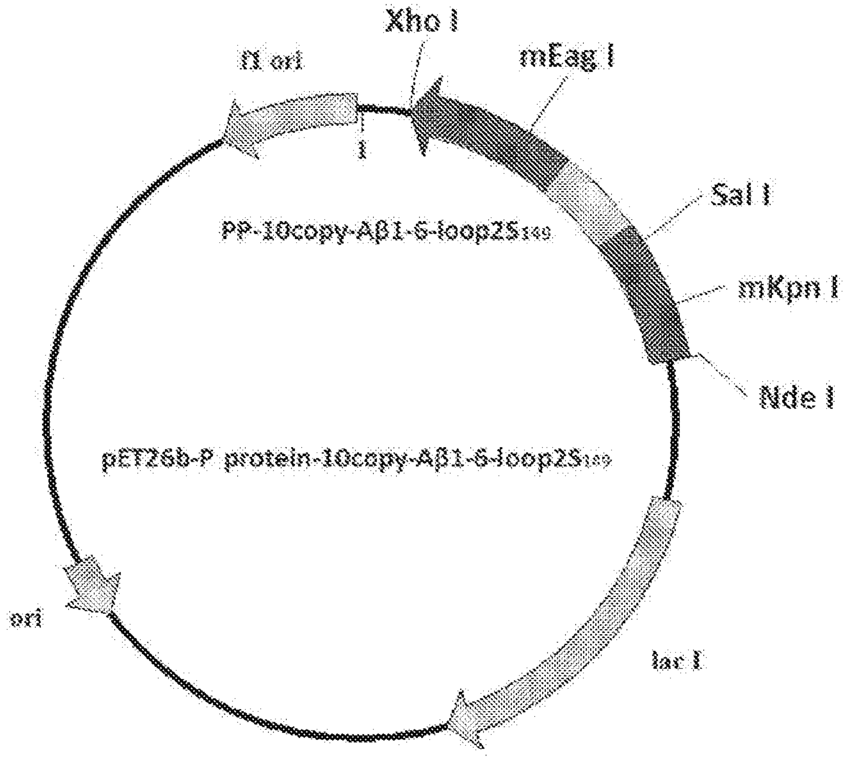

4.2.2 Construction of a Plasmid Vector Expressing PP-10Copy-Aβ1-6-loop2$S_{149}$ Protein A plasmid vector expressing PP-10copy-Aβ1-6-loop2$S_{149}$ protein was constructed, using the same method as 4.2.1. The plasmid is shown in FIG. 1F.

Figure 1G:
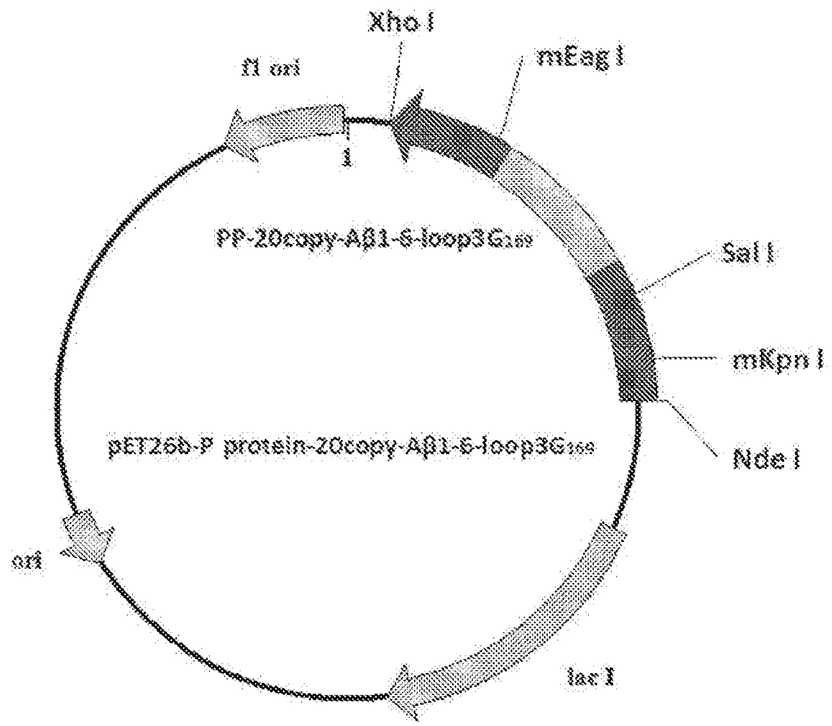

4.2.3 Construction of a Plasmid Vector Expressing PP-20Copy-Aβ1-6-loop3$G_{169}$ Protein A plasmid vector expressing PP-20copy-Aβ1-6-loop3$G_{169}$ protein was constructed, using the same method as 4.2.1. The plasmid is shown in FIG. 1G.

Figure 1H:
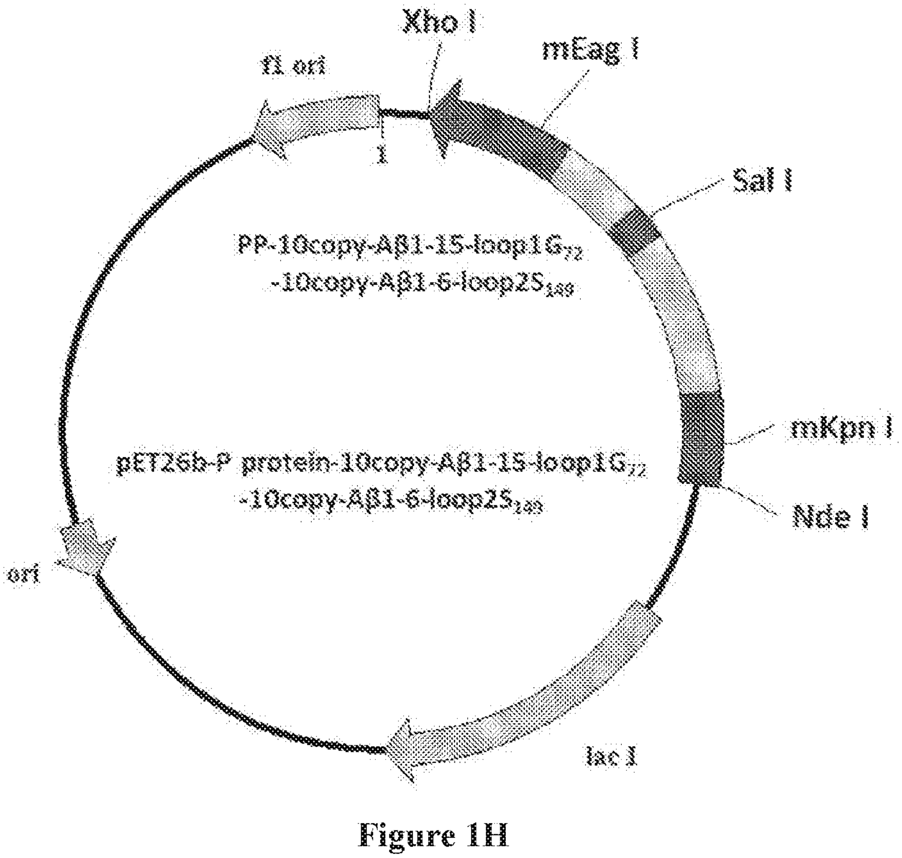
Figure 1I:
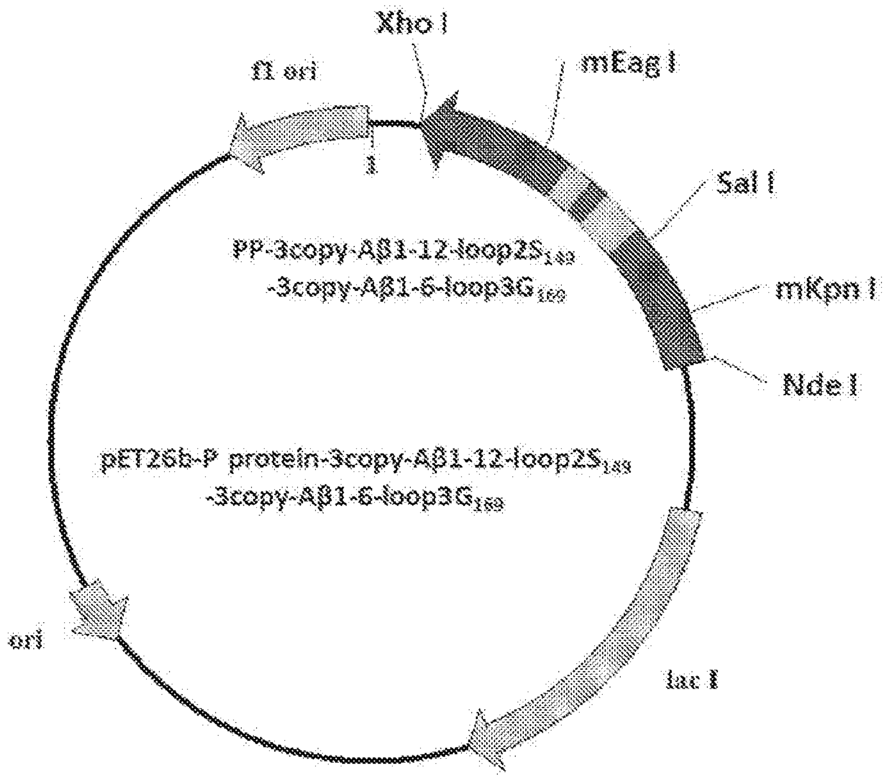

4.2.4 Construction of a Plasmid Vector Expressing PP-3Copy-Aβ1-12-loop$S_{149}$-3Copy-Aβ1-6-loop3$G_{169}$ Protein A plasmid vector expressing PP-3copy-Aβ1-12-loop$S_{149}$-3copy-Aβ1-6-loop3$G_{169}$ protein was constructed, using the same method as 4.2.1. The plasmid is shown in FIG. 1I.

4.3 Scheme III

The pET26b-P protein-mEagI-mKpnI plasmid vector obtained in Example 2 was subjected to mKpnI/mEagI double-enzyme digestion, using the mEagI restriction enzyme site and the mKpnI restriction enzyme site obtained by mutation, in order to excise the original loop1, loop2 and loop3 regions. The plasmid was recovered as the vector.

Meanwhile, the recombinant loop1, loop2 and loop3 DNA fragments comprising multiple copies of the human Aβ1-m sequence synthesized in Example 3 was subjected to mKpnI/mEagI double-enzyme digestion in order to obtain the DNA fragment of interest.

The digested DNA fragment of interest was ligated to the digested vector in order to obtain a pET26b plasmid that can express a recombinant P protein embedded with an Aβ1-m immunogen. Finally, the plasmid was verified by sequencing, and thus a correct plasmid was obtained.

4.3.1 Construction of a Plasmid Vector Expressing PP-3Copy-Aβ1-6-Loop 1-$G_{72}$-3Copy-Aβ1-6-loop2$S_{149}$-3Copy-Aβ1-6-loop3$G_{169}$ Protein 1 μL of KpnI enzyme and 1 μL of EagI enzyme (purchased from Takara Corporation) and an appropriate amount of digestion buffer (purchased from Takara Corporation) were added respectively to 4 μg of the pET26b-P protein-mEagI-mKpnI vector plasmid obtained in Example 2, and finally sterile water was added to reach a final volume of 50 μL. Digestion was carried out at 37° C. for 5 hours. The digested products were subjected to agarose gel electrophoresis, and recovered using gel recovery kit (purchased from Tiangen Biotech Co., Ltd.) to obtain a plasmid vector having sticky ends.

Meanwhile, the DNA fragment 3copy-Aβ1-6-loop1$G_{72}$-3copy-Aβ1-6-loop2$S_{149}$-3copy-Aβ1-6-loop3$G_{169}$ synthesized in Example 3 was subjected to EagI/KpnI double-enzyme digestion by the same method to obtain the gene fragment of interest.

Figure 1J:
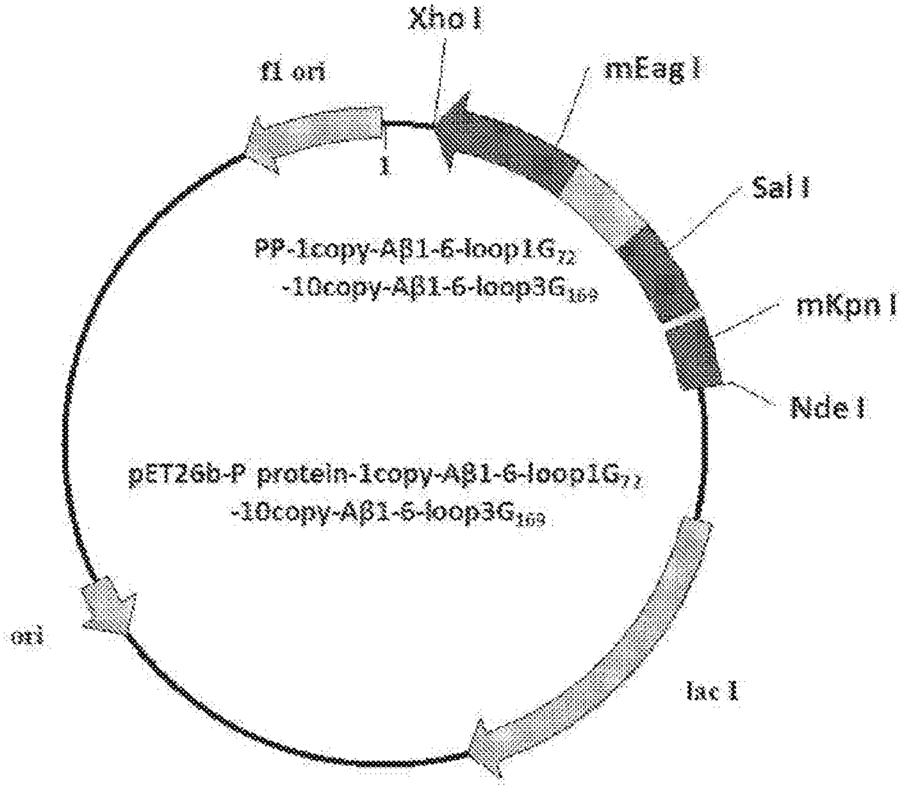
Figure 1K:
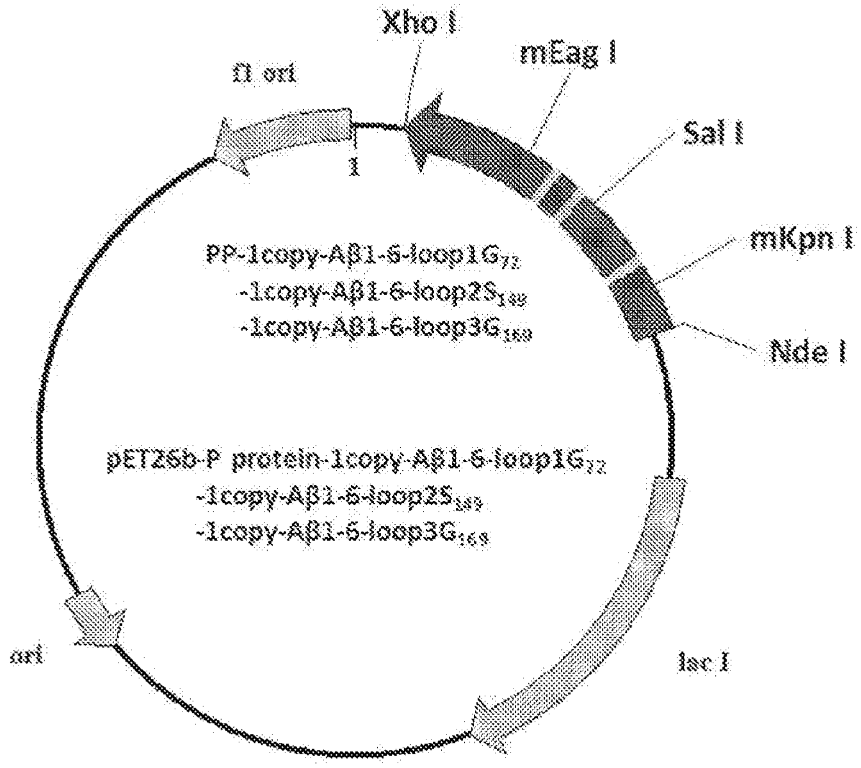
Figure 1L:
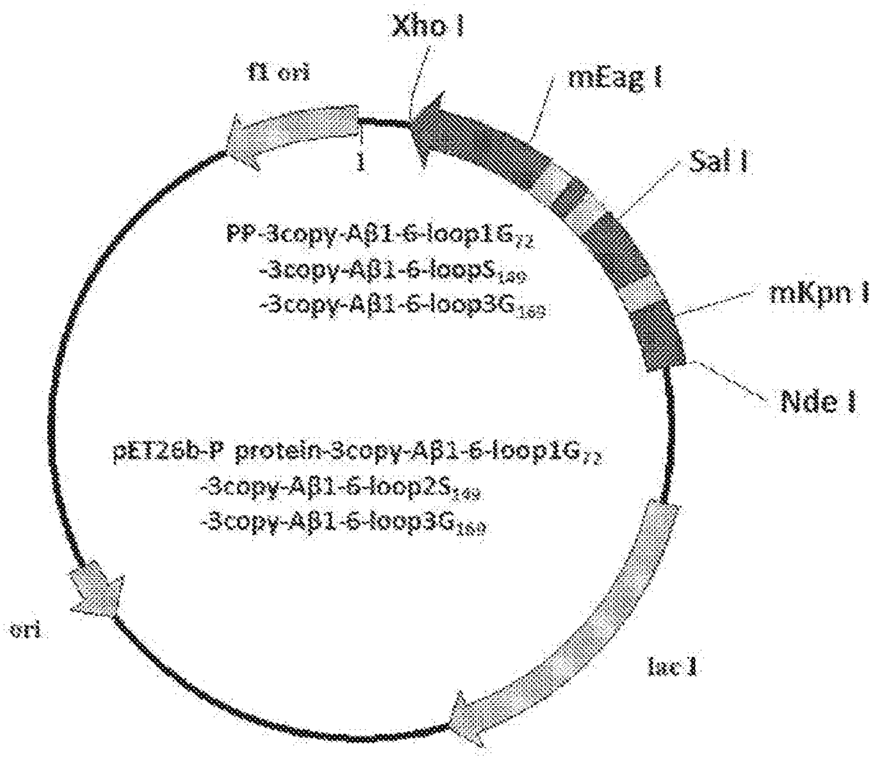

The digested vector was mixed with the digested gene fragment of interest. 0.75 μL of T4 ligase (purchased from Takara Corporation) and 1.5 μL of ligase buffer (purchased from Takara Corporation) were added to the mixture. The ligation was carried out at 16° C. overnight to obtain a plasmid vector expressing PP-1copy-Aβ1-6-loop2$S_{149}$ protein. The plasmid was verified by sequencing, as shown in FIG. 1L.

4.3.2 Construction of a plasmid vector expressing PP-10copy-Aβ1-15-loop1$G_{72}$-10copy-Aβ1-6-loop2$S_{149}$ protein A plasmid vector expressing PP-10copy-Aβ1-15-loop1$G_{72}$-10copy-Aβ1-6-loop2$S_{149}$ protein was constructed, using the same method as 4.3.1. The plasmid is shown in FIG. 1H.

4.3.3 Construction of a Plasmid Vector Expressing PP-1Copy-Aβ1-6-loop1$G_{72}$-10Copy-Aβ1-6-loop3$G_{169}$ Protein A plasmid vector expressing PP-1copy-Aβ1-6-loop1$G_{72}$-10copy-Aβ1-6-loop3$G_{169}$ protein was constructed, using the same method as 4.3.1. The plasmid is shown in FIG. 1J.

4.3.4 Construction of a Plasmid Vector Expressing PP-1Copy-Aβ1-6-loop1$G_{72}$-1Copy-Aβ1-6-loop2$S_{149}$-1Copy-Aβ1-6-loop3$G_{169}$ Protein A plasmid vector expressing PP-1copy-Aβ1-6-loop1$G_{72}$-1copy-Aβ1-6-loop2$S_{149}$-11copy-Aβ1-6-loop3$G_{169}$ protein was constructed, using the same method as 4.3.1. The plasmid is shown in FIG. 1K.

4.3.5 Construction of a Plasmid Vector Expressing PP-10Copy-Aβ1-6-loop1$G_{72}$-10Copy-Aβ1-6-loop2$S_{149}$-10 Copy-Aβ1-6-loop3$G_{169}$ Protein A plasmid vector expressing PP-10copy-Aβ1-6-loop1$G_{72}$-10copy-Aβ1-6-loop2$S_{149}$-10copy-Aβ1-6-loop3$G_{169}$ protein was constructed, using the same method as 4.3.1. The plasmid is shown in FIG. 1M.

Furthermore, in addition to the above 10 recombinant P proteins, construction methods of other 117 plasmids expressing recombinant P proteins respectively involve the above three schemes, specifically as shown in Table 2. The obtained recombinant plasmids are not shown.

Example 5 Expression and Purification of a P Protein Embedded with a Human Aβ1-m Immunogen 5.1 Expression of a Recombinant P Particle Protein 1 μL of the recombinant plasmids prepared in the above examples were respectively added to 100 μL of *E. coli* BL21 competent cells (purchased from TransGen Corporation), ice-bathed for 30 min, heat shocked for 90 s in a water-bath at 42° C., and then ice-bathed for 2 min. 600 μL of LB medium was added to the mixture, and cultured at 180 rpm/min at 37° C. for 1 h. The mixture was coated evenly on a LB solid medium containing kanamycin (15 μg/mL) resistance and cultured at 37° C. for 24 h to obtain strains that can stably express recombinant proteins. A growing colony was picked and inoculated into 20 mL of LB medium. The mixture was cultured at 220 rpm at 37° C. When the OD value of the culture mixture reached 1.0, induction by Isopropyl β-D-Thiogalactoside (IPTG at a final concentration of 0.33 mmol/L) was carried out at 220 rpm at 16° C. overnight. After the induction, the culture broth was centrifuged at 4000 rpm for 20 min. The supernatant was discarded, and the bacterial precipitates were resuspended with PBS. Centrifugation was conducted again at 4000 rpm for 20 min and the supernatant was discarded to obtain the bacterial precipitates containing proteins of interest.

5.2 Extraction and Purification of Recombinant P Particle Proteins

The bacterial precipitates obtained in 5.1 were resuspended by adding 20 mL of protein buffer (pH8.0, containing 50 mM Tris and 300 mM KCl). The bacteria were lysed by sonication on ice for 30 min. The mixture was centrifuged at 12,000 rpm at 4° C. for 30 min. Subsequently, the supernatant was taken and allowed to pass through 0.45 μm filter membrane to obtain crude extracts of proteins.

The structures of recombinant P particle proteins are shown as FIG. 3A-J.

The crude extracts of proteins were purified using a cation exchange column (purchased from GE Corporation). The specific scheme was as follows: First, the exchange column was rinsed with ultrapure water in a volume of about 100 mL, followed by equilibration with PB solution (pH 5.0) at a flow rate of 2 mL/min. Then 20 mL of the crude extracts of proteins were added to the exchange column at a flow rate of 1 ml/min. After the sample was completely loaded onto the column, the exchange column was rinsed with PB solution (pH 7.0) to remove protein impurities, and then eluted with PB solution containing 1 mol/L NaCl. The proteins at peak value were collected to obtain the proteins of interest.

The proteins were further purified by a hydrophobic chromatography column (purchased from GE Corporation). The specific scheme was as follows: First, the column was rinsed with ultrapure water, and then with PB solution (pH 7.0) at a flow rate of 2 mL/min. After the column was equilibrated well, the protein sample was loaded onto it. After the sample was completely loaded onto the column, the column was eluted by gradient with PB (pH 7.0) and 1 mol/L NaCl solution for 2 hours. The concentration of NaCl decreases from 1 mol/L to 0.1 mol/L. The proteins were collected at peak value.

The sizes of 10 P particle protein monomers were identified by reductive SDS-PAGE. The upper panels of FIGS. 4A-J respectively show that the size of PP-10copy-Aβ1-6-loop1G72 protein is 45 KD; the size of PP-1copy-Aβ1-6-loop2$S_{149}$ protein is 37 KD; the size of PP-10copy-Aβ1-6- loopS$_{149}$ protein is 45 KD; the size of PP-20copy-Aβ1-6-loop3G$_{169}$ protein is 55 KD; the size of PP-10copy-Aβ1-15-loop1G$_{72}$-10copy-Aβ1-6-loop2S$_{149}$ protein is 66 KD; the size of PP-3copy-Aβ1-12-loop2S$_{149}$-3copy-Aβ1-6-loop3G$_{169}$ protein is 38 KD; the size of PP-1copy-Aβ1-6-loop1G$_{72}$-10copy-Aβ1-6-loop3G$_{169}$ protein is 47 KD; the size of PP-1copy-Aβ1-6-loop1G$_{72}$-1copy-Aβ1-6-loop2S$_{149}$-1copy-Aβ1-6-loop3G$_{169}$ protein is 3 KD; the size of PP-3copy-Aβ1-6-loop1G$_{72}$-3copy-Aβ1-6-loop2S$_{149}$-3copy-Aβ1-6-loop3G$_{169}$ protein is KD; and the size of PP-10copy-Aβ1-6-loop1G$_{72}$-10copy-Aβ1-6-loop2S$_{149}$-10copy-Aβ1-6-loop3G$_{169}$ is 66 KD.

Then the tetracosamers of P protein particles were further isolated and purified using a Superdex 200 molecular sieve (purchased from GE Corporation). The procedures were as follows: The column was rinsed with ultrapure water at a flow rate of 1 mL/min for one volume of the column, and then again with about 120 mL of PB buffer (pH 5). After that, 2 mL of protein extraction solution was added to the column and washed with PB buffer at a flow rate of 1 mL/min. The proteins at peak value were collected to obtain the tetracosamers of P particle proteins. Three proteins were tested for their polymer structures by native polyacrylamide gel electrophoresis, as shown in the middle panels of FIGS. 4A-J. All ten protein bands are above 225 KDa, which indicates that recombinant proteins can self-assemble into tetracosamers of P protein particles, and they can remain their polymer form after being purified.

Example 6 Characterization of a P Protein Particle Embedded with a Human Aβ1-m Immunogen Inventors further analyzed the particle diameter and morphology of 10 protein polymers. The particle diameter was tested using a nanoparticle diameter analyzer (purchased from Malvern Corporation) in accordance with the instructions of the manufacturer. The analysis results showed that there were particles having an average diameter of about 20 nm in the solution of the above 10 recombinant P particles. As shown in the lower panels of FIGS. 4A-J, PP-10copy-Aβ1-6-loop1G$_{72}$ protein particle has a particle diameter of 27.88 nm; PP-1copy-Aβ1-6-loop2S$_{149}$ protein particle has a particle diameter of 17.44 nm; PP-10copy-Aβ1-6-loop2S$_{149}$ protein particle has a particle diameter of 27.64 nm; PP-20copy-Aβ1-6-loop3G$_{169}$ protein particle has a particle diameter of 32.55 nm; PP-10copy-Aβ1-15-loop1G$_{72}$-10copy-Aβ1-6-loop2S$_{149}$ protein particle has a particle diameter of 35.88 nm; PP-3copy-Aβ1-12-loop2S$_{149}$-3copy-Aβ1-6-loop3G$_{169}$ protein particle has a particle diameter of 17.02 nm; PP-1copy-Aβ1-6-loop1G$_{72}$-10copy-Aβ1-6-loop3G$_{169}$ protein particle has a particle diameter of 28.92 nm; PP-1copy-Aβ1-6-loop1G$_{72}$-1copy-Aβ1-6-loop2S$_{149}$-1copy-Aβ1-6-loop3G$_{169}$ protein particle has a particle diameter of 18.14 nm; PP-3copy-Aβ1-6-loop1G$_{72}$-3copy-Aβ1-6-loop2S$_{149}$-3copy-Aβ1-6-loop3G$_{169}$ protein particle has a particle diameter of 25.56 nm; and PP-10copy-Aβ1-6-loop1G$_{72}$-10copy-Aβ1-6-loop2S$_{149}$-10copy-Aβ1-6-loop3G$_{169}$ protein particle has a particle diameter of 36.09 nm. Meanwhile, the results of electron microscope tests show that the recombinant P proteins are in the form of approximately spherical particles, and in the form of polymers. According to the ruler, 10 protein polymers mainly comprise particles of about 20 nm. Thus, all the above 10 recombinant P proteins can self-assemble in vitro to form tetracosamers of P particles.

The sizes and P particle diameters of the 127 P particle proteins according to the invention are shown as Table 3.

TABLE 3

The sizes and P particle diameters of 127 different forms of recombinant P particle proteins

| NO. | Size of protein (KD) | P particle diameter (nm) |
|---|---|---|
| 1 | 36.2 | 17.75 |
| 2 | 48.4 | 31.23 |
| 3 | 68.2 | 36.37 |
| 4 | 114.4 | 39.86 |
| 5 | 36.6 | 16.98 |
| 6 | 51.7 | 31.53 |
| 7 | 74.8 | 38.13 |
| 8 | 74.8 | 38.2 |
| 9 | 36.2 | 16.98 |
| 10 | 45.1 | 27.88 |
| 11 | 55.0 | 32.07 |
| 12 | 74.8 | 37.89 |
| 13 | 36.9 | 17.89 |
| 14 | 55.0 | 31.99 |
| 15 | 55.0 | 31.68 |
| 16 | 88.0 | 39.54 |
| 17 | 37.2 | 17.89 |
| 28 | 45.1 | 18.03 |
| 19 | 61.6 | 34.66 |
| 20 | 101.2 | 39.75 |
| 21 | 36.5 | 16.77 |
| 22 | 48.4 | 31.15 |
| 23 | 61.6 | 34.15 |
| 24 | 88.0 | 39.65 |
| 25 | 36.2 | 17.44 |
| 26 | 45.1 | 27.64 |
| 27 | 55.0 | 31.97 |
| 28 | 74.8 | 38.17 |
| 29 | 36.9 | 17.95 |
| 30 | 51.7 | 31.67 |
| 31 | 68.2 | 36.34 |
| 32 | 101.2 | 39.67 |
| 33 | 37.2 | 18.01 |
| 34 | 55.0 | 32.01 |
| 35 | 74.8 | 38.22 |
| 36 | 114.4 | 39.92 |
| 37 | 36.9 | 18.02 |
| 38 | 51.7 | 31.42 |
| 39 | 68.2 | 36.41 |
| 40 | 101.2 | 40.11 |
| 41 | 36.2 | 17.51 |
| 42 | 45.1 | 27.61 |
| 43 | 55.0 | 32.55 |
| 44 | 74.8 | 38.21 |
| 45 | 37.2 | 18.13 |
| 46 | 55.0 | 31.87 |
| 47 | 74.8 | 38.17 |
| 48 | 114.4 | 40.17 |
| 49 | 36.5 | 18.16 |
| 50 | 48.4 | 31.26 |
| 51 | 61.6 | 36.18 |
| 52 | 88.0 | 39.18 |
| 53 | 41.5 | 25.06 |
| 54 | 61.9 | 34.09 |
| 55 | 101.5 | 40.06 |
| 56 | 193.9 | 45.3 |
| 57 | 38.2 | 19.2 |
| 58 | 42.5 | 26.2 |
| 59 | 65.2 | 35.88 |
| 60 | 101.5 | 39.83 |
| 61 | 144.4 | 43.7 |
| 62 | 154.3 | 44.01 |
| 63 | 46.4 | 30.31 |
| 64 | 75.1 | 31.88 |
| 65 | 134.5 | 42.67 |
| 66 | 134.5 | 43.12 |
| 67 | 53.0 | 31.99 |
| 68 | 68.5 | 36.28 |
| 69 | 114.7 | 39.67 |
| 70 | 127.9 | 40.02 |
| 71 | 91.6 | 39.77 |
| 72 | 53.4 | 31.89 |
| 73 | 49.4 | 18.24 |
| 74 | 68.5 | 36.44 |

TABLE 3-continued

The sizes and P particle diameters of 127 different forms of recombinant P particle proteins

| NO. | Size of protein (KD) | P particle diameter (nm) |
|---|---|---|
| 75 | 75.1 | 38.17 |
| 76 | 141.1 | 42.55 |
| 77 | 37.8 | 17.1 |
| 78 | 43.5 | 17.02 |
| 79 | 68.5 | 35.21 |
| 80 | 94.9 | 39.62 |
| 81 | 124.6 | 41.41 |
| 82 | 180.7 | 45.23 |
| 83 | 46.4 | 28.31 |
| 84 | 75.1 | 38.21 |
| 85 | 134.5 | 42.71 |
| 86 | 134.5 | 41.93 |
| 87 | 49.7 | 31.19 |
| 88 | 75.1 | 38.38 |
| 89 | 147.7 | 44.22 |
| 90 | 147.7 | 43.91 |
| 91 | 78.4 | 39.4 |
| 92 | 50.7 | 31.87 |
| 93 | 39.4 | 18.31 |
| 94 | 61.9 | 34.67 |
| 95 | 75.1 | 38.09 |
| 96 | 167.5 | 45.8 |
| 97 | 37.8 | 18.45 |
| 98 | 43.4 | 27.67 |
| 99 | 68.5 | 36.38 |
| 100 | 94.9 | 40.01 |
| 101 | 144.4 | 43.96 |
| 102 | 154.3 | 44.38 |
| 103 | 46.4 | 28.92 |
| 104 | 75.1 | 38.22 |
| 105 | 134.5 | 42.51 |
| 106 | 134.5 | 42.79 |
| 107 | 49.7 | 31.33 |
| 108 | 55.0 | 32.09 |
| 109 | 54.0 | 32.91 |
| 110 | 141.1 | 43.68 |
| 111 | 121.3 | 40.03 |
| 112 | 109.8 | 38.88 |
| 113 | 83.1 | 39.44 |
| 114 | 141.5 | 43.21 |
| 115 | 60.6 | 35.87 |
| 116 | 134.9 | 42.57 |
| 117 | 65.6 | 36.12 |

TABLE 3-continued

The sizes and P particle diameters of 127 different forms of recombinant P particle proteins

| NO. | Size of protein (KD) | P particle diameter (nm) |
|---|---|---|
| 118 | 38.8 | 18.14 |
| 119 | 44.8 | 25.56 |
| 120 | 65.6 | 36.09 |
| 121 | 154.7 | 44.11 |
| 122 | 41.5 | 20.45 |
| 123 | 42.7 | 24.24 |
| 124 | 47.5 | 28.99 |
| 125 | 53.6 | 32.01 |
| 126 | 45.1 | 27.64 |
| 127 | 38.9 | 18.15 |

3. Immunological Effects of Recombinant P Particle Protein Vaccines 3.1 Determination of Immune Dosages and Adjuvants of P Particle Protein Vaccines The PP-10copy-Aβ1-6-loop2$S_{149}$ protein vaccine was selected for use in female C57BL/6 mice aged 6-8 weeks (purchased from Beijing HFK Bioscience Co., LTD) to determine the immune dosage and immune adjuvant. The immune dosages were respectively 12.5 μg, 25 μg and 50 μg/animal, and were increased to 100 μL/animal with sterile PBS. Each group contained 6 mice. The immunization was performed by subcutaneous injection. The immune adjuvants were an aluminium adjuvant (purchased from Brenntag Biosector Corporation) and an CpG adjuvant that can specifically stimulate the body to produce humoral immunity (purchased from Takara Corporation). The nucleotide sequence of CpG adjuvant was as follows: TGTCGTCGTCGTTTGTCGTTTGTCGTT (SEQ ID NO: 153). The immunization was carried out at day 1, day 15 and day 29 (three times in total). Blood was taken on the day before every immunization. The mice were sacrificed two weeks after the third immunization. The recombinant P particle protein vaccine was tested for immunological responses of the induced humoral immunity and cellular immunity in mice. There were 7 test groups and 3 control groups. The immune dosage, adjuvant and immunizing antigen for each group are shown in Table 4.

TABLE 4

Immunization scheme of PP-10copy-Aβ1-6-loop2$S_{149}$

| Group | Immune dosage (100 μl) | Adjuvant | Immunizing antigen |
|---|---|---|---|
| Negative | — | — | — |
| control group | — | aluminium adjuvant (200 μg) | — |
| | — | CpG (10 μg) | — |
| Test group | 12.5 μg | — | PP-10copy-Aβ1-6-loop2$S_{149}$ |
| | 25 μg | — | PP-10copy-Aβ1-6-loop2$S_{149}$ |
| | 50 μg | — | PP-10copy-Aβ1-6-loop2$S_{149}$ |
| | 25 μg | aluminium adjuvant (200 μg) | PP-10copy-Aβ1-6-loop2$S_{149}$ |
| | 25 μg | CpG (10 μg) | PP-10copy-Aβ1-6-loop2$S_{149}$ |
| | 25 μg | aluminium adjuvant + CpG (10 μg) | PP-10copy-Aβ1-6-loop2$S_{149}$ |
| | 100 μg | Freund's adjuvant (100 μl) | Aβ1-42 |

3.1.1 Humoral Immunity-ELISA Detection Experiment

Tails of the mice were cut and blood was taken on the day before every immunization. Blood samples were placed at 37° C. for 2 h, then placed at 4° C. for 1 h, and centrifuged at 3,000 rpm to take the supernatant serum. The serum was frozen for use. Aβ1-42 (purchased from GL Biochem (Shanghai) Ltd.) was used as antigen and formulated into 1 mg/mL solution with sterile PBS. The solution was diluted to 1 ng/L with antigen coating solution and used for coating a 96-well plate (100 μL/well). The plate was coated at 4° C. overnight. After each well was washed three times with 300 μL of PBST (pH 7.4, 0.01 mol/L PBS, containing 0.05% Tween-20), blocking solution (pH 7.4, 0.01 mol/L PBS, 20% fetal bovine serum) was added. Blocking was carried out at 37° C. for 2 hours. Each well was washed three times with PBST. To the wells were added different dilution gradients (1:200, 1:800, 1:3200, 1:12800, 1:51200 and 1:204800) of antiserum (100 μL/well), and incubation was carried out at 37° C. for 1 hour. Each well was washed three times with PBST. To the wells were added 0.3 μg/ml of HPR (horse radish peroxidase) goat-anti-mouse secondary antibody (purchased from Beijing Dingguochangsheng Biotechnology Co. LTD) (100 μL/well), and incubation was carried out at 37° C. for 1 hour. Each well was washed three times with PBST. To the wells were added the substrate tetramethylbenzidine (TMB) (purchased from Tiangen Biotech Co., Ltd.) (100 μL/well), and color was developed in the dark for 25 min. 50 μL of 2M sulfuric acid was added to each well to terminate the reaction. Absorbance was detected at 450 nm using a microplate reader (purchased from Bio-red Corporation).

Experimental results are shown in FIG. 5A. When CpG is used as immune adjuvant and the immune dosage is 25 μg, or the immune dosage is 50 μg and no immune adjuvant is used, PP-10copy-Aβ1-6-loop2-$S_{149}$ protein vaccine at all the shown dilutions can stimulate the mouse to produce relatively high titers of specific antibodies against Aβ42.

3.1.2 Cellular Immunity-ELISPOT Detection

A 96-well plate was coated with the monoclonal antibody against cytokine interferon γ (from elispot kit purchased from BD Corporation) in a concentration of 5 μg/mL (50 μL/well), and covered at 4° C. overnight. After discarding the coating antibody and washing once with a complete medium containing 10% fetal bovine serum, 200 μL of this complete medium was added to each well. Blocking was carried out at 37° C. for 1 hour, and then the medium was discarded. Mice used in the experiment were sacrificed by neck-pulling. Spleen cells of the mice were taken out and formulated into a cell suspension in a concentration of $10^7$/mL. The cell suspension was added to the coated 96-well plate (100 μL/well). 100 μL of 1 μg/mL specific antigen Aβ1-42 was added to each well. The plate was then cultured at 37° C. in an incubator containing 5% $CO_2$ for 24 h to stimulate and activate the cells. 24 h later, the plate was washed two times with sterile water, and six times with sterile PBST (pH7.4, 0.01 mol/L PBS, containing 0.05% Tween-20) buffer to wash the cells away. 50 μL of 2 μg/mL antibody against interferon γ (from elispot kit purchased from BD Corporation) was added to each well and incubated at room temperature for 2 hours. The 96-well plate was washed, and horse radish peroxidase labeled biotin secondary antibody (from elispot kit purchased from BD Corporation) was added (50 μL/well). The plate was cultured at room temperature for 2 h, and washed four times with PBST, and two times with PBS. 50 μL of Elispot color developing solution (AEC substrate) was added to each well and reacted in the dark at room temperature for 5-60 min. The staining solution was discarded, and the plate was washed with distilled water. After being dried overnight, the sample was calculated for the number of activated cells using a microscope.

The results are shown in FIG. 5B. In the T cell response-positive control group Aβ42 group, a large number of spots emerge, which demonstrates a strong T cell response. In the 25 μg protein+aluminium adjuvant group, a large number of spots also emerge, which demonstrates that the aluminium adjuvant could stimulate the body to produce a certain T cell response. Nevertheless, the 25 μg PP-10copy-Aβ1-6-loop2-$S_{149}$+CpG adjuvant group and 50 μg group have no or fewer positive spots, which demonstrates no evident T cell response occurring in the body, and as described in 3.1.1, this immunization strategy can stimulate the mice to produce the highest titer of specific antibodies against Aβ42. Considering the safety of vaccines, 25 g PP-10copy-Aβ1-6-loop2$S_{149}$+CpG adjuvant was selected as the optimal immunization strategy.

3.2 Comparison of Immunological Effects of Three Recombinant P Particle Protein Vaccines After the experiments for determining immune dosages and immune adjuvants of protein vaccines, the applicant first selected three representative recombinant proteins, adopted the strategy of a protein vaccine dosage of 25 μg/animal and CpG as the adjuvant, compared immunological effects of the three recombinant P particle protein vaccines in female C57BL/6 mice aged 6-8 weeks by the two immunization routes via nasal and subcutaneous injections in order to compare the effects of nasal and subcutaneous immunizations, and identify the differences in immunological effects of various proteins. Similar to the method in 3.1.1, immunization was carried out every two weeks and four times in total. Tails of the mice were cut and blood was taken before every immunization. Serum was tested by ELISA detection. The mice were divided into 7 test groups and 3 control groups. The immunogen and immunization route for each group are shown as in FIG. 5.

TABLE 5

Immunization schemes of 3 representative P particle proteins

| Group | Immunogen | immunization route |
|---|---|---|
| Control group | PBS | subcutaneous |
| | PBS | nasal |
| | CpG | subcutaneous |
| | CpG | nasal |
| test group | PP-1copy-Aβ1-6-loop2$S_{149}$ + CpG | subcutaneous |
| | PP-10copy-Aβ1-6-loop2$S_{149}$ + CpG | subcutaneous |
| | PP-3copy-Aβ1-6-loop1$G_{72}$-3copy-Aβ1-6-loop2$S_{149}$-3copy-Aβ1-6-loop3$S_{169}$ + CpG | subcutaneous |
| | PP-1copy-Aβ1-6-loop2$S_{149}$ + CpG | nasal |

TABLE 5-continued

| Immunization schemes of 3 representative P particle proteins | | |
|---|---|---|
| Group | Immunogen | immunization route |
| | PP-10copy-Aβ1-6-loop2$S_{149}$ + CpG | nasal |
| | PP-3copy-Aβ1-6-loop1$G_{72}$-3copy-Aβ1-6-loop2$S_{149}$-3copy-Aβ1-6-loop3$S_{169}$ + CpG | nasal |

An ELISA plate was coated with Aβ1-42 as the antigen, using the method described in 3.1.1. A reaction was carried out using the immunized mouse serum as the primary antibody, HRP goat-anti-mouse antibody as the secondary antibody, TMB as the substrate, and sulfuric acid as the termination solution. After the termination of reaction, absorbance was detected at 450 nm using a microplate reader. The contents of antibodies in the serum were compared based on the absorbance. Experiment was carried out using PBS as the negative control, and the commercial antibody 6e10 (purchased from Covance Corporation) as the positive control, and using the sera before and after immunizing mice with three proteins as the test groups. Results are shown in FIG. 6. All the three proteins can stimulate the mouse body to produce specific antibodies against Aβ42, which demonstrates that the vaccines of the present invention have good immunogenicity. Standard curve was plotted using the commercial antibody 6e10 as the positive control in order to calculate the concentration of antibodies. The comparison results of immunological effects are shown in FIG. 6. The two immunization routes of the three proteins can all produce specific antibodies against Aβ42, the OD values of which are all significantly higher than those of the PBS group and CpG group. Moreover, with the increase of immunization times, the concentration of the antibody continuously increases and can reach the highest value at the fourth immunization. By comparison, it can be seen that the subcutaneous immunization has better effect than the nasal immunization.

3.3 Comparison of Immunological Effects of Various Recombinant P Particle Protein Vaccines The applicant determined that the adopted immune dosage was 25 μg/animal and the immunization route was subcutaneous injection by the experiments for determining immune dosages and immune adjuvants of protein vaccines, and immunological experiments of three representative recombinant proteins, and determined the immunological effects of 127 candidate vaccines in female C57BL/6 mice aged 6-8 weeks. Immunization procedures and method are as described in 3.2. Comparison results of immunological effects are shown in Table 6.

TABLE 6

| Concentrations of Aβ42 antibody produced by mice stimulated with protein vaccines having 127 different forms of P particles as the immunogens | |
|---|---|
| group number | Concentration of the produced Aβ42 antibody after the fourth immunization |
| 1 | 94.88 |
| 2 | 90.28 |
| 3 | 64.55 |
| 4 | 29.09 |
| 5 | 85.62 |
| 6 | 77.10 |
| 7 | 65.75 |
| 8 | 55.98 |

TABLE 6-continued

| Concentrations of Aβ42 antibody produced by mice stimulated with protein vaccines having 127 different forms of P particles as the immunogens | |
|---|---|
| group number | Concentration of the produced Aβ42 antibody after the fourth immunization |
| 9 | 101.79 |
| 10 | 153.34 |
| 11 | 103.01 |
| 12 | 63.67 |
| 13 | 38.57 |
| 14 | 40.87 |
| 15 | 48.89 |
| 16 | 34.82 |
| 17 | 89.98 |
| 28 | 111.76 |
| 19 | 77.09 |
| 20 | 38.78 |
| 21 | 105.87 |
| 22 | 162.36 |
| 23 | 55.38 |
| 24 | 44.70 |
| 25 | 162.78 |
| 26 | 189.83 |
| 27 | 137.62 |
| 28 | 82.09 |
| 29 | 187.23 |
| 30 | 83.42 |
| 31 | 56.67 |
| 32 | 54.31 |
| 33 | 87.47 |
| 34 | 77.21 |
| 35 | 68.47 |
| 36 | 42.12 |
| 37 | 98.09 |
| 38 | 67.92 |
| 39 | 21.83 |
| 40 | 34.01 |
| 41 | 108.53 |
| 42 | 145.61 |
| 43 | 158.96 |
| 44 | 43.57 |
| 45 | 76.37 |
| 46 | 64.89 |
| 47 | 56.17 |
| 48 | 29.02 |
| 49 | 68.78 |
| 50 | 75.26 |
| 51 | 77.15 |
| 52 | 39.58 |
| 53 | 130.09 |
| 54 | 144.98 |
| 55 | 36.75 |
| 56 | 24.98 |
| 57 | 99.90 |
| 58 | 78.79 |
| 59 | 178.46 |
| 60 | 71.14 |
| 61 | 88.82 |
| 62 | 22.19 |
| 63 | 109.70 |
| 64 | 142.06 |
| 65 | 20.08 |
| 66 | 19.98 |
| 67 | 111.49 |
| 68 | 109.15 |

TABLE 6-continued

Concentrations of Aβ42 antibody produced by mice stimulated with protein vaccines having 127 different forms of P particles as the immunogens

| group number | Concentration of the produced Aβ42 antibody after the fourth immunization |
|---|---|
| 69 | 41.78 |
| 70 | 39.75 |
| 71 | 96.58 |
| 72 | 123.43 |
| 73 | 169.92 |
| 74 | 178.83 |
| 75 | 120.47 |
| 76 | 21.10 |
| 77 | 102.80 |
| 78 | 197.09 |
| 79 | 95.03 |
| 80 | 76.78 |
| 81 | 55.87 |
| 82 | 23.56 |
| 83 | 139.92 |
| 84 | 159.80 |
| 85 | 25.73 |
| 86 | 33.09 |
| 87 | 87.82 |
| 88 | 58.97 |
| 89 | 27.41 |
| 90 | 24.46 |
| 91 | 73.45 |
| 92 | 82.67 |
| 93 | 168.21 |
| 94 | 116.81 |
| 95 | 82.39 |
| 96 | 43.08 |
| 97 | 142.97 |
| 98 | 158.03 |
| 99 | 103.64 |
| 100 | 59.82 |
| 101 | 21.11 |
| 102 | 11.87 |
| 103 | 165.27 |
| 104 | 66.72 |
| 105 | 47.86 |
| 106 | 34.56 |
| 107 | 150.98 |
| 108 | 75.73 |
| 109 | 99.17 |
| 110 | 45.43 |
| 111 | 31.25 |
| 112 | 67.87 |
| 113 | 155.87 |
| 114 | 101.23 |
| 115 | 135.15 |
| 116 | 79.75 |
| 117 | 202.44 |
| 118 | 215.93 |
| 119 | 245.12 |
| 120 | 222.76 |
| 121 | 23.89 |
| 122 | 149.78 |
| 123 | 152.29 |
| 124 | 166.09 |
| 125 | 113.11 |
| 126 | 189.83 |
| 127 | 160.08 |

In the above P particles, the 17 P particles, PP-10copy-Aβ1-6-loop1$G_{72}$, PP-1copy-Aβ1-6-loop2$S_{149}$, PP-10copy-Aβ1-6-loop2$S_{149}$, PP-10copy-Aβ1-6-loop3$G_{169}$, PP-20copy-Aβ1-6-loop3$G_{169}$, PP-3copy-Aβ1-6-loop1$G_{72}$-3 copy-Aβ1-6-loop2$S_{149}$, PP-10copy-Aβ1-15-loop1$G_{72}$-10copy-Aβ1-6-loop2$S_{149}$, PP-20copy-Aβ1-15-loop1$G_{72}$-40copy-Aβ1-6-loop2$S_{149}$, PP-3copy-Aβ1-12-loop2$S_{149}$-3copy-Aβ1-6-loop3$G_{169}$, PP-1 copy-Aβ1-6-loop2$S_{149}$-10copy-Aβ1-6-loop3$G_{169}$, PP-20copy-Aβ1-12-loop2$S_{149}$-10copy-Aβ1-6-loop3$G_{169}$, PP-3copy-Aβ1-6-loop1$G_{72}$-3copy-Aβ1-12-loop3$G_{169}$, PP-1copy-Aβ1-6-loop1$G_{72}$-10copy-Aβ1-6-loop3$G_{169}$, PP-3copy-Aβ1-6-loop1$G_{72}$-10copy-Aβ1-12-loop3$G_{169}$, PP-1copy-Aβ1-6-loop1$G_{72}$-1copy-Aβ1-6-loop2$S_{149}$-1copy-Aβ1-6-loop3 $G_{169}$, PP-3copy-Aβ1-6-loop1$G_{72}$-3copy-Aβ1-6-loop2$S_{149}$-3copy-Aβ1-6-loop3$G_{169}$, PP-10copy-Aβ1-6-loop1$G_{72}$-10copy-Aβ1-6-loop2$S_{149}$-10copy-Aβ1-6-loop3$G_{169}$, have good immunological effects and can induce the production of high concentrations of antibodies.

The standard curve is plotted in accordance with positive antibody 6e10, and its linear fitting curve is $y=47.692x+0.2964$, $R2=0.99$. According to this standard curve, the concentration of the antibody produced by induction can be calculated within the linear range, wherein PP-3copy-Aβ1-6-loop1$G_{72}$-3copy-Aβ1-6-loop2$S_{149}$-3copy-Aβ1-6-loop3$G_{169}$ produce antibodies in a concentration of about 245.12 μg/mL after the fourth immunization. Therefore, the present invention has good immunological effects and induces a high concentration of Aβ1-42 antibody in mouse serum after immunization. The present invention has very good therapeutical effects and is a protein vaccine with great potentials for treating AD.

The invention claimed is:

1. A recombinant P particle formed from a norovirus capsid P protein chimerized with a Aβ1-m peptide, wherein m is an integer ranging from 6 to 15, and the recombinant P particle forms an ordered and repetitive antigen array, and the amino acid sequence of at least one of the Aβ1-m peptides is embedded into loop1, loop2 and/or loop3 of the norovirus capsid P protein, wherein the amino acid sequence of the norovirus capsid P protein comprises the sequence of SEQ ID NO: 1, and wherein N1 Aβ1-m peptide sequences are embedded behind one or more amino acid sites selected from the group consisting of amino acids 70-74 of SEQ ID NO: 1, i.e. 170, A71, G72, T73 and Q74; N2 Aβ1-m peptide sequences are embedded behind one or more amino acid sites selected from the group consisting of amino acids 148-151 of SEQ ID NO: 1, i.e. T148, S149, N150 and D151; and N3 Aβ1-m peptide sequences are embedded behind one or more amino acid sites selected from the group consisting of amino acids 168-171 of SEQ ID NO: 1, i.e. D168, G169, S170 and T171; wherein N1, N2 and N3 each are independently selected from an integer ranging from 0-40, and $N1+N2+N3 \geq 1$.

2. The recombinant P particle according to claim 1, wherein multiple consecutive Aβ1-m peptide sequences embedded into the norovirus capsid P protein are linked directly or via a polypeptide linker.

3. The recombinant P particle according to claim 1, wherein the Aβ1-m peptide is linked to the norovirus capsid P protein directly or via a polypeptide linker.

4. The recombinant P particle according to claim 1, wherein the Aβ1-m peptide sequence is an amino acid sequence comprised in sequences selected from SEQ ID NOs: 2-8.

5. The recombinant P particle according to claim 1, wherein the chimerized norovirus capsid P protein is encoded by nucleic acid sequences of SEQ ID NO: 15-SEQ ID NO: 141.

6. A nucleic acid encoding the recombinant P particle according to claim 1, wherein the nucleic acid has sequences of SEQ ID NO: 15-SEQ ID NO: 141.

7. A pharmaceutical composition used for preventing or treating Alzheimer's disease, comprising the recombinant P particle according to claim 1 and a pharmaceutically acceptable carrier.

8. Use of the recombinant P particle according to claim 1 in the manufacture of a medicament for treating or preventing Alzheimer's disease, wherein the medicament is a vaccine.

9. A method for preparing the recombinant P particle according to claim 1, comprising the following steps:

i) obtaining an expression vector comprising a nucleic acid encoding a norovirus capsid P protein chimerized with a Aβ1-m peptide, wherein m is an integer ranging from 6 to 15;

ii) transferring the expression vector into a receptor cell;

iii) expressing the chimerized norovirus capsid P protein, and allowing it to self-assemble into a recombinant P particle.

* * * * *

SEQUENCE LISTING

<160> NUMBER OF SEQ ID NOS: 153

<210> SEQ ID NO 1
<211> LENGTH: 317
<212> TYPE: PRT
<213> ORGANISM: NOROVIRUS

<400> SEQUENCE: 1

```
Met Lys Pro Phe Ser Val Pro Ile Leu Thr Val Glu Glu Met Thr Asn
1               5                   10                  15

Ser Arg Phe Pro Ile Pro Leu Glu Lys Leu Phe Thr Gly Pro Ser Ser
            20                  25                  30

Ala Phe Val Val Gln Pro Gln Asn Gly Arg Cys Thr Thr Asp Gly Val
        35                  40                  45
```

-continued

Leu Leu Gly Thr Thr Gln Leu Ser Pro Val Asn Ile Cys Thr Phe Arg
    50                  55                  60

Gly Asp Val Thr His Ile Ala Gly Thr Gln Asn Tyr Thr Met Asn Leu
65                  70                  75                  80

Ala Ser Gln Asn Trp Asn Asn Tyr Asp Pro Thr Glu Glu Ile Pro Ala
                85                  90                  95

Pro Leu Gly Thr Pro Asp Phe Val Gly Arg Ile Gln Gly Val Leu Thr
            100                 105                 110

Gln Thr Thr Arg Arg Asp Gly Ser Thr Arg Gly His Lys Ala Thr Val
        115                 120                 125

Ser Thr Gly Ser Val His Phe Thr Pro Lys Leu Gly Ser Val Gln Phe
    130                 135                 140

Ser Thr Asp Thr Ser Asn Asp Phe Glu Thr Gly Gln Asn Thr Arg Phe
145                 150                 155                 160

Thr Pro Val Gly Val Val Gln Asp Gly Ser Thr Thr His Gln Asn Glu
                165                 170                 175

Pro Gln Gln Trp Val Leu Pro Asp Tyr Ser Gly Arg Asp Ser His Asn
            180                 185                 190

Val His Leu Ala Pro Ala Val Ala Pro Thr Phe Pro Gly Glu Gln Leu
        195                 200                 205

Leu Phe Phe Arg Ser Thr Met Pro Gly Cys Ser Gly Tyr Pro Asn Met
    210                 215                 220

Asn Leu Asp Cys Leu Leu Pro Gln Glu Trp Val Gln His Phe Tyr Gln
225                 230                 235                 240

Glu Ser Ala Pro Ala Gln Ser Asp Val Ala Leu Leu Arg Phe Val Asn
                245                 250                 255

Pro Asp Thr Gly Arg Val Leu Phe Glu Cys Lys Leu His Lys Ser Gly
            260                 265                 270

Tyr Val Thr Val Ala His Thr Gly Gln His Asp Leu Val Ile Pro Pro
        275                 280                 285

Asn Gly Tyr Phe Arg Phe Asp Ser Trp Val Asn Gln Phe Tyr Thr Leu
    290                 295                 300

Ala Pro Met Gly Asn Gly Ala Gly Arg Arg Arg Ala Leu
305                 310                 315

<210> SEQ ID NO 2
<211> LENGTH: 15
<212> TYPE: PRT
<213> ORGANISM: Homo sapiens

<400> SEQUENCE: 2

Asp Ala Glu Phe Arg His Asp Ser Gly Tyr Glu Val His His Gln
1               5                   10                  15

<210> SEQ ID NO 3
<211> LENGTH: 15
<212> TYPE: PRT
<213> ORGANISM: Mus musculus

<400> SEQUENCE: 3

Asp Ala Glu Phe Gly His Asp Ser Gly Phe Glu Val Arg His Gln
1               5                   10                  15

<210> SEQ ID NO 4
<211> LENGTH: 15
<212> TYPE: PRT
<213> ORGANISM: Gorillas

<400> SEQUENCE: 4

Asp Ala Glu Phe Arg His Asp Ser Gly Tyr Glu Val His His Gln
1 5 10 15

<210> SEQ ID NO 5
<211> LENGTH: 15
<212> TYPE: PRT
<213> ORGANISM: Oryctolagus cuniculus

<400> SEQUENCE: 5

Asp Ala Glu Phe Arg His Asp Ser Gly Tyr Glu Val His His Gln
1 5 10 15

<210> SEQ ID NO 6
<211> LENGTH: 15
<212> TYPE: PRT
<213> ORGANISM: Xenopus laevis

<400> SEQUENCE: 6

Asp Ser Glu Tyr Arg His Asp Thr Ala Tyr Glu Val His His Gln
1 5 10 15

<210> SEQ ID NO 7
<211> LENGTH: 15
<212> TYPE: PRT
<213> ORGANISM: Rattus norvegicus

<400> SEQUENCE: 7

Asp Ser Glu Tyr Arg His Asp Thr Ala Tyr Glu Val His His Gln
1 5 10 15

<210> SEQ ID NO 8
<211> LENGTH: 15
<212> TYPE: PRT
<213> ORGANISM: Cavia porcellus

<400> SEQUENCE: 8

Asp Ala Glu Phe Arg His Asp Ser Gly Tyr Glu Val His His Gln
1 5 10 15

<210> SEQ ID NO 9
<211> LENGTH: 954
<212> TYPE: DNA
<213> ORGANISM: artificial sequence
<220> FEATURE:
<223> OTHER INFORMATION: synthetic nucleotide sequence encoding a norovirus capsid P protein

<400> SEQUENCE: 9
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggcacaaccc agctctcacc tgtgaacatc 180
tgtactttcc gcggcgacgt cacacacatc gctggaacac aaaactacac catgaacttg 240
gcctcgcaga actggaacaa ctacgatcca accgaggaaa tccccgctcc tttgggaact 300
cccgacttcg tgggacgtat ccaaggtgtc ctgacacaga ctacacgtcg cgacggctct 360
actcgcggac acaaggccac tgtgtcgaca ggttccgtcc acttcacccc taagctgggc 420
tctgtgcaat tcagcacaga cacctcaaac gatttcgaga ctggccagaa caccaggttc 480
actcccgtgg gtgtcgttca agacggcagc accactcacc agaacgaacc ccagcaatgg 540

-continued gtcctccctg actactcggg cagggattcc cacaacgttc acttggctcc cgccgtggct 600
ccaaccttcc ctggagagca gttgctgttc ttcagatcca ctatgccagg ctgctctgga 660
tacccgaaca tgaacctcga ctgtctcttg cctcaggagt gggtgcaaca cttctaccag 720
gaatctgccc cagctcaaag cgacgtcgct ctgctccgtt tcgttaaccc cgataccggt 780
cgcgtgctct tcgagtgtaa gttgcacaag tctggttacg tcactgttgc ccacacaggc 840
cagcacgacc tggtcatccc tcccaacggc tacttccgct tcgatagctg ggtcaaccag 900
ttctacacac tcgccccgat gggaaacgga gccggtcgtc gcagagcctt gtaa 954

<210> SEQ ID NO 10
<211> LENGTH: 45
<212> TYPE: DNA
<213> ORGANISM: artificial sequence
<220> FEATURE:
<223> OTHER INFORMATION: synthetic nucleotide sequence encoding an Abeta1-15 peptide from human

<400> SEQUENCE: 10
gatgcagaat tccgacatga ctcaggatat gaagttcatc atcaa 45

<210> SEQ ID NO 11
<211> LENGTH: 31
<212> TYPE: DNA
<213> ORGANISM: artificial sequence
<220> FEATURE:
<223> OTHER INFORMATION: a synthetic site-directed mutation forward primer for pET26b-P protein-mEagI plasmid

<400> SEQUENCE: 11
cgttcacttg gctccggccg tggctccaac c 31

<210> SEQ ID NO 12
<211> LENGTH: 31
<212> TYPE: DNA
<213> ORGANISM: artificial sequence
<220> FEATURE:
<223> OTHER INFORMATION: a synthetic site-directed mutation reverse primer for pET26b-P protein-mEagI plasmid

<400> SEQUENCE: 12
ggttggagcc acggccggag ccaagtgaac g 31

<210> SEQ ID NO 13
<211> LENGTH: 32
<212> TYPE: DNA
<213> ORGANISM: artificial sequence
<220> FEATURE:
<223> OTHER INFORMATION: a synthetic site-directed mutation forward primer for pET26b-P protein-mEagI&mKpnI plasmid

<400> SEQUENCE: 13
ggtgtcctgc tcggtaccac ccagctctca cc 32

<210> SEQ ID NO 14
<211> LENGTH: 32
<212> TYPE: DNA
<213> ORGANISM: artificial sequence
<220> FEATURE:
<223> OTHER INFORMATION: a synthetic site-directed mutation reverse primer for pET26b-Pprotein-mEagI&mKpnI plasmid

<400> SEQUENCE: 14
ggtgagagct gggtggtacc gagcaggaca cc 32

-continued

<210> SEQ ID NO 15
<211> LENGTH: 990
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 15
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc ggaggaggag atgcagaatt ccgacatgga 240
ggaggagctg gaacacaaaa ctacaccatg aacttggcct cgcagaactg gaacaactac 300
gatccaaccg aggaaatccc cgctcctttg ggaactcccg acttcgtggg acgtatccaa 360
ggtgtcctga cacagactac acgtcgcgac ggctctactc gcggacacaa ggccactgtg 420
tcgacaggtt ccgtccactt cacccctaag ctgggctctg tgcaattcag cacagacacc 480
tcaaacgatt tcgagactgg ccagaacacc aggttcactc ccgtgggtgt cgttcaagac 540
ggcagcacca ctcaccagaa cgaaccccag caatgggtcc tccctgacta ctcgggcagg 600
gattcccaca acgttcactt ggctccggcc gtggctccaa ccttccctgg agagcagttg 660
ctgttcttca gatccactat gccaggctgc tctggatacc cgaacatgaa cctcgactgt 720
ctcttgcctc aggagtgggt gcaacacttc taccaggaat ctgccccagc tcaaagcgac 780
gtcgctctgc tccgtttcgt taaccccgat accggtcgcg tgctcttcga gtgtaagttg 840
cacaagtctg gttacgtcac tgttgcccac acaggccagc acgacctggt catccctccc 900
aacggctact tccgcttcga tagctgggtc aaccagttct acacactcgc cccgatggga 960
aacggagccg gtcgtcgcag agccttgtaa 990

<210> SEQ ID NO 16
<211> LENGTH: 1323
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 16
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc ggaggaggag atgcagaatt ccgacatgac 240
tcaggaggag gaggagatgc agaattccga catgactcag gaggaggagg agatgcagaa 300
ttccgacatg actcaggagg aggaggagat gcagaattcc gacatgactc aggaggagga 360
ggagatgcag aattccgaca tgactcagga ggaggaggag atgcagaatt ccgacatgac 420
tcaggaggag gaggagatgc agaattccga catgactcag gaggaggagg agatgcagaa 480
ttccgacatg actcaggagg aggaggagat gcagaattcc gacatgactc aggaggagga 540
ggagatgcag aattccgaca tgactcagga ggaggaggag ctggaacaca aaactacacc 600
atgaacttgg cctcgcagaa ctggaacaac tacgatccaa ccgaggaaat ccccgctcct 660
ttgggaactc ccgacttcgt gggacgtatc caaggtgtcc tgacacagac tacacgtcgc 720
gacggctcta ctcgcggaca caaggccact gtgtcgacag gttccgtcca cttcacccct 780
aagctgggct ctgtgcaatt cagcacagac acctcaaacg atttcgagac tggccagaac 840
accaggttca ctcccgtggg tgtcgttcaa gacggcagca ccactcacca gaacgaaccc 900
cagcaatggg tcctccctga ctactcgggc agggattccc acaacgttca cttggctccg 960
gccgtggctc caaccttccc tggagagcag ttgctgttct tcagatccac tatgccaggc 1020
tgctctggat acccgaacat gaacctcgac tgtctcttgc ctcaggagtg ggtgcaacac 1080
ttctaccagg aatctgcccc agctcaaagc gacgtcgctc tgctccgttt cgttaacccc 1140
gataccggtc gcgtgctctt cgagtgtaag ttgcacaagt ctggttacgt cactgttgcc 1200
cacacaggcc agcacgacct ggtcatccct cccaacggct acttccgctt cgatagctgg 1260
gtcaaccagt tctacacact cgccccgatg ggaaacggag ccggtcgtcg cagagccttg 1320
taa 1323

<210> SEQ ID NO 17
<211> LENGTH: 1863
<212> TYPE: DNA
<213> ORGANISM: artificial sequence
<220> FEATURE:
<223> OTHER INFORMATION: synthetic nucleotide sequence encoding the
      recombinant P protein

<400> SEQUENCE: 17
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc ggaggaggag atgcagaatt ccgacatgac 240
tcaggatatg aagttggagg aggagatgca gaattccgac atgactcagg atatgaagtt 300
ggaggaggag atgcagaatt ccgacatgac tcaggatatg aagttggagg aggagatgca 360
gaattccgac atgactcagg atatgaagtt ggaggaggag atgcagaatt ccgacatgac 420
tcaggatatg aagttggagg aggagatgca gaattccgac atgactcagg atatgaagtt 480
ggaggaggag atgcagaatt ccgacatgac tcaggatatg aagttggagg aggagatgca 540
gaattccgac atgactcagg atatgaagtt ggaggaggag atgcagaatt ccgacatgac 600
tcaggatatg aagttggagg aggagatgca gaattccgac atgactcagg atatgaagtt 660
ggaggaggag atgcagaatt ccgacatgac tcaggatatg aagttggagg aggagatgca 720
gaattccgac atgactcagg atatgaagtt ggaggaggag atgcagaatt ccgacatgac 780
tcaggatatg aagttggagg aggagatgca gaattccgac atgactcagg atatgaagtt 840
ggaggaggag atgcagaatt ccgacatgac tcaggatatg aagttggagg aggagatgca 900
gaattccgac atgactcagg atatgaagtt ggaggaggag atgcagaatt ccgacatgac 960
tcaggatatg aagttggagg aggagatgca gaattccgac atgactcagg atatgaagtt 1020
ggaggaggag atgcagaatt ccgacatgac tcaggatatg aagttggagg aggagatgca 1080
gaattccgac atgactcagg atatgaagtt ggaggaggag ctggaacaca aaactacacc 1140
atgaacttgg cctcgcagaa ctggaacaac tacgatccaa ccgaggaaat ccccgctcct 1200
ttgggaactc ccgacttcgt gggacgtatc caaggtgtcc tgacacagac tacacgtcgc 1260
gacggctcta ctcgcggaca caaggccact gtgtcgacag gttccgtcca cttcacccct 1320
aagctgggct ctgtgcaatt cagcacagac acctcaaacg atttcgagac tggccagaac 1380

-continued

```
accaggttca ctcccgtggg tgtcgttcaa gacggcagca ccactcacca gaacgaaccc   1440
cagcaatggg tcctccctga ctactcgggc agggattccc acaacgttca cttggctccg   1500
gccgtggctc caaccttccc tggagagcag ttgctgttct tcagatccac tatgccaggc   1560
tgctctggat acccgaacat gaacctcgac tgtctcttgc ctcaggagtg ggtgcaacac   1620
ttctaccagg aatctgcccc agctcaaagc gacgtcgctc tgctccgttt cgttaacccc   1680
gataccggtc gcgtgctctt cgagtgtaag ttgcacaagt ctggttacgt cactgttgcc   1740
cacacaggcc agcacgacct ggtcatccct cccaacggct acttccgctt cgatagctgg   1800
gtcaaccagt tctacacact cgccccgatg ggaaacggag ccggtcgtcg cagagccttg   1860
taa                                                                 1863
```

<210> SEQ ID NO 18
<211> LENGTH: 3123
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 18

```
atgaagccct tctcggtccc tatcctgaca gttgaggaaa tgaccaactc tagattccca     60
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc ggaggaggag atgcagaatt ccgacatgac    240
tcaggatatg aagttcatca tcaaggagga ggagatgcag aattccgaca tgactcagga    300
tatgaagttc atcatcaagg aggaggagat gcagaattcc gacatgactc aggatatgaa    360
gttcatcatc aaggaggagg agatgcagaa ttccgacatg actcaggata tgaagttcat    420
catcaaggag gaggagatgc agaattccga catgactcag gatatgaagt tcatcatcaa    480
ggaggaggag atgcagaatt ccgacatgac tcaggatatg aagttcatca tcaaggagga    540
ggagatgcag aattccgaca tgactcagga tatgaagttc atcatcaagg aggaggagat    600
gcagaattcc gacatgactc aggatatgaa gttcatcatc aaggaggagg agatgcagaa    660
ttccgacatg actcaggata tgaagttcat catcaaggag gaggagatgc agaattccga    720
catgactcag gatatgaagt tcatcatcaa ggaggaggag atgcagaatt ccgacatgac    780
tcaggatatg aagttcatca tcaaggagga ggagatgcag aattccgaca tgactcagga    840
tatgaagttc atcatcaagg aggaggagat gcagaattcc gacatgactc aggatatgaa    900
gttcatcatc aaggaggagg agatgcagaa ttccgacatg actcaggata tgaagttcat    960
catcaaggag gaggagatgc agaattccga catgactcag gatatgaagt tcatcatcaa   1020
ggaggaggag atgcagaatt ccgacatgac tcaggatatg aagttcatca tcaaggagga   1080
ggagatgcag aattccgaca tgactcagga tatgaagttc atcatcaagg aggaggagat   1140
gcagaattcc gacatgactc aggatatgaa gttcatcatc aaggaggagg agatgcagaa   1200
ttccgacatg actcaggata tgaagttcat catcaaggag gaggagatgc agaattccga   1260
catgactcag gatatgaagt tcatcatcaa ggaggaggag atgcagaatt ccgacatgac   1320
tcaggatatg aagttcatca tcaaggagga ggagatgcag aattccgaca tgactcagga   1380
tatgaagttc atcatcaagg aggaggagat gcagaattcc gacatgactc aggatatgaa   1440
gttcatcatc aaggaggagg agatgcagaa ttccgacatg actcaggata tgaagttcat   1500
```

-continued catcaaggag gaggagatgc agaattccga catgactcag gatatgaagt tcatcatcaa 1560
ggaggaggag atgcagaatt ccgacatgac tcaggatatg aagttcatca tcaaggagga 1620
ggagatgcag aattccgaca tgactcagga tatgaagttc atcatcaagg aggaggagat 1680
gcagaattcc gacatgactc aggatatgaa gttcatcatc aaggaggagg agatgcagaa 1740
ttccgacatg actcaggata tgaagttcat catcaaggag gaggagatgc agaattccga 1800
catgactcag gatatgaagt tcatcatcaa ggaggaggag atgcagaatt ccgacatgac 1860
tcaggatatg aagttcatca tcaaggagga ggagatgcag aattccgaca tgactcagga 1920
tatgaagttc atcatcaagg aggaggagat gcagaattcc gacatgactc aggatatgaa 1980
gttcatcatc aaggaggagg agatgcagaa ttccgacatg actcaggata tgaagttcat 2040
catcaaggag gaggagatgc agaattccga catgactcag gatatgaagt tcatcatcaa 2100
ggaggaggag atgcagaatt ccgacatgac tcaggatatg aagttcatca tcaaggagga 2160
ggagatgcag aattccgaca tgactcagga tatgaagttc atcatcaagg aggaggagat 2220
gcagaattcc gacatgactc aggatatgaa gttcatcatc aaggaggagg agatgcagaa 2280
ttccgacatg actcaggata tgaagttcat catcaaggag gaggagatgc agaattccga 2340
catgactcag gatatgaagt tcatcatcaa ggaggaggag ctggaacaca aaactacacc 2400
atgaacttgg cctcgcagaa ctggaacaac tacgatccaa ccgaggaaat ccccgctcct 2460
ttgggaactc ccgacttcgt gggacgtatc caaggtgtcc tgacacagac tacacgtcgc 2520
gacggctcta ctcgcggaca caaggccact gtgtcgacag gttccgtcca cttcacccct 2580
aagctgggct ctgtgcaatt cagcacagac acctcaaacg atttcgagac tggccagaac 2640
accaggttca ctcccgtggg tgtcgttcaa gacggcagca ccactcacca gaacgaaccc 2700
cagcaatggg tcctccctga ctactcgggc agggattccc acaacgttca cttggctccg 2760
gccgtggctc caaccttccc tggagagcag ttgctgttct tcagatccac tatgccaggc 2820
tgctctggat acccgaacat gaacctcgac tgtctcttgc ctcaggagtg ggtgcaacac 2880
ttctaccagg aatctgcccc agctcaaagc gacgtcgctc tgctccgttt cgttaacccc 2940
gataccggtc gcgtgctctt cgagtgtaag ttgcacaagt ctggttacgt cactgttgcc 3000
cacacaggcc agcacgacct ggtcatccct cccaacggct acttccgctt cgatagctgg 3060
gtcaaccagt tctacacact cgccccgatg ggaaacggag ccggtcgtcg cagagccttg 3120
taa 3123

<210> SEQ ID NO 19
<211> LENGTH: 999
<212> TYPE: DNA
<213> ORGANISM: artificial sequence
<220> FEATURE:
<223> OTHER INFORMATION: synthetic nucleotide sequence encoding the
recombinant P protein

<400> SEQUENCE: 19
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaggag gagatgcaga attccgacat 240
gactcaggag gaggaggagg aacacaaaac tacaccatga acttggcctc gcagaactgg 300
aacaactacg atccaaccga ggaaatcccc gctcctttgg gaactcccga cttcgtggga 360

```
cgtatccaag gtgtcctgac acagactaca cgtcgcgacg gctctactcg cggacacaag    420
gccactgtgt cgacaggttc cgtccacttc acccctaagc tgggctctgt gcaattcagc    480
acagacacct caaacgattt cgagactggc cagaacacca ggttcactcc cgtgggtgtc    540
gttcaagacg gcagcaccac tcaccagaac gaaccccagc aatgggtcct ccctgactac    600
tcgggcaggg attcccacaa cgttcacttg gctccggccg tggctccaac cttccctgga    660
gagcagttgc tgttcttcag atccactatg ccaggctgct ctggataccc gaacatgaac    720
ctcgactgtc tcttgcctca ggagtgggtg caacacttct accaggaatc tgccccagct    780
caaagcgacg tcgctctgct ccgtttcgtt aaccccgata ccggtcgcgt gctcttcgag    840
tgtaagttgc acaagtctgg ttacgtcact gttgcccaca caggccagca cgacctggtc    900
atccctccca acggctactt ccgcttcgat agctgggtca accagttcta cacactcgcc    960
ccgatgggaa acggagccgg tcgtcgcaga gccttgtaa                           999
```

```
<210> SEQ ID NO 20
<211> LENGTH: 1413
<212> TYPE: DNA
<213> ORGANISM: artificial sequence
<220> FEATURE:
<223> OTHER INFORMATION: synthetic nucleotide sequence encoding the
      recombinant P protein

<400> SEQUENCE: 20
atgaagccct tctcggtccc tatcctgaca gttgaggaaa tgaccaactc tagattccca     60
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc gctggaggag gagatgcaga attccgacat    240
gactcaggat atgaagttgg aggaggagat gcagaattcc gacatgactc aggatatgaa    300
gttggaggag gagatgcaga attccgacat gactcaggat atgaagttgg aggaggagat    360
gcagaattcc gacatgactc aggatatgaa gttggaggag gagatgcaga attccgacat    420
gactcaggat atgaagttgg aggaggagat gcagaattcc gacatgactc aggatatgaa    480
gttggaggag gagatgcaga attccgacat gactcaggat atgaagttgg aggaggagat    540
gcagaattcc gacatgactc aggatatgaa gttggaggag gagatgcaga attccgacat    600
gactcaggat atgaagttgg aggaggagat gcagaattcc gacatgactc aggatatgaa    660
gttggaggag gaggaacaca aaactacacc atgaacttgg cctcgcagaa ctggaacaac    720
tacgatccaa ccgaggaaat ccccgctcct ttgggaactc ccgacttcgt gggacgtatc    780
caaggtgtcc tgacacagac tacacgtcgc gacggctcta ctcgcggaca caaggccact    840
gtgtcgacag gttccgtcca cttcacccct aagctgggct ctgtgcaatt cagcacagac    900
acctcaaacg atttcgagac tggccagaac accaggttca ctcccgtggg tgtcgttcaa    960
gacggcagca ccactcacca gaacgaaccc cagcaatggg tcctccctga ctactcgggc   1020
agggattccc acaacgttca cttggctccg gccgtggctc caaccttccc tggagagcag   1080
ttgctgttct tcagatccac tatgccaggc tgctctggat acccgaacat gaacctcgac   1140
tgtctcttgc ctcaggagtg ggtgcaacac ttctaccagg aatctgcccc agctcaaagc   1200
gacgtcgctc tgctccgttt cgttaacccc gataccggtc gcgtgctctt cgagtgtaag   1260
ttgcacaagt ctggttacgt cactgttgcc cacacaggcc agcacgacct ggtcatccct   1320
cccaacggct acttccgctt cgatagctgg gtcaaccagt tctacacact cgccccgatg   1380
```

-continued

```
ggaaacggag ccggtcgtcg cagagccttg taa                        1413

<210> SEQ ID NO 21
<211> LENGTH: 2043
<212> TYPE: DNA
<213> ORGANISM: artificial sequence
<220> FEATURE:
<223> OTHER INFORMATION: synthetic nucleotide sequence encoding the
      recombinant P protein

<400> SEQUENCE: 21
atgaagccct tctcggtccc tatcctgaca gttgaggaaa tgaccaactc tagattccca     60
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc gctggaggag gagatgcaga attccgacat    240
gactcaggat atgaagttca tcatcaagga ggaggagatg cagaattccg acatgactca    300
ggatatgaag ttcatcatca aggaggagga gatgcagaat tccgacatga ctcaggatat    360
gaagttcatc atcaaggagg aggagatgca gaattccgac atgactcagg atatgaagtt    420
catcatcaag gaggaggaga tgcagaattc cgacatgact caggatatga agttcatcat    480
caaggaggag gagatgcaga attccgacat gactcaggat atgaagttca tcatcaagga    540
ggaggagatg cagaattccg acatgactca ggatatgaag ttcatcatca aggaggagga    600
gatgcagaat tccgacatga ctcaggatat gaagttcatc atcaaggagg aggagatgca    660
gaattccgac atgactcagg atatgaagtt catcatcaag gaggaggaga tgcagaattc    720
cgacatgact caggatatga agttcatcat caaggaggag gagatgcaga attccgacat    780
gactcaggat atgaagttca tcatcaagga ggaggagatg cagaattccg acatgactca    840
ggatatgaag ttcatcatca aggaggagga gatgcagaat tccgacatga ctcaggatat    900
gaagttcatc atcaaggagg aggagatgca gaattccgac atgactcagg atatgaagtt    960
catcatcaag gaggaggaga tgcagaattc cgacatgact caggatatga agttcatcat   1020
caaggaggag gagatgcaga attccgacat gactcaggat atgaagttca tcatcaagga   1080
ggaggagatg cagaattccg acatgactca ggatatgaag ttcatcatca aggaggagga   1140
gatgcagaat tccgacatga ctcaggatat gaagttcatc atcaaggagg aggagatgca   1200
gaattccgac atgactcagg atatgaagtt catcatcaag gaggaggaga tgcagaattc   1260
cgacatgact caggatatga agttcatcat caaggaggag gaggaacaca aaactacacc   1320
atgaacttgg cctcgcagaa ctggaacaac tacgatccaa ccgaggaaat ccccgctcct   1380
ttgggaactc ccgacttcgt gggacgtatc caaggtgtcc tgacacagac tacacgtcgc   1440
gacggctcta ctcgcggaca caaggccact gtgtcgacag gttccgtcca cttcacccct   1500
aagctgggct ctgtgcaatt cagcacagac acctcaaacg atttcgagac tggccagaac   1560
accaggttca ctcccgtggg tgtcgttcaa gacggcagca ccactcacca gaacgaaccc   1620
cagcaatggg tcctccctga ctactcgggc agggattccc acaacgttca cttggctccg   1680
gccgtggctc caaccttccc tggagagcag ttgctgttct tcagatccac tatgccaggc   1740
tgctctggat acccgaacat gaacctcgac tgtctcttgc ctcaggagtg ggtgcaacac   1800
ttctaccagg aatctgcccc agctcaaagc gacgtcgctc tgctccgttt cgttaacccc   1860
gataccggtc gcgtgctctt cgagtgtaag ttgcacaagt ctggttacgt cactgttgcc   1920
cacacaggcc agcacgacct ggtcatccct cccaacggct acttccgctt cgatagctgg   1980
```
gtcaaccagt tctacacact cgccccgatg ggaaacggag ccggtcgtcg cagagccttg 2040
taa 2043

<210> SEQ ID NO 22
<211> LENGTH: 2043
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 22
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaggag gagatgcaga attccgacat 240
ggaggaggag atgcagaatt ccgacatgga ggaggagatg cagaattccg acatggagga 300
ggagatgcag aattccgaca tggaggagga gatgcagaat tccgacatgg aggaggagat 360
gcagaattcc gacatggagg aggagatgca gaattccgac atggaggagg agatgcagaa 420
ttccgacatg gaggaggaga tgcagaattc cgacatggag gaggagatgc agaattccga 480
catggaggag gagatgcaga attccgacat ggaggaggag atgcagaatt ccgacatgga 540
ggaggagatg cagaattccg acatggagga ggagatgcag aattccgaca tggaggagga 600
gatgcagaat tccgacatgg aggaggagat gcagaattcc gacatggagg aggagatgca 660
gaattccgac atggaggagg agatgcagaa ttccgacatg gaggaggaga tgcagaattc 720
cgacatggag gaggagatgc agaattccga catggaggag gagatgcaga attccgacat 780
ggaggaggag atgcagaatt ccgacatgga ggaggagatg cagaattccg acatggagga 840
ggagatgcag aattccgaca tggaggagga gatgcagaat tccgacatgg aggaggagat 900
gcagaattcc gacatggagg aggagatgca gaattccgac atggaggagg agatgcagaa 960
ttccgacatg gaggaggaga tgcagaattc cgacatggag gaggagatgc agaattccga 1020
catggaggag gagatgcaga attccgacat ggaggaggag atgcagaatt ccgacatgga 1080
ggaggagatg cagaattccg acatggagga ggagatgcag aattccgaca tggaggagga 1140
gatgcagaat tccgacatgg aggaggagat gcagaattcc gacatggagg aggagatgca 1200
gaattccgac atggaggagg agatgcagaa ttccgacatg gaggaggaga tgcagaattc 1260
cgacatggag gaggagatgc agaattccga catggaggag gaggaacaca aaactacacc 1320
atgaacttgg cctcgcagaa ctggaacaac tacgatccaa ccgaggaaat ccccgctcct 1380
ttgggaactc ccgacttcgt gggacgtatc caaggtgtcc tgacacagac tacacgtcgc 1440
gacggctcta ctcgcggaca caaggccact gtgtcgacag gttccgtcca cttcacccct 1500
aagctgggct ctgtgcaatt cagcacagac acctcaaacg atttcgagac tggccagaac 1560
accaggttca ctcccgtggg tgtcgttcaa gacggcagca ccactcacca gaacgaaccc 1620
cagcaatggg tcctccctga ctactcgggc agggattccc acaacgttca cttggctccg 1680
gccgtggctc caaccttccc tggagagcag ttgctgttct tcagatccac tatgccaggc 1740
tgctctggat acccgaacat gaacctcgac tgtctcttgc ctcaggagtg ggtgcaacac 1800
ttctaccagg aatctgcccc agctcaaagc gacgtcgctc tgctccgttt cgttaacccc 1860
gataccggtc gcgtgctctt cgagtgtaag ttgcacaagt ctggttacgt cactgttgcc 1920
cacacaggcc agcacgacct ggtcatccct cccaacggct acttccgctt cgatagctgg 1980
gtcaaccagt tctacacact cgccccgatg ggaaacggag ccggtcgtcg cagagccttg 2040
taa 2043

<210> SEQ ID NO 23
<211> LENGTH: 990
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 23
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaggag gaggagatgc agaattccga 240
catggaggag gaacacaaaa ctacaccatg aacttggcct cgcagaactg gaacaactac 300
gatccaaccg aggaaatccc cgctcctttg ggaactcccg acttcgtggg acgtatccaa 360
ggtgtcctga cacagactac acgtcgcgac ggctctactc gcggacacaa ggccactgtg 420
tcgacaggtt ccgtccactt cacccctaag ctgggctctg tgcaattcag cacagacacc 480
tcaaacgatt tcgagactgg ccagaacacc aggttcactc ccgtgggtgt cgttcaagac 540
ggcagcacca ctcaccagaa cgaaccccag caatgggtcc tccctgacta ctcgggcagg 600
gattcccaca acgttcactt ggctccggcc gtggctccaa ccttccctgg agagcagttg 660
ctgttcttca gatccactat gccaggctgc tctggatacc cgaacatgaa cctcgactgt 720
ctcttgcctc aggagtgggt gcaacacttc taccaggaat ctgccccagc tcaaagcgac 780
gtcgctctgc tccgtttcgt taaccccgat accggtcgcg tgctcttcga gtgtaagttg 840
cacaagtctg gttacgtcac tgttgcccac acaggccagc acgacctggt catccctccc 900
aacggctact tccgcttcga tagctgggtc aaccagttct acacactcgc cccgatggga 960
aacggagccg gtcgtcgcag agccttgtaa 990

<210> SEQ ID NO 24
<211> LENGTH: 1233
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 24
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaggag gaggagatgc agaattccga 240
catggaggag gagatgcaga attccgacat ggaggaggag atgcagaatt ccgacatgga 300
ggaggagatg cagaattccg acatggagga ggagatgcag aattccgaca tggaggagga 360
gatgcagaat tccgacatgg aggaggagat gcagaattcc gacatggagg aggagatgca 420
gaattccgac atggaggagg agatgcagaa ttccgacatg gaggaggaga tgcagaattc 480

```
cgacatggag gaggaacaca aaactacacc atgaacttgg cctcgcagaa ctggaacaac    540
tacgatccaa ccgaggaaat ccccgctcct ttgggaactc ccgacttcgt gggacgtatc    600
caaggtgtcc tgacacagac tacacgtcgc gacggctcta ctcgcggaca caaggccact    660
gtgtcgacag gttccgtcca cttcacccct aagctgggct ctgtgcaatt cagcacagac    720
acctcaaacg atttcgagac tggccagaac accaggttca ctcccgtggg tgtcgttcaa    780
gacggcagca ccactcacca gaacgaaccc cagcaatggg tcctccctga ctactcgggc    840
agggattccc acaacgttca cttggctccg gccgtggctc caaccttccc tggagagcag    900
ttgctgttct tcagatccac tatgccaggc tgctctggat acccgaacat gaacctcgac    960
tgtctcttgc ctcaggagtg ggtgcaacac ttctaccagg aatctgcccc agctcaaagc   1020
gacgtcgctc tgctccgttt cgttaacccc gataccggtc gcgtgctctt cgagtgtaag   1080
ttgcacaagt ctggttacgt cactgttgcc cacacaggcc agcacgacct ggtcatccct   1140
cccaacggct acttccgctt cgatagctgg gtcaaccagt tctacacact cgccccgatg   1200
ggaaacggag ccggtcgtcg cagagccttg taa                                1233
```

<210> SEQ ID NO 25
<211> LENGTH: 1503
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 25

```
atgaagccct tctcggtccc tatcctgaca gttgaggaaa tgaccaactc tagattccca     60
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc gctggaggag gaggagatgc agaattccga    240
catggaggag gagatgcaga attccgacat ggaggaggag atgcagaatt ccgacatgga    300
ggaggagatg cagaattccg acatggagga ggagatgcag aattccgaca tggaggagga    360
gatgcagaat tccgacatgg aggaggagat gcagaattcc gacatggagg aggagatgca    420
gaattccgac atggaggagg agatgcagaa ttccgacatg gaggaggaga tgcagaattc    480
cgacatggag gaggagatgc agaattccga catggaggag gagatgcaga attccgacat    540
ggaggaggag atgcagaatt ccgacatgga ggaggagatg cagaattccg acatggagga    600
ggagatgcag aattccgaca tggaggagga gatgcagaat tccgacatgg aggaggagat    660
gcagaattcc gacatggagg aggagatgca gaattccgac atggaggagg agatgcagaa    720
ttccgacatg gaggaggaga tgcagaattc cgacatggag gaggaacaca aaactacacc    780
atgaacttgg cctcgcagaa ctggaacaac tacgatccaa ccgaggaaat ccccgctcct    840
ttgggaactc ccgacttcgt gggacgtatc caaggtgtcc tgacacagac tacacgtcgc    900
gacggctcta ctcgcggaca caaggccact gtgtcgacag gttccgtcca cttcacccct    960
aagctgggct ctgtgcaatt cagcacagac acctcaaacg atttcgagac tggccagaac   1020
accaggttca ctcccgtggg tgtcgttcaa gacggcagca ccactcacca gaacgaaccc   1080
cagcaatggg tcctccctga ctactcgggc agggattccc acaacgttca cttggctccg   1140
gccgtggctc caaccttccc tggagagcag ttgctgttct tcagatccac tatgccaggc   1200
tgctctggat acccgaacat gaacctcgac tgtctcttgc ctcaggagtg ggtgcaacac   1260
```

-continued ttctaccagg aatctgcccc agctcaaagc gacgtcgctc tgctccgttt cgttaacccc 1320
gataccggtc gcgtgctctt cgagtgtaag ttgcacaagt ctggttacgt cactgttgcc 1380
cacacaggcc agcacgacct ggtcatccct cccaacggct acttccgctt cgatagctgg 1440
gtcaaccagt tctacacact cgccccgatg ggaaacggag ccggtcgtcg cagagccttg 1500
taa 1503

<210> SEQ ID NO 26
<211> LENGTH: 2043
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 26
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaggag gaggagatgc agaattccga 240
catggaggag gagatgcaga attccgacat ggaggaggag atgcagaatt ccgacatgga 300
ggaggagatg cagaattccg acatggagga ggagatgcag aattccgaca tggaggagga 360
gatgcagaat tccgacatgg aggaggagat gcagaattcc gacatggagg aggagatgca 420
gaattccgac atggaggagg agatgcagaa ttccgacatg gaggaggaga tgcagaattc 480
cgacatggag gaggagatgc agaattccga catggaggag gagatgcaga attccgacat 540
ggaggaggag atgcagaatt ccgacatgga ggaggagatg cagaattccg acatggagga 600
ggagatgcag aattccgaca tggaggagga gatgcagaat tccgacatgg aggaggagat 660
gcagaattcc gacatggagg aggagatgca gaattccgac atggaggagg agatgcagaa 720
ttccgacatg gaggaggaga tgcagaattc cgacatggag gaggagatgc agaattccga 780
catggaggag gagatgcaga attccgacat ggaggaggag atgcagaatt ccgacatgga 840
ggaggagatg cagaattccg acatggagga ggagatgcag aattccgaca tggaggagga 900
gatgcagaat tccgacatgg aggaggagat gcagaattcc gacatggagg aggagatgca 960
gaattccgac atggaggagg agatgcagaa ttccgacatg gaggaggaga tgcagaattc 1020
cgacatggag gaggagatgc agaattccga catggaggag gagatgcaga attccgacat 1080
ggaggaggag atgcagaatt ccgacatgga ggaggagatg cagaattccg acatggagga 1140
ggagatgcag aattccgaca tggaggagga gatgcagaat tccgacatgg aggaggagat 1200
gcagaattcc gacatggagg aggagatgca gaattccgac atggaggagg agatgcagaa 1260
ttccgacatg gaggaggaga tgcagaattc cgacatggag gaggaacaca aaactacacc 1320
atgaacttgg cctcgcagaa ctggaacaac tacgatccaa ccgaggaaat ccccgctcct 1380
ttgggaactc ccgacttcgt gggacgtatc caaggtgtcc tgacacagac tacacgtcgc 1440
gacggctcta ctcgcggaca caaggccact gtgtcgacag gttccgtcca cttcacccct 1500
aagctgggct ctgtgcaatt cagcacagac acctcaaacg atttcgagac tggccagaac 1560
accaggttca ctcccgtggg tgtcgttcaa gacggcagca ccactcacca gaacgaaccc 1620
cagcaatggg tcctccctga ctactcgggc agggattccc acaacgttca cttggctccg 1680
gccgtggctc caaccttccc tggagagcag ttgctgttct tcagatccac tatgccaggc 1740

-continued

```
tgctctggat acccgaacat gaacctcgac tgtctcttgc ctcaggagtg ggtgcaacac   1800
ttctaccagg aatctgcccc agctcaaagc gacgtcgctc tgctccgttt cgttaacccc   1860
gataccggtc gcgtgctctt cgagtgtaag ttgcacaagt ctggttacgt cactgttgcc   1920
cacacaggcc agcacgacct ggtcatccct cccaacggct acttccgctt cgatagctgg   1980
gtcaaccagt tctacacact cgccccgatg ggaaacggag ccggtcgtcg cagagccttg   2040
taa                                                                 2043
```

```
<210> SEQ ID NO 27
<211> LENGTH: 1008
<212> TYPE: DNA
<213> ORGANISM: artificial sequence
<220> FEATURE:
<223> OTHER INFORMATION: synthetic nucleotide sequence encoding the
      recombinant P protein

<400> SEQUENCE: 27
atgaagccct tctcggtccc tatcctgaca gttgaggaaa tgaccaactc tagattccca     60
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc gctggaacag gaggaggaga tgcagaattc    240
cgacatgact caggatatga agttggagga ggacaaaact acaccatgaa cttggcctcg    300
cagaactgga acaactacga tccaaccgag gaaatccccg ctcctttggg aactcccgac    360
ttcgtgggac gtatccaagg tgtcctgaca cagactacac gtcgcgacgg ctctactcgc    420
ggacacaagg ccactgtgtc gacaggttcc gtccacttca cccctaagct gggctctgtg    480
caattcagca cagacacctc aaacgatttc gagactggcc agaacaccag gttcactccc    540
gtgggtgtcg ttcaagacgg cagcaccact caccagaacg aaccccagca atgggtcctc    600
cctgactact cgggcaggga ttcccacaac gttcacttgg ctccggccgt ggctccaacc    660
ttccctggag agcagttgct gttcttcaga tccactatgc caggctgctc tggatacccg    720
aacatgaacc tcgactgtct cttgcctcag gagtgggtgc aacacttcta ccaggaatct    780
gccccagctc aaagcgacgt cgctctgctc cgtttcgtta accccgatac cggtcgcgtg    840
ctcttcgagt gtaagttgca caagtctggt tacgtcactg ttgcccacac aggccagcac    900
gacctggtca tccctcccaa cggctacttc cgcttcgata gctgggtcaa ccagttctac    960
acactcgccc cgatgggaaa cggagccggt cgtcgcagag ccttgtaa                1008
```

```
<210> SEQ ID NO 28
<211> LENGTH: 1503
<212> TYPE: DNA
<213> ORGANISM: artificial sequence
<220> FEATURE:
<223> OTHER INFORMATION: synthetic nucleotide sequence encoding the
      recombinant P protein

<400> SEQUENCE: 28
atgaagccct tctcggtccc tatcctgaca gttgaggaaa tgaccaactc tagattccca     60
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc gctggaacag gaggaggaga tgcagaattc    240
cgacatgact caggatatga agttcatcat caaggaggag gagatgcaga attccgacat    300
gactcaggat atgaagttca tcatcaagga ggaggagatg cagaattccg acatgactca    360
```

-continued

```
ggatatgaag ttcatcatca aggaggagga gatgcagaat tccgacatga ctcaggatat    420
gaagttcatc atcaaggagg aggagatgca gaattccgac atgactcagg atatgaagtt    480
catcatcaag gaggaggaga tgcagaattc cgacatgact caggatatga agttcatcat    540
caaggaggag gagatgcaga attccgacat gactcaggat atgaagttca tcatcaagga    600
ggaggagatg cagaattccg acatgactca ggatatgaag ttcatcatca aggaggagga    660
gatgcagaat tccgacatga ctcaggatat gaagttcatc atcaaggagg aggagatgca    720
gaattccgac atgactcagg atatgaagtt catcatcaag gaggaggaca aaactacacc    780
atgaacttgg cctcgcagaa ctggaacaac tacgatccaa ccgaggaaat ccccgctcct    840
ttgggaactc ccgacttcgt gggacgtatc caaggtgtcc tgacacagac tacacgtcgc    900
gacggctcta ctcgcggaca caaggccact gtgtcgacag gttccgtcca cttcacccct    960
aagctgggct ctgtgcaatt cagcacagac acctcaaacg atttcgagac tggccagaac   1020
accaggttca ctcccgtggg tgtcgttcaa gacggcagca ccactcacca gaacgaaccc   1080
cagcaatggg tcctccctga ctactcgggc agggattccc acaacgttca cttggctccg   1140
gccgtggctc caaccttccc tggagagcag ttgctgttct tcagatccac tatgccaggc   1200
tgctctggat acccgaacat gaacctcgac tgtctcttgc ctcaggagtg ggtgcaacac   1260
ttctaccagg aatctgcccc agctcaaagc gacgtcgctc tgctccgttt cgttaacccc   1320
gataccggtc gcgtgctctt cgagtgtaag ttgcacaagt ctggttacgt cactgttgcc   1380
cacacaggcc agcacgacct ggtcatccct cccaacggct acttccgctt cgatagctgg   1440
gtcaaccagt tctacacact cgccccgatg ggaaacggag ccggtcgtcg cagagccttg   1500
taa                                                                 1503
```

<210> SEQ ID NO 29
<211> LENGTH: 1503
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 29

```
atgaagccct tctcggtccc tatcctgaca gttgaggaaa tgaccaactc tagattccca     60
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc gctggaacag gaggaggaga tgcagaattc    240
cgacatggag gaggagatgc agaattccga catggaggag gagatgcaga attccgacat    300
ggaggaggag atgcagaatt ccgacatgga ggaggagatg cagaattccg acatggagga    360
ggagatgcag aattccgaca tggaggagga gatgcagaat tccgacatgg aggaggagat    420
gcagaattcc gacatggagg aggagatgca gaattccgac atggaggagg agatgcagaa    480
ttccgacatg gaggaggaga tgcagaattc cgacatggag gaggagatgc agaattccga    540
catggaggag gagatgcaga attccgacat ggaggaggag atgcagaatt ccgacatgga    600
ggaggagatg cagaattccg acatggagga ggagatgcag aattccgaca tggaggagga    660
gatgcagaat tccgacatgg aggaggagat gcagaattcc gacatggagg aggagatgca    720
gaattccgac atggaggagg agatgcagaa ttccgacatg gaggaggaca aaactacacc    780
atgaacttgg cctcgcagaa ctggaacaac tacgatccaa ccgaggaaat ccccgctcct    840
```

-continued

```
ttgggaactc ccgacttcgt gggacgtatc caaggtgtcc tgacacagac tacacgtcgc    900
gacggctcta ctcgcggaca caaggccact gtgtcgacag gttccgtcca cttcacccct    960
aagctgggct ctgtgcaatt cagcacagac acctcaaacg atttcgagac tggccagaac   1020
accaggttca ctcccgtggg tgtcgttcaa gacggcagca ccactcacca gaacgaaccc   1080
cagcaatggg tcctccctga ctactcgggc agggattccc acaacgttca cttggctccg   1140
gccgtggctc caaccttccc tggagagcag ttgctgttct tcagatccac tatgccaggc   1200
tgctctggat acccgaacat gaacctcgac tgtctcttgc ctcaggagtg ggtgcaacac   1260
ttctaccagg aatctgcccc agctcaaagc gacgtcgctc tgctccgttt cgttaacccc   1320
gataccggtc gcgtgctctt cgagtgtaag ttgcacaagt ctggttacgt cactgttgcc   1380
cacacaggcc agcacgacct ggtcatccct cccaacggct acttccgctt cgatagctgg   1440
gtcaaccagt tctacacact cgccccgatg ggaaacggag ccggtcgtcg cagagccttg   1500
taa                                                                 1503
```

```
<210> SEQ ID NO 30
<211> LENGTH: 2403
<212> TYPE: DNA
<213> ORGANISM: artificial sequence
<220> FEATURE:
<223> OTHER INFORMATION: synthetic nucleotide sequence encoding the
      recombinant P protein

<400> SEQUENCE: 30
atgaagccct tctcggtccc tatcctgaca gttgaggaaa tgaccaactc tagattccca     60
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc gctggaacag gaggaggaga tgcagaattc    240
cgacatgact caggaggagg aggagatgca gaattccgac atgactcagg aggaggagga    300
gatgcagaat tccgacatga ctcaggagga ggaggagatg cagaattccg acatgactca    360
ggaggaggag gagatgcaga attccgacat gactcaggag gaggaggaga tgcagaattc    420
cgacatgact caggaggagg aggagatgca gaattccgac atgactcagg aggaggagga    480
gatgcagaat tccgacatga ctcaggagga ggaggagatg cagaattccg acatgactca    540
ggaggaggag gagatgcaga attccgacat gactcaggag gaggaggaga tgcagaattc    600
cgacatgact caggaggagg aggagatgca gaattccgac atgactcagg aggaggagga    660
gatgcagaat tccgacatga ctcaggagga ggaggagatg cagaattccg acatgactca    720
ggaggaggag gagatgcaga attccgacat gactcaggag gaggaggaga tgcagaattc    780
cgacatgact caggaggagg aggagatgca gaattccgac atgactcagg aggaggagga    840
gatgcagaat tccgacatga ctcaggagga ggaggagatg cagaattccg acatgactca    900
ggaggaggag gagatgcaga attccgacat gactcaggag gaggaggaga tgcagaattc    960
cgacatgact caggaggagg aggagatgca gaattccgac atgactcagg aggaggagga   1020
gatgcagaat tccgacatga ctcaggagga ggaggagatg cagaattccg acatgactca   1080
ggaggaggag gagatgcaga attccgacat gactcaggag gaggaggaga tgcagaattc   1140
cgacatgact caggaggagg aggagatgca gaattccgac atgactcagg aggaggagga   1200
gatgcagaat tccgacatga ctcaggagga ggaggagatg cagaattccg acatgactca   1260
ggaggaggag gagatgcaga attccgacat gactcaggag gaggaggaga tgcagaattc   1320
```

```
cgacatgact caggaggagg aggagatgca gaattccgac atgactcagg aggaggagga   1380
gatgcagaat tccgacatga ctcaggagga ggaggagatg cagaattccg acatgactca   1440
ggaggaggag gagatgcaga attccgacat gactcaggag gaggaggaga tgcagaattc   1500
cgacatgact caggaggagg aggagatgca gaattccgac atgactcagg aggaggagga   1560
gatgcagaat tccgacatga ctcaggagga ggaggagatg cagaattccg acatgactca   1620
ggaggaggag gagatgcaga attccgacat gactcaggag gaggaggaca aaactacacc   1680
atgaacttgg cctcgcagaa ctggaacaac tacgatccaa ccgaggaaat ccccgctcct   1740
ttgggaactc ccgacttcgt gggacgtatc caaggtgtcc tgacacagac tacacgtcgc   1800
gacggctcta ctcgcggaca caaggccact gtgtcgacag gttccgtcca cttcacccct   1860
aagctgggct ctgtgcaatt cagcacagac acctcaaacg atttcgagac tggccagaac   1920
accaggttca ctcccgtggg tgtcgttcaa gacggcagca ccactcacca gaacgaaccc   1980
cagcaatggg tcctccctga ctactcgggc agggattccc acaacgttca cttggctccg   2040
gccgtggctc caaccttccc tggagagcag ttgctgttct tcagatccac tatgccaggc   2100
tgctctggat acccgaacat gaacctcgac tgtctcttgc ctcaggagtg ggtgcaacac   2160
ttctaccagg aatctgcccc agctcaaagc gacgtcgctc tgctccgttt cgttaacccc   2220
gataccggtc gcgtgctctt cgagtgtaag ttgcacaagt ctggttacgt cactgttgcc   2280
cacacaggcc agcacgacct ggtcatccct cccaacggct acttccgctt cgatagctgg   2340
gtcaaccagt tctacacact cgccccgatg ggaaacggag ccggtcgtcg cagagccttg   2400
taa                                                                 2403
```

```
<210> SEQ ID NO 31
<211> LENGTH: 1017
<212> TYPE: DNA
<213> ORGANISM: artificial sequence
<220> FEATURE:
<223> OTHER INFORMATION: synthetic nucleotide sequence encoding the
      recombinant P protein

<400> SEQUENCE: 31
atgaagccct tctcggtccc tatcctgaca gttgaggaaa tgaccaactc tagattccca     60
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc gctggaacac aaggaggagg agatgcagaa    240
ttccgacatg actcaggata tgaagttcat catcaaggag gaggaaacta caccatgaac    300
ttggcctcgc agaactggaa caactacgat ccaaccgagg aaatccccgc tcctttggga    360
actcccgact tcgtgggacg tatccaaggt gtcctgacac agactacacg tcgcgacggc    420
tctactcgcg gacacaaggc cactgtgtcg acaggttccg tccacttcac ccctaagctg    480
ggctctgtgc aattcagcac agacacctca aacgatttcg agactggcca gaacaccagg    540
ttcactcccg tgggtgtcgt tcaagacggc agcaccactc accagaacga accccagcaa    600
tgggtcctcc ctgactactc gggcagggat tcccacaacg ttcacttggc tccggccgtg    660
gctccaacct tccctggaga gcagttgctg ttcttcagat ccactatgcc aggctgctct    720
ggatacccga acatgaacct cgactgtctc ttgcctcagg agtgggtgca acacttctac    780
caggaatctg ccccagctca aagcgacgtc gctctgctcc gtttcgttaa ccccgatacc    840
ggtcgcgtgc tcttcgagtg taagttgcac aagtctggtt acgtcactgt tgcccacaca    900
```
ggccagcacg acctggtcat ccctcccaac ggctacttcc gcttcgatag ctgggtcaac 960
cagttctaca cactcgcccc gatgggaaac ggagccggtc gtcgcagagc cttgtaa 1017

<210> SEQ ID NO 32
<211> LENGTH: 1233
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 32
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaacac aaggaggagg agatgcagaa 240
ttccgacatg gaggaggaga tgcagaattc cgacatggag gaggagatgc agaattccga 300
catggaggag gagatgcaga attccgacat ggaggaggag atgcagaatt ccgacatgga 360
ggaggagatg cagaattccg acatggagga ggagatgcag aattccgaca tggaggagga 420
gatgcagaat tccgacatgg aggaggagat gcagaattcc gacatggagg aggagatgca 480
gaattccgac atggaggagg aaactacacc atgaacttgg cctcgcagaa ctggaacaac 540
tacgatccaa ccgaggaaat ccccgctcct ttgggaactc ccgacttcgt gggacgtatc 600
caaggtgtcc tgacacagac tacacgtcgc gacggctcta ctcgcggaca caaggccact 660
gtgtcgacag gttccgtcca cttcacccct aagctgggct ctgtgcaatt cagcacagac 720
acctcaaacg atttcgagac tggccagaac accaggttca ctcccgtggg tgtcgttcaa 780
gacggcagca ccactcacca gaacgaaccc cagcaatggg tcctccctga ctactcgggc 840
agggattccc acaacgttca cttggctccg gccgtggctc caaccttccc tggagagcag 900
ttgctgttct tcagatccac tatgccaggc tgctctggat acccgaacat gaacctcgac 960
tgtctcttgc ctcaggagtg ggtgcaacac ttctaccagg aatctgcccc agctcaaagc 1020
gacgtcgctc tgctccgttt cgttaacccc gataccggtc gcgtgctctt cgagtgtaag 1080
ttgcacaagt ctggttacgt cactgttgcc cacacaggcc agcacgacct ggtcatccct 1140
cccaacggct acttccgctt cgatagctgg gtcaaccagt tctacacact cgccccgatg 1200
ggaaacggag ccggtcgtcg cagagccttg taa 1233

<210> SEQ ID NO 33
<211> LENGTH: 1683
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 33
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaacac aaggaggagg agatgcagaa 240
ttccgacatg actcaggagg aggaggagat gcagaattcc gacatgactc aggaggagga 300

-continued ggagatgcag aattccgaca tgactcagga ggaggaggag atgcagaatt ccgacatgac 360
tcaggaggag gaggagatgc agaattccga catgactcag gaggaggagg agatgcagaa 420
ttccgacatg actcaggagg aggaggagat gcagaattcc gacatgactc aggaggagga 480
ggagatgcag aattccgaca tgactcagga ggaggaggag atgcagaatt ccgacatgac 540
tcaggaggag gaggagatgc agaattccga catgactcag gaggaggagg agatgcagaa 600
ttccgacatg actcaggagg aggaggagat gcagaattcc gacatgactc aggaggagga 660
ggagatgcag aattccgaca tgactcagga ggaggaggag atgcagaatt ccgacatgac 720
tcaggaggag gaggagatgc agaattccga catgactcag gaggaggagg agatgcagaa 780
ttccgacatg actcaggagg aggaggagat gcagaattcc gacatgactc aggaggagga 840
ggagatgcag aattccgaca tgactcagga ggaggaggag atgcagaatt ccgacatgac 900
tcaggaggag gaggagatgc agaattccga catgactcag gaggaggagg aaactacacc 960
atgaacttgg cctcgcagaa ctggaacaac tacgatccaa ccgaggaaat ccccgctcct 1020
ttgggaactc ccgacttcgt gggacgtatc caaggtgtcc tgacacagac tacacgtcgc 1080
gacggctcta ctcgcggaca caaggccact gtgtcgacag gttccgtcca cttcacccct 1140
aagctgggct ctgtgcaatt cagcacagac acctcaaacg atttcgagac tggccagaac 1200
accaggttca ctcccgtggg tgtcgttcaa gacggcagca ccactcacca gaacgaaccc 1260
cagcaatggg tcctccctga ctactcgggc agggattccc acaacgttca cttggctccg 1320
gccgtggctc caaccttccc tggagagcag ttgctgttct tcagatccac tatgccaggc 1380
tgctctggat acccgaacat gaacctcgac tgtctcttgc ctcaggagtg ggtgcaacac 1440
ttctaccagg aatctgcccc agctcaaagc gacgtcgctc tgctccgttt cgttaacccc 1500
gataccggtc gcgtgctctt cgagtgtaag ttgcacaagt ctggttacgt cactgttgcc 1560
cacacaggcc agcacgacct ggtcatccct cccaacggct acttccgctt cgatagctgg 1620
gtcaaccagt tctacacact cgccccgatg ggaaacggag ccggtcgtcg cagagccttg 1680
taa 1683

<210> SEQ ID NO 34
<211> LENGTH: 2763
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 34
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaacac aaggaggagg agatgcagaa 240
ttccgacatg actcaggata tgaagttgga ggaggagatg cagaattccg acatgactca 300
ggatatgaag ttggaggagg agatgcagaa ttccgacatg actcaggata tgaagttgga 360
ggaggagatg cagaattccg acatgactca ggatatgaag ttggaggagg agatgcagaa 420
ttccgacatg actcaggata tgaagttgga ggaggagatg cagaattccg acatgactca 480
ggatatgaag ttggaggagg agatgcagaa ttccgacatg actcaggata tgaagttgga 540
ggaggagatg cagaattccg acatgactca ggatatgaag ttggaggagg agatgcagaa 600

-continued

```
ttccgacatg actcaggata tgaagttgga ggaggagatg cagaattccg acatgactca    660
ggatatgaag ttggaggagg agatgcagaa ttccgacatg actcaggata tgaagttgga    720
ggaggagatg cagaattccg acatgactca ggatatgaag ttggaggagg agatgcagaa    780
ttccgacatg actcaggata tgaagttgga ggaggagatg cagaattccg acatgactca    840
ggatatgaag ttggaggagg agatgcagaa ttccgacatg actcaggata tgaagttgga    900
ggaggagatg cagaattccg acatgactca ggatatgaag ttggaggagg agatgcagaa    960
ttccgacatg actcaggata tgaagttgga ggaggagatg cagaattccg acatgactca   1020
ggatatgaag ttggaggagg agatgcagaa ttccgacatg actcaggata tgaagttgga   1080
ggaggagatg cagaattccg acatgactca ggatatgaag ttggaggagg agatgcagaa   1140
ttccgacatg actcaggata tgaagttgga ggaggagatg cagaattccg acatgactca   1200
ggatatgaag ttggaggagg agatgcagaa ttccgacatg actcaggata tgaagttgga   1260
ggaggagatg cagaattccg acatgactca ggatatgaag ttggaggagg agatgcagaa   1320
ttccgacatg actcaggata tgaagttgga ggaggagatg cagaattccg acatgactca   1380
ggatatgaag ttggaggagg agatgcagaa ttccgacatg actcaggata tgaagttgga   1440
ggaggagatg cagaattccg acatgactca ggatatgaag ttggaggagg agatgcagaa   1500
ttccgacatg actcaggata tgaagttgga ggaggagatg cagaattccg acatgactca   1560
ggatatgaag ttggaggagg agatgcagaa ttccgacatg actcaggata tgaagttgga   1620
ggaggagatg cagaattccg acatgactca ggatatgaag ttggaggagg agatgcagaa   1680
ttccgacatg actcaggata tgaagttgga ggaggagatg cagaattccg acatgactca   1740
ggatatgaag ttggaggagg agatgcagaa ttccgacatg actcaggata tgaagttgga   1800
ggaggagatg cagaattccg acatgactca ggatatgaag ttggaggagg agatgcagaa   1860
ttccgacatg actcaggata tgaagttgga ggaggagatg cagaattccg acatgactca   1920
ggatatgaag ttggaggagg agatgcagaa ttccgacatg actcaggata tgaagttgga   1980
ggaggagatg cagaattccg acatgactca ggatatgaag ttggaggagg aaactacacc   2040
atgaacttgg cctcgcagaa ctggaacaac tacgatccaa ccgaggaaat ccccgctcct   2100
ttgggaactc ccgacttcgt gggacgtatc caaggtgtcc tgacacagac tacacgtcgc   2160
gacggctcta ctcgcggaca caaggccact gtgtcgacag gttccgtcca cttcacccct   2220
aagctgggct ctgtgcaatt cagcacagac acctcaaacg atttcgagac tggccagaac   2280
accaggttca ctcccgtggg tgtcgttcaa gacggcagca ccactcacca gaacgaaccc   2340
cagcaatggg tcctccctga ctactcgggc agggattccc acaacgttca cttggctccg   2400
gccgtggctc caaccttccc tggagagcag ttgctgttct tcagatccac tatgccaggc   2460
tgctctggat acccgaacat gaacctcgac tgtctcttgc ctcaggagtg ggtgcaacac   2520
ttctaccagg aatctgcccc agctcaaagc gacgtcgctc tgctccgttt cgttaacccc   2580
gataccggtc gcgtgctctt cgagtgtaag ttgcacaagt ctggttacgt cactgttgcc   2640
cacacaggcc agcacgacct ggtcatccct cccaacggct acttccgctt cgatagctgg   2700
gtcaaccagt tctacacact cgccccgatg ggaaacggag ccggtcgtcg cagagccttg   2760
taa                                                                 2763
```

<210> SEQ ID NO 35
<211> LENGTH: 999
<212> TYPE: DNA
<213> ORGANISM: artificial sequence -continued
<220> FEATURE:
<223> OTHER INFORMATION: synthetic nucleotide sequence encoding the
      recombinant P protein

<400> SEQUENCE: 35
atgaagccct tctcggtccc tatcctgaca gttgaggaaa tgaccaactc tagattccca     60
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc gctggaacac aaaactacac catgaacttg    240
gcctcgcaga actggaacaa ctacgatcca accgaggaaa tccccgctcc tttgggaact    300
cccgacttcg tgggacgtat ccaaggtgtc ctgacacaga ctacacgtcg cgacggctct    360
actcgcggac acaaggccac tgtgtcgaca ggttccgtcc acttcacccc taagctgggc    420
tctgtgcaat tcagcacaga caccggagga ggagatgcag aattccgaca tgactcagga    480
ggaggaggat caaacgattt cgagactggc cagaacacca ggttcactcc cgtgggtgtc    540
gttcaagacg gcagcaccac tcaccagaac gaaccccagc aatgggtcct ccctgactac    600
tcgggcaggg attcccacaa cgttcacttg gctccggccg tggctccaac cttccctgga    660
gagcagttgc tgttcttcag atccactatg ccaggctgct ctggataccc gaacatgaac    720
ctcgactgtc tcttgcctca ggagtgggtg caacacttct accaggaatc tgccccagct    780
caaagcgacg tcgctctgct ccgtttcgtt aaccccgata ccggtcgcgt gctcttcgag    840
tgtaagttgc acaagtctgg ttacgtcact gttgcccaca caggccagca cgacctggtc    900
atccctccca acggctactt ccgcttcgat agctgggtca accagttcta cacactcgcc    960
ccgatgggaa acggagccgg tcgtcgcaga gccttgtaa                           999

<210> SEQ ID NO 36
<211> LENGTH: 1323
<212> TYPE: DNA
<213> ORGANISM: artificial sequence
<220> FEATURE:
<223> OTHER INFORMATION: synthetic nucleotide sequence encoding the
      recombinant P protein

<400> SEQUENCE: 36
atgaagccct tctcggtccc tatcctgaca gttgaggaaa tgaccaactc tagattccca     60
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc gctggaacac aaaactacac catgaacttg    240
gcctcgcaga actggaacaa ctacgatcca accgaggaaa tccccgctcc tttgggaact    300
cccgacttcg tgggacgtat ccaaggtgtc ctgacacaga ctacacgtcg cgacggctct    360
actcgcggac acaaggccac tgtgtcgaca ggttccgtcc acttcacccc taagctgggc    420
tctgtgcaat tcagcacaga caccggagga ggagatgcag aattccgaca tgactcagga    480
ggaggaggag atgcagaatt ccgacatgac tcaggaggag gaggagatgc agaattccga    540
catgactcag gaggaggagg agatgcagaa ttccgacatg actcaggagg aggaggagat    600
gcagaattcc gacatgactc aggaggagga ggagatgcag aattccgaca tgactcagga    660
ggaggaggag atgcagaatt ccgacatgac tcaggaggag gaggagatgc agaattccga    720
catgactcag gaggaggagg agatgcagaa ttccgacatg actcaggagg aggaggagat    780
gcagaattcc gacatgactc aggaggagga ggatcaaacg atttcgagac tggccagaac    840

-continued

```
accaggttca ctcccgtggg tgtcgttcaa gacggcagca ccactcacca gaacgaaccc     900
cagcaatggg tcctccctga ctactcgggc agggattccc acaacgttca cttggctccg     960
gccgtggctc caaccttccc tggagagcag ttgctgttct tcagatccac tatgccaggc    1020
tgctctggat acccgaacat gaacctcgac tgtctcttgc ctcaggagtg ggtgcaacac    1080
ttctaccagg aatctgcccc agctcaaagc gacgtcgctc tgctccgttt cgttaacccc    1140
gataccggtc gcgtgctctt cgagtgtaag ttgcacaagt ctggttacgt cactgttgcc    1200
cacacaggcc agcacgacct ggtcatccct cccaacggct acttccgctt cgatagctgg    1260
gtcaaccagt tctacacact cgccccgatg ggaaacggag ccggtcgtcg cagagccttg    1320
taa                                                                  1323
```

<210> SEQ ID NO 37
<211> LENGTH: 1683
<212> TYPE: DNA
<213> ORGANISM: artificial sequence
<220> FEATURE:
<223> OTHER INFORMATION: synthetic nucleotide sequence encoding the
recombinant P protein

<400> SEQUENCE: 37

```
atgaagccct tctcggtccc tatcctgaca gttgaggaaa tgaccaactc tagattccca      60
atcccgctgg aaaagctctt caccggaccc tcctctgctt tcgttgtgca gcctcaaaac     120
ggtcgttgca ccactgatgg tgtcctgctc ggtaccaccc agctctcacc tgtgaacatc     180
tgtactttcc gcggcgacgt cacacacatc gctggaacac aaaactacac catgaacttg     240
gcctcgcaga actggaacaa ctacgatcca accgaggaaa tccccgctcc tttgggaact     300
cccgacttcg tgggacgtat ccaaggtgtc ctgacacaga ctacacgtcg cgacggctct     360
actcgcggac acaaggccac tgtgtcgaca ggttccgtcc acttcacccc taagctgggc     420
tctgtgcaat tcagcacaga caccggagga ggagatgcag aattccgaca tgactcagga     480
ggaggaggag atgcagaatt ccgacatgac tcaggaggag gaggagatgc agaattccga     540
catgactcag gaggaggagg agatgcagaa ttccgacatg actcaggagg aggaggagat     600
gcagaattcc gacatgactc aggaggagga ggagatgcag aattccgaca tgactcagga     660
ggaggaggag atgcagaatt ccgacatgac tcaggaggag gaggagatgc agaattccga     720
catgactcag gaggaggagg agatgcagaa ttccgacatg actcaggagg aggaggagat     780
gcagaattcc gacatgactc aggaggagga ggagatgcag aattccgaca tgactcagga     840
ggaggaggag atgcagaatt ccgacatgac tcaggaggag gaggagatgc agaattccga     900
catgactcag gaggaggagg agatgcagaa ttccgacatg actcaggagg aggaggagat     960
gcagaattcc gacatgactc aggaggagga ggagatgcag aattccgaca tgactcagga    1020
ggaggaggag atgcagaatt ccgacatgac tcaggaggag gaggagatgc agaattccga    1080
catgactcag gaggaggagg agatgcagaa ttccgacatg actcaggagg aggaggagat    1140
gcagaattcc gacatgactc aggaggagga ggatcaaacg atttcgagac tggccagaac    1200
accaggttca ctcccgtggg tgtcgttcaa gacggcagca ccactcacca gaacgaaccc    1260
cagcaatggg tcctccctga ctactcgggc agggattccc acaacgttca cttggctccg    1320
gccgtggctc caaccttccc tggagagcag ttgctgttct tcagatccac tatgccaggc    1380
tgctctggat acccgaacat gaacctcgac tgtctcttgc ctcaggagtg ggtgcaacac    1440
ttctaccagg aatctgcccc agctcaaagc gacgtcgctc tgctccgttt cgttaacccc    1500
```

-continued gataccggtc gcgtgctctt cgagtgtaag ttgcacaagt ctggttacgt cactgttgcc 1560
cacacaggcc agcacgacct ggtcatccct cccaacggct acttccgctt cgatagctgg 1620
gtcaaccagt tctacacact cgccccgatg ggaaacggag ccggtcgtcg cagagccttg 1680
taa 1683

<210> SEQ ID NO 38
<211> LENGTH: 2403
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 38
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaacac aaaactacac catgaacttg 240
gcctcgcaga actggaacaa ctacgatcca accgaggaaa tccccgctcc tttgggaact 300
cccgacttcg tgggacgtat ccaaggtgtc ctgacacaga ctacacgtcg cgacggctct 360
actcgcggac acaaggccac tgtgtcgaca ggttccgtcc acttcacccc taagctgggc 420
tctgtgcaat tcagcacaga caccggagga ggagatgcag aattccgaca tgactcagga 480
ggaggaggag atgcagaatt ccgacatgac tcaggaggag gaggagatgc agaattccga 540
catgactcag gaggaggagg agatgcagaa ttccgacatg actcaggagg aggaggagat 600
gcagaattcc gacatgactc aggaggagga ggagatgcag aattccgaca tgactcagga 660
ggaggaggag atgcagaatt ccgacatgac tcaggaggag gaggagatgc agaattccga 720
catgactcag gaggaggagg agatgcagaa ttccgacatg actcaggagg aggaggagat 780
gcagaattcc gacatgactc aggaggagga ggagatgcag aattccgaca tgactcagga 840
ggaggaggag atgcagaatt ccgacatgac tcaggaggag gaggagatgc agaattccga 900
catgactcag gaggaggagg agatgcagaa ttccgacatg actcaggagg aggaggagat 960
gcagaattcc gacatgactc aggaggagga ggagatgcag aattccgaca tgactcagga 1020
ggaggaggag atgcagaatt ccgacatgac tcaggaggag gaggagatgc agaattccga 1080
catgactcag gaggaggagg agatgcagaa ttccgacatg actcaggagg aggaggagat 1140
gcagaattcc gacatgactc aggaggagga ggagatgcag aattccgaca tgactcagga 1200
ggaggaggag atgcagaatt ccgacatgac tcaggaggag gaggagatgc agaattccga 1260
catgactcag gaggaggagg agatgcagaa ttccgacatg actcaggagg aggaggagat 1320
gcagaattcc gacatgactc aggaggagga ggagatgcag aattccgaca tgactcagga 1380
ggaggaggag atgcagaatt ccgacatgac tcaggaggag gaggagatgc agaattccga 1440
catgactcag gaggaggagg agatgcagaa ttccgacatg actcaggagg aggaggagat 1500
gcagaattcc gacatgactc aggaggagga ggagatgcag aattccgaca tgactcagga 1560
ggaggaggag atgcagaatt ccgacatgac tcaggaggag gaggagatgc agaattccga 1620
catgactcag gaggaggagg agatgcagaa ttccgacatg actcaggagg aggaggagat 1680
gcagaattcc gacatgactc aggaggagga ggagatgcag aattccgaca tgactcagga 1740
ggaggaggag atgcagaatt ccgacatgac tcaggaggag gaggagatgc agaattccga 1800

-continued catgactcag gaggaggagg agatgcagaa ttccgacatg actcaggagg aggaggagat 1860
gcagaattcc gacatgactc aggaggagga ggatcaaacg atttcgagac tggccagaac 1920
accaggttca ctcccgtggg tgtcgttcaa gacggcagca ccactcacca gaacgaaccc 1980
cagcaatggg tcctccctga ctactcgggc agggattccc acaacgttca cttggctccg 2040
gccgtggctc caaccttccc tggagagcag ttgctgttct tcagatccac tatgccaggc 2100
tgctctggat acccgaacat gaacctcgac tgtctcttgc ctcaggagtg ggtgcaacac 2160
ttctaccagg aatctgcccc agctcaaagc gacgtcgctc tgctccgttt cgttaacccc 2220
gataccggtc gcgtgctctt cgagtgtaag ttgcacaagt ctggttacgt cactgttgcc 2280
cacacaggcc agcacgacct ggtcatccct cccaacggct acttccgctt cgatagctgg 2340
gtcaaccagt tctacacact cgccccgatg ggaaacggag ccggtcgtcg cagagccttg 2400
taa 2403

<210> SEQ ID NO 39
<211> LENGTH: 990
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 39
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaacac aaaactacac catgaacttg 240
gcctcgcaga actggaacaa ctacgatcca accgaggaaa tccccgctcc tttgggaact 300
cccgacttcg tgggacgtat ccaaggtgtc ctgacacaga ctacacgtcg cgacggctct 360
actcgcggac acaaggccac tgtgtcgaca ggttccgtcc acttcacccc taagctgggc 420
tctgtgcaat tcagcacaga cacctcagga ggaggagatg cagaattccg acatggagga 480
ggaaacgatt tcgagactgg ccagaacacc aggttcactc ccgtgggtgt cgttcaagac 540
ggcagcacca ctcaccagaa cgaaccccag caatgggtcc tccctgacta ctcgggcagg 600
gattcccaca acgttcactt ggctccggcc gtggctccaa ccttccctgg agagcagttg 660
ctgttcttca gatccactat gccaggctgc tctggatacc cgaacatgaa cctcgactgt 720
ctcttgcctc aggagtgggt gcaacacttc taccaggaat ctgccccagc tcaaagcgac 780
gtcgctctgc tccgtttcgt taaccccgat accggtcgcg tgctcttcga gtgtaagttg 840
cacaagtctg gttacgtcac tgttgcccac acaggccagc acgacctggt catccctccc 900
aacggctact tccgcttcga tagctgggtc aaccagttct acacactcgc cccgatggga 960
aacggagccg gtcgtcgcag agccttgtaa 990

<210> SEQ ID NO 40
<211> LENGTH: 1233
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 40
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaacac aaaactacac catgaacttg 240
gcctcgcaga actggaacaa ctacgatcca accgaggaaa tccccgctcc tttgggaact 300
cccgacttcg tgggacgtat ccaaggtgtc ctgacacaga ctacacgtcg cgacggctct 360
actcgcggac acaaggccac tgtgtcgaca ggttccgtcc acttcacccc taagctgggc 420
tctgtgcaat tcagcacaga cacctcagga ggaggagatg cagaattccg acatggagga 480
ggagatgcag aattccgaca tggaggagga gatgcagaat tccgacatgg aggaggagat 540
gcagaattcc gacatggagg aggagatgca gaattccgac atggaggagg agatgcagaa 600
ttccgacatg gaggaggaga tgcagaattc cgacatggag gaggagatgc agaattccga 660
catggaggag gagatgcaga attccgacat ggaggaggag atgcagaatt ccgacatgga 720
ggaggaaacg atttcgagac tggccagaac accaggttca ctcccgtggg tgtcgttcaa 780
gacggcagca ccactcacca gaacgaaccc cagcaatggg tcctccctga ctactcgggc 840
agggattccc acaacgttca cttggctccg gccgtggctc caaccttccc tggagagcag 900
ttgctgttct tcagatccac tatgccaggc tgctctggat acccgaacat gaacctcgac 960
tgtctcttgc ctcaggagtg ggtgcaacac ttctaccagg aatctgcccc agctcaaagc 1020
gacgtcgctc tgctccgttt cgttaacccc gataccggtc gcgtgctctt cgagtgtaag 1080
ttgcacaagt ctggttacgt cactgttgcc cacacaggcc agcacgacct ggtcatccct 1140
cccaacggct acttccgctt cgatagctgg gtcaaccagt tctacacact cgccccgatg 1200
ggaaacggag ccggtcgtcg cagagccttg taa 1233

<210> SEQ ID NO 41
<211> LENGTH: 1503
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 41
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaacac aaaactacac catgaacttg 240
gcctcgcaga actggaacaa ctacgatcca accgaggaaa tccccgctcc tttgggaact 300
cccgacttcg tgggacgtat ccaaggtgtc ctgacacaga ctacacgtcg cgacggctct 360
actcgcggac acaaggccac tgtgtcgaca ggttccgtcc acttcacccc taagctgggc 420
tctgtgcaat tcagcacaga cacctcagga ggaggagatg cagaattccg acatggagga 480
ggagatgcag aattccgaca tggaggagga gatgcagaat tccgacatgg aggaggagat 540
gcagaattcc gacatggagg aggagatgca gaattccgac atggaggagg agatgcagaa 600
ttccgacatg gaggaggaga tgcagaattc cgacatggag gaggagatgc agaattccga 660
catggaggag gagatgcaga attccgacat ggaggaggag atgcagaatt ccgacatgga 720
ggaggagatg cagaattccg acatggagga ggagatgcag aattccgaca tggaggagga 780
gatgcagaat tccgacatgg aggaggagat gcagaattcc gacatggagg aggagatgca 840
gaattccgac atggaggagg agatgcagaa ttccgacatg gaggaggaga tgcagaattc 900
cgacatggag gaggagatgc agaattccga catggaggag gagatgcaga attccgacat 960
ggaggaggag atgcagaatt ccgacatgga ggaggaaacg atttcgagac tggccagaac 1020
accaggttca ctcccgtggg tgtcgttcaa gacggcagca ccactcacca gaacgaaccc 1080
cagcaatggg tcctccctga ctactcgggc agggattccc acaacgttca cttggctccg 1140
gccgtggctc caaccttccc tggagagcag ttgctgttct tcagatccac tatgccaggc 1200
tgctctggat acccgaacat gaacctcgac tgtctcttgc ctcaggagtg ggtgcaacac 1260
ttctaccagg aatctgcccc agctcaaagc gacgtcgctc tgctccgttt cgttaacccc 1320
gataccggtc gcgtgctctt cgagtgtaag ttgcacaagt ctggttacgt cactgttgcc 1380
cacacaggcc agcacgacct ggtcatccct cccaacggct acttccgctt cgatagctgg 1440
gtcaaccagt tctacacact cgccccgatg ggaaacggag ccggtcgtcg cagagccttg 1500
taa 1503

<210> SEQ ID NO 42
<211> LENGTH: 2043
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 42
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaacac aaaactacac catgaacttg 240
gcctcgcaga actggaacaa ctacgatcca accgaggaaa tccccgctcc tttgggaact 300
cccgacttcg tgggacgtat ccaaggtgtc ctgacacaga ctacacgtcg cgacggctct 360
actcgcggac acaaggccac tgtgtcgaca ggttccgtcc acttcacccc taagctgggc 420
tctgtgcaat tcagcacaga cacctcagga ggaggagatg cagaattccg acatggagga 480
ggagatgcag aattccgaca tggaggagga gatgcagaat tccgacatgg aggaggagat 540
gcagaattcc gacatggagg aggagatgca gaattccgac atggaggagg agatgcagaa 600
ttccgacatg gaggaggaga tgcagaattc cgacatggag gaggagatgc agaattccga 660
catggaggag gagatgcaga attccgacat ggaggaggag atgcagaatt ccgacatgga 720
ggaggagatg cagaattccg acatggagga ggagatgcag aattccgaca tggaggagga 780
gatgcagaat tccgacatgg aggaggagat gcagaattcc gacatggagg aggagatgca 840
gaattccgac atggaggagg agatgcagaa ttccgacatg gaggaggaga tgcagaattc 900
cgacatggag gaggagatgc agaattccga catggaggag gagatgcaga attccgacat 960
ggaggaggag atgcagaatt ccgacatgga ggaggagatg cagaattccg acatggagga 1020
ggagatgcag aattccgaca tggaggagga gatgcagaat tccgacatgg aggaggagat 1080
gcagaattcc gacatggagg aggagatgca gaattccgac atggaggagg agatgcagaa 1140
ttccgacatg gaggaggaga tgcagaattc cgacatggag gaggagatgc agaattccga 1200
catggaggag gagatgcaga attccgacat ggaggaggag atgcagaatt ccgacatgga 1260
ggaggagatg cagaattccg acatggagga ggagatgcag aattccgaca tggaggagga 1320

```
gatgcagaat tccgacatgg aggaggagat gcagaattcc gacatggagg aggagatgca   1380
gaattccgac atggaggagg agatgcagaa ttccgacatg gaggaggaga tgcagaattc   1440
cgacatggag gaggagatgc agaattccga catggaggag gagatgcaga attccgacat   1500
ggaggaggag atgcagaatt ccgacatgga ggaggaaacg atttcgagac tggccagaac   1560
accaggttca ctcccgtggg tgtcgttcaa gacggcagca ccactcacca gaacgaaccc   1620
cagcaatggg tcctccctga ctactcgggc agggattccc acaacgttca cttggctccg   1680
gccgtggctc caaccttccc tggagagcag ttgctgttct tcagatccac tatgccaggc   1740
tgctctggat acccgaacat gaacctcgac tgtctcttgc ctcaggagtg ggtgcaacac   1800
ttctaccagg aatctgcccc agctcaaagc gacgtcgctc tgctccgttt cgttaacccc   1860
gataccggtc gcgtgctctt cgagtgtaag ttgcacaagt ctggttacgt cactgttgcc   1920
cacacaggcc agcacgacct ggtcatccct cccaacggct acttccgctt cgatagctgg   1980
gtcaaccagt tctacacact cgccccgatg ggaaacggag ccggtcgtcg cagagccttg   2040
taa                                                                 2043
```

<210> SEQ ID NO 43
<211> LENGTH: 1008
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 43

```
atgaagccct tctcggtccc tatcctgaca gttgaggaaa tgaccaactc tagattccca     60
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc gctggaacac aaaactacac catgaacttg    240
gcctcgcaga actggaacaa ctacgatcca accgaggaaa tccccgctcc tttgggaact    300
cccgacttcg tgggacgtat ccaaggtgtc ctgacacaga ctacacgtcg cgacggctct    360
actcgcggac acaaggccac tgtgtcgaca ggttccgtcc acttcacccc taagctgggc    420
tctgtgcaat tcagcacaga cacctcaaac ggaggaggag atgcagaatt ccgacatgac    480
tcaggatatg aagttggagg aggagatttc gagactggcc agaacaccag gttcactccc    540
gtgggtgtcg ttcaagacgg cagcaccact caccagaacg aaccccagca atgggtcctc    600
cctgactact cgggcaggga ttcccacaac gttcacttgg ctccggccgt ggctccaacc    660
ttccctggag agcagttgct gttcttcaga tccactatgc caggctgctc tggatacccg    720
aacatgaacc tcgactgtct cttgcctcag gagtgggtgc aacacttcta ccaggaatct    780
gccccagctc aaagcgacgt cgctctgctc cgtttcgtta accccgatac cggtcgcgtg    840
ctcttcgagt gtaagttgca caagtctggt tacgtcactg ttgcccacac aggccagcac    900
gacctggtca tccctcccaa cggctacttc cgcttcgata gctgggtcaa ccagttctac    960
acactcgccc cgatgggaaa cggagccggt cgtcgcagag ccttgtaa                1008
```

<210> SEQ ID NO 44
<211> LENGTH: 1413
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 44
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaacac aaaactacac catgaacttg 240
gcctcgcaga actggaacaa ctacgatcca accgaggaaa tccccgctcc tttgggaact 300
cccgacttcg tgggacgtat ccaaggtgtc ctgacacaga ctacacgtcg cgacggctct 360
actcgcggac acaaggccac tgtgtcgaca ggttccgtcc acttcacccc taagctgggc 420
tctgtgcaat tcagcacaga cacctcaaac ggaggaggag atgcagaatt ccgacatgac 480
tcaggatatg aagttggagg aggagatgca gaattccgac atgactcagg atatgaagtt 540
ggaggaggag atgcagaatt ccgacatgac tcaggatatg aagttggagg aggagatgca 600
gaattccgac atgactcagg atatgaagtt ggaggaggag atgcagaatt ccgacatgac 660
tcaggatatg aagttggagg aggagatgca gaattccgac atgactcagg atatgaagtt 720
ggaggaggag atgcagaatt ccgacatgac tcaggatatg aagttggagg aggagatgca 780
gaattccgac atgactcagg atatgaagtt ggaggaggag atgcagaatt ccgacatgac 840
tcaggatatg aagttggagg aggagatgca gaattccgac atgactcagg atatgaagtt 900
ggaggaggag atttcgagac tggccagaac accaggttca ctcccgtggg tgtcgttcaa 960
gacggcagca ccactcacca gaacgaaccc cagcaatggg tcctccctga ctactcgggc 1020
agggattccc acaacgttca cttggctccg gccgtggctc caaccttccc tggagagcag 1080
ttgctgttct tcagatccac tatgccaggc tgctctggat acccgaacat gaacctcgac 1140
tgtctcttgc ctcaggagtg ggtgcaacac ttctaccagg aatctgcccc agctcaaagc 1200
gacgtcgctc tgctccgttt cgttaacccc gataccggtc gcgtgctctt cgagtgtaag 1260
ttgcacaagt ctggttacgt cactgttgcc cacacaggcc agcacgacct ggtcatccct 1320
cccaacggct acttccgctt cgatagctgg gtcaaccagt tctacacact cgccccgatg 1380
ggaaacggag ccggtcgtcg cagagccttg taa 1413

<210> SEQ ID NO 45
<211> LENGTH: 1863
<212> TYPE: DNA
<213> ORGANISM: artificial sequence
<220> FEATURE:
<223> OTHER INFORMATION: synthetic nucleotide sequence encoding the
recombinant P protein

<400> SEQUENCE: 45
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaacac aaaactacac catgaacttg 240
gcctcgcaga actggaacaa ctacgatcca accgaggaaa tccccgctcc tttgggaact 300
cccgacttcg tgggacgtat ccaaggtgtc ctgacacaga ctacacgtcg cgacggctct 360
actcgcggac acaaggccac tgtgtcgaca ggttccgtcc acttcacccc taagctgggc 420
tctgtgcaat tcagcacaga cacctcaaac ggaggaggag atgcagaatt ccgacatgac 480

```
tcaggatatg aagttggagg aggagatgca gaattccgac atgactcagg atatgaagtt    540
ggaggaggag atgcagaatt ccgacatgac tcaggatatg aagttggagg aggagatgca    600
gaattccgac atgactcagg atatgaagtt ggaggaggag atgcagaatt ccgacatgac    660
tcaggatatg aagttggagg aggagatgca gaattccgac atgactcagg atatgaagtt    720
ggaggaggag atgcagaatt ccgacatgac tcaggatatg aagttggagg aggagatgca    780
gaattccgac atgactcagg atatgaagtt ggaggaggag atgcagaatt ccgacatgac    840
tcaggatatg aagttggagg aggagatgca gaattccgac atgactcagg atatgaagtt    900
ggaggaggag atgcagaatt ccgacatgac tcaggatatg aagttggagg aggagatgca    960
gaattccgac atgactcagg atatgaagtt ggaggaggag atgcagaatt ccgacatgac   1020
tcaggatatg aagttggagg aggagatgca gaattccgac atgactcagg atatgaagtt   1080
ggaggaggag atgcagaatt ccgacatgac tcaggatatg aagttggagg aggagatgca   1140
gaattccgac atgactcagg atatgaagtt ggaggaggag atgcagaatt ccgacatgac   1200
tcaggatatg aagttggagg aggagatgca gaattccgac atgactcagg atatgaagtt   1260
ggaggaggag atgcagaatt ccgacatgac tcaggatatg aagttggagg aggagatgca   1320
gaattccgac atgactcagg atatgaagtt ggaggaggag atttcgagac tggccagaac   1380
accaggttca ctcccgtggg tgtcgttcaa gacggcagca ccactcacca gaacgaaccc   1440
cagcaatggg tcctccctga ctactcgggc agggattccc acaacgttca cttggctccg   1500
gccgtggctc caaccttccc tggagagcag ttgctgttct tcagatccac tatgccaggc   1560
tgctctggat acccgaacat gaacctcgac tgtctcttgc ctcaggagtg ggtgcaacac   1620
ttctaccagg aatctgcccc agctcaaagc gacgtcgctc tgctccgttt cgttaacccc   1680
gataccggtc gcgtgctctt cgagtgtaag ttgcacaagt ctggttacgt cactgttgcc   1740
cacacaggcc agcacgacct ggtcatccct cccaacggct acttccgctt cgatagctgg   1800
gtcaaccagt tctacacact cgccccgatg ggaaacggag ccggtcgtcg cagagccttg   1860
taa                                                                 1863
```

<210> SEQ ID NO 46
<211> LENGTH: 2763
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 46

```
atgaagccct tctcggtccc tatcctgaca gttgaggaaa tgaccaactc tagattccca     60
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc gctggaacac aaaactacac catgaacttg    240
gcctcgcaga actggaacaa ctacgatcca accgaggaaa tccccgctcc tttgggaact    300
cccgacttcg tgggacgtat ccaaggtgtc ctgacacaga ctacacgtcg cgacggctct    360
actcgcggac acaaggccac tgtgtcgaca ggttccgtcc acttcacccc taagctgggc    420
tctgtgcaat tcagcacaga cacctcaaac ggaggaggag atgcagaatt ccgacatgac    480
tcaggatatg aagttggagg aggagatgca gaattccgac atgactcagg atatgaagtt    540
ggaggaggag atgcagaatt ccgacatgac tcaggatatg aagttggagg aggagatgca    600
```

-continued

```
gaattccgac atgactcagg atatgaagtt ggaggaggag atgcagaatt ccgacatgac    660
tcaggatatg aagttggagg aggagatgca gaattccgac atgactcagg atatgaagtt    720
ggaggaggag atgcagaatt ccgacatgac tcaggatatg aagttggagg aggagatgca    780
gaattccgac atgactcagg atatgaagtt ggaggaggag atgcagaatt ccgacatgac    840
tcaggatatg aagttggagg aggagatgca gaattccgac atgactcagg atatgaagtt    900
ggaggaggag atgcagaatt ccgacatgac tcaggatatg aagttggagg aggagatgca    960
gaattccgac atgactcagg atatgaagtt ggaggaggag atgcagaatt ccgacatgac   1020
tcaggatatg aagttggagg aggagatgca gaattccgac atgactcagg atatgaagtt   1080
ggaggaggag atgcagaatt ccgacatgac tcaggatatg aagttggagg aggagatgca   1140
gaattccgac atgactcagg atatgaagtt ggaggaggag atgcagaatt ccgacatgac   1200
tcaggatatg aagttggagg aggagatgca gaattccgac atgactcagg atatgaagtt   1260
ggaggaggag atgcagaatt ccgacatgac tcaggatatg aagttggagg aggagatgca   1320
gaattccgac atgactcagg atatgaagtt ggaggaggag atgcagaatt ccgacatgac   1380
tcaggatatg aagttggagg aggagatgca gaattccgac atgactcagg atatgaagtt   1440
ggaggaggag atgcagaatt ccgacatgac tcaggatatg aagttggagg aggagatgca   1500
gaattccgac atgactcagg atatgaagtt ggaggaggag atgcagaatt ccgacatgac   1560
tcaggatatg aagttggagg aggagatgca gaattccgac atgactcagg atatgaagtt   1620
ggaggaggag atgcagaatt ccgacatgac tcaggatatg aagttggagg aggagatgca   1680
gaattccgac atgactcagg atatgaagtt ggaggaggag atgcagaatt ccgacatgac   1740
tcaggatatg aagttggagg aggagatgca gaattccgac atgactcagg atatgaagtt   1800
ggaggaggag atgcagaatt ccgacatgac tcaggatatg aagttggagg aggagatgca   1860
gaattccgac atgactcagg atatgaagtt ggaggaggag atgcagaatt ccgacatgac   1920
tcaggatatg aagttggagg aggagatgca gaattccgac atgactcagg atatgaagtt   1980
ggaggaggag atgcagaatt ccgacatgac tcaggatatg aagttggagg aggagatgca   2040
gaattccgac atgactcagg atatgaagtt ggaggaggag atgcagaatt ccgacatgac   2100
tcaggatatg aagttggagg aggagatgca gaattccgac atgactcagg atatgaagtt   2160
ggaggaggag atgcagaatt ccgacatgac tcaggatatg aagttggagg aggagatgca   2220
gaattccgac atgactcagg atatgaagtt ggaggaggag atttcgagac tggccagaac   2280
accaggttca ctcccgtggg tgtcgttcaa gacggcagca ccactcacca gaacgaaccc   2340
cagcaatggg tcctccctga ctactcgggc agggattccc acaacgttca cttggctccg   2400
gccgtggctc caaccttccc tggagagcag ttgctgttct tcagatccac tatgccaggc   2460
tgctctggat acccgaacat gaacctcgac tgtctcttgc ctcaggagtg ggtgcaacac   2520
ttctaccagg aatctgcccc agctcaaagc gacgtcgctc tgctccgttt cgttaacccc   2580
gataccggtc gcgtgctctt cgagtgtaag ttgcacaagt ctggttacgt cactgttgcc   2640
cacacaggcc agcacgacct ggtcatccct cccaacggct acttccgctt cgatagctgg   2700
gtcaaccagt tctacacact cgccccgatg ggaaacggag ccggtcgtcg cagagccttg   2760
taa                                                                  2763
```

<210> SEQ ID NO 47
<211> LENGTH: 1017
<212> TYPE: DNA
<213> ORGANISM: artificial sequence
<220> FEATURE:
<223> OTHER INFORMATION: synthetic nucleotide sequence encoding the
      recombinant P protein

<400> SEQUENCE: 47
atgaagccct tctcggtccc tatcctgaca gttgaggaaa tgaccaactc tagattccca      60
atcccgctgg aaaagctctt caccggaccc tcctctgctt tcgttgtgca gcctcaaaac     120
ggtcgttgca ccactgatgg tgtcctgctc ggtaccaccc agctctcacc tgtgaacatc     180
tgtactttcc gcggcgacgt cacacacatc gctggaacac aaaactacac catgaacttg     240
gcctcgcaga actggaacaa ctacgatcca accgaggaaa tccccgctcc tttgggaact     300
cccgacttcg tgggacgtat ccaaggtgtc ctgacacaga ctacacgtcg cgacggctct     360
actcgcggac acaaggccac tgtgtcgaca ggttccgtcc acttcacccc taagctgggc     420
tctgtgcaat tcagcacaga cacctcaaac gatggaggag gagatgcaga attccgacat     480
gactcaggat atgaagttca tcatcaagga ggaggattcg agactggcca gaacaccagg     540
ttcactcccg tgggtgtcgt tcaagacggc agcaccactc accagaacga accccagcaa     600
tgggtcctcc ctgactactc gggcagggat tcccacaacg ttcacttggc tccggccgtg     660
gctccaacct tccctggaga gcagttgctg ttcttcagat ccactatgcc aggctgctct     720
ggatacccga acatgaacct cgactgtctc ttgcctcagg agtgggtgca acacttctac     780
caggaatctg ccccagctca aagcgacgtc gctctgctcc gtttcgttaa ccccgatacc     840
ggtcgcgtgc tcttcgagtg taagttgcac aagtctggtt acgtcactgt tgcccacaca     900
ggccagcacg acctggtcat ccctcccaac ggctacttcc gcttcgatag ctgggtcaac     960
cagttctaca cactcgcccc gatgggaaac ggagccggtc gtcgcagagc cttgtaa       1017

<210> SEQ ID NO 48
<211> LENGTH: 1503
<212> TYPE: DNA
<213> ORGANISM: artificial sequence
<220> FEATURE:
<223> OTHER INFORMATION: synthetic nucleotide sequence encoding the
      recombinant P protein

<400> SEQUENCE: 48
atgaagccct tctcggtccc tatcctgaca gttgaggaaa tgaccaactc tagattccca      60
atcccgctgg aaaagctctt caccggaccc tcctctgctt tcgttgtgca gcctcaaaac     120
ggtcgttgca ccactgatgg tgtcctgctc ggtaccaccc agctctcacc tgtgaacatc     180
tgtactttcc gcggcgacgt cacacacatc gctggaacac aaaactacac catgaacttg     240
gcctcgcaga actggaacaa ctacgatcca accgaggaaa tccccgctcc tttgggaact     300
cccgacttcg tgggacgtat ccaaggtgtc ctgacacaga ctacacgtcg cgacggctct     360
actcgcggac acaaggccac tgtgtcgaca ggttccgtcc acttcacccc taagctgggc     420
tctgtgcaat tcagcacaga cacctcaaac gatggaggag gagatgcaga attccgacat     480
gactcaggat atgaagttca tcatcaagga ggaggagatg cagaattccg acatgactca     540
ggatatgaag ttcatcatca aggaggagga gatgcagaat tccgacatga ctcaggatat     600
gaagttcatc atcaaggagg aggagatgca gaattccgac atgactcagg atatgaagtt     660
catcatcaag gaggaggaga tgcagaattc cgacatgact caggatatga agttcatcat     720
caaggaggag gagatgcaga attccgacat gactcaggat atgaagttca tcatcaagga     780
ggaggagatg cagaattccg acatgactca ggatatgaag ttcatcatca aggaggagga     840

-continued

```
gatgcagaat tccgacatga ctcaggatat gaagttcatc atcaaggagg aggagatgca    900
gaattccgac atgactcagg atatgaagtt catcatcaag gaggaggaga tgcagaattc    960
cgacatgact caggatatga agttcatcat caaggaggag gattcgagac tggccagaac   1020
accaggttca ctcccgtggg tgtcgttcaa gacggcagca ccactcacca gaacgaaccc   1080
cagcaatggg tcctccctga ctactcgggc agggattccc acaacgttca cttggctccg   1140
gccgtggctc caaccttccc tggagagcag ttgctgttct tcagatccac tatgccaggc   1200
tgctctggat acccgaacat gaacctcgac tgtctcttgc ctcaggagtg ggtgcaacac   1260
ttctaccagg aatctgcccc agctcaaagc gacgtcgctc tgctccgttt cgttaacccc   1320
gataccggtc gcgtgctctt cgagtgtaag ttgcacaagt ctggttacgt cactgttgcc   1380
cacacaggcc agcacgacct ggtcatccct cccaacggct acttccgctt cgatagctgg   1440
gtcaaccagt tctacacact cgccccgatg ggaaacggag ccggtcgtcg cagagccttg   1500
taa                                                                 1503
```

```
<210> SEQ ID NO 49
<211> LENGTH: 2043
<212> TYPE: DNA
<213> ORGANISM: artificial sequence
<220> FEATURE:
<223> OTHER INFORMATION: synthetic nucleotide sequence encoding the
      recombinant P protein

<400> SEQUENCE: 49
atgaagccct tctcggtccc tatcctgaca gttgaggaaa tgaccaactc tagattccca     60
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc gctggaacac aaaactacac catgaacttg    240
gcctcgcaga actggaacaa ctacgatcca accgaggaaa tccccgctcc tttgggaact    300
cccgacttcg tgggacgtat ccaaggtgtc ctgacacaga ctacacgtcg cgacggctct    360
actcgcggac acaaggccac tgtgtcgaca ggttccgtcc acttcacccc taagctgggc    420
tctgtgcaat tcagcacaga cacctcaaac gatggaggag gagatgcaga attccgacat    480
gactcaggat atgaagttca tcatcaagga ggaggagatg cagaattccg acatgactca    540
ggatatgaag ttcatcatca aggaggagga gatgcagaat tccgacatga ctcaggatat    600
gaagttcatc atcaaggagg aggagatgca gaattccgac atgactcagg atatgaagtt    660
catcatcaag gaggaggaga tgcagaattc cgacatgact caggatatga agttcatcat    720
caaggaggag gagatgcaga attccgacat gactcaggat atgaagttca tcatcaagga    780
ggaggagatg cagaattccg acatgactca ggatatgaag ttcatcatca aggaggagga    840
gatgcagaat tccgacatga ctcaggatat gaagttcatc atcaaggagg aggagatgca    900
gaattccgac atgactcagg atatgaagtt catcatcaag gaggaggaga tgcagaattc    960
cgacatgact caggatatga agttcatcat caaggaggag gagatgcaga attccgacat   1020
gactcaggat atgaagttca tcatcaagga ggaggagatg cagaattccg acatgactca   1080
ggatatgaag ttcatcatca aggaggagga gatgcagaat tccgacatga ctcaggatat   1140
gaagttcatc atcaaggagg aggagatgca gaattccgac atgactcagg atatgaagtt   1200
catcatcaag gaggaggaga tgcagaattc cgacatgact caggatatga agttcatcat   1260
caaggaggag gagatgcaga attccgacat gactcaggat atgaagttca tcatcaagga   1320
```

-continued ggaggagatg cagaattccg acatgactca ggatatgaag ttcatcatca aggaggagga 1380
gatgcagaat tccgacatga ctcaggatat gaagttcatc atcaaggagg aggagatgca 1440
gaattccgac atgactcagg atatgaagtt catcatcaag gaggaggaga tgcagaattc 1500
cgacatgact caggatatga agttcatcat caaggaggag gattcgagac tggccagaac 1560
accaggttca ctcccgtggg tgtcgttcaa gacggcagca ccactcacca gaacgaaccc 1620
cagcaatggg tcctccctga ctactcgggc agggattccc acaacgttca cttggctccg 1680
gccgtggctc caaccttccc tggagagcag ttgctgttct tcagatccac tatgccaggc 1740
tgctctggat acccgaacat gaacctcgac tgtctcttgc ctcaggagtg ggtgcaacac 1800
ttctaccagg aatctgcccc agctcaaagc gacgtcgctc tgctccgttt cgttaacccc 1860
gataccggtc gcgtgctctt cgagtgtaag ttgcacaagt ctggttacgt cactgttgcc 1920
cacacaggcc agcacgacct ggtcatccct cccaacggct acttccgctt cgatagctgg 1980
gtcaaccagt tctacacact cgccccgatg ggaaacggag ccggtcgtcg cagagccttg 2040
taa 2043

<210> SEQ ID NO 50
<211> LENGTH: 3123
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 50
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaacac aaaactacac catgaacttg 240
gcctcgcaga actggaacaa ctacgatcca accgaggaaa tccccgctcc tttgggaact 300
cccgacttcg tgggacgtat ccaaggtgtc ctgacacaga ctacacgtcg cgacggctct 360
actcgcggac acaaggccac tgtgtcgaca ggttccgtcc acttcacccc taagctgggc 420
tctgtgcaat tcagcacaga cacctcaaac gatggaggag gagatgcaga attccgacat 480
gactcaggat atgaagttca tcatcaagga ggaggagatg cagaattccg acatgactca 540
ggatatgaag ttcatcatca aggaggagga gatgcagaat tccgacatga ctcaggatat 600
gaagttcatc atcaaggagg aggagatgca gaattccgac atgactcagg atatgaagtt 660
catcatcaag gaggaggaga tgcagaattc cgacatgact caggatatga agttcatcat 720
caaggaggag gagatgcaga attccgacat gactcaggat atgaagttca tcatcaagga 780
ggaggagatg cagaattccg acatgactca ggatatgaag ttcatcatca aggaggagga 840
gatgcagaat tccgacatga ctcaggatat gaagttcatc atcaaggagg aggagatgca 900
gaattccgac atgactcagg atatgaagtt catcatcaag gaggaggaga tgcagaattc 960
cgacatgact caggatatga agttcatcat caaggaggag gagatgcaga attccgacat 1020
gactcaggat atgaagttca tcatcaagga ggaggagatg cagaattccg acatgactca 1080
ggatatgaag ttcatcatca aggaggagga gatgcagaat tccgacatga ctcaggatat 1140
gaagttcatc atcaaggagg aggagatgca gaattccgac atgactcagg atatgaagtt 1200
catcatcaag gaggaggaga tgcagaattc cgacatgact caggatatga agttcatcat 1260

-continued

```
caaggaggag gagatgcaga attccgacat gactcaggat atgaagttca tcatcaagga   1320
ggaggagatg cagaattccg acatgactca ggatatgaag ttcatcatca aggaggagga   1380
gatgcagaat tccgacatga ctcaggatat gaagttcatc atcaaggagg aggagatgca   1440
gaattccgac atgactcagg atatgaagtt catcatcaag gaggaggaga tgcagaattc   1500
cgacatgact caggatatga agttcatcat caaggaggag gagatgcaga attccgacat   1560
gactcaggat atgaagttca tcatcaagga ggaggagatg cagaattccg acatgactca   1620
ggatatgaag ttcatcatca aggaggagga gatgcagaat tccgacatga ctcaggatat   1680
gaagttcatc atcaaggagg aggagatgca gaattccgac atgactcagg atatgaagtt   1740
catcatcaag gaggaggaga tgcagaattc cgacatgact caggatatga agttcatcat   1800
caaggaggag gagatgcaga attccgacat gactcaggat atgaagttca tcatcaagga   1860
ggaggagatg cagaattccg acatgactca ggatatgaag ttcatcatca aggaggagga   1920
gatgcagaat tccgacatga ctcaggatat gaagttcatc atcaaggagg aggagatgca   1980
gaattccgac atgactcagg atatgaagtt catcatcaag gaggaggaga tgcagaattc   2040
cgacatgact caggatatga agttcatcat caaggaggag gagatgcaga attccgacat   2100
gactcaggat atgaagttca tcatcaagga ggaggagatg cagaattccg acatgactca   2160
ggatatgaag ttcatcatca aggaggagga gatgcagaat tccgacatga ctcaggatat   2220
gaagttcatc atcaaggagg aggagatgca gaattccgac atgactcagg atatgaagtt   2280
catcatcaag gaggaggaga tgcagaattc cgacatgact caggatatga agttcatcat   2340
caaggaggag gagatgcaga attccgacat gactcaggat atgaagttca tcatcaagga   2400
ggaggagatg cagaattccg acatgactca ggatatgaag ttcatcatca aggaggagga   2460
gatgcagaat tccgacatga ctcaggatat gaagttcatc atcaaggagg aggagatgca   2520
gaattccgac atgactcagg atatgaagtt catcatcaag gaggaggaga tgcagaattc   2580
cgacatgact caggatatga agttcatcat caaggaggag gattcgagac tggccagaac   2640
accaggttca ctcccgtggg tgtcgttcaa gacggcagca ccactcacca gaacgaaccc   2700
cagcaatggg tcctccctga ctactcgggc agggattccc acaacgttca cttggctccg   2760
gccgtggctc caaccttccc tggagagcag ttgctgttct tcagatccac tatgccaggc   2820
tgctctggat acccgaacat gaacctcgac tgtctcttgc ctcaggagtg ggtgcaacac   2880
ttctaccagg aatctgcccc agctcaaagc gacgtcgctc tgctccgttt cgttaacccc   2940
gataccggtc gcgtgctctt cgagtgtaag ttgcacaagt ctggttacgt cactgttgcc   3000
cacacaggcc agcacgacct ggtcatccct cccaacggct acttccgctt cgatagctgg   3060
gtcaaccagt tctacacact cgccccgatg ggaaacggag ccggtcgtcg cagagccttg   3120
taa                                                                 3123
```

<210> SEQ ID NO 51
<211> LENGTH: 1008
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 51

```
atgaagccct tctcggtccc tatcctgaca gttgaggaaa tgaccaactc tagattccca     60
atcccgctgg aaaagctctt caccggaccc tcctctgctt tcgttgtgca gcctcaaaac    120
```

```
ggtcgttgca ccactgatgg tgtcctgctc ggtaccaccc agctctcacc tgtgaacatc    180
tgtactttcc gcggcgacgt cacacacatc gctggaacac aaaactacac catgaacttg    240
gcctcgcaga actggaacaa ctacgatcca accgaggaaa tccccgctcc tttgggaact    300
cccgacttcg tgggacgtat ccaaggtgtc ctgacacaga ctacacgtcg cgacggctct    360
actcgcggac acaaggccac tgtgtcgaca ggttccgtcc acttcacccc taagctgggc    420
tctgtgcaat tcagcacaga cacctcaaac gatttcgaga ctggccagaa caccaggttc    480
actcccgtgg gtgtcgttca agacggagga ggagatgcag aattccgaca tgactcagga    540
tatgaagttg gaggaggagg cagcaccact caccagaacg aaccccagca atgggtcctc    600
cctgactact cgggcaggga ttcccacaac gttcacttgg ctccggccgt ggctccaacc    660
ttccctggag agcagttgct gttcttcaga tccactatgc caggctgctc tggataccccg    720 aacatgaacc tcgactgtct cttgcctcag gagtgggtgc aacacttcta ccaggaatct    780
gccccagctc aaagcgacgt cgctctgctc cgtttcgtta accccgatac cggtcgcgtg    840
ctcttcgagt gtaagttgca caagtctggt tacgtcactg ttgcccacac aggccagcac    900
gacctggtca tccctcccaa cggctacttc cgcttcgata gctgggtcaa ccagttctac    960
acactcgccc cgatgggaaa cggagccggt cgtcgcagag ccttgtaa                1008
```

```
<210> SEQ ID NO 52
<211> LENGTH: 1413
<212> TYPE: DNA
<213> ORGANISM: artificial sequence
<220> FEATURE:
<223> OTHER INFORMATION: synthetic nucleotide sequence encoding the
      recombinant P protein

<400> SEQUENCE: 52
```

```
atgaagccct tctcggtccc tatcctgaca gttgaggaaa tgaccaactc tagattccca     60
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc gctggaacac aaaactacac catgaacttg    240
gcctcgcaga actggaacaa ctacgatcca accgaggaaa tccccgctcc tttgggaact    300
cccgacttcg tgggacgtat ccaaggtgtc ctgacacaga ctacacgtcg cgacggctct    360
actcgcggac acaaggccac tgtgtcgaca ggttccgtcc acttcacccc taagctgggc    420
tctgtgcaat tcagcacaga cacctcaaac gatttcgaga ctggccagaa caccaggttc    480
actcccgtgg gtgtcgttca agacggagga ggagatgcag aattccgaca tgactcagga    540
tatgaagttg gaggaggaga tgcagaattc cgacatgact caggatatga agttggagga    600
ggagatgcag aattccgaca tgactcagga tatgaagttg gaggaggaga tgcagaattc    660
cgacatgact caggatatga agttggagga ggagatgcag aattccgaca tgactcagga    720
tatgaagttg gaggaggaga tgcagaattc cgacatgact caggatatga agttggagga    780
ggagatgcag aattccgaca tgactcagga tatgaagttg gaggaggaga tgcagaattc    840
cgacatgact caggatatga agttggagga ggagatgcag aattccgaca tgactcagga    900
tatgaagttg gaggaggaga tgcagaattc cgacatgact caggatatga agttggagga    960
ggaggcagca ccactcacca gaacgaaccc cagcaatggg tcctccctga ctactcgggc   1020
agggattccc acaacgttca cttggctccg gccgtggctc caaccttccc tggagagcag   1080
ttgctgttct tcagatccac tatgccaggc tgctctggat acccgaacat gaacctcgac   1140
```

-continued

```
tgtctcttgc ctcaggagtg ggtgcaacac ttctaccagg aatctgcccc agctcaaagc   1200
gacgtcgctc tgctccgttt cgttaacccc gataccggtc gcgtgctctt cgagtgtaag   1260
ttgcacaagt ctggttacgt cactgttgcc cacacaggcc agcacgacct ggtcatccct   1320
cccaacggct acttccgctt cgatagctgg gtcaaccagt tctacacact cgccccgatg   1380
ggaaacggag ccggtcgtcg cagagccttg taa                                 1413
```

<210> SEQ ID NO 53
<211> LENGTH: 1863
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 53

```
atgaagccct tctcggtccc tatcctgaca gttgaggaaa tgaccaactc tagattccca     60
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc gctggaacac aaaactacac catgaacttg    240
gcctcgcaga actggaacaa ctacgatcca accgaggaaa tccccgctcc tttgggaact    300
cccgacttcg tgggacgtat ccaaggtgtc ctgacacaga ctacacgtcg cgacggctct    360
actcgcggac acaaggccac tgtgtcgaca ggttccgtcc acttcacccc taagctgggc    420
tctgtgcaat tcagcacaga cacctcaaac gatttcgaga ctggccagaa caccaggttc    480
actcccgtgg gtgtcgttca agacggagga ggagatgcag aattccgaca tgactcagga    540
tatgaagttg gaggaggaga tgcagaattc cgacatgact caggatatga agttggagga    600
ggagatgcag aattccgaca tgactcagga tatgaagttg gaggaggaga tgcagaattc    660
cgacatgact caggatatga agttggagga ggagatgcag aattccgaca tgactcagga    720
tatgaagttg gaggaggaga tgcagaattc cgacatgact caggatatga agttggagga    780
ggagatgcag aattccgaca tgactcagga tatgaagttg gaggaggaga tgcagaattc    840
cgacatgact caggatatga agttggagga ggagatgcag aattccgaca tgactcagga    900
tatgaagttg gaggaggaga tgcagaattc cgacatgact caggatatga agttggagga    960
ggagatgcag aattccgaca tgactcagga tatgaagttg gaggaggaga tgcagaattc   1020
cgacatgact caggatatga agttggagga ggagatgcag aattccgaca tgactcagga   1080
tatgaagttg gaggaggaga tgcagaattc cgacatgact caggatatga agttggagga   1140
ggagatgcag aattccgaca tgactcagga tatgaagttg gaggaggaga tgcagaattc   1200
cgacatgact caggatatga agttggagga ggagatgcag aattccgaca tgactcagga   1260
tatgaagttg gaggaggaga tgcagaattc cgacatgact caggatatga agttggagga   1320
ggagatgcag aattccgaca tgactcagga tatgaagttg gaggaggaga tgcagaattc   1380
cgacatgact caggatatga agttggagga ggaggcagca ccactcacca gaacgaaccc   1440
cagcaatggg tcctccctga ctactcgggc agggattccc acaacgttca cttggctccg   1500
gccgtggctc caaccttccc tggagagcag ttgctgttct tcagatccac tatgccaggc   1560
tgctctggat acccgaacat gaacctcgac tgtctcttgc ctcaggagtg ggtgcaacac   1620
ttctaccagg aatctgcccc agctcaaagc gacgtcgctc tgctccgttt cgttaacccc   1680
gataccggtc gcgtgctctt cgagtgtaag ttgcacaagt ctggttacgt cactgttgcc   1740
```

-continued cacacaggcc agcacgacct ggtcatccct cccaacggct acttccgctt cgatagctgg 1800
gtcaaccagt tctacacact cgccccgatg ggaaacggag ccggtcgtcg cagagccttg 1860
taa 1863

<210> SEQ ID NO 54
<211> LENGTH: 2763
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 54
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaacac aaaactacac catgaacttg 240
gcctcgcaga actggaacaa ctacgatcca accgaggaaa tccccgctcc tttgggaact 300
cccgacttcg tgggacgtat ccaaggtgtc ctgacacaga ctacacgtcg cgacggctct 360
actcgcggac acaaggccac tgtgtcgaca ggttccgtcc acttcacccc taagctgggc 420
tctgtgcaat tcagcacaga cacctcaaac gatttcgaga ctggccagaa caccaggttc 480
actcccgtgg gtgtcgttca agacggagga ggagatgcag aattccgaca tgactcagga 540
tatgaagttg gaggaggaga tgcagaattc cgacatgact caggatatga agttggagga 600
ggagatgcag aattccgaca tgactcagga tatgaagttg gaggaggaga tgcagaattc 660
cgacatgact caggatatga agttggagga ggagatgcag aattccgaca tgactcagga 720
tatgaagttg gaggaggaga tgcagaattc cgacatgact caggatatga agttggagga 780
ggagatgcag aattccgaca tgactcagga tatgaagttg gaggaggaga tgcagaattc 840
cgacatgact caggatatga agttggagga ggagatgcag aattccgaca tgactcagga 900
tatgaagttg gaggaggaga tgcagaattc cgacatgact caggatatga agttggagga 960
ggagatgcag aattccgaca tgactcagga tatgaagttg gaggaggaga tgcagaattc 1020
cgacatgact caggatatga agttggagga ggagatgcag aattccgaca tgactcagga 1080
tatgaagttg gaggaggaga tgcagaattc cgacatgact caggatatga agttggagga 1140
ggagatgcag aattccgaca tgactcagga tatgaagttg gaggaggaga tgcagaattc 1200
cgacatgact caggatatga agttggagga ggagatgcag aattccgaca tgactcagga 1260
tatgaagttg gaggaggaga tgcagaattc cgacatgact caggatatga agttggagga 1320
ggagatgcag aattccgaca tgactcagga tatgaagttg gaggaggaga tgcagaattc 1380
cgacatgact caggatatga agttggagga ggagatgcag aattccgaca tgactcagga 1440
tatgaagttg gaggaggaga tgcagaattc cgacatgact caggatatga agttggagga 1500
ggagatgcag aattccgaca tgactcagga tatgaagttg gaggaggaga tgcagaattc 1560
cgacatgact caggatatga agttggagga ggagatgcag aattccgaca tgactcagga 1620
tatgaagttg gaggaggaga tgcagaattc cgacatgact caggatatga agttggagga 1680
ggagatgcag aattccgaca tgactcagga tatgaagttg gaggaggaga tgcagaattc 1740
cgacatgact caggatatga agttggagga ggagatgcag aattccgaca tgactcagga 1800
tatgaagttg gaggaggaga tgcagaattc cgacatgact caggatatga agttggagga 1860

-continued

```
ggagatgcag aattccgaca tgactcagga tatgaagttg gaggaggaga tgcagaattc   1920
cgacatgact caggatatga agttggagga ggagatgcag aattccgaca tgactcagga   1980
tatgaagttg gaggaggaga tgcagaattc cgacatgact caggatatga agttggagga   2040
ggagatgcag aattccgaca tgactcagga tatgaagttg gaggaggaga tgcagaattc   2100
cgacatgact caggatatga agttggagga ggagatgcag aattccgaca tgactcagga   2160
tatgaagttg gaggaggaga tgcagaattc cgacatgact caggatatga agttggagga   2220
ggagatgcag aattccgaca tgactcagga tatgaagttg gaggaggaga tgcagaattc   2280
cgacatgact caggatatga agttggagga ggaggcagca ccactcacca gaacgaaccc   2340
cagcaatggg tcctccctga ctactcgggc agggattccc acaacgttca cttggctccg   2400
gccgtggctc caaccttccc tggagagcag ttgctgttct tcagatccac tatgccaggc   2460
tgctctggat acccgaacat gaacctcgac tgtctcttgc ctcaggagtg ggtgcaacac   2520
ttctaccagg aatctgcccc agctcaaagc gacgtcgctc tgctccgttt cgttaacccc   2580
gataccggtc gcgtgctctt cgagtgtaag ttgcacaagt ctggttacgt cactgttgcc   2640
cacacaggcc agcacgacct ggtcatccct cccaacggct acttccgctt cgatagctgg   2700
gtcaaccagt tctacacact cgccccgatg ggaaacggag ccggtcgtcg cagagccttg   2760
taa                                                                 2763
```

<210> SEQ ID NO 55
<211> LENGTH: 990
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 55

```
atgaagccct tctcggtccc tatcctgaca gttgaggaaa tgaccaactc tagattccca     60
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc gctggaacac aaaactacac catgaacttg    240
gcctcgcaga actggaacaa ctacgatcca accgaggaaa tccccgctcc tttgggaact    300
cccgacttcg tgggacgtat ccaaggtgtc ctgacacaga ctacacgtcg cgacggctct    360
actcgcggac acaaggccac tgtgtcgaca ggttccgtcc acttcacccc taagctgggc    420
tctgtgcaat tcagcacaga cacctcaaac gatttcgaga ctggccagaa caccaggttc    480
actcccgtgg gtgtcgttca agacggcgga ggaggagatg cagaattccg acatggagga    540
ggaagcacca ctcaccagaa cgaaccccag caatgggtcc tccctgacta ctcgggcagg    600
gattcccaca acgttcactt ggctccggcc gtggctccaa ccttccctgg agagcagttg    660
ctgttcttca gatccactat gccaggctgc tctggatacc cgaacatgaa cctcgactgt    720
ctcttgcctc aggagtgggt gcaacacttc taccaggaat ctgccccagc tcaaagcgac    780
gtcgctctgc tccgtttcgt taaccccgat accggtcgcg tgctcttcga gtgtaagttg    840
cacaagtctg gttacgtcac tgttgcccac acaggccagc acgacctggt catccctccc    900
aacggctact tccgcttcga tagctgggtc aaccagttct acacactcgc cccgatggga    960
aacggagccg gtcgtcgcag agccttgtaa                                     990
```

<210> SEQ ID NO 56

-continued

<211> LENGTH: 1233
<212> TYPE: DNA
<213> ORGANISM: artificial sequence
<220> FEATURE:
<223> OTHER INFORMATION: synthetic nucleotide sequence encoding the
recombinant P protein

<400> SEQUENCE: 56
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaacac aaaactacac catgaacttg 240
gcctcgcaga actggaacaa ctacgatcca accgaggaaa tccccgctcc tttgggaact 300
cccgacttcg tgggacgtat ccaaggtgtc ctgacacaga ctacacgtcg cgacggctct 360
actcgcggac acaaggccac tgtgtcgaca ggttccgtcc acttcacccc taagctgggc 420
tctgtgcaat tcagcacaga cacctcaaac gatttcgaga ctggccagaa caccaggttc 480
actcccgtgg gtgtcgttca agacggcgga ggaggagatg cagaattccg acatggagga 540
ggagatgcag aattccgaca tggaggagga gatgcagaat tccgacatgg aggaggagat 600
gcagaattcc gacatggagg aggagatgca gaattccgac atggaggagg agatgcagaa 660
ttccgacatg gaggaggaga tgcagaattc cgacatggag gaggagatgc agaattccga 720
catggaggag gagatgcaga attccgacat ggaggaggag atgcagaatt ccgacatgga 780
ggaggaagca ccactcacca gaacgaaccc cagcaatggg tcctccctga ctactcgggc 840
agggattccc acaacgttca cttggctccg gccgtggctc caaccttccc tggagagcag 900
ttgctgttct tcagatccac tatgccaggc tgctctggat acccgaacat gaacctcgac 960
tgtctcttgc ctcaggagtg ggtgcaacac ttctaccagg aatctgcccc agctcaaagc 1020
gacgtcgctc tgctccgttt cgttaacccc gataccggtc gcgtgctctt cgagtgtaag 1080
ttgcacaagt ctggttacgt cactgttgcc cacacaggcc agcacgacct ggtcatccct 1140
cccaacggct acttccgctt cgatagctgg gtcaaccagt tctacacact cgccccgatg 1200
ggaaacggag ccggtcgtcg cagagccttg taa 1233

<210> SEQ ID NO 57
<211> LENGTH: 1503
<212> TYPE: DNA
<213> ORGANISM: artificial sequence
<220> FEATURE:
<223> OTHER INFORMATION: synthetic nucleotide sequence encoding the
recombinant P protein

<400> SEQUENCE: 57
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaacac aaaactacac catgaacttg 240
gcctcgcaga actggaacaa ctacgatcca accgaggaaa tccccgctcc tttgggaact 300
cccgacttcg tgggacgtat ccaaggtgtc ctgacacaga ctacacgtcg cgacggctct 360
actcgcggac acaaggccac tgtgtcgaca ggttccgtcc acttcacccc taagctgggc 420
tctgtgcaat tcagcacaga cacctcaaac gatttcgaga ctggccagaa caccaggttc 480
actcccgtgg gtgtcgttca agacggcgga ggaggagatg cagaattccg acatggagga 540

```
ggagatgcag aattccgaca tggaggagga gatgcagaat tccgacatgg aggaggagat    600
gcagaattcc gacatggagg aggagatgca gaattccgac atggaggagg agatgcagaa    660
ttccgacatg gaggaggaga tgcagaattc cgacatggag gaggagatgc agaattccga    720
catggaggag gagatgcaga attccgacat ggaggaggag atgcagaatt ccgacatgga    780
ggaggagatg cagaattccg acatggagga ggagatgcag aattccgaca tggaggagga    840
gatgcagaat tccgacatgg aggaggagat gcagaattcc gacatggagg aggagatgca    900
gaattccgac atggaggagg agatgcagaa ttccgacatg gaggaggaga tgcagaattc    960
cgacatggag gaggagatgc agaattccga catggaggag gagatgcaga attccgacat   1020
ggaggaggag atgcagaatt ccgacatgga ggaggaagca ccactcacca gaacgaaccc   1080
cagcaatggg tcctccctga ctactcgggc agggattccc acaacgttca cttggctccg   1140
gccgtggctc caaccttccc tggagagcag ttgctgttct tcagatccac tatgccaggc   1200
tgctctggat acccgaacat gaacctcgac tgtctcttgc ctcaggagtg ggtgcaacac   1260
ttctaccagg aatctgcccc agctcaaagc gacgtcgctc tgctccgttt cgttaacccc   1320
gataccggtc gcgtgctctt cgagtgtaag ttgcacaagt ctggttacgt cactgttgcc   1380
cacacaggcc agcacgacct ggtcatccct cccaacggct acttccgctt cgatagctgg   1440
gtcaaccagt tctacacact cgccccgatg ggaaacggag ccggtcgtcg cagagccttg   1500
taa                                                                1503
```

<210> SEQ ID NO 58
<211> LENGTH: 2043
<212> TYPE: DNA
<213> ORGANISM: artificial sequence
<220> FEATURE:
<223> OTHER INFORMATION: synthetic nucleotide sequence encoding the
      recombinant P protein

<400> SEQUENCE: 58

```
atgaagccct tctcggtccc tatcctgaca gttgaggaaa tgaccaactc tagattccca     60
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc gctggaacac aaaactacac catgaacttg    240
gcctcgcaga actggaacaa ctacgatcca accgaggaaa tccccgctcc tttgggaact    300
cccgacttcg tgggacgtat ccaaggtgtc ctgacacaga ctacacgtcg cgacggctct    360
actcgcggac acaaggccac tgtgtcgaca ggttccgtcc acttcacccc taagctgggc    420
tctgtgcaat tcagcacaga cacctcaaac gatttcgaga ctggccagaa caccaggttc    480
actcccgtgg gtgtcgttca agacggcgga ggaggagatg cagaattccg acatggagga    540
ggagatgcag aattccgaca tggaggagga gatgcagaat tccgacatgg aggaggagat    600
gcagaattcc gacatggagg aggagatgca gaattccgac atggaggagg agatgcagaa    660
ttccgacatg gaggaggaga tgcagaattc cgacatggag gaggagatgc agaattccga    720
catggaggag gagatgcaga attccgacat ggaggaggag atgcagaatt ccgacatgga    780
ggaggagatg cagaattccg acatggagga ggagatgcag aattccgaca tggaggagga    840
gatgcagaat tccgacatgg aggaggagat gcagaattcc gacatggagg aggagatgca    900
gaattccgac atggaggagg agatgcagaa ttccgacatg gaggaggaga tgcagaattc    960
cgacatggag gaggagatgc agaattccga catggaggag gagatgcaga attccgacat   1020
```

```
ggaggaggag atgcagaatt ccgacatgga ggaggagatg cagaattccg acatggagga   1080
ggagatgcag aattccgaca tggaggagga gatgcagaat tccgacatgg aggaggagat   1140
gcagaattcc gacatggagg aggagatgca gaattccgac atggaggagg agatgcagaa   1200
ttccgacatg gaggaggaga tgcagaattc cgacatggag gaggagatgc agaattccga   1260
catggaggag gagatgcaga attccgacat ggaggaggag atgcagaatt ccgacatgga   1320
ggaggagatg cagaattccg acatggagga ggagatgcag aattccgaca tggaggagga   1380
gatgcagaat tccgacatgg aggaggagat gcagaattcc gacatggagg aggagatgca   1440
gaattccgac atggaggagg agatgcagaa ttccgacatg gaggaggaga tgcagaattc   1500
cgacatggag gaggagatgc agaattccga catggaggag gagatgcaga attccgacat   1560
ggaggaggag atgcagaatt ccgacatgga ggaggaagca ccactcacca gaacgaaccc   1620
cagcaatggg tcctccctga ctactcgggc agggattccc acaacgttca cttggctccg   1680
gccgtggctc caaccttccc tggagagcag ttgctgttct tcagatccac tatgccaggc   1740
tgctctggat acccgaacat gaacctcgac tgtctcttgc ctcaggagtg ggtgcaacac   1800
ttctaccagg aatctgcccc agctcaaagc gacgtcgctc tgctccgttt cgttaacccc   1860
gataccggtc gcgtgctctt cgagtgtaag ttgcacaagt ctggttacgt cactgttgcc   1920
cacacaggcc agcacgacct ggtcatccct cccaacggct acttccgctt cgatagctgg   1980
gtcaaccagt tctacacact cgccccgatg ggaaacggag ccggtcgtcg cagagccttg   2040
taa                                                                2043

<210> SEQ ID NO 59
<211> LENGTH: 1017
<212> TYPE: DNA
<213> ORGANISM: artificial sequence
<220> FEATURE:
<223> OTHER INFORMATION: synthetic nucleotide sequence encoding the
      recombinant P protein

<400> SEQUENCE: 59
atgaagccct tctcggtccc tatcctgaca gttgaggaaa tgaccaactc tagattccca     60
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc gctggaacac aaaactacac catgaacttg    240
gcctcgcaga actggaacaa ctacgatcca accgaggaaa tccccgctcc tttgggaact    300
cccgacttcg tgggacgtat ccaaggtgtc ctgacacaga ctacacgtcg cgacggctct    360
actcgcggac acaaggccac tgtgtcgaca ggttccgtcc acttcacccc taagctgggc    420
tctgtgcaat tcagcacaga cacctcaaac gatttcgaga ctggccagaa caccaggttc    480
actcccgtgg gtgtcgttca agacggcagc ggaggaggag atgcagaatt ccgacatgac    540
tcaggatatg aagttcatca tcaaggagga ggaaccactc accagaacga accccagcaa    600
tgggtcctcc ctgactactc gggcagggat tcccacaacg ttcacttggc tccggccgtg    660
gctccaacct tccctggaga gcagttgctg ttcttcagat ccactatgcc aggctgctct    720
ggatacccga acatgaacct cgactgtctc ttgcctcagg agtgggtgca acacttctac    780
caggaatctg ccccagctca aagcgacgtc gctctgctcc gtttcgttaa ccccgatacc    840
ggtcgcgtgc tcttcgagtg taagttgcac aagtctggtt acgtcactgt tgcccacaca    900
ggccagcacg acctggtcat ccctcccaac ggctacttcc gcttcgatag ctgggtcaac    960
```
cagttctaca cactcgcccc gatgggaaac ggagccggtc gtcgcagagc cttgtaa 1017

<210> SEQ ID NO 60
<211> LENGTH: 1503
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 60
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaacac aaaactacac catgaacttg 240
gcctcgcaga actggaacaa ctacgatcca accgaggaaa tccccgctcc tttgggaact 300
cccgacttcg tgggacgtat ccaaggtgtc ctgacacaga ctacacgtcg cgacggctct 360
actcgcggac acaaggccac tgtgtcgaca ggttccgtcc acttcacccc taagctgggc 420
tctgtgcaat tcagcacaga cacctcaaac gatttcgaga ctggccagaa caccaggttc 480
actcccgtgg gtgtcgttca agacggcagc ggaggaggag atgcagaatt ccgacatgac 540
tcaggatatg aagttcatca tcaaggagga ggagatgcag aattccgaca tgactcagga 600
tatgaagttc atcatcaagg aggaggagat gcagaattcc gacatgactc aggatatgaa 660
gttcatcatc aaggaggagg agatgcagaa ttccgacatg actcaggata tgaagttcat 720
catcaaggag gaggagatgc agaattccga catgactcag gatatgaagt tcatcatcaa 780
ggaggaggag atgcagaatt ccgacatgac tcaggatatg aagttcatca tcaaggagga 840
ggagatgcag aattccgaca tgactcagga tatgaagttc atcatcaagg aggaggagat 900
gcagaattcc gacatgactc aggatatgaa gttcatcatc aaggaggagg agatgcagaa 960
ttccgacatg actcaggata tgaagttcat catcaaggag gaggagatgc agaattccga 1020
catgactcag gatatgaagt tcatcatcaa ggaggaggaa ccactcacca gaacgaaccc 1080
cagcaatggg tcctccctga ctactcgggc agggattccc acaacgttca cttggctccg 1140
gccgtggctc caaccttccc tggagagcag ttgctgttct tcagatccac tatgccaggc 1200
tgctctggat acccgaacat gaacctcgac tgtctcttgc ctcaggagtg ggtgcaacac 1260
ttctaccagg aatctgcccc agctcaaagc gacgtcgctc tgctccgttt cgttaacccc 1320
gataccggtc gcgtgctctt cgagtgtaag ttgcacaagt ctggttacgt cactgttgcc 1380
cacacaggcc agcacgacct ggtcatccct cccaacggct acttccgctt cgatagctgg 1440
gtcaaccagt tctacacact cgccccgatg ggaaacggag ccggtcgtcg cagagccttg 1500
taa 1503

<210> SEQ ID NO 61
<211> LENGTH: 2043
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 61
atgaagccct tctcggtccc tatcctgaca gttgaggaaa tgaccaactc tagattccca 60

-continued

```
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc gctggaacac aaaactacac catgaacttg    240
gcctcgcaga actggaacaa ctacgatcca accgaggaaa tccccgctcc tttgggaact    300
cccgacttcg tgggacgtat ccaaggtgtc ctgacacaga ctacacgtcg cgacggctct    360
actcgcggac acaaggccac tgtgtcgaca ggttccgtcc acttcacccc taagctgggc    420
tctgtgcaat tcagcacaga cacctcaaac gatttcgaga ctggccagaa caccaggttc    480
actcccgtgg gtgtcgttca agacggcagc ggaggaggag atgcagaatt ccgacatgac    540
tcaggatatg aagttcatca tcaaggagga ggagatgcag aattccgaca tgactcagga    600
tatgaagttc atcatcaagg aggaggagat gcagaattcc gacatgactc aggatatgaa    660
gttcatcatc aaggaggagg agatgcagaa ttccgacatg actcaggata tgaagttcat    720
catcaaggag gaggagatgc agaattccga catgactcag gatatgaagt tcatcatcaa    780
ggaggaggag atgcagaatt ccgacatgac tcaggatatg aagttcatca tcaaggagga    840
ggagatgcag aattccgaca tgactcagga tatgaagttc atcatcaagg aggaggagat    900
gcagaattcc gacatgactc aggatatgaa gttcatcatc aaggaggagg agatgcagaa    960
ttccgacatg actcaggata tgaagttcat catcaaggag gaggagatgc agaattccga   1020
catgactcag gatatgaagt tcatcatcaa ggaggaggag atgcagaatt ccgacatgac   1080
tcaggatatg aagttcatca tcaaggagga ggagatgcag aattccgaca tgactcagga   1140
tatgaagttc atcatcaagg aggaggagat gcagaattcc gacatgactc aggatatgaa   1200
gttcatcatc aaggaggagg agatgcagaa ttccgacatg actcaggata tgaagttcat   1260
catcaaggag gaggagatgc agaattccga catgactcag gatatgaagt tcatcatcaa   1320
ggaggaggag atgcagaatt ccgacatgac tcaggatatg aagttcatca tcaaggagga   1380
ggagatgcag aattccgaca tgactcagga tatgaagttc atcatcaagg aggaggagat   1440
gcagaattcc gacatgactc aggatatgaa gttcatcatc aaggaggagg agatgcagaa   1500
ttccgacatg actcaggata tgaagttcat catcaaggag gaggagatgc agaattccga   1560
catgactcag gatatgaagt tcatcatcaa ggaggaggaa ccactcacca gaacgaaccc   1620
cagcaatggg tcctccctga ctactcgggc agggattccc acaacgttca cttggctccg   1680
gccgtggctc caaccttccc tggagagcag ttgctgttct tcagatccac tatgccaggc   1740
tgctctggat acccgaacat gaacctcgac tgtctcttgc ctcaggagtg ggtgcaacac   1800
ttctaccagg aatctgcccc agctcaaagc gacgtcgctc tgctccgttt cgttaacccc   1860
gataccggtc gcgtgctctt cgagtgtaag ttgcacaagt ctggttacgt cactgttgcc   1920
cacacaggcc agcacgacct ggtcatccct cccaacggct acttccgctt cgatagctgg   1980
gtcaaccagt tctacacact cgccccgatg ggaaacggag ccggtcgtcg cagagccttg   2040
taa                                                                 2043
```

<210> SEQ ID NO 62
<211> LENGTH: 3123
<212> TYPE: DNA
<213> ORGANISM: artificial sequence
<220> FEATURE:
<223> OTHER INFORMATION: synthetic nucleotide sequence encoding the
      recombinant P protein

<400> SEQUENCE: 62

-continued

```
atgaagccct tctcggtccc tatcctgaca gttgaggaaa tgaccaactc tagattccca     60
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc gctggaacac aaaactacac catgaacttg    240
gcctcgcaga actggaacaa ctacgatcca accgaggaaa tccccgctcc tttgggaact    300
cccgacttcg tgggacgtat ccaaggtgtc ctgacacaga ctacacgtcg cgacggctct    360
actcgcggac acaaggccac tgtgtcgaca ggttccgtcc acttcacccc taagctgggc    420
tctgtgcaat tcagcacaga cacctcaaac gatttcgaga ctggccagaa caccaggttc    480
actcccgtgg gtgtcgttca agacggcagc ggaggaggag atgcagaatt ccgacatgac    540
tcaggatatg aagttcatca tcaaggagga ggagatgcag aattccgaca tgactcagga    600
tatgaagttc atcatcaagg aggaggagat gcagaattcc gacatgactc aggatatgaa    660
gttcatcatc aaggaggagg agatgcagaa ttccgacatg actcaggata tgaagttcat    720
catcaaggag gaggagatgc agaattccga catgactcag gatatgaagt tcatcatcaa    780
ggaggaggag atgcagaatt ccgacatgac tcaggatatg aagttcatca tcaaggagga    840
ggagatgcag aattccgaca tgactcagga tatgaagttc atcatcaagg aggaggagat    900
gcagaattcc gacatgactc aggatatgaa gttcatcatc aaggaggagg agatgcagaa    960
ttccgacatg actcaggata tgaagttcat catcaaggag gaggagatgc agaattccga   1020
catgactcag gatatgaagt tcatcatcaa ggaggaggag atgcagaatt ccgacatgac   1080
tcaggatatg aagttcatca tcaaggagga ggagatgcag aattccgaca tgactcagga   1140
tatgaagttc atcatcaagg aggaggagat gcagaattcc gacatgactc aggatatgaa   1200
gttcatcatc aaggaggagg agatgcagaa ttccgacatg actcaggata tgaagttcat   1260
catcaaggag gaggagatgc agaattccga catgactcag gatatgaagt tcatcatcaa   1320
ggaggaggag atgcagaatt ccgacatgac tcaggatatg aagttcatca tcaaggagga   1380
ggagatgcag aattccgaca tgactcagga tatgaagttc atcatcaagg aggaggagat   1440
gcagaattcc gacatgactc aggatatgaa gttcatcatc aaggaggagg agatgcagaa   1500
ttccgacatg actcaggata tgaagttcat catcaaggag gaggagatgc agaattccga   1560
catgactcag gatatgaagt tcatcatcaa ggaggaggag atgcagaatt ccgacatgac   1620
tcaggatatg aagttcatca tcaaggagga ggagatgcag aattccgaca tgactcagga   1680
tatgaagttc atcatcaagg aggaggagat gcagaattcc gacatgactc aggatatgaa   1740
gttcatcatc aaggaggagg agatgcagaa ttccgacatg actcaggata tgaagttcat   1800
catcaaggag gaggagatgc agaattccga catgactcag gatatgaagt tcatcatcaa   1860
ggaggaggag atgcagaatt ccgacatgac tcaggatatg aagttcatca tcaaggagga   1920
ggagatgcag aattccgaca tgactcagga tatgaagttc atcatcaagg aggaggagat   1980
gcagaattcc gacatgactc aggatatgaa gttcatcatc aaggaggagg agatgcagaa   2040
ttccgacatg actcaggata tgaagttcat catcaaggag gaggagatgc agaattccga   2100
catgactcag gatatgaagt tcatcatcaa ggaggaggag atgcagaatt ccgacatgac   2160
tcaggatatg aagttcatca tcaaggagga ggagatgcag aattccgaca tgactcagga   2220
tatgaagttc atcatcaagg aggaggagat gcagaattcc gacatgactc aggatatgaa   2280
gttcatcatc aaggaggagg agatgcagaa ttccgacatg actcaggata tgaagttcat   2340
catcaaggag gaggagatgc agaattccga catgactcag gatatgaagt tcatcatcaa   2400
```

```
ggaggaggag atgcagaatt ccgacatgac tcaggatatg aagttcatca tcaaggagga   2460
ggagatgcag aattccgaca tgactcagga tatgaagttc atcatcaagg aggaggagat   2520
gcagaattcc gacatgactc aggatatgaa gttcatcatc aaggaggagg agatgcagaa   2580
ttccgacatg actcaggata tgaagttcat catcaaggag gaggagatgc agaattccga   2640
catgactcag gatatgaagt tcatcatcaa ggaggaggaa ccactcacca gaacgaaccc   2700
cagcaatggg tcctccctga ctactcgggc agggattccc acaacgttca cttggctccg   2760
gccgtggctc caaccttccc tggagagcag ttgctgttct tcagatccac tatgccaggc   2820
tgctctggat acccgaacat gaacctcgac tgtctcttgc ctcaggagtg ggtgcaacac   2880
ttctaccagg aatctgcccc agctcaaagc gacgtcgctc tgctccgttt cgttaacccc   2940
gataccggtc gcgtgctctt cgagtgtaag ttgcacaagt ctggttacgt cactgttgcc   3000
cacacaggcc agcacgacct ggtcatccct cccaacggct acttccgctt cgatagctgg   3060
gtcaaccagt tctacacact cgccccgatg ggaaacggag ccggtcgtcg cagagccttg   3120
taa                                                                 3123
```

<210> SEQ ID NO 63
<211> LENGTH: 999
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 63

```
atgaagccct tctcggtccc tatcctgaca gttgaggaaa tgaccaactc tagattccca     60
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc gctggaacac aaaactacac catgaacttg    240
gcctcgcaga actggaacaa ctacgatcca accgaggaaa tccccgctcc tttgggaact    300
cccgacttcg tgggacgtat ccaaggtgtc ctgacacaga ctacacgtcg cgacggctct    360
actcgcggac acaaggccac tgtgtcgaca ggttccgtcc acttcacccc taagctgggc    420
tctgtgcaat tcagcacaga cacctcaaac gatttcgaga ctggccagaa caccaggttc    480
actcccgtgg gtgtcgttca agacggcagc accggaggag gagatgcaga attccgacat    540
gactcaggag gaggaggaac tcaccagaac gaaccccagc aatgggtcct ccctgactac    600
tcgggcaggg attcccacaa cgttcacttg gctccggccg tggctccaac cttccctgga    660
gagcagttgc tgttcttcag atccactatg ccaggctgct ctggataccc gaacatgaac    720
ctcgactgtc tcttgcctca ggagtgggtg caacacttct accaggaatc tgccccagct    780
caaagcgacg tcgctctgct ccgtttcgtt aaccccgata ccggtcgcgt gctcttcgag    840
tgtaagttgc acaagtctgg ttacgtcact gttgcccaca caggccagca cgacctggtc    900
atccctccca acggctactt ccgcttcgat agctgggtca accagttcta cacactcgcc    960
ccgatgggaa acggagccgg tcgtcgcaga gccttgtaa                           999
```

<210> SEQ ID NO 64
<211> LENGTH: 1323
<212> TYPE: DNA
<213> ORGANISM: artificial sequence
<220> FEATURE:
<223> OTHER INFORMATION: synthetic nucleotide sequence encoding the -continued recombinant P protein

<400> SEQUENCE: 64
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaacac aaaactacac catgaacttg 240
gcctcgcaga actggaacaa ctacgatcca accgaggaaa tccccgctcc tttgggaact 300
cccgacttcg tgggacgtat ccaaggtgtc ctgacacaga ctacacgtcg cgacggctct 360
actcgcggac acaaggccac tgtgtcgaca ggttccgtcc acttcacccc taagctgggc 420
tctgtgcaat tcagcacaga cacctcaaac gatttcgaga ctggccagaa caccaggttc 480
actcccgtgg gtgtcgttca agacggcagc accggaggag gagatgcaga attccgacat 540
gactcaggag gaggaggaga tgcagaattc cgacatgact caggaggagg aggagatgca 600
gaattccgac atgactcagg aggaggagga gatgcagaat tccgacatga ctcaggagga 660
ggaggagatg cagaattccg acatgactca ggaggaggag gagatgcaga attccgacat 720
gactcaggag gaggaggaga tgcagaattc cgacatgact caggaggagg aggagatgca 780
gaattccgac atgactcagg aggaggagga gatgcagaat tccgacatga ctcaggagga 840
ggaggagatg cagaattccg acatgactca ggaggaggag gaactcacca gaacgaaccc 900
cagcaatggg tcctccctga ctactcgggc agggattccc acaacgttca cttggctccg 960
gccgtggctc caaccttccc tggagagcag ttgctgttct tcagatccac tatgccaggc 1020
tgctctggat acccgaacat gaacctcgac tgtctcttgc ctcaggagtg ggtgcaacac 1080
ttctaccagg aatctgcccc agctcaaagc gacgtcgctc tgctccgttt cgttaacccc 1140
gataccggtc gcgtgctctt cgagtgtaag ttgcacaagt ctggttacgt cactgttgcc 1200
cacacaggcc agcacgacct ggtcatccct cccaacggct acttccgctt cgatagctgg 1260
gtcaaccagt tctacacact cgccccgatg ggaaacggag ccggtcgtcg cagagccttg 1320
taa 1323

<210> SEQ ID NO 65
<211> LENGTH: 1683
<212> TYPE: DNA
<213> ORGANISM: artificial sequence
<220> FEATURE:
<223> OTHER INFORMATION: synthetic nucleotide sequence encoding the
recombinant P protein

<400> SEQUENCE: 65
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaacac aaaactacac catgaacttg 240
gcctcgcaga actggaacaa ctacgatcca accgaggaaa tccccgctcc tttgggaact 300
cccgacttcg tgggacgtat ccaaggtgtc ctgacacaga ctacacgtcg cgacggctct 360
actcgcggac acaaggccac tgtgtcgaca ggttccgtcc acttcacccc taagctgggc 420
tctgtgcaat tcagcacaga cacctcaaac gatttcgaga ctggccagaa caccaggttc 480
actcccgtgg gtgtcgttca agacggcagc accggaggag gagatgcaga attccgacat 540

```
gactcaggag gaggaggaga tgcagaattc cgacatgact caggaggagg aggagatgca    600
gaattccgac atgactcagg aggaggagga gatgcagaat tccgacatga ctcaggagga    660
ggaggagatg cagaattccg acatgactca ggaggaggag gagatgcaga attccgacat    720
gactcaggag gaggaggaga tgcagaattc cgacatgact caggaggagg aggagatgca    780
gaattccgac atgactcagg aggaggagga gatgcagaat tccgacatga ctcaggagga    840
ggaggagatg cagaattccg acatgactca ggaggaggag gagatgcaga attccgacat    900
gactcaggag gaggaggaga tgcagaattc cgacatgact caggaggagg aggagatgca    960
gaattccgac atgactcagg aggaggagga gatgcagaat tccgacatga ctcaggagga   1020
ggaggagatg cagaattccg acatgactca ggaggaggag gagatgcaga attccgacat   1080
gactcaggag gaggaggaga tgcagaattc cgacatgact caggaggagg aggagatgca   1140
gaattccgac atgactcagg aggaggagga gatgcagaat tccgacatga ctcaggagga   1200
ggaggagatg cagaattccg acatgactca ggaggaggag gaactcacca gaacgaaccc   1260
cagcaatggg tcctccctga ctactcgggc agggattccc acaacgttca cttggctccg   1320
gccgtggctc caaccttccc tggagagcag ttgctgttct tcagatccac tatgccaggc   1380
tgctctggat acccgaacat gaacctcgac tgtctcttgc ctcaggagtg ggtgcaacac   1440
ttctaccagg aatctgcccc agctcaaagc gacgtcgctc tgctccgttt cgttaacccc   1500
gataccggtc gcgtgctctt cgagtgtaag ttgcacaagt ctggttacgt cactgttgcc   1560
cacacaggcc agcacgacct ggtcatccct cccaacggct acttccgctt cgatagctgg   1620
gtcaaccagt tctacacact cgccccgatg ggaaacggag ccggtcgtcg cagagccttg   1680
taa                                                                 1683
```

<210> SEQ ID NO 66
<211> LENGTH: 2403
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 66

```
atgaagccct tctcggtccc tatcctgaca gttgaggaaa tgaccaactc tagattccca     60
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc gctggaacac aaaactacac catgaacttg    240
gcctcgcaga actggaacaa ctacgatcca accgaggaaa tccccgctcc tttgggaact    300
cccgacttcg tgggacgtat ccaaggtgtc ctgacacaga ctacacgtcg cgacggctct    360
actcgcggac acaaggccac tgtgtcgaca ggttccgtcc acttcacccc taagctgggc    420
tctgtgcaat tcagcacaga cacctcaaac gatttcgaga ctggccagaa caccaggttc    480
actcccgtgg gtgtcgttca agacggcagc accggaggag gagatgcaga attccgacat    540
gactcaggag gaggaggaga tgcagaattc cgacatgact caggaggagg aggagatgca    600
gaattccgac atgactcagg aggaggagga gatgcagaat tccgacatga ctcaggagga    660
ggaggagatg cagaattccg acatgactca ggaggaggag gagatgcaga attccgacat    720
gactcaggag gaggaggaga tgcagaattc cgacatgact caggaggagg aggagatgca    780
gaattccgac atgactcagg aggaggagga gatgcagaat tccgacatga ctcaggagga    840
```

```
ggaggagatg cagaattccg acatgactca ggaggaggag gagatgcaga attccgacat    900
gactcaggag gaggaggaga tgcagaattc cgacatgact caggaggagg aggagatgca    960
gaattccgac atgactcagg aggaggagga gatgcagaat tccgacatga ctcaggagga   1020
ggaggagatg cagaattccg acatgactca ggaggaggag gagatgcaga attccgacat   1080
gactcaggag gaggaggaga tgcagaattc cgacatgact caggaggagg aggagatgca   1140
gaattccgac atgactcagg aggaggagga gatgcagaat tccgacatga ctcaggagga   1200
ggaggagatg cagaattccg acatgactca ggaggaggag gagatgcaga attccgacat   1260
gactcaggag gaggaggaga tgcagaattc cgacatgact caggaggagg aggagatgca   1320
gaattccgac atgactcagg aggaggagga gatgcagaat tccgacatga ctcaggagga   1380
ggaggagatg cagaattccg acatgactca ggaggaggag gagatgcaga attccgacat   1440
gactcaggag gaggaggaga tgcagaattc cgacatgact caggaggagg aggagatgca   1500
gaattccgac atgactcagg aggaggagga gatgcagaat tccgacatga ctcaggagga   1560
ggaggagatg cagaattccg acatgactca ggaggaggag gagatgcaga attccgacat   1620
gactcaggag gaggaggaga tgcagaattc cgacatgact caggaggagg aggagatgca   1680
gaattccgac atgactcagg aggaggagga gatgcagaat tccgacatga ctcaggagga   1740
ggaggagatg cagaattccg acatgactca ggaggaggag gagatgcaga attccgacat   1800
gactcaggag gaggaggaga tgcagaattc cgacatgact caggaggagg aggagatgca   1860
gaattccgac atgactcagg aggaggagga gatgcagaat tccgacatga ctcaggagga   1920
ggaggagatg cagaattccg acatgactca ggaggaggag gaactcacca gaacgaaccc   1980
cagcaatggg tcctccctga ctactcgggc agggattccc acaacgttca cttggctccg   2040
gccgtggctc caaccttccc tggagagcag ttgctgttct tcagatccac tatgccaggc   2100
tgctctggat acccgaacat gaacctcgac tgtctcttgc ctcaggagtg ggtgcaacac   2160
ttctaccagg aatctgcccc agctcaaagc gacgtcgctc tgctccgttt cgttaacccc   2220
gataccggtc gcgtgctctt cgagtgtaag ttgcacaagt ctggttacgt cactgttgcc   2280
cacacaggcc agcacgacct ggtcatccct cccaacggct acttccgctt cgatagctgg   2340
gtcaaccagt tctacacact cgccccgatg ggaaacggag ccggtcgtcg cagagccttg   2400
taa                                                                 2403
```

<210> SEQ ID NO 67
<211> LENGTH: 1134
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 67

```
atgaagccct tctcggtccc tatcctgaca gttgaggaaa tgaccaactc tagattccca     60
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc gctggaggag gagatgcaga attccgacat    240
ggaggaggag atgcagaatt ccgacatgga ggaggagatg cagaattccg acatggagga    300
ggaggaacac aaaactacac catgaacttg gcctcgcaga actggaacaa ctacgatcca    360
accgaggaaa tccccgctcc tttgggaact cccgacttcg tgggacgtat ccaaggtgtc    420
```

```
ctgacacaga ctacacgtcg cgacggctct actcgcggac acaaggccac tgtgtcgaca    480
ggttccgtcc acttcacccc taagctgggc tctgtgcaat tcagcacaga cacctcagga    540
ggaggagatg cagaattccg acatggagga ggagatgcag aattccgaca tggaggagga    600
gatgcagaat tccgacatgg aggaggaaac gatttcgaga ctggccagaa caccaggttc    660
actcccgtgg gtgtcgttca agacggcagc accactcacc agaacgaacc ccagcaatgg    720
gtcctccctg actactcggg cagggattcc cacaacgttc acttggctcc ggccgtggct    780
ccaaccttcc ctggagagca gttgctgttc ttcagatcca ctatgccagg ctgctctgga    840
tacccgaaca tgaacctcga ctgtctcttg cctcaggagt gggtgcaaca cttctaccag    900
gaatctgccc cagctcaaag cgacgtcgct ctgctccgtt tcgttaaccc cgataccggt    960
cgcgtgctct tcgagtgtaa gttgcacaag tctggttacg tcactgttgc ccacacaggc   1020
cagcacgacc tggtcatccc tcccaacggc tacttccgct tcgatagctg ggtcaaccag   1080
ttctacacac tcgccccgat gggaaacgga gccggtcgtc gcagagcctt gtaa         1134
```

```
<210> SEQ ID NO 68
<211> LENGTH: 1692
<212> TYPE: DNA
<213> ORGANISM: artificial sequence
<220> FEATURE:
<223> OTHER INFORMATION: synthetic nucleotide sequence encoding the
      recombinant P protein

<400> SEQUENCE: 68
```

```
atgaagccct tctcggtccc tatcctgaca gttgaggaaa tgaccaactc tagattccca     60
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc gctggaggag gagatgcaga attccgacat    240
gactcaggag gaggaggaga tgcagaattc cgacatgact caggaggagg aggagatgca    300
gaattccgac atgactcagg aggaggagga gatgcagaat tccgacatga ctcaggagga    360
ggaggagatg cagaattccg acatgactca ggaggaggag gagatgcaga attccgacat    420
gactcaggag gaggaggaga tgcagaattc cgacatgact caggaggagg aggagatgca    480
gaattccgac atgactcagg aggaggagga gatgcagaat tccgacatga ctcaggagga    540
ggaggagatg cagaattccg acatgactca ggaggaggag gaggaacaca aaactacacc    600
atgaacttgg cctcgcagaa ctggaacaac tacgatccaa ccgaggaaat ccccgctcct    660
ttgggaactc ccgacttcgt gggacgtatc caaggtgtcc tgacacagac tacacgtcgc    720
gacggctcta ctcgcggaca caaggccact gtgtcgacag gttccgtcca cttcacccct    780
aagctgggct ctgtgcaatt cagcacagac acctcaggag gaggagatgc agaattccga    840
catgactcag gaggaggagg agatgcagaa ttccgacatg actcaggagg aggaggagat    900
gcagaattcc gacatgactc aggaggagga ggagatgcag aattccgaca tgactcagga    960
ggaggaggag atgcagaatt ccgacatgac tcaggaggag gaggagatgc agaattccga   1020
catgactcag gaggaggagg agatgcagaa ttccgacatg actcaggagg aggaggagat   1080
gcagaattcc gacatgactc aggaggagga ggagatgcag aattccgaca tgactcagga   1140
ggaggaggag atgcagaatt ccgacatgac tcaggaggag gaggaaacga tttcgagact   1200
ggccagaaca ccaggttcac tcccgtgggt gtcgttcaag acggcagcac cactcaccag   1260
aacgaacccc agcaatgggt cctccctgac tactcgggca gggattccca caacgttcac   1320
```

```
ttggctccgg ccgtggctcc aaccttccct ggagagcagt tgctgttctt cagatccact   1380
atgccaggct gctctggata cccgaacatg aacctcgact gtctcttgcc tcaggagtgg   1440
gtgcaacact tctaccagga atctgcccca gctcaaagcg acgtcgctct gctccgtttc   1500
gttaaccccg ataccggtcg cgtgctcttc gagtgtaagt tgcacaagtc tggttacgtc   1560
actgttgccc acacaggcca gcacgacctg gtcatccctc ccaacggcta cttccgcttc   1620
gatagctggg tcaaccagtt ctacacactc gccccgatgg gaaacggagc cggtcgtcgc   1680
agagccttgt aa                                                       1692
```

```
<210> SEQ ID NO 69
<211> LENGTH: 2772
<212> TYPE: DNA
<213> ORGANISM: artificial sequence
<220> FEATURE:
<223> OTHER INFORMATION: synthetic nucleotide sequence encoding the
      recombinant P protein

<400> SEQUENCE: 69
atgaagccct tctcggtccc tatcctgaca gttgaggaaa tgaccaactc tagattccca     60
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc gctggaggag gagatgcaga attccgacat    240
gactcaggat atgaagttgg aggaggagat gcagaattcc gacatgactc aggatatgaa    300
gttggaggag gagatgcaga attccgacat gactcaggat atgaagttgg aggaggagat    360
gcagaattcc gacatgactc aggatatgaa gttggaggag gagatgcaga attccgacat    420
gactcaggat atgaagttgg aggaggagat gcagaattcc gacatgactc aggatatgaa    480
gttggaggag gagatgcaga attccgacat gactcaggat atgaagttgg aggaggagat    540
gcagaattcc gacatgactc aggatatgaa gttggaggag gagatgcaga attccgacat    600
gactcaggat atgaagttgg aggaggagat gcagaattcc gacatgactc aggatatgaa    660
gttggaggag gagatgcaga attccgacat gactcaggat atgaagttgg aggaggagat    720
gcagaattcc gacatgactc aggatatgaa gttggaggag gagatgcaga attccgacat    780
gactcaggat atgaagttgg aggaggagat gcagaattcc gacatgactc aggatatgaa    840
gttggaggag gagatgcaga attccgacat gactcaggat atgaagttgg aggaggagat    900
gcagaattcc gacatgactc aggatatgaa gttggaggag gagatgcaga attccgacat    960
gactcaggat atgaagttgg aggaggagat gcagaattcc gacatgactc aggatatgaa   1020
gttggaggag gagatgcaga attccgacat gactcaggat atgaagttgg aggaggagat   1080
gcagaattcc gacatgactc aggatatgaa gttggaggag gaggaacaca aaactacacc   1140
atgaacttgg cctcgcagaa ctggaacaac tacgatccaa ccgaggaaat ccccgctcct   1200
ttgggaactc ccgacttcgt gggacgtatc caaggtgtcc tgacacagac tacacgtcgc   1260
gacggctcta ctcgcggaca caaggccact gtgtcgacag gttccgtcca cttcacccct   1320
aagctgggct ctgtgcaatt cagcacagac acctcaggag gaggagatgc agaattccga   1380
catgactcag gatatgaagt tggaggagga gatgcagaat tccgacatga ctcaggatat   1440
gaagttggag gaggagatgc agaattccga catgactcag gatatgaagt tggaggagga   1500
gatgcagaat tccgacatga ctcaggatat gaagttggag gaggagatgc agaattccga   1560
catgactcag gatatgaagt tggaggagga gatgcagaat tccgacatga ctcaggatat   1620
```

-continued gaagttggag gaggagatgc agaattccga catgactcag gatatgaagt tggaggagga 1680
gatgcagaat tccgacatga ctcaggatat gaagttggag gaggagatgc agaattccga 1740
catgactcag gatatgaagt tggaggagga gatgcagaat tccgacatga ctcaggatat 1800
gaagttggag gaggagatgc agaattccga catgactcag gatatgaagt tggaggagga 1860
gatgcagaat tccgacatga ctcaggatat gaagttggag gaggagatgc agaattccga 1920
catgactcag gatatgaagt tggaggagga gatgcagaat tccgacatga ctcaggatat 1980
gaagttggag gaggagatgc agaattccga catgactcag gatatgaagt tggaggagga 2040
gatgcagaat tccgacatga ctcaggatat gaagttggag gaggagatgc agaattccga 2100
catgactcag gatatgaagt tggaggagga gatgcagaat tccgacatga ctcaggatat 2160
gaagttggag gaggagatgc agaattccga catgactcag gatatgaagt tggaggagga 2220
gatgcagaat tccgacatga ctcaggatat gaagttggag gaggaaacga tttcgagact 2280
ggccagaaca ccaggttcac tcccgtgggt gtcgttcaag acggcagcac cactcaccag 2340
aacgaacccc agcaatgggt cctccctgac tactcgggca gggattccca caacgttcac 2400
ttggctccgg ccgtggctcc aaccttccct ggagagcagt tgctgttctt cagatccact 2460
atgccaggct gctctggata cccgaacatg aacctcgact gtctcttgcc tcaggagtgg 2520
gtgcaacact tctaccagga atctgcccca gctcaaagcg acgtcgctct gctccgtttc 2580
gttaaccccg ataccggtcg cgtgctcttc gagtgtaagt tgcacaagtc tggttacgtc 2640
actgttgccc acacaggcca gcacgacctg gtcatccctc ccaacggcta cttccgcttc 2700
gatagctggg tcaaccagtt ctacacactc gccccgatgg gaaacggagc cggtcgtcgc 2760
agagccttgt aa 2772

<210> SEQ ID NO 70
<211> LENGTH: 5292
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 70
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaggag gagatgcaga attccgacat 240
gactcaggat atgaagttca tcatcaagga ggaggagatg cagaattccg acatgactca 300
ggatatgaag ttcatcatca aggaggagga gatgcagaat tccgacatga ctcaggatat 360
gaagttcatc atcaaggagg aggagatgca gaattccgac atgactcagg atatgaagtt 420
catcatcaag gaggaggaga tgcagaattc cgacatgact caggatatga agttcatcat 480
caaggaggag gagatgcaga attccgacat gactcaggat atgaagttca tcatcaagga 540
ggaggagatg cagaattccg acatgactca ggatatgaag ttcatcatca aggaggagga 600
gatgcagaat tccgacatga ctcaggatat gaagttcatc atcaaggagg aggagatgca 660
gaattccgac atgactcagg atatgaagtt catcatcaag gaggaggaga tgcagaattc 720
cgacatgact caggatatga agttcatcat caaggaggag gagatgcaga attccgacat 780
gactcaggat atgaagttca tcatcaagga ggaggagatg cagaattccg acatgactca 840

-continued

```
ggatatgaag ttcatcatca aggaggagga gatgcagaat tccgacatga ctcaggatat    900
gaagttcatc atcaaggagg aggagatgca gaattccgac atgactcagg atatgaagtt    960
catcatcaag gaggaggaga tgcagaattc cgacatgact caggatatga agttcatcat   1020
caaggaggag gagatgcaga attccgacat gactcaggat atgaagttca tcatcaagga   1080
ggaggagatg cagaattccg acatgactca ggatatgaag ttcatcatca aggaggagga   1140
gatgcagaat tccgacatga ctcaggatat gaagttcatc atcaaggagg aggagatgca   1200
gaattccgac atgactcagg atatgaagtt catcatcaag gaggaggaga tgcagaattc   1260
cgacatgact caggatatga agttcatcat caaggaggag gagatgcaga attccgacat   1320
gactcaggat atgaagttca tcatcaagga ggaggagatg cagaattccg acatgactca   1380
ggatatgaag ttcatcatca aggaggagga gatgcagaat tccgacatga ctcaggatat   1440
gaagttcatc atcaaggagg aggagatgca gaattccgac atgactcagg atatgaagtt   1500
catcatcaag gaggaggaga tgcagaattc cgacatgact caggatatga agttcatcat   1560
caaggaggag gagatgcaga attccgacat gactcaggat atgaagttca tcatcaagga   1620
ggaggagatg cagaattccg acatgactca ggatatgaag ttcatcatca aggaggagga   1680
gatgcagaat tccgacatga ctcaggatat gaagttcatc atcaaggagg aggagatgca   1740
gaattccgac atgactcagg atatgaagtt catcatcaag gaggaggaga tgcagaattc   1800
cgacatgact caggatatga agttcatcat caaggaggag gagatgcaga attccgacat   1860
gactcaggat atgaagttca tcatcaagga ggaggagatg cagaattccg acatgactca   1920
ggatatgaag ttcatcatca aggaggagga gatgcagaat tccgacatga ctcaggatat   1980
gaagttcatc atcaaggagg aggagatgca gaattccgac atgactcagg atatgaagtt   2040
catcatcaag gaggaggaga tgcagaattc cgacatgact caggatatga agttcatcat   2100
caaggaggag gagatgcaga attccgacat gactcaggat atgaagttca tcatcaagga   2160
ggaggagatg cagaattccg acatgactca ggatatgaag ttcatcatca aggaggagga   2220
gatgcagaat tccgacatga ctcaggatat gaagttcatc atcaaggagg aggagatgca   2280
gaattccgac atgactcagg atatgaagtt catcatcaag gaggaggaga tgcagaattc   2340
cgacatgact caggatatga agttcatcat caaggaggag gaggaacaca aaactacacc   2400
atgaacttgg cctcgcagaa ctggaacaac tacgatccaa ccgaggaaat ccccgctcct   2460
ttgggaactc ccgacttcgt gggacgtatc caaggtgtcc tgacacagac tacacgtcgc   2520
gacggctcta ctcgcggaca caaggccact gtgtcgacag gttccgtcca cttcacccct   2580
aagctgggct ctgtgcaatt cagcacagac acctcaggag gaggagatgc agaattccga   2640
catgactcag gatatgaagt tcatcatcaa ggaggaggag atgcagaatt ccgacatgac   2700
tcaggatatg aagttcatca tcaaggagga ggagatgcag aattccgaca tgactcagga   2760
tatgaagttc atcatcaagg aggaggagat gcagaattcc gacatgactc aggatatgaa   2820
gttcatcatc aaggaggagg agatgcagaa ttccgacatg actcaggata tgaagttcat   2880
catcaaggag gaggagatgc agaattccga catgactcag gatatgaagt tcatcatcaa   2940
ggaggaggag atgcagaatt ccgacatgac tcaggatatg aagttcatca tcaaggagga   3000
ggagatgcag aattccgaca tgactcagga tatgaagttc atcatcaagg aggaggagat   3060
gcagaattcc gacatgactc aggatatgaa gttcatcatc aaggaggagg agatgcagaa   3120
ttccgacatg actcaggata tgaagttcat catcaaggag gaggagatgc agaattccga   3180
catgactcag gatatgaagt tcatcatcaa ggaggaggag atgcagaatt ccgacatgac   3240
```

```
tcaggatatg aagttcatca tcaaggagga ggagatgcag aattccgaca tgactcagga   3300
tatgaagttc atcatcaagg aggaggagat gcagaattcc gacatgactc aggatatgaa   3360
gttcatcatc aaggaggagg agatgcagaa ttccgacatg actcaggata tgaagttcat   3420
catcaaggag gaggagatgc agaattccga catgactcag gatatgaagt tcatcatcaa   3480
ggaggaggag atgcagaatt ccgacatgac tcaggatatg aagttcatca tcaaggagga   3540
ggagatgcag aattccgaca tgactcagga tatgaagttc atcatcaagg aggaggagat   3600
gcagaattcc gacatgactc aggatatgaa gttcatcatc aaggaggagg agatgcagaa   3660
ttccgacatg actcaggata tgaagttcat catcaaggag gaggagatgc agaattccga   3720
catgactcag gatatgaagt tcatcatcaa ggaggaggag atgcagaatt ccgacatgac   3780
tcaggatatg aagttcatca tcaaggagga ggagatgcag aattccgaca tgactcagga   3840
tatgaagttc atcatcaagg aggaggagat gcagaattcc gacatgactc aggatatgaa   3900
gttcatcatc aaggaggagg agatgcagaa ttccgacatg actcaggata tgaagttcat   3960
catcaaggag gaggagatgc agaattccga catgactcag gatatgaagt tcatcatcaa   4020
ggaggaggag atgcagaatt ccgacatgac tcaggatatg aagttcatca tcaaggagga   4080
ggagatgcag aattccgaca tgactcagga tatgaagttc atcatcaagg aggaggagat   4140
gcagaattcc gacatgactc aggatatgaa gttcatcatc aaggaggagg agatgcagaa   4200
ttccgacatg actcaggata tgaagttcat catcaaggag gaggagatgc agaattccga   4260
catgactcag gatatgaagt tcatcatcaa ggaggaggag atgcagaatt ccgacatgac   4320
tcaggatatg aagttcatca tcaaggagga ggagatgcag aattccgaca tgactcagga   4380
tatgaagttc atcatcaagg aggaggagat gcagaattcc gacatgactc aggatatgaa   4440
gttcatcatc aaggaggagg agatgcagaa ttccgacatg actcaggata tgaagttcat   4500
catcaaggag gaggagatgc agaattccga catgactcag gatatgaagt tcatcatcaa   4560
ggaggaggag atgcagaatt ccgacatgac tcaggatatg aagttcatca tcaaggagga   4620
ggagatgcag aattccgaca tgactcagga tatgaagttc atcatcaagg aggaggagat   4680
gcagaattcc gacatgactc aggatatgaa gttcatcatc aaggaggagg agatgcagaa   4740
ttccgacatg actcaggata tgaagttcat catcaaggag gaggaaacga tttcgagact   4800
ggccagaaca ccaggttcac tcccgtgggt gtcgttcaag acggcagcac cactcaccag   4860
aacgaacccc agcaatgggt cctccctgac tactcgggca gggattccca caacgttcac   4920
ttggctccgg ccgtggctcc aaccttccct ggagagcagt tgctgttctt cagatccact   4980
atgccaggct gctctggata cccgaacatg aacctcgact gtctcttgcc tcaggagtgg   5040
gtgcaacact tctaccagga atctgcccca gctcaaagcg acgtcgctct gctccgtttc   5100
gttaaccccg ataccggtcg cgtgctcttc gagtgtaagt tgcacaagtc tggttacgtc   5160
actgttgccc acacaggcca gcacgacctg gtcatccctc ccaacggcta cttccgcttc   5220
gatagctggg tcaaccagtt ctacacactc gccccgatgg gaaacggagc cggtcgtcgc   5280
agagccttgt aa                                                      5292
```

<210> SEQ ID NO 71
<211> LENGTH: 1044
<212> TYPE: DNA
<213> ORGANISM: artificial sequence
<220> FEATURE:
<223> OTHER INFORMATION: synthetic nucleotide sequence encoding the
      recombinant P protein

<400> SEQUENCE: 71
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc ggaggaggag atgcagaatt ccgacatgga 240
ggaggagctg gaacacaaaa ctacaccatg aacttggcct cgcagaactg gaacaactac 300
gatccaaccg aggaaatccc cgctcctttg ggaactcccg acttcgtggg acgtatccaa 360
ggtgtcctga cacagactac acgtcgcgac ggctctactc gcggacacaa ggccactgtg 420
tcgacaggtt ccgtccactt cacccctaag ctgggctctg tgcaattcag cacagacacc 480
ggaggaggag atgcagaatt ccgacatgac tcaggatatg aagttggagg aggatcaaac 540
gatttcgaga ctggccagaa caccaggttc actcccgtgg gtgtcgttca agacggcagc 600
accactcacc agaacgaacc ccagcaatgg gtcctccctg actactcggg cagggattcc 660
cacaacgttc acttggctcc ggccgtggct ccaaccttcc ctggagagca gttgctgttc 720
ttcagatcca ctatgccagg ctgctctgga tacccgaaca tgaacctcga ctgtctcttg 780
cctcaggagt gggtgcaaca cttctaccag gaatctgccc cagctcaaag cgacgtcgct 840
ctgctccgtt tcgttaaccc cgataccggt cgcgtgctct tcgagtgtaa gttgcacaag 900
tctggttacg tcactgttgc ccacacaggc cagcacgacc tggtcatccc tcccaacggc 960
tacttccgct tcgatagctg ggtcaaccag ttctacacac tcgccccgat gggaaacgga 1020
gccggtcgtc gcagagcctt gtaa 1044

<210> SEQ ID NO 72
<211> LENGTH: 1161
<212> TYPE: DNA
<213> ORGANISM: artificial sequence
<220> FEATURE:
<223> OTHER INFORMATION: synthetic nucleotide sequence encoding the
recombinant P protein

<400> SEQUENCE: 72
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaggag gagatgcaga attccgacat 240
gactcaggag gaggaggaga tgcagaattc cgacatgact caggaggagg aggagatgca 300
gaattccgac atgactcagg aggaggagga ggaacacaaa actacaccat gaacttggcc 360
tcgcagaact ggaacaacta cgatccaacc gaggaaatcc ccgctccttt gggaactccc 420
gacttcgtgg gacgtatcca aggtgtcctg acacagacta cacgtcgcga cggctctact 480
cgcggacaca aggccactgt gtcgacaggt tccgtccact tcacccctaa gctgggctct 540
gtgcaattca gcacagacac ctcaggagga ggagatgcag aattccgaca tggaggagga 600
gatgcagaat tccgacatgg aggaggagat gcagaattcc gacatggagg aggaaacgat 660
ttcgagactg gccagaacac caggttcact cccgtgggtg tcgttcaaga cggcagcacc 720
actcaccaga acgaacccca gcaatgggtc ctccctgact actcgggcag ggattcccac 780
aacgttcact tggctccggc cgtggctcca accttccctg gagagcagtt gctgttcttc 840
agatccacta tgccaggctg ctctggatac ccgaacatga acctcgactg tctcttgcct 900

```
caggagtggg tgcaacactt ctaccaggaa tctgccccag ctcaaagcga cgtcgctctg    960
ctccgtttcg ttaaccccga taccggtcgc gtgctcttcg agtgtaagtt gcacaagtct   1020
ggttacgtca ctgttgccca cacaggccag cacgacctgg tcatccctcc caacggctac   1080
ttccgcttcg atagctgggt caaccagttc tacacactcg ccccgatggg aaacggagcc   1140
ggtcgtcgca gagccttgta a                                             1161
```

<210> SEQ ID NO 73
<211> LENGTH: 1782
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 73

```
atgaagccct tctcggtccc tatcctgaca gttgaggaaa tgaccaactc tagattccca     60
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc gctggaggag gaggagatgc agaattccga    240
catgactcag gatatgaagt tcatcatcaa ggaggaggag atgcagaatt ccgacatgac    300
tcaggatatg aagttcatca tcaaggagga ggagatgcag aattccgaca tgactcagga    360
tatgaagttc atcatcaagg aggaggagat gcagaattcc gacatgactc aggatatgaa    420
gttcatcatc aaggaggagg agatgcagaa ttccgacatg actcaggata tgaagttcat    480
catcaaggag gaggagatgc agaattccga catgactcag gatatgaagt tcatcatcaa    540
ggaggaggag atgcagaatt ccgacatgac tcaggatatg aagttcatca tcaaggagga    600
ggagatgcag aattccgaca tgactcagga tatgaagttc atcatcaagg aggaggagat    660
gcagaattcc gacatgactc aggatatgaa gttcatcatc aaggaggagg agatgcagaa    720
ttccgacatg actcaggata tgaagttcat catcaaggag gaggaacaca aaactacacc    780
atgaacttgg cctcgcagaa ctggaacaac tacgatccaa ccgaggaaat ccccgctcct    840
ttgggaactc ccgacttcgt gggacgtatc caaggtgtcc tgacacagac tacacgtcgc    900
gacggctcta ctcgcggaca caaggccact gtgtcgacag gttccgtcca cttcacccct    960
aagctgggct ctgtgcaatt cagcacagac acctcaggag gaggagatgc agaattccga   1020
catggaggag gagatgcaga attccgacat ggaggaggag atgcagaatt ccgacatgga   1080
ggaggagatg cagaattccg acatggagga ggagatgcag aattccgaca tggaggagga   1140
gatgcagaat tccgacatgg aggaggagat gcagaattcc gacatggagg aggagatgca   1200
gaattccgac atggaggagg agatgcagaa ttccgacatg gaggaggaga tgcagaattc   1260
cgacatggag gaggaaacga tttcgagact ggccagaaca ccaggttcac tcccgtgggt   1320
gtcgttcaag acggcagcac cactcaccag aacgaacccc agcaatgggt cctccctgac   1380
tactcgggca gggattccca caacgttcac ttggctccgg ccgtggctcc aaccttccct   1440
ggagagcagt tgctgttctt cagatccact atgccaggct gctctggata cccgaacatg   1500
aacctcgact gtctcttgcc tcaggagtgg gtgcaacact tctaccagga atctgcccca   1560
gctcaaagcg acgtcgctct gctccgtttc gttaaccccg ataccggtcg cgtgctcttc   1620
gagtgtaagt tgcacaagtc tggttacgtc actgttgccc acacaggcca gcacgacctg   1680
gtcatccctc ccaacggcta cttccgcttc gatagctggg tcaaccagtt ctacacactc   1740
```
gccccgatgg gaaacggagc cggtcgtcgc agagccttgt aa 1782

<210> SEQ ID NO 74
<211> LENGTH: 2772
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 74
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaggag gaggagatgc agaattccga 240
catgactcag gaggaggagg agatgcagaa ttccgacatg actcaggagg aggaggagat 300
gcagaattcc gacatgactc aggaggagga ggagatgcag aattccgaca tgactcagga 360
ggaggaggag atgcagaatt ccgacatgac tcaggaggag gaggagatgc agaattccga 420
catgactcag gaggaggagg agatgcagaa ttccgacatg actcaggagg aggaggagat 480
gcagaattcc gacatgactc aggaggagga ggagatgcag aattccgaca tgactcagga 540
ggaggaggag atgcagaatt ccgacatgac tcaggaggag gaggagatgc agaattccga 600
catgactcag gaggaggagg agatgcagaa ttccgacatg actcaggagg aggaggagat 660
gcagaattcc gacatgactc aggaggagga ggagatgcag aattccgaca tgactcagga 720
ggaggaggag atgcagaatt ccgacatgac tcaggaggag gaggagatgc agaattccga 780
catgactcag gaggaggagg agatgcagaa ttccgacatg actcaggagg aggaggagat 840
gcagaattcc gacatgactc aggaggagga ggagatgcag aattccgaca tgactcagga 900
ggaggaggag atgcagaatt ccgacatgac tcaggaggag gaggaacaca aaactacacc 960
atgaacttgg cctcgcagaa ctggaacaac tacgatccaa ccgaggaaat ccccgctcct 1020
ttgggaactc ccgacttcgt gggacgtatc caaggtgtcc tgacacagac tacacgtcgc 1080
gacggctcta ctcgcggaca caaggccact gtgtcgacag gttccgtcca cttcacccct 1140
aagctgggct ctgtgcaatt cagcacagac acctcaaacg gaggaggaga tgcagaattc 1200
cgacatgact caggatatga agttcatcat caaggaggag gagatgcaga attccgacat 1260
gactcaggat atgaagttca tcatcaagga ggaggagatg cagaattccg acatgactca 1320
ggatatgaag ttcatcatca aggaggagga gatgcagaat tccgacatga ctcaggatat 1380
gaagttcatc atcaaggagg aggagatgca gaattccgac atgactcagg atatgaagtt 1440
catcatcaag gaggaggaga tgcagaattc cgacatgact caggatatga agttcatcat 1500
caaggaggag gagatgcaga attccgacat gactcaggat atgaagttca tcatcaagga 1560
ggaggagatg cagaattccg acatgactca ggatatgaag ttcatcatca aggaggagga 1620
gatgcagaat tccgacatga ctcaggatat gaagttcatc atcaaggagg aggagatgca 1680
gaattccgac atgactcagg atatgaagtt catcatcaag gaggaggaga tgcagaattc 1740
cgacatgact caggatatga agttcatcat caaggaggag gagatgcaga attccgacat 1800
gactcaggat atgaagttca tcatcaagga ggaggagatg cagaattccg acatgactca 1860
ggatatgaag ttcatcatca aggaggagga gatgcagaat tccgacatga ctcaggatat 1920
gaagttcatc atcaaggagg aggagatgca gaattccgac atgactcagg atatgaagtt 1980
catcatcaag gaggaggaga tgcagaattc cgacatgact caggatatga agttcatcat 2040
caaggaggag gagatgcaga attccgacat gactcaggat atgaagttca tcatcaagga 2100
ggaggagatg cagaattccg acatgactca ggatatgaag ttcatcatca aggaggagga 2160
gatgcagaat tccgacatga ctcaggatat gaagttcatc atcaaggagg aggagatgca 2220
gaattccgac atgactcagg atatgaagtt catcatcaag gaggaggaga tttcgagact 2280
ggccagaaca ccaggttcac tcccgtgggt gtcgttcaag acggcagcac cactcaccag 2340
aacgaacccc agcaatgggt cctccctgac tactcgggca gggattccca caacgttcac 2400
ttggctccgg ccgtggctcc aaccttccct ggagagcagt tgctgttctt cagatccact 2460
atgccaggct gctctggata cccgaacatg aacctcgact gtctcttgcc tcaggagtgg 2520
gtgcaacact tctaccagga atctgcccca gctcaaagcg acgtcgctct gctccgtttc 2580
gttaaccccg ataccggtcg cgtgctcttc gagtgtaagt tgcacaagtc tggttacgtc 2640
actgttgccc acacaggcca gcacgacctg gtcatccctc ccaacggcta cttccgcttc 2700
gatagctggg tcaaccagtt ctacacactc gccccgatgg gaaacggagc cggtcgtcgc 2760
agagccttgt aa 2772

<210> SEQ ID NO 75
<211> LENGTH: 3942
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 75
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaacag gaggaggaga tgcagaattc 240
cgacatgact caggatatga agttcatcat caaggaggag gagatgcaga attccgacat 300
gactcaggat atgaagttca tcatcaagga ggaggagatg cagaattccg acatgactca 360
ggatatgaag ttcatcatca aggaggagga gatgcagaat tccgacatga ctcaggatat 420
gaagttcatc atcaaggagg aggagatgca gaattccgac atgactcagg atatgaagtt 480
catcatcaag gaggaggaga tgcagaattc cgacatgact caggatatga agttcatcat 540
caaggaggag gagatgcaga attccgacat gactcaggat atgaagttca tcatcaagga 600
ggaggagatg cagaattccg acatgactca ggatatgaag ttcatcatca aggaggagga 660
gatgcagaat tccgacatga ctcaggatat gaagttcatc atcaaggagg aggagatgca 720
gaattccgac atgactcagg atatgaagtt catcatcaag gaggaggaga tgcagaattc 780
cgacatgact caggatatga agttcatcat caaggaggag gagatgcaga attccgacat 840
gactcaggat atgaagttca tcatcaagga ggaggagatg cagaattccg acatgactca 900
ggatatgaag ttcatcatca aggaggagga gatgcagaat tccgacatga ctcaggatat 960
gaagttcatc atcaaggagg aggagatgca gaattccgac atgactcagg atatgaagtt 1020
catcatcaag gaggaggaga tgcagaattc cgacatgact caggatatga agttcatcat 1080
caaggaggag gagatgcaga attccgacat gactcaggat atgaagttca tcatcaagga 1140
ggaggagatg cagaattccg acatgactca ggatatgaag ttcatcatca aggaggagga 1200
gatgcagaat tccgacatga ctcaggatat gaagttcatc atcaaggagg aggagatgca 1260
gaattccgac atgactcagg atatgaagtt catcatcaag gaggaggaga tgcagaattc 1320
cgacatgact caggatatga agttcatcat caaggaggag gagatgcaga attccgacat 1380
gactcaggat atgaagttca tcatcaagga ggaggagatg cagaattccg acatgactca 1440
ggatatgaag ttcatcatca aggaggagga gatgcagaat tccgacatga ctcaggatat 1500
gaagttcatc atcaaggagg aggagatgca gaattccgac atgactcagg atatgaagtt 1560
catcatcaag gaggaggaga tgcagaattc cgacatgact caggatatga agttcatcat 1620
caaggaggag gagatgcaga attccgacat gactcaggat atgaagttca tcatcaagga 1680
ggaggagatg cagaattccg acatgactca ggatatgaag ttcatcatca aggaggagga 1740
gatgcagaat tccgacatga ctcaggatat gaagttcatc atcaaggagg aggagatgca 1800
gaattccgac atgactcagg atatgaagtt catcatcaag gaggaggaca aaactacacc 1860
atgaacttgg cctcgcagaa ctggaacaac tacgatccaa ccgaggaaat ccccgctcct 1920
ttgggaactc ccgacttcgt gggacgtatc caaggtgtcc tgacacagac tacacgtcgc 1980
gacggctcta ctcgcggaca caaggccact gtgtcgacag gttccgtcca cttcacccct 2040
aagctgggct ctgtgcaatt cagcacagac acctcaaacg atggaggagg agatgcagaa 2100
ttccgacatg actcaggata tgaagttgga ggaggagatg cagaattccg acatgactca 2160
ggatatgaag ttggaggagg agatgcagaa ttccgacatg actcaggata tgaagttgga 2220
ggaggagatg cagaattccg acatgactca ggatatgaag ttggaggagg agatgcagaa 2280
ttccgacatg actcaggata tgaagttgga ggaggagatg cagaattccg acatgactca 2340
ggatatgaag ttggaggagg agatgcagaa ttccgacatg actcaggata tgaagttgga 2400
ggaggagatg cagaattccg acatgactca ggatatgaag ttggaggagg agatgcagaa 2460
ttccgacatg actcaggata tgaagttgga ggaggagatg cagaattccg acatgactca 2520
ggatatgaag ttggaggagg agatgcagaa ttccgacatg actcaggata tgaagttgga 2580
ggaggagatg cagaattccg acatgactca ggatatgaag ttggaggagg agatgcagaa 2640
ttccgacatg actcaggata tgaagttgga ggaggagatg cagaattccg acatgactca 2700
ggatatgaag ttggaggagg agatgcagaa ttccgacatg actcaggata tgaagttgga 2760
ggaggagatg cagaattccg acatgactca ggatatgaag ttggaggagg agatgcagaa 2820
ttccgacatg actcaggata tgaagttgga ggaggagatg cagaattccg acatgactca 2880
ggatatgaag ttggaggagg agatgcagaa ttccgacatg actcaggata tgaagttgga 2940
ggaggagatg cagaattccg acatgactca ggatatgaag ttggaggagg agatgcagaa 3000
ttccgacatg actcaggata tgaagttgga ggaggagatg cagaattccg acatgactca 3060
ggatatgaag ttggaggagg agatgcagaa ttccgacatg actcaggata tgaagttgga 3120
ggaggagatg cagaattccg acatgactca ggatatgaag ttggaggagg agatgcagaa 3180
ttccgacatg actcaggata tgaagttgga ggaggagatg cagaattccg acatgactca 3240
ggatatgaag ttggaggagg agatgcagaa ttccgacatg actcaggata tgaagttgga 3300
ggaggagatg cagaattccg acatgactca ggatatgaag ttggaggagg agatgcagaa 3360
ttccgacatg actcaggata tgaagttgga ggaggagatg cagaattccg acatgactca 3420
ggatatgaag ttggaggagg attcgagact ggccagaaca ccaggttcac tcccgtgggt 3480
gtcgttcaag acggcagcac cactcaccag aacgaacccc agcaatgggt cctccctgac 3540

-continued

```
tactcgggca gggattccca caacgttcac ttggctccgg ccgtggctcc aaccttccct   3600
ggagagcagt tgctgttctt cagatccact atgccaggct gctctggata cccgaacatg   3660
aacctcgact gtctcttgcc tcaggagtgg gtgcaacact tctaccagga atctgcccca   3720
gctcaaagcg acgtcgctct gctccgtttc gttaaccccg ataccggtcg cgtgctcttc   3780
gagtgtaagt tgcacaagtc tggttacgtc actgttgccc acacaggcca gcacgacctg   3840
gtcatccctc ccaacggcta cttccgcttc gatagctggg tcaaccagtt ctacacactc   3900
gccccgatgg gaaacggagc cggtcgtcgc agagccttgt aa                      3942
```

```
<210> SEQ ID NO 76
<211> LENGTH: 4212
<212> TYPE: DNA
<213> ORGANISM: artificial sequence
<220> FEATURE:
<223> OTHER INFORMATION: synthetic nucleotide sequence encoding the
      recombinant P protein

<400> SEQUENCE: 76
atgaagccct tctcggtccc tatcctgaca gttgaggaaa tgaccaactc tagattccca     60
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc gctggaacac aaggaggagg agatgcagaa    240
ttccgacatg actcaggata tgaagttgga ggaggagatg cagaattccg acatgactca    300
ggatatgaag ttggaggagg agatgcagaa ttccgacatg actcaggata tgaagttgga    360
ggaggagatg cagaattccg acatgactca ggatatgaag ttggaggagg agatgcagaa    420
ttccgacatg actcaggata tgaagttgga ggaggagatg cagaattccg acatgactca    480
ggatatgaag ttggaggagg agatgcagaa ttccgacatg actcaggata tgaagttgga    540
ggaggagatg cagaattccg acatgactca ggatatgaag ttggaggagg agatgcagaa    600
ttccgacatg actcaggata tgaagttgga ggaggagatg cagaattccg acatgactca    660
ggatatgaag ttggaggagg agatgcagaa ttccgacatg actcaggata tgaagttgga    720
ggaggagatg cagaattccg acatgactca ggatatgaag ttggaggagg agatgcagaa    780
ttccgacatg actcaggata tgaagttgga ggaggagatg cagaattccg acatgactca    840
ggatatgaag ttggaggagg agatgcagaa ttccgacatg actcaggata tgaagttgga    900
ggaggagatg cagaattccg acatgactca ggatatgaag ttggaggagg agatgcagaa    960
ttccgacatg actcaggata tgaagttgga ggaggagatg cagaattccg acatgactca   1020
ggatatgaag ttggaggagg agatgcagaa ttccgacatg actcaggata tgaagttgga   1080
ggaggagatg cagaattccg acatgactca ggatatgaag ttggaggagg agatgcagaa   1140
ttccgacatg actcaggata tgaagttgga ggaggagatg cagaattccg acatgactca   1200
ggatatgaag ttggaggagg agatgcagaa ttccgacatg actcaggata tgaagttgga   1260
ggaggagatg cagaattccg acatgactca ggatatgaag ttggaggagg agatgcagaa   1320
ttccgacatg actcaggata tgaagttgga ggaggagatg cagaattccg acatgactca   1380
ggatatgaag ttggaggagg agatgcagaa ttccgacatg actcaggata tgaagttgga   1440
ggaggagatg cagaattccg acatgactca ggatatgaag ttggaggagg agatgcagaa   1500
ttccgacatg actcaggata tgaagttgga ggaggagatg cagaattccg acatgactca   1560
ggatatgaag ttggaggagg agatgcagaa ttccgacatg actcaggata tgaagttgga   1620
```

```
ggaggagatg cagaattccg acatgactca ggatatgaag ttggaggagg agatgcagaa   1680
ttccgacatg actcaggata tgaagttgga ggaggagatg cagaattccg acatgactca   1740
ggatatgaag ttggaggagg agatgcagaa ttccgacatg actcaggata tgaagttgga   1800
ggaggagatg cagaattccg acatgactca ggatatgaag ttggaggagg agatgcagaa   1860
ttccgacatg actcaggata tgaagttgga ggaggagatg cagaattccg acatgactca   1920
ggatatgaag ttggaggagg agatgcagaa ttccgacatg actcaggata tgaagttgga   1980
ggaggagatg cagaattccg acatgactca ggatatgaag ttggaggagg aaactacacc   2040
atgaacttgg cctcgcagaa ctggaacaac tacgatccaa ccgaggaaat ccccgctcct   2100
ttgggaactc ccgacttcgt gggacgtatc caaggtgtcc tgacacagac tacacgtcgc   2160
gacggctcta ctcgcggaca caaggccact gtgtcgacag gttccgtcca cttcacccct   2220
aagctgggct ctgtgcaatt cagcacagac acctcaggag gaggagatgc agaattccga   2280
catgactcag gaggaggagg agatgcagaa ttccgacatg actcaggagg aggaggagat   2340
gcagaattcc gacatgactc aggaggagga ggagatgcag aattccgaca tgactcagga   2400
ggaggaggag atgcagaatt ccgacatgac tcaggaggag gaggagatgc agaattccga   2460
catgactcag gaggaggagg agatgcagaa ttccgacatg actcaggagg aggaggagat   2520
gcagaattcc gacatgactc aggaggagga ggagatgcag aattccgaca tgactcagga   2580
ggaggaggag atgcagaatt ccgacatgac tcaggaggag gaggagatgc agaattccga   2640
catgactcag gaggaggagg agatgcagaa ttccgacatg actcaggagg aggaggagat   2700
gcagaattcc gacatgactc aggaggagga ggagatgcag aattccgaca tgactcagga   2760
ggaggaggag atgcagaatt ccgacatgac tcaggaggag gaggagatgc agaattccga   2820
catgactcag gaggaggagg agatgcagaa ttccgacatg actcaggagg aggaggagat   2880
gcagaattcc gacatgactc aggaggagga ggagatgcag aattccgaca tgactcagga   2940
ggaggaggag atgcagaatt ccgacatgac tcaggaggag gaggagatgc agaattccga   3000
catgactcag gaggaggagg agatgcagaa ttccgacatg actcaggagg aggaggagat   3060
gcagaattcc gacatgactc aggaggagga ggagatgcag aattccgaca tgactcagga   3120
ggaggaggag atgcagaatt ccgacatgac tcaggaggag gaggagatgc agaattccga   3180
catgactcag gaggaggagg agatgcagaa ttccgacatg actcaggagg aggaggagat   3240
gcagaattcc gacatgactc aggaggagga ggagatgcag aattccgaca tgactcagga   3300
ggaggaggag atgcagaatt ccgacatgac tcaggaggag gaggagatgc agaattccga   3360
catgactcag gaggaggagg agatgcagaa ttccgacatg actcaggagg aggaggagat   3420
gcagaattcc gacatgactc aggaggagga ggagatgcag aattccgaca tgactcagga   3480
ggaggaggag atgcagaatt ccgacatgac tcaggaggag gaggagatgc agaattccga   3540
catgactcag gaggaggagg agatgcagaa ttccgacatg actcaggagg aggaggagat   3600
gcagaattcc gacatgactc aggaggagga ggagatgcag aattccgaca tgactcagga   3660
ggaggaggag atgcagaatt ccgacatgac tcaggaggag gaggaaacga tttcgagact   3720
ggccagaaca ccaggttcac tcccgtgggt gtcgttcaag acggcagcac cactcaccag   3780
aacgaacccc agcaatgggt cctccctgac tactcgggca gggattccca caacgttcac   3840
ttggctccgg ccgtggctcc aaccttccct ggagagcagt tgctgttctt cagatccact   3900
atgccaggct gctctggata cccgaacatg aacctcgact gtctcttgcc tcaggagtgg   3960
gtgcaacact tctaccagga atctgcccca gctcaaagcg acgtcgctct gctccgtttc   4020
```
gttaaccccg ataccggtcg cgtgctcttc gagtgtaagt tgcacaagtc tggttacgtc 4080
actgttgccc acacaggcca gcacgacctg gtcatccctc ccaacggcta cttccgcttc 4140
gatagctggg tcaaccagtt ctacacactc gccccgatgg gaaacggagc cggtcgtcgc 4200
agagccttgt aa 4212

<210> SEQ ID NO 77
<211> LENGTH: 1269
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 77
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaggag gaggagatgc agaattccga 240
catggaggag gaacacaaaa ctacaccatg aacttggcct cgcagaactg gaacaactac 300
gatccaaccg aggaaatccc cgctcctttg ggaactcccg acttcgtggg acgtatccaa 360
ggtgtcctga cacagactac acgtcgcgac ggctctactc gcggacacaa ggccactgtg 420
tcgacaggtt ccgtccactt cacccctaag ctgggctctg tgcaattcag cacagacacc 480
tcaggaggag gagatgcaga attccgacat ggaggaggag atgcagaatt ccgacatgga 540
ggaggagatg cagaattccg acatggagga ggagatgcag aattccgaca tggaggagga 600
gatgcagaat tccgacatgg aggaggagat gcagaattcc gacatggagg aggagatgca 660
gaattccgac atggaggagg agatgcagaa ttccgacatg gaggaggaga tgcagaattc 720
cgacatggag gaggagatgc agaattccga catggaggag gaaacgattt cgagactggc 780
cagaacacca ggttcactcc cgtgggtgtc gttcaagacg gcagcaccac tcaccagaac 840
gaaccccagc aatgggtcct ccctgactac tcgggcaggg attcccacaa cgttcacttg 900
gctccggccg tggctccaac cttccctgga gagcagttgc tgttcttcag atccactatg 960
ccaggctgct ctggataccc gaacatgaac ctcgactgtc tcttgcctca ggagtgggtg 1020
caacacttct accaggaatc tgccccagct caaagcgacg tcgctctgct ccgtttcgtt 1080
aaccccgata ccggtcgcgt gctcttcgag tgtaagttgc acaagtctgg ttacgtcact 1140
gttgcccaca caggccagca cgacctggtc atccctccca acggctactt ccgcttcgat 1200
agctgggtca accagttcta cacactcgcc ccgatgggaa acggagccgg tcgtcgcaga 1260
gccttgtaa 1269

<210> SEQ ID NO 78
<211> LENGTH: 2052
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 78
atgaagccct tctcggtccc tatcctgaca gttgaggaaa tgaccaactc tagattccca 60
atcccgctgg aaaagctctt caccggaccc tcctctgctt tcgttgtgca gcctcaaaac 120

```
ggtcgttgca ccactgatgg tgtcctgctc ggtaccaccc agctctcacc tgtgaacatc    180
tgtactttcc gcggcgacgt cacacacatc gctggaggag gaggagatgc agaattccga    240
catgactcag gaggaggagg agatgcagaa ttccgacatg actcaggagg aggaggagat    300
gcagaattcc gacatgactc aggaggagga ggagatgcag aattccgaca tgactcagga    360
ggaggaggag atgcagaatt ccgacatgac tcaggaggag gaggagatgc agaattccga    420
catgactcag gaggaggagg agatgcagaa ttccgacatg actcaggagg aggaggagat    480
gcagaattcc gacatgactc aggaggagga ggagatgcag aattccgaca tgactcagga    540
ggaggaggag atgcagaatt ccgacatgac tcaggaggag gaggaacaca aaactacacc    600
atgaacttgg cctcgcagaa ctggaacaac tacgatccaa ccgaggaaat ccccgctcct    660
ttgggaactc ccgacttcgt gggacgtatc caaggtgtcc tgacacagac tacacgtcgc    720
gacggctcta ctcgcggaca caaggccact gtgtcgacag gttccgtcca cttcacccct    780
aagctgggct ctgtgcaatt cagcacagac acctcaggag gaggagatgc agaattccga    840
catgactcag gaggaggagg agatgcagaa ttccgacatg actcaggagg aggaggagat    900
gcagaattcc gacatgactc aggaggagga ggagatgcag aattccgaca tgactcagga    960
ggaggaggag atgcagaatt ccgacatgac tcaggaggag gaggagatgc agaattccga   1020
catgactcag gaggaggagg agatgcagaa ttccgacatg actcaggagg aggaggagat   1080
gcagaattcc gacatgactc aggaggagga ggagatgcag aattccgaca tgactcagga   1140
ggaggaggag atgcagaatt ccgacatgac tcaggaggag gaggagatgc agaattccga   1200
catgactcag gaggaggagg agatgcagaa ttccgacatg actcaggagg aggaggagat   1260
gcagaattcc gacatgactc aggaggagga ggagatgcag aattccgaca tgactcagga   1320
ggaggaggag atgcagaatt ccgacatgac tcaggaggag gaggagatgc agaattccga   1380
catgactcag gaggaggagg agatgcagaa ttccgacatg actcaggagg aggaggagat   1440
gcagaattcc gacatgactc aggaggagga ggagatgcag aattccgaca tgactcagga   1500
ggaggaggag atgcagaatt ccgacatgac tcaggaggag gaggaaacga tttcgagact   1560
ggccagaaca ccaggttcac tcccgtgggt gtcgttcaag acggcagcac cactcaccag   1620
aacgaacccc agcaatgggt cctccctgac tactcgggca gggattccca caacgttcac   1680
ttggctccgg ccgtggctcc aaccttccct ggagagcagt tgctgttctt cagatccact   1740
atgccaggct gctctggata cccgaacatg aacctcgact gtctcttgcc tcaggagtgg   1800
gtgcaacact tctaccagga atctgcccca gctcaaagcg acgtcgctct gctccgtttc   1860
gttaaccccg ataccggtcg cgtgctcttc gagtgtaagt tgcacaagtc tggttacgtc   1920
actgttgccc acacaggcca gcacgacctg gtcatccctc ccaacggcta cttccgcttc   1980
gatagctggg tcaaccagtt ctacacactc gccccgatgg gaaacggagc cggtcgtcgc   2040
agagccttgt aa                                                       2052
```

```
<210> SEQ ID NO 79
<211> LENGTH: 3672
<212> TYPE: DNA
<213> ORGANISM: artificial sequence
<220> FEATURE:
<223> OTHER INFORMATION: synthetic nucleotide sequence encoding the
      recombinant P protein

<400> SEQUENCE: 79
atgaagccct tctcggtccc tatcctgaca gttgaggaaa tgaccaactc tagattccca     60
```

-continued

```
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc gctggaggag gaggagatgc agaattccga    240
catgactcag gatatgaagt tggaggagga gatgcagaat tccgacatga ctcaggatat    300
gaagttggag gaggagatgc agaattccga catgactcag gatatgaagt tggaggagga    360
gatgcagaat tccgacatga ctcaggatat gaagttggag gaggagatgc agaattccga    420
catgactcag gatatgaagt tggaggagga gatgcagaat tccgacatga ctcaggatat    480
gaagttggag gaggagatgc agaattccga catgactcag gatatgaagt tggaggagga    540
gatgcagaat tccgacatga ctcaggatat gaagttggag gaggagatgc agaattccga    600
catgactcag gatatgaagt tggaggagga gatgcagaat tccgacatga ctcaggatat    660
gaagttggag gaggagatgc agaattccga catgactcag gatatgaagt tggaggagga    720
gatgcagaat tccgacatga ctcaggatat gaagttggag gaggagatgc agaattccga    780
catgactcag gatatgaagt tggaggagga gatgcagaat tccgacatga ctcaggatat    840
gaagttggag gaggagatgc agaattccga catgactcag gatatgaagt tggaggagga    900
gatgcagaat tccgacatga ctcaggatat gaagttggag gaggagatgc agaattccga    960
catgactcag gatatgaagt tggaggagga gatgcagaat tccgacatga ctcaggatat   1020
gaagttggag gaggagatgc agaattccga catgactcag gatatgaagt tggaggagga   1080
gatgcagaat tccgacatga ctcaggatat gaagttggag gaggaacaca aaactacacc   1140
atgaacttgg cctcgcagaa ctggaacaac tacgatccaa ccgaggaaat ccccgctcct   1200
ttgggaactc ccgacttcgt gggacgtatc caaggtgtcc tgacacagac tacacgtcgc   1260
gacggctcta ctcgcggaca caaggccact gtgtcgacag gttccgtcca cttcacccct   1320
aagctgggct ctgtgcaatt cagcacagac acctcaggag gaggagatgc agaattccga   1380
catgactcag gatatgaagt tggaggagga gatgcagaat tccgacatga ctcaggatat   1440
gaagttggag gaggagatgc agaattccga catgactcag gatatgaagt tggaggagga   1500
gatgcagaat tccgacatga ctcaggatat gaagttggag gaggagatgc agaattccga   1560
catgactcag gatatgaagt tggaggagga gatgcagaat tccgacatga ctcaggatat   1620
gaagttggag gaggagatgc agaattccga catgactcag gatatgaagt tggaggagga   1680
gatgcagaat tccgacatga ctcaggatat gaagttggag gaggagatgc agaattccga   1740
catgactcag gatatgaagt tggaggagga gatgcagaat tccgacatga ctcaggatat   1800
gaagttggag gaggagatgc agaattccga catgactcag gatatgaagt tggaggagga   1860
gatgcagaat tccgacatga ctcaggatat gaagttggag gaggagatgc agaattccga   1920
catgactcag gatatgaagt tggaggagga gatgcagaat tccgacatga ctcaggatat   1980
gaagttggag gaggagatgc agaattccga catgactcag gatatgaagt tggaggagga   2040
gatgcagaat tccgacatga ctcaggatat gaagttggag gaggagatgc agaattccga   2100
catgactcag gatatgaagt tggaggagga gatgcagaat tccgacatga ctcaggatat   2160
gaagttggag gaggagatgc agaattccga catgactcag gatatgaagt tggaggagga   2220
gatgcagaat tccgacatga ctcaggatat gaagttggag gaggagatgc agaattccga   2280
catgactcag gatatgaagt tggaggagga gatgcagaat tccgacatga ctcaggatat   2340
gaagttggag gaggagatgc agaattccga catgactcag gatatgaagt tggaggagga   2400
gatgcagaat tccgacatga ctcaggatat gaagttggag gaggagatgc agaattccga   2460
```
catgactcag gatatgaagt tggaggagga gatgcagaat tccgacatga ctcaggatat 2520
gaagttggag gaggagatgc agaattccga catgactcag gatatgaagt tggaggagga 2580
gatgcagaat tccgacatga ctcaggatat gaagttggag gaggagatgc agaattccga 2640
catgactcag gatatgaagt tggaggagga gatgcagaat tccgacatga ctcaggatat 2700
gaagttggag gaggagatgc agaattccga catgactcag gatatgaagt tggaggagga 2760
gatgcagaat tccgacatga ctcaggatat gaagttggag gaggagatgc agaattccga 2820
catgactcag gatatgaagt tggaggagga gatgcagaat tccgacatga ctcaggatat 2880
gaagttggag gaggagatgc agaattccga catgactcag gatatgaagt tggaggagga 2940
gatgcagaat tccgacatga ctcaggatat gaagttggag gaggagatgc agaattccga 3000
catgactcag gatatgaagt tggaggagga gatgcagaat tccgacatga ctcaggatat 3060
gaagttggag gaggagatgc agaattccga catgactcag gatatgaagt tggaggagga 3120
gatgcagaat tccgacatga ctcaggatat gaagttggag gaggaaacga tttcgagact 3180
ggccagaaca ccaggttcac tcccgtgggt gtcgttcaag acggcagcac cactcaccag 3240
aacgaacccc agcaatgggt cctccctgac tactcgggca gggattccca caacgttcac 3300
ttggctccgg ccgtggctcc aaccttccct ggagagcagt tgctgttctt cagatccact 3360
atgccaggct gctctggata cccgaacatg aacctcgact gtctcttgcc tcaggagtgg 3420
gtgcaacact tctaccagga atctgcccca gctcaaagcg acgtcgctct gctccgtttc 3480
gttaaccccg ataccggtcg cgtgctcttc gagtgtaagt tgcacaagtc tggttacgtc 3540
actgttgccc acacaggcca gcacgacctg gtcatccctc ccaacggcta cttccgcttc 3600
gatagctggg tcaaccagtt ctacacactc gccccgatgg gaaacggagc cggtcgtcgc 3660
agagccttgt aa 3672

<210> SEQ ID NO 80
<211> LENGTH: 3672
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 80
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaggag gaggagatgc agaattccga 240
catgactcag gatatgaagt tcatcatcaa ggaggaggag atgcagaatt ccgacatgac 300
tcaggatatg aagttcatca tcaaggagga ggagatgcag aattccgaca tgactcagga 360
tatgaagttc atcatcaagg aggaggagat gcagaattcc gacatgactc aggatatgaa 420
gttcatcatc aaggaggagg agatgcagaa ttccgacatg actcaggata tgaagttcat 480
catcaaggag gaggagatgc agaattccga catgactcag gatatgaagt tcatcatcaa 540
ggaggaggag atgcagaatt ccgacatgac tcaggatatg aagttcatca tcaaggagga 600
ggagatgcag aattccgaca tgactcagga tatgaagttc atcatcaagg aggaggagat 660
gcagaattcc gacatgactc aggatatgaa gttcatcatc aaggaggagg agatgcagaa 720
ttccgacatg actcaggata tgaagttcat catcaaggag gaggagatgc agaattccga 780

-continued

```
catgactcag gatatgaagt tcatcatcaa ggaggaggag atgcagaatt ccgacatgac    840
tcaggatatg aagttcatca tcaaggagga ggagatgcag aattccgaca tgactcagga    900
tatgaagttc atcatcaagg aggaggagat gcagaattcc gacatgactc aggatatgaa    960
gttcatcatc aaggaggagg agatgcagaa ttccgacatg actcaggata tgaagttcat   1020
catcaaggag gaggagatgc agaattccga catgactcag gatatgaagt tcatcatcaa   1080
ggaggaggag atgcagaatt ccgacatgac tcaggatatg aagttcatca tcaaggagga   1140
ggagatgcag aattccgaca tgactcagga tatgaagttc atcatcaagg aggaggagat   1200
gcagaattcc gacatgactc aggatatgaa gttcatcatc aaggaggagg agatgcagaa   1260
ttccgacatg actcaggata tgaagttcat catcaaggag gaggagatgc agaattccga   1320
catgactcag gatatgaagt tcatcatcaa ggaggaggag atgcagaatt ccgacatgac   1380
tcaggatatg aagttcatca tcaaggagga ggagatgcag aattccgaca tgactcagga   1440
tatgaagttc atcatcaagg aggaggagat gcagaattcc gacatgactc aggatatgaa   1500
gttcatcatc aaggaggagg agatgcagaa ttccgacatg actcaggata tgaagttcat   1560
catcaaggag gaggagatgc agaattccga catgactcag gatatgaagt tcatcatcaa   1620
ggaggaggag atgcagaatt ccgacatgac tcaggatatg aagttcatca tcaaggagga   1680
ggagatgcag aattccgaca tgactcagga tatgaagttc atcatcaagg aggaggagat   1740
gcagaattcc gacatgactc aggatatgaa gttcatcatc aaggaggagg agatgcagaa   1800
ttccgacatg actcaggata tgaagttcat catcaaggag gaggagatgc agaattccga   1860
catgactcag gatatgaagt tcatcatcaa ggaggaggag atgcagaatt ccgacatgac   1920
tcaggatatg aagttcatca tcaaggagga ggagatgcag aattccgaca tgactcagga   1980
tatgaagttc atcatcaagg aggaggagat gcagaattcc gacatgactc aggatatgaa   2040
gttcatcatc aaggaggagg agatgcagaa ttccgacatg actcaggata tgaagttcat   2100
catcaaggag gaggagatgc agaattccga catgactcag gatatgaagt tcatcatcaa   2160
ggaggaggag atgcagaatt ccgacatgac tcaggatatg aagttcatca tcaaggagga   2220
ggagatgcag aattccgaca tgactcagga tatgaagttc atcatcaagg aggaggagat   2280
gcagaattcc gacatgactc aggatatgaa gttcatcatc aaggaggagg agatgcagaa   2340
ttccgacatg actcaggata tgaagttcat catcaaggag gaggaacaca aaactacacc   2400
atgaacttgg cctcgcagaa ctggaacaac tacgatccaa ccgaggaaat ccccgctcct   2460
ttgggaactc ccgacttcgt gggacgtatc caaggtgtcc tgacacagac tacacgtcgc   2520
gacggctcta ctcgcggaca caaggccact gtgtcgacag gttccgtcca cttcacccct   2580
aagctgggct ctgtgcaatt cagcacagac acctcaggag gaggagatgc agaattccga   2640
catgactcag gatatgaagt tcatcatcaa ggaggaggag atgcagaatt ccgacatgac   2700
tcaggatatg aagttcatca tcaaggagga ggagatgcag aattccgaca tgactcagga   2760
tatgaagttc atcatcaagg aggaggagat gcagaattcc gacatgactc aggatatgaa   2820
gttcatcatc aaggaggagg agatgcagaa ttccgacatg actcaggata tgaagttcat   2880
catcaaggag gaggagatgc agaattccga catgactcag gatatgaagt tcatcatcaa   2940
ggaggaggag atgcagaatt ccgacatgac tcaggatatg aagttcatca tcaaggagga   3000
ggagatgcag aattccgaca tgactcagga tatgaagttc atcatcaagg aggaggagat   3060
gcagaattcc gacatgactc aggatatgaa gttcatcatc aaggaggagg agatgcagaa   3120
```

-continued

```
ttccgacatg actcaggata tgaagttcat catcaaggag gaggaaacga tttcgagact   3180
ggccagaaca ccaggttcac tcccgtgggt gtcgttcaag acggcagcac cactcaccag   3240
aacgaacccc agcaatgggt cctccctgac tactcgggca gggattccca caacgttcac   3300
ttggctccgg ccgtggctcc aaccttccct ggagagcagt tgctgttctt cagatccact   3360
atgccaggct gctctggata cccgaacatg aacctcgact gtctcttgcc tcaggagtgg   3420
gtgcaacact tctaccagga atctgcccca gctcaaagcg acgtcgctct gctccgtttc   3480
gttaaccccg ataccggtcg cgtgctcttc gagtgtaagt tgcacaagtc tggttacgtc   3540
actgttgccc acacaggcca gcacgacctg gtcatccctc ccaacggcta cttccgcttc   3600
gatagctggg tcaaccagtt ctacacactc gccccgatgg gaaacggagc cggtcgtcgc   3660
agagccttgt aa                                                      3672
```

<210> SEQ ID NO 81
<211> LENGTH: 1449
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 81

```
atgaagccct tctcggtccc tatcctgaca gttgaggaaa tgaccaactc tagattccca     60
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc ggaggaggag atgcagaatt ccgacatgga    240
ggaggagctg gaacacaaaa ctacaccatg aacttggcct cgcagaactg gaacaactac    300
gatccaaccg aggaaatccc cgctcctttg ggaactcccg acttcgtggg acgtatccaa    360
ggtgtcctga cacagactac acgtcgcgac ggctctactc gcggacacaa ggccactgtg    420
tcgacaggtt ccgtccactt caccccctaag ctgggctctg tgcaattcag cacagacacc    480
ggaggaggag atgcagaatt ccgacatgac tcaggatatg aagttggagg aggagatgca    540
gaattccgac atgactcagg atatgaagtt ggaggaggag atgcagaatt ccgacatgac    600
tcaggatatg aagttggagg aggagatgca gaattccgac atgactcagg atatgaagtt    660
ggaggaggag atgcagaatt ccgacatgac tcaggatatg aagttggagg aggagatgca    720
gaattccgac atgactcagg atatgaagtt ggaggaggag atgcagaatt ccgacatgac    780
tcaggatatg aagttggagg aggagatgca gaattccgac atgactcagg atatgaagtt    840
ggaggaggag atgcagaatt ccgacatgac tcaggatatg aagttggagg aggagatgca    900
gaattccgac atgactcagg atatgaagtt ggaggaggat caaacgattt cgagactggc    960
cagaacacca ggttcactcc cgtgggtgtc gttcaagacg gcagcaccac tcaccagaac   1020
gaaccccagc aatgggtcct ccctgactac tcgggcaggg attcccacaa cgttcacttg   1080
gctccggccg tggctccaac cttccctgga gagcagttgc tgttcttcag atccactatg   1140
ccaggctgct ctggataccc gaacatgaac ctcgactgtc tcttgcctca ggagtgggtg   1200
caacacttct accaggaatc tgccccagct caaagcgacg tcgctctgct ccgtttcgtt   1260
aaccccgata ccggtcgcgt gctcttcgag tgtaagttgc acaagtctgg ttacgtcact   1320
gttgcccaca caggccagca cgacctggtc atccctccca acggctactt ccgcttcgat   1380
agctgggtca accagttcta cacactcgcc ccgatgggaa acggagccgg tcgtcgcaga   1440
``` gccttgtaa 1449

<210> SEQ ID NO 82
<211> LENGTH: 1872
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 82
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaggag gagatgcaga attccgacat 240
gactcaggag gaggaggaga tgcagaattc cgacatgact caggaggagg aggagatgca 300
gaattccgac atgactcagg aggaggagga gatgcagaat tccgacatga ctcaggagga 360
ggaggagatg cagaattccg acatgactca ggaggaggag gagatgcaga attccgacat 420
gactcaggag gaggaggaga tgcagaattc cgacatgact caggaggagg aggagatgca 480
gaattccgac atgactcagg aggaggagga gatgcagaat tccgacatga ctcaggagga 540
ggaggagatg cagaattccg acatgactca ggaggaggag gaggaacaca aaactacacc 600
atgaacttgg cctcgcagaa ctggaacaac tacgatccaa ccgaggaaat ccccgctcct 660
ttgggaactc ccgacttcgt gggacgtatc caaggtgtcc tgacacagac tacacgtcgc 720
gacggctcta ctcgcggaca caaggccact gtgtcgacag gttccgtcca cttcacccct 780
aagctgggct ctgtgcaatt cagcacagac acctcaggag gaggagatgc agaattccga 840
catggaggag gagatgcaga attccgacat ggaggaggag atgcagaatt ccgacatgga 900
ggaggagatg cagaattccg acatggagga ggagatgcag aattccgaca tggaggagga 960
gatgcagaat tccgacatgg aggaggagat gcagaattcc gacatggagg aggagatgca 1020
gaattccgac atggaggagg agatgcagaa ttccgacatg gaggaggaga tgcagaattc 1080
cgacatggag gaggagatgc agaattccga catggaggag gagatgcaga attccgacat 1140
ggaggaggag atgcagaatt ccgacatgga ggaggagatg cagaattccg acatggagga 1200
ggagatgcag aattccgaca tggaggagga gatgcagaat tccgacatgg aggaggagat 1260
gcagaattcc gacatggagg aggagatgca gaattccgac atggaggagg agatgcagaa 1320
ttccgacatg gaggaggaga tgcagaattc cgacatggag gaggaaacga tttcgagact 1380
ggccagaaca ccaggttcac tcccgtgggt gtcgttcaag acggcagcac cactcaccag 1440
aacgaacccc agcaatgggt cctccctgac tactcgggca gggattccca caacgttcac 1500
ttggctccgg ccgtggctcc aaccttccct ggagagcagt tgctgttctt cagatccact 1560
atgccaggct gctctggata cccgaacatg aacctcgact gtctcttgcc tcaggagtgg 1620
gtgcaacact tctaccagga atctgcccca gctcaaagcg acgtcgctct gctccgtttc 1680
gttaaccccg ataccggtcg cgtgctcttc gagtgtaagt tgcacaagtc tggttacgtc 1740
actgttgccc acacaggcca gcacgacctg gtcatccctc ccaacggcta cttccgcttc 1800
gatagctggg tcaaccagtt ctacacactc gccccgatgg gaaacggagc cggtcgtcgc 1860
agagccttgt aa 1872

<210> SEQ ID NO 83

```
<211> LENGTH: 3132
<212> TYPE: DNA
<213> ORGANISM: artificial sequence
<220> FEATURE:
<223> OTHER INFORMATION: synthetic nucleotide sequence encoding the
      recombinant P protein

<400> SEQUENCE: 83
atgaagccct tctcggtccc tatcctgaca gttgaggaaa tgaccaactc tagattccca     60
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc gctggaggag gaggagatgc agaattccga    240
catgactcag gatatgaagt tcatcatcaa ggaggaggag atgcagaatt ccgacatgac    300
tcaggatatg aagttcatca tcaaggagga ggagatgcag aattccgaca tgactcagga    360
tatgaagttc atcatcaagg aggaggagat gcagaattcc gacatgactc aggatatgaa    420
gttcatcatc aaggaggagg agatgcagaa ttccgacatg actcaggata tgaagttcat    480
catcaaggag gaggagatgc agaattccga catgactcag gatatgaagt tcatcatcaa    540
ggaggaggag atgcagaatt ccgacatgac tcaggatatg aagttcatca tcaaggagga    600
ggagatgcag aattccgaca tgactcagga tatgaagttc atcatcaagg aggaggagat    660
gcagaattcc gacatgactc aggatatgaa gttcatcatc aaggaggagg agatgcagaa    720
ttccgacatg actcaggata tgaagttcat catcaaggag gaggagatgc agaattccga    780
catgactcag gatatgaagt tcatcatcaa ggaggaggag atgcagaatt ccgacatgac    840
tcaggatatg aagttcatca tcaaggagga ggagatgcag aattccgaca tgactcagga    900
tatgaagttc atcatcaagg aggaggagat gcagaattcc gacatgactc aggatatgaa    960
gttcatcatc aaggaggagg agatgcagaa ttccgacatg actcaggata tgaagttcat   1020
catcaaggag gaggagatgc agaattccga catgactcag gatatgaagt tcatcatcaa   1080
ggaggaggag atgcagaatt ccgacatgac tcaggatatg aagttcatca tcaaggagga   1140
ggagatgcag aattccgaca tgactcagga tatgaagttc atcatcaagg aggaggagat   1200
gcagaattcc gacatgactc aggatatgaa gttcatcatc aaggaggagg agatgcagaa   1260
ttccgacatg actcaggata tgaagttcat catcaaggag gaggaacaca aaactacacc   1320
atgaacttgg cctcgcagaa ctggaacaac tacgatccaa ccgaggaaat ccccgctcct   1380
ttgggaactc ccgacttcgt gggacgtatc caaggtgtcc tgacacagac tacacgtcgc   1440
gacggctcta ctcgcggaca caaggccact gtgtcgacag gttccgtcca cttcacccct   1500
aagctgggct ctgtgcaatt cagcacagac acctcaggag gaggagatgc agaattccga   1560
catggaggag gagatgcaga attccgacat ggaggaggag atgcagaatt ccgacatgga   1620
ggaggagatg cagaattccg acatggagga ggagatgcag aattccgaca tggaggagga   1680
gatgcagaat tccgacatgg aggaggagat gcagaattcc gacatggagg aggagatgca   1740
gaattccgac atggaggagg agatgcagaa ttccgacatg gaggaggaga tgcagaattc   1800
cgacatggag gaggagatgc agaattccga catggaggag gagatgcaga attccgacat   1860
ggaggaggag atgcagaatt ccgacatgga ggaggagatg cagaattccg acatggagga   1920
ggagatgcag aattccgaca tggaggagga gatgcagaat tccgacatgg aggaggagat   1980
gcagaattcc gacatggagg aggagatgca gaattccgac atggaggagg agatgcagaa   2040
ttccgacatg gaggaggaga tgcagaattc cgacatggag gaggagatgc agaattccga   2100
```

-continued catggaggag gagatgcaga attccgacat ggaggaggag atgcagaatt ccgacatgga 2160
ggaggagatg cagaattccg acatggagga ggagatgcag aattccgaca tggaggagga 2220
gatgcagaat tccgacatgg aggaggagat gcagaattcc gacatggagg aggagatgca 2280
gaattccgac atggaggagg agatgcagaa ttccgacatg gaggaggaga tgcagaattc 2340
cgacatggag gaggagatgc agaattccga catggaggag gagatgcaga attccgacat 2400
ggaggaggag atgcagaatt ccgacatgga ggaggagatg cagaattccg acatggagga 2460
ggagatgcag aattccgaca tggaggagga gatgcagaat tccgacatgg aggaggagat 2520
gcagaattcc gacatggagg aggagatgca gaattccgac atggaggagg agatgcagaa 2580
ttccgacatg gaggaggaga tgcagaattc cgacatggag gaggaaacga tttcgagact 2640
ggccagaaca ccaggttcac tcccgtgggt gtcgttcaag acggcagcac cactcaccag 2700
aacgaacccc agcaatgggt cctccctgac tactcgggca gggattccca caacgttcac 2760
ttggctccgg ccgtggctcc aaccttccct ggagagcagt tgctgttctt cagatccact 2820
atgccaggct gctctggata cccgaacatg aacctcgact gtctcttgcc tcaggagtgg 2880
gtgcaacact tctaccagga atctgcccca gctcaaagcg acgtcgctct gctccgtttc 2940
gttaaccccg ataccggtcg cgtgctcttc gagtgtaagt tgcacaagtc tggttacgtc 3000
actgttgccc acacaggcca gcacgacctg gtcatccctc ccaacggcta cttccgcttc 3060
gatagctggg tcaaccagtt ctacacactc gccccgatgg gaaacggagc cggtcgtcgc 3120
agagccttgt aa 3132

<210> SEQ ID NO 84
<211> LENGTH: 3492
<212> TYPE: DNA
<213> ORGANISM: artificial sequence
<220> FEATURE:
<223> OTHER INFORMATION: synthetic nucleotide sequence encoding the
      recombinant P protein

<400> SEQUENCE: 84
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaggag gaggagatgc agaattccga 240
catgactcag gaggaggagg agatgcagaa ttccgacatg actcaggagg aggaggagat 300
gcagaattcc gacatgactc aggaggagga ggagatgcag aattccgaca tgactcagga 360
ggaggaggag atgcagaatt ccgacatgac tcaggaggag gaggagatgc agaattccga 420
catgactcag gaggaggagg agatgcagaa ttccgacatg actcaggagg aggaggagat 480
gcagaattcc gacatgactc aggaggagga ggagatgcag aattccgaca tgactcagga 540
ggaggaggag atgcagaatt ccgacatgac tcaggaggag gaggagatgc agaattccga 600
catgactcag gaggaggagg agatgcagaa ttccgacatg actcaggagg aggaggagat 660
gcagaattcc gacatgactc aggaggagga ggagatgcag aattccgaca tgactcagga 720
ggaggaggag atgcagaatt ccgacatgac tcaggaggag gaggagatgc agaattccga 780
catgactcag gaggaggagg agatgcagaa ttccgacatg actcaggagg aggaggagat 840
gcagaattcc gacatgactc aggaggagga ggagatgcag aattccgaca tgactcagga 900
ggaggaggag atgcagaatt ccgacatgac tcaggaggag gaggagatgc agaattccga 960

-continued

```
catgactcag gaggaggagg agatgcagaa ttccgacatg actcaggagg aggaggagat   1020
gcagaattcc gacatgactc aggaggagga ggagatgcag aattccgaca tgactcagga   1080
ggaggaggag atgcagaatt ccgacatgac tcaggaggag gaggagatgc agaattccga   1140
catgactcag gaggaggagg agatgcagaa ttccgacatg actcaggagg aggaggagat   1200
gcagaattcc gacatgactc aggaggagga ggagatgcag aattccgaca tgactcagga   1260
ggaggaggag atgcagaatt ccgacatgac tcaggaggag gaggagatgc agaattccga   1320
catgactcag gaggaggagg agatgcagaa ttccgacatg actcaggagg aggaggagat   1380
gcagaattcc gacatgactc aggaggagga ggagatgcag aattccgaca tgactcagga   1440
ggaggaggag atgcagaatt ccgacatgac tcaggaggag gaggagatgc agaattccga   1500
catgactcag gaggaggagg agatgcagaa ttccgacatg actcaggagg aggaggagat   1560
gcagaattcc gacatgactc aggaggagga ggagatgcag aattccgaca tgactcagga   1620
ggaggaggag atgcagaatt ccgacatgac tcaggaggag gaggaacaca aaactacacc   1680
atgaacttgg cctcgcagaa ctggaacaac tacgatccaa ccgaggaaat ccccgctcct   1740
ttgggaactc ccgacttcgt gggacgtatc caaggtgtcc tgacacagac tacacgtcgc   1800
gacggctcta ctcgcggaca caaggccact gtgtcgacag gttccgtcca cttcacccct   1860
aagctgggct ctgtgcaatt cagcacagac acctcaaacg gaggaggaga tgcagaattc   1920
cgacatgact caggatatga agttcatcat caaggaggag gagatgcaga attccgacat   1980
gactcaggat atgaagttca tcatcaagga ggaggagatg cagaattccg acatgactca   2040
ggatatgaag ttcatcatca aggaggagga gatgcagaat tccgacatga ctcaggatat   2100
gaagttcatc atcaaggagg aggagatgca gaattccgac atgactcagg atatgaagtt   2160
catcatcaag gaggaggaga tgcagaattc cgacatgact caggatatga agttcatcat   2220
caaggaggag gagatgcaga attccgacat gactcaggat atgaagttca tcatcaagga   2280
ggaggagatg cagaattccg acatgactca ggatatgaag ttcatcatca aggaggagga   2340
gatgcagaat tccgacatga ctcaggatat gaagttcatc atcaaggagg aggagatgca   2400
gaattccgac atgactcagg atatgaagtt catcatcaag gaggaggaga tgcagaattc   2460
cgacatgact caggatatga agttcatcat caaggaggag gagatgcaga attccgacat   2520
gactcaggat atgaagttca tcatcaagga ggaggagatg cagaattccg acatgactca   2580
ggatatgaag ttcatcatca aggaggagga gatgcagaat tccgacatga ctcaggatat   2640
gaagttcatc atcaaggagg aggagatgca gaattccgac atgactcagg atatgaagtt   2700
catcatcaag gaggaggaga tgcagaattc cgacatgact caggatatga agttcatcat   2760
caaggaggag gagatgcaga attccgacat gactcaggat atgaagttca tcatcaagga   2820
ggaggagatg cagaattccg acatgactca ggatatgaag ttcatcatca aggaggagga   2880
gatgcagaat tccgacatga ctcaggatat gaagttcatc atcaaggagg aggagatgca   2940
gaattccgac atgactcagg atatgaagtt catcatcaag gaggaggaga tttcgagact   3000
ggccagaaca ccaggttcac tcccgtgggt gtcgttcaag acggcagcac cactcaccag   3060
aacgaacccc agcaatgggt cctccctgac tactcgggca gggattccca caacgttcac   3120
ttggctccgg ccgtggctcc aaccttccct ggagagcagt tgctgttctt cagatccact   3180
atgccaggct gctctggata cccgaacatg aacctcgact gtctcttgcc tcaggagtgg   3240
gtgcaacact tctaccagga atctgcccca gctcaaagcg acgtcgctct gctccgtttc   3300
gttaaccccg ataccggtcg cgtgctcttc gagtgtaagt tgcacaagtc tggttacgtc   3360
```
actgttgccc acacaggcca gcacgacctg gtcatccctc ccaacggcta cttccgcttc 3420
gatagctggg tcaaccagtt ctacacactc gccccgatgg gaaacggagc cggtcgtcgc 3480
agagccttgt aa 3492

<210> SEQ ID NO 85
<211> LENGTH: 2502
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 85
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaacag gaggaggaga tgcagaattc 240
cgacatgact caggatatga agttcatcat caaggaggag gagatgcaga attccgacat 300
gactcaggat atgaagttca tcatcaagga ggaggagatg cagaattccg acatgactca 360
ggatatgaag ttcatcatca aggaggagga gatgcagaat tccgacatga ctcaggatat 420
gaagttcatc atcaaggagg aggagatgca gaattccgac atgactcagg atatgaagtt 480
catcatcaag gaggaggaga tgcagaattc cgacatgact caggatatga agttcatcat 540
caaggaggag gagatgcaga attccgacat gactcaggat atgaagttca tcatcaagga 600
ggaggagatg cagaattccg acatgactca ggatatgaag ttcatcatca aggaggagga 660
gatgcagaat tccgacatga ctcaggatat gaagttcatc atcaaggagg aggagatgca 720
gaattccgac atgactcagg atatgaagtt catcatcaag gaggaggaga tgcagaattc 780
cgacatgact caggatatga agttcatcat caaggaggag gagatgcaga attccgacat 840
gactcaggat atgaagttca tcatcaagga ggaggagatg cagaattccg acatgactca 900
ggatatgaag ttcatcatca aggaggagga gatgcagaat tccgacatga ctcaggatat 960
gaagttcatc atcaaggagg aggagatgca gaattccgac atgactcagg atatgaagtt 1020
catcatcaag gaggaggaga tgcagaattc cgacatgact caggatatga agttcatcat 1080
caaggaggag gagatgcaga attccgacat gactcaggat atgaagttca tcatcaagga 1140
ggaggagatg cagaattccg acatgactca ggatatgaag ttcatcatca aggaggagga 1200
gatgcagaat tccgacatga ctcaggatat gaagttcatc atcaaggagg aggagatgca 1260
gaattccgac atgactcagg atatgaagtt catcatcaag gaggaggaca aaactacacc 1320
atgaacttgg cctcgcagaa ctggaacaac tacgatccaa ccgaggaaat ccccgctcct 1380
ttgggaactc ccgacttcgt gggacgtatc caaggtgtcc tgacacagac tacacgtcgc 1440
gacggctcta ctcgcggaca caaggccact gtgtcgacag gttccgtcca cttcacccct 1500
aagctgggct ctgtgcaatt cagcacagac acctcaaacg atggaggagg agatgcagaa 1560
ttccgacatg actcaggata tgaagttgga ggaggagatg cagaattccg acatgactca 1620
ggatatgaag ttggaggagg agatgcagaa ttccgacatg actcaggata tgaagttgga 1680
ggaggagatg cagaattccg acatgactca ggatatgaag ttggaggagg agatgcagaa 1740
ttccgacatg actcaggata tgaagttgga ggaggagatg cagaattccg acatgactca 1800
ggatatgaag ttggaggagg agatgcagaa ttccgacatg actcaggata tgaagttgga 1860

```
ggaggagatg cagaattccg acatgactca ggatatgaag ttggaggagg agatgcagaa   1920
ttccgacatg actcaggata tgaagttgga ggaggagatg cagaattccg acatgactca   1980
ggatatgaag ttggaggagg attcgagact ggccagaaca ccaggttcac tcccgtgggt   2040
gtcgttcaag acggcagcac cactcaccag aacgaacccc agcaatgggt cctccctgac   2100
tactcgggca gggattccca caacgttcac ttggctccgg ccgtggctcc aaccttccct   2160
ggagagcagt tgctgttctt cagatccact atgccaggct gctctggata cccgaacatg   2220
aacctcgact gtctcttgcc tcaggagtgg gtgcaacact tctaccagga atctgcccca   2280
gctcaaagcg acgtcgctct gctccgtttc gttaaccccg ataccggtcg cgtgctcttc   2340
gagtgtaagt tgcacaagtc tggttacgtc actgttgccc acacaggcca gcacgacctg   2400
gtcatccctc ccaacggcta cttccgcttc gatagctggg tcaaccagtt ctacacactc   2460
gccccgatgg gaaacggagc cggtcgtcgc agagccttgt aa                       2502
```

<210> SEQ ID NO 86
<211> LENGTH: 1458
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 86

```
atgaagccct tctcggtccc tatcctgaca gttgaggaaa tgaccaactc tagattccca     60
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc gctggaacac aaggaggagg agatgcagaa    240
ttccgacatg actcaggata tgaagttgga ggaggagatg cagaattccg acatgactca    300
ggatatgaag ttggaggagg agatgcagaa ttccgacatg actcaggata tgaagttgga    360
ggaggagatg cagaattccg acatgactca ggatatgaag ttggaggagg agatgcagaa    420
ttccgacatg actcaggata tgaagttgga ggaggagatg cagaattccg acatgactca    480
ggatatgaag ttggaggagg agatgcagaa ttccgacatg actcaggata tgaagttgga    540
ggaggagatg cagaattccg acatgactca ggatatgaag ttggaggagg agatgcagaa    600
ttccgacatg actcaggata tgaagttgga ggaggagatg cagaattccg acatgactca    660
ggatatgaag ttggaggagg aaactacacc atgaacttgg cctcgcagaa ctggaacaac    720
tacgatccaa ccgaggaaat ccccgctcct ttgggaactc ccgacttcgt gggacgtatc    780
caaggtgtcc tgacacagac tacacgtcgc gacggctcta ctcgcggaca caaggccact    840
gtgtcgacag gttccgtcca cttcacccct aagctgggct ctgtgcaatt cagcacagac    900
acctcaggag gaggagatgc agaattccga catgactcag gaggaggagg aaacgatttc    960
gagactggcc agaacaccag gttcactccc gtgggtgtcg ttcaagacgg cagcaccact   1020
caccagaacg aaccccagca atgggtcctc cctgactact cgggcaggga ttcccacaac   1080
gttcacttgg ctccggccgt ggctccaacc ttccctggag agcagttgct gttcttcaga   1140
tccactatgc caggctgctc tggatacccg aacatgaacc tcgactgtct cttgcctcag   1200
gagtgggtgc aacacttcta ccaggaatct gccccagctc aaagcgacgt cgctctgctc   1260
cgtttcgtta accccgatac cggtcgcgtg ctcttcgagt gtaagttgca caagtctggt   1320
tacgtcactg ttgcccacac aggccagcac gacctggtca tccctcccaa cggctacttc   1380
```
cgcttcgata gctgggtcaa ccagttctac acactcgccc cgatgggaaa cggagccggt 1440
cgtcgcagag ccttgtaa 1458

<210> SEQ ID NO 87
<211> LENGTH: 1080
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 87
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaacac aaaactacac catgaacttg 240
gcctcgcaga actggaacaa ctacgatcca accgaggaaa tccccgctcc tttgggaact 300
cccgacttcg tgggacgtat ccaaggtgtc ctgacacaga ctacacgtcg cgacggctct 360
actcgcggac acaaggccac tgtgtcgaca ggttccgtcc acttcacccc taagctgggc 420
tctgtgcaat tcagcacaga cacctcagga ggaggagatg cagaattccg acatgactca 480
ggatatgaag ttcatcatca aggaggagga aacgatttcg agactggcca gaacaccagg 540
ttcactcccg tgggtgtcgt tcaagacggc ggaggaggag atgcagaatt ccgacatgac 600
tcaggatatg aagttcatca tcaaggagga ggaagcacca ctcaccagaa cgaaccccag 660
caatgggtcc tccctgacta ctcgggcagg gattcccaca acgttcactt ggctccggcc 720
gtggctccaa ccttccctgg agagcagttg ctgttcttca gatccactat gccaggctgc 780
tctggatacc cgaacatgaa cctcgactgt ctcttgcctc aggagtgggt gcaacacttc 840
taccaggaat ctgccccagc tcaaagcgac gtcgctctgc tccgtttcgt taaccccgat 900
accggtcgcg tgctcttcga gtgtaagttg cacaagtctg gttacgtcac tgttgcccac 960
acaggccagc acgacctggt catccctccc aacggctact tccgcttcga tagctgggtc 1020
aaccagttct acacactcgc cccgatggga aacggagccg gtcgtcgcag agccttgtaa 1080

<210> SEQ ID NO 88
<211> LENGTH: 1872
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 88
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaacac aaaactacac catgaacttg 240
gcctcgcaga actggaacaa ctacgatcca accgaggaaa tccccgctcc tttgggaact 300
cccgacttcg tgggacgtat ccaaggtgtc ctgacacaga ctacacgtcg cgacggctct 360
actcgcggac acaaggccac tgtgtcgaca ggttccgtcc acttcacccc taagctgggc 420
tctgtgcaat tcagcacaga cacctcagga ggaggagatg cagaattccg acatgactca 480
ggatatgaag ttggaggagg agatgcagaa ttccgacatg actcaggata tgaagttgga 540
ggaggagatg cagaattccg acatgactca ggatatgaag ttggaggagg agatgcagaa 600
ttccgacatg actcaggata tgaagttgga ggaggagatg cagaattccg acatgactca 660
ggatatgaag ttggaggagg agatgcagaa ttccgacatg actcaggata tgaagttgga 720
ggaggagatg cagaattccg acatgactca ggatatgaag ttggaggagg agatgcagaa 780
ttccgacatg actcaggata tgaagttgga ggaggagatg cagaattccg acatgactca 840
ggatatgaag ttggaggagg agatgcagaa ttccgacatg actcaggata tgaagttgga 900
ggaggaaacg atttcgagac tggccagaac accaggttca ctcccgtggg tgtcgttcaa 960
gacggcggag gaggagatgc agaattccga catgactcag gatatgaagt tggaggagga 1020
gatgcagaat tccgacatga ctcaggatat gaagttggag gaggagatgc agaattccga 1080
catgactcag gatatgaagt tggaggagga gatgcagaat tccgacatga ctcaggatat 1140
gaagttggag gaggagatgc agaattccga catgactcag gatatgaagt tggaggagga 1200
gatgcagaat tccgacatga ctcaggatat gaagttggag gaggagatgc agaattccga 1260
catgactcag gatatgaagt tggaggagga gatgcagaat tccgacatga ctcaggatat 1320
gaagttggag gaggagatgc agaattccga catgactcag gatatgaagt tggaggagga 1380
gatgcagaat tccgacatga ctcaggatat gaagttggag gaggaagcac cactcaccag 1440
aacgaacccc agcaatgggt cctccctgac tactcgggca gggattccca caacgttcac 1500
ttggctccgg ccgtggctcc aaccttccct ggagagcagt tgctgttctt cagatccact 1560
atgccaggct gctctggata cccgaacatg aacctcgact gtctcttgcc tcaggagtgg 1620
gtgcaacact tctaccagga atctgcccca gctcaaagcg acgtcgctct gctccgtttc 1680
gttaaccccg ataccggtcg cgtgctcttc gagtgtaagt tgcacaagtc tggttacgtc 1740
actgttgccc acacaggcca gcacgacctg gtcatccctc ccaacggcta cttccgcttc 1800
gatagctggg tcaaccagtt ctacacactc gccccgatgg gaaacggagc cggtcgtcgc 1860
agagccttgt aa 1872

<210> SEQ ID NO 89
<211> LENGTH: 2052
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 89
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaacac aaaactacac catgaacttg 240
gcctcgcaga actggaacaa ctacgatcca accgaggaaa tccccgctcc tttgggaact 300
cccgacttcg tgggacgtat ccaaggtgtc ctgacacaga ctacacgtcg cgacggctct 360
actcgcggac acaaggccac tgtgtcgaca ggttccgtcc acttcacccc taagctgggc 420
tctgtgcaat tcagcacaga cacctcagga ggaggagatg cagaattccg acatggagga 480
ggagatgcag aattccgaca tggaggagga gatgcagaat tccgacatgg aggaggagat 540
gcagaattcc gacatggagg aggagatgca gaattccgac atggaggagg agatgcagaa 600

-continued ttccgacatg gaggaggaga tgcagaattc cgacatggag gaggagatgc agaattccga 660
catggaggag gagatgcaga attccgacat ggaggaggag atgcagaatt ccgacatgga 720
ggaggagatg cagaattccg acatggagga ggagatgcag aattccgaca tggaggagga 780
gatgcagaat tccgacatgg aggaggagat gcagaattcc gacatggagg aggagatgca 840
gaattccgac atggaggagg agatgcagaa ttccgacatg gaggaggaga tgcagaattc 900
cgacatggag gaggagatgc agaattccga catggaggag gagatgcaga attccgacat 960
ggaggaggag atgcagaatt ccgacatgga ggaggaaacg atttcgagac tggccagaac 1020
accaggttca ctcccgtggg tgtcgttcaa gacggcggag gaggagatgc agaattccga 1080
catggaggag gagatgcaga attccgacat ggaggaggag atgcagaatt ccgacatgga 1140
ggaggagatg cagaattccg acatggagga ggagatgcag aattccgaca tggaggagga 1200
gatgcagaat tccgacatgg aggaggagat gcagaattcc gacatggagg aggagatgca 1260
gaattccgac atggaggagg agatgcagaa ttccgacatg gaggaggaga tgcagaattc 1320
cgacatggag gaggagatgc agaattccga catggaggag gagatgcaga attccgacat 1380
ggaggaggag atgcagaatt ccgacatgga ggaggagatg cagaattccg acatggagga 1440
ggagatgcag aattccgaca tggaggagga gatgcagaat tccgacatgg aggaggagat 1500
gcagaattcc gacatggagg aggagatgca gaattccgac atggaggagg agatgcagaa 1560
ttccgacatg gaggaggaga tgcagaattc cgacatggag gaggaagcac cactcaccag 1620
aacgaacccc agcaatgggt cctccctgac tactcgggca gggattccca caacgttcac 1680
ttggctccgg ccgtggctcc aaccttccct ggagagcagt tgctgttctt cagatccact 1740
atgccaggct gctctggata cccgaacatg aacctcgact gtctcttgcc tcaggagtgg 1800
gtgcaacact tctaccagga atctgcccca gctcaaagcg acgtcgctct gctccgtttc 1860
gttaaccccg ataccggtcg cgtgctcttc gagtgtaagt tgcacaagtc tggttacgtc 1920
actgttgccc acacaggcca gcacgacctg gtcatccctc ccaacggcta cttccgcttc 1980
gatagctggg tcaaccagtt ctacacactc gccccgatgg gaaacggagc cggtcgtcgc 2040
agagccttgt aa 2052

<210> SEQ ID NO 90
<211> LENGTH: 3852
<212> TYPE: DNA
<213> ORGANISM: artificial sequence
<220> FEATURE:
<223> OTHER INFORMATION: synthetic nucleotide sequence encoding the
      recombinant P protein

<400> SEQUENCE: 90
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaacac aaaactacac catgaacttg 240
gcctcgcaga actggaacaa ctacgatcca accgaggaaa tccccgctcc tttgggaact 300
cccgacttcg tgggacgtat ccaaggtgtc ctgacacaga ctacacgtcg cgacggctct 360
actcgcggac acaaggccac tgtgtcgaca ggttccgtcc acttcacccc taagctgggc 420
tctgtgcaat tcagcacaga cacctcagga ggaggagatg cagaattccg acatgactca 480
ggaggaggag gagatgcaga attccgacat gactcaggag gaggaggaga tgcagaattc 540

-continued

```
cgacatgact caggaggagg aggagatgca gaattccgac atgactcagg aggaggagga    600
gatgcagaat tccgacatga ctcaggagga ggaggagatg cagaattccg acatgactca    660
ggaggaggag gagatgcaga attccgacat gactcaggag gaggaggaga tgcagaattc    720
cgacatgact caggaggagg aggagatgca gaattccgac atgactcagg aggaggagga    780
gatgcagaat tccgacatga ctcaggagga ggaggagatg cagaattccg acatgactca    840
ggaggaggag gagatgcaga attccgacat gactcaggag gaggaggaga tgcagaattc    900
cgacatgact caggaggagg aggagatgca gaattccgac atgactcagg aggaggagga    960
gatgcagaat tccgacatga ctcaggagga ggaggagatg cagaattccg acatgactca   1020
ggaggaggag gagatgcaga attccgacat gactcaggag gaggaggaga tgcagaattc   1080
cgacatgact caggaggagg aggagatgca gaattccgac atgactcagg aggaggagga   1140
gatgcagaat tccgacatga ctcaggagga ggaggagatg cagaattccg acatgactca   1200
ggaggaggag gagatgcaga attccgacat gactcaggag gaggaggaga tgcagaattc   1260
cgacatgact caggaggagg aggagatgca gaattccgac atgactcagg aggaggagga   1320
gatgcagaat tccgacatga ctcaggagga ggaggagatg cagaattccg acatgactca   1380
ggaggaggag gagatgcaga attccgacat gactcaggag gaggaggaga tgcagaattc   1440
cgacatgact caggaggagg aggagatgca gaattccgac atgactcagg aggaggagga   1500
gatgcagaat tccgacatga ctcaggagga ggaggagatg cagaattccg acatgactca   1560
ggaggaggag gagatgcaga attccgacat gactcaggag gaggaggaga tgcagaattc   1620
cgacatgact caggaggagg aggagatgca gaattccgac atgactcagg aggaggagga   1680
gatgcagaat tccgacatga ctcaggagga ggaggagatg cagaattccg acatgactca   1740
ggaggaggag gagatgcaga attccgacat gactcaggag gaggaggaga tgcagaattc   1800
cgacatgact caggaggagg aggagatgca gaattccgac atgactcagg aggaggagga   1860
gatgcagaat tccgacatga ctcaggagga ggaggaaacg atttcgagac tggccagaac   1920
accaggttca ctcccgtggg tgtcgttcaa gacggcggag gaggagatgc agaattccga   1980
catgactcag gaggaggagg agatgcagaa ttccgacatg actcaggagg aggaggagat   2040
gcagaattcc gacatgactc aggaggagga ggagatgcag aattccgaca tgactcagga   2100
ggaggaggag atgcagaatt ccgacatgac tcaggaggag gaggagatgc agaattccga   2160
catgactcag gaggaggagg agatgcagaa ttccgacatg actcaggagg aggaggagat   2220
gcagaattcc gacatgactc aggaggagga ggagatgcag aattccgaca tgactcagga   2280
ggaggaggag atgcagaatt ccgacatgac tcaggaggag gaggagatgc agaattccga   2340
catgactcag gaggaggagg agatgcagaa ttccgacatg actcaggagg aggaggagat   2400
gcagaattcc gacatgactc aggaggagga ggagatgcag aattccgaca tgactcagga   2460
ggaggaggag atgcagaatt ccgacatgac tcaggaggag gaggagatgc agaattccga   2520
catgactcag gaggaggagg agatgcagaa ttccgacatg actcaggagg aggaggagat   2580
gcagaattcc gacatgactc aggaggagga ggagatgcag aattccgaca tgactcagga   2640
ggaggaggag atgcagaatt ccgacatgac tcaggaggag gaggagatgc agaattccga   2700
catgactcag gaggaggagg agatgcagaa ttccgacatg actcaggagg aggaggagat   2760
gcagaattcc gacatgactc aggaggagga ggagatgcag aattccgaca tgactcagga   2820
ggaggaggag atgcagaatt ccgacatgac tcaggaggag gaggagatgc agaattccga   2880
catgactcag gaggaggagg agatgcagaa ttccgacatg actcaggagg aggaggagat   2940
```

```
gcagaattcc gacatgactc aggaggagga ggagatgcag aattccgaca tgactcagga   3000
ggaggaggag atgcagaatt ccgacatgac tcaggaggag gaggagatgc agaattccga   3060
catgactcag gaggaggagg agatgcagaa ttccgacatg actcaggagg aggaggagat   3120
gcagaattcc gacatgactc aggaggagga ggagatgcag aattccgaca tgactcagga   3180
ggaggaggag atgcagaatt ccgacatgac tcaggaggag gaggagatgc agaattccga   3240
catgactcag gaggaggagg agatgcagaa ttccgacatg actcaggagg aggaggagat   3300
gcagaattcc gacatgactc aggaggagga ggagatgcag aattccgaca tgactcagga   3360
ggaggaggag atgcagaatt ccgacatgac tcaggaggag gaggaagcac cactcaccag   3420
aacgaacccc agcaatgggt cctccctgac tactcgggca gggattccca caacgttcac   3480
ttggctccgg ccgtggctcc aaccttccct ggagagcagt tgctgttctt cagatccact   3540
atgccaggct gctctggata cccgaacatg aacctcgact gtctcttgcc tcaggagtgg   3600
gtgcaacact tctaccagga atctgcccca gctcaaagcg acgtcgctct gctccgtttc   3660
gttaaccccg ataccggtcg cgtgctcttc gagtgtaagt tgcacaagtc tggttacgtc   3720
actgttgccc acacaggcca gcacgacctg gtcatccctc ccaacggcta cttccgcttc   3780
gatagctggg tcaaccagtt ctacacactc gccccgatgg gaaacggagc cggtcgtcgc   3840
agagccttgt aa                                                        3852
```

```
<210> SEQ ID NO 91
<211> LENGTH: 1035
<212> TYPE: DNA
<213> ORGANISM: artificial sequence
<220> FEATURE:
<223> OTHER INFORMATION: synthetic nucleotide sequence encoding the
      recombinant P protein

<400> SEQUENCE: 91
```

```
atgaagccct tctcggtccc tatcctgaca gttgaggaaa tgaccaactc tagattccca     60
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc gctggaacac aaaactacac catgaacttg    240
gcctcgcaga actggaacaa ctacgatcca accgaggaaa tccccgctcc tttgggaact    300
cccgacttcg tgggacgtat ccaaggtgtc ctgacacaga ctacacgtcg cgacggctct    360
actcgcggac acaaggccac tgtgtcgaca ggttccgtcc acttcacccc taagctgggc    420
tctgtgcaat tcagcacaga caccggagga ggagatgcag aattccgaca tggaggagga    480
tcaaacgatt tcgagactgg ccagaacacc aggttcactc ccgtgggtgt cgttcaagac    540
ggaggaggag atgcagaatt ccgacatgac tcaggaggag gaggaggcag caccactcac    600
cagaacgaac cccagcaatg ggtcctccct gactactcgg gcagggattc ccacaacgtt    660
cacttggctc cggccgtggc tccaaccttc cctggagagc agttgctgtt cttcagatcc    720
actatgccag gctgctctgg atacccgaac atgaacctcg actgtctctt gcctcaggag    780
tgggtgcaac acttctacca ggaatctgcc ccagctcaaa gcgacgtcgc tctgctccgt    840
ttcgttaacc ccgataccgg tcgcgtgctc ttcgagtgta agttgcacaa gtctggttac    900
gtcactgttg cccacacagg ccagcacgac ctggtcatcc ctcccaacgg ctacttccgc    960
ttcgatagct gggtcaacca gttctacaca ctcgccccga tgggaaacgg agccggtcgt   1020
cgcagagcct tgtaa                                                    1035
```

<210> SEQ ID NO 92
<211> LENGTH: 1188
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 92
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaacac aaaactacac catgaacttg 240
gcctcgcaga actggaacaa ctacgatcca accgaggaaa tccccgctcc tttgggaact 300
cccgacttcg tgggacgtat ccaaggtgtc ctgacacaga ctacacgtcg cgacggctct 360
actcgcggac acaaggccac tgtgtcgaca ggttccgtcc acttcacccc taagctgggc 420
tctgtgcaat tcagcacaga cacctcagga ggaggagatg cagaattccg acatgactca 480
ggatatgaag ttggaggagg agatgcagaa ttccgacatg actcaggata tgaagttgga 540
ggaggagatg cagaattccg acatgactca ggatatgaag ttggaggagg aaacgatttc 600
gagactggcc agaacaccag gttcactccc gtgggtgtcg ttcaagacgg cggaggagga 660
gatgcagaat tccgacatgg aggaggagat gcagaattcc gacatggagg aggagatgca 720
gaattccgac atggaggagg aagcaccact caccagaacg aaccccagca atgggtcctc 780
cctgactact cgggcaggga ttcccacaac gttcacttgg ctccggccgt ggctccaacc 840
ttccctggag agcagttgct gttcttcaga tccactatgc caggctgctc tggatacccg 900
aacatgaacc tcgactgtct cttgcctcag gagtgggtgc aacacttcta ccaggaatct 960
gccccagctc aaagcgacgt cgctctgctc cgtttcgtta accccgatac cggtcgcgtg 1020
ctcttcgagt gtaagttgca caagtctggt tacgtcactg ttgcccacac aggccagcac 1080
gacctggtca tccctcccaa cggctacttc cgcttcgata gctgggtcaa ccagttctac 1140
acactcgccc cgatgggaaa cggagccggt cgtcgcagag ccttgtaa 1188

<210> SEQ ID NO 93
<211> LENGTH: 1872
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 93
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaacac aaaactacac catgaacttg 240
gcctcgcaga actggaacaa ctacgatcca accgaggaaa tccccgctcc tttgggaact 300
cccgacttcg tgggacgtat ccaaggtgtc ctgacacaga ctacacgtcg cgacggctct 360
actcgcggac acaaggccac tgtgtcgaca ggttccgtcc acttcacccc taagctgggc 420
tctgtgcaat tcagcacaga cacctcagga ggaggagatg cagaattccg acatgactca 480

```
ggaggaggag gagatgcaga attccgacat gactcaggag gaggaggaga tgcagaattc    540
cgacatgact caggaggagg aggagatgca gaattccgac atgactcagg aggaggagga    600
gatgcagaat tccgacatga ctcaggagga ggaggagatg cagaattccg acatgactca    660
ggaggaggag gagatgcaga attccgacat gactcaggag gaggaggaga tgcagaattc    720
cgacatgact caggaggagg aggagatgca gaattccgac atgactcagg aggaggagga    780
gatgcagaat tccgacatga ctcaggagga ggaggaaacg atttcgagac tggccagaac    840
accaggttca ctcccgtggg tgtcgttcaa gacggcggag gaggagatgc agaattccga    900
catgactcag gatatgaagt tcatcatcaa ggaggaggag atgcagaatt ccgacatgac    960
tcaggatatg aagttcatca tcaaggagga ggagatgcag aattccgaca tgactcagga   1020
tatgaagttc atcatcaagg aggaggagat gcagaattcc gacatgactc aggatatgaa   1080
gttcatcatc aaggaggagg agatgcagaa ttccgacatg actcaggata tgaagttcat   1140
catcaaggag gaggagatgc agaattccga catgactcag gatatgaagt tcatcatcaa   1200
ggaggaggag atgcagaatt ccgacatgac tcaggatatg aagttcatca tcaaggagga   1260
ggagatgcag aattccgaca tgactcagga tatgaagttc atcatcaagg aggaggagat   1320
gcagaattcc gacatgactc aggatatgaa gttcatcatc aaggaggagg agatgcagaa   1380
ttccgacatg actcaggata tgaagttcat catcaaggag gaggaagcac cactcaccag   1440
aacgaacccc agcaatgggt cctccctgac tactcgggca gggattccca caacgttcac   1500
ttggctccgg ccgtggctcc aaccttccct ggagagcagt tgctgttctt cagatccact   1560
atgccaggct gctctggata cccgaacatg aacctcgact gtctcttgcc tcaggagtgg   1620
gtgcaacact tctaccagga atctgcccca gctcaaagcg acgtcgctct gctccgtttc   1680
gttaaccccg ataccggtcg cgtgctcttc gagtgtaagt tgcacaagtc tggttacgtc   1740
actgttgccc acacaggcca gcacgacctg gtcatccctc ccaacggcta cttccgcttc   1800
gatagctggg tcaaccagtt ctacacactc gccccgatgg gaaacggagc cggtcgtcgc   1860
agagccttgt aa                                                       1872
```

<210> SEQ ID NO 94
<211> LENGTH: 2592
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 94

```
atgaagccct tctcggtccc tatcctgaca gttgaggaaa tgaccaactc tagattccca     60
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc gctggaacac aaaactacac catgaacttg    240
gcctcgcaga actggaacaa ctacgatcca accgaggaaa tccccgctcc tttgggaact    300
cccgacttcg tgggacgtat ccaaggtgtc ctgacacaga ctacacgtcg cgacggctct    360
actcgcggac acaaggccac tgtgtcgaca ggttccgtcc acttcacccc taagctgggc    420
tctgtgcaat tcagcacaga cacctcagga ggaggagatg cagaattccg acatgactca    480
ggatatgaag ttcatcatca aggaggagga gatgcagaat tccgacatga ctcaggatat    540
gaagttcatc atcaaggagg aggagatgca gaattccgac atgactcagg atatgaagtt    600
```

```
catcatcaag gaggaggaga tgcagaattc cgacatgact caggatatga agttcatcat    660
caaggaggag gagatgcaga attccgacat gactcaggat atgaagttca tcatcaagga    720
ggaggagatg cagaattccg acatgactca ggatatgaag ttcatcatca aggaggagga    780
gatgcagaat tccgacatga ctcaggatat gaagttcatc atcaaggagg aggagatgca    840
gaattccgac atgactcagg atatgaagtt catcatcaag gaggaggaga tgcagaattc    900
cgacatgact caggatatga agttcatcat caaggaggag gagatgcaga attccgacat    960
gactcaggat atgaagttca tcatcaagga ggaggagatg cagaattccg acatgactca   1020
ggatatgaag ttcatcatca aggaggagga gatgcagaat tccgacatga ctcaggatat   1080
gaagttcatc atcaaggagg aggagatgca gaattccgac atgactcagg atatgaagtt   1140
catcatcaag gaggaggaga tgcagaattc cgacatgact caggatatga agttcatcat   1200
caaggaggag gagatgcaga attccgacat gactcaggat atgaagttca tcatcaagga   1260
ggaggagatg cagaattccg acatgactca ggatatgaag ttcatcatca aggaggagga   1320
gatgcagaat tccgacatga ctcaggatat gaagttcatc atcaaggagg aggagatgca   1380
gaattccgac atgactcagg atatgaagtt catcatcaag gaggaggaga tgcagaattc   1440
cgacatgact caggatatga agttcatcat caaggaggag gagatgcaga attccgacat   1500
gactcaggat atgaagttca tcatcaagga ggaggaaacg atttcgagac tggccagaac   1560
accaggttca ctcccgtggg tgtcgttcaa gacggcggag gaggagatgc agaattccga   1620
catggaggag gagatgcaga attccgacat ggaggaggag atgcagaatt ccgacatgga   1680
ggaggagatg cagaattccg acatggagga ggagatgcag aattccgaca tggaggagga   1740
gatgcagaat tccgacatgg aggaggagat gcagaattcc gacatggagg aggagatgca   1800
gaattccgac atggaggagg agatgcagaa ttccgacatg gaggaggaga tgcagaattc   1860
cgacatggag gaggagatgc agaattccga catggaggag gagatgcaga attccgacat   1920
ggaggaggag atgcagaatt ccgacatgga ggaggagatg cagaattccg acatggagga   1980
ggagatgcag aattccgaca tggaggagga gatgcagaat tccgacatgg aggaggagat   2040
gcagaattcc gacatggagg aggagatgca gaattccgac atggaggagg agatgcagaa   2100
ttccgacatg gaggaggaga tgcagaattc cgacatggag gaggaagcac cactcaccag   2160
aacgaacccc agcaatgggt cctccctgac tactcgggca gggattccca caacgttcac   2220
ttggctccgg ccgtggctcc aaccttccct ggagagcagt tgctgttctt cagatccact   2280
atgccaggct gctctggata cccgaacatg aacctcgact gtctcttgcc tcaggagtgg   2340
gtgcaacact tctaccagga atctgcccca gctcaaagcg acgtcgctct gctccgtttc   2400
gttaaccccg ataccggtcg cgtgctcttc gagtgtaagt tgcacaagtc tggttacgtc   2460
actgttgccc acacaggcca gcacgacctg gtcatccctc ccaacggcta cttccgcttc   2520
gatagctggg tcaaccagtt ctacacactc gccccgatgg gaaacggagc cggtcgtcgc   2580
agagccttgt aa                                                       2592
```

<210> SEQ ID NO 95
<211> LENGTH: 3402
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 95

-continued

```
atgaagccct tctcggtccc tatcctgaca gttgaggaaa tgaccaactc tagattccca     60
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc gctggaacac aaaactacac catgaacttg    240
gcctcgcaga actggaacaa ctacgatcca accgaggaaa tccccgctcc tttgggaact    300
cccgacttcg tgggacgtat ccaaggtgtc ctgacacaga ctacacgtcg cgacggctct    360
actcgcggac acaaggccac tgtgtcgaca ggttccgtcc acttcacccc taagctgggc    420
tctgtgcaat tcagcacaga cacctcaaac ggaggaggag atgcagaatt ccgacatgac    480
tcaggaggag gaggagatgc agaattccga catgactcag gaggaggagg agatgcagaa    540
ttccgacatg actcaggagg aggaggagat gcagaattcc gacatgactc aggaggagga    600
ggagatgcag aattccgaca tgactcagga ggaggaggag atgcagaatt ccgacatgac    660
tcaggaggag gaggagatgc agaattccga catgactcag gaggaggagg agatgcagaa    720
ttccgacatg actcaggagg aggaggagat gcagaattcc gacatgactc aggaggagga    780
ggagatgcag aattccgaca tgactcagga ggaggaggag atgcagaatt ccgacatgac    840
tcaggaggag gaggagatgc agaattccga catgactcag gaggaggagg agatgcagaa    900
ttccgacatg actcaggagg aggaggagat gcagaattcc gacatgactc aggaggagga    960
ggagatgcag aattccgaca tgactcagga ggaggaggag atgcagaatt ccgacatgac   1020
tcaggaggag gaggagatgc agaattccga catgactcag gaggaggagg agatgcagaa   1080
ttccgacatg actcaggagg aggaggagat gcagaattcc gacatgactc aggaggagga   1140
ggagatgcag aattccgaca tgactcagga ggaggaggag atgcagaatt ccgacatgac   1200
tcaggaggag gaggagatgc agaattccga catgactcag gaggaggagg agatgcagaa   1260
ttccgacatg actcaggagg aggaggagat gcagaattcc gacatgactc aggaggagga   1320
ggagatgcag aattccgaca tgactcagga ggaggaggag atgcagaatt ccgacatgac   1380
tcaggaggag gaggagatgc agaattccga catgactcag gaggaggagg agatgcagaa   1440
ttccgacatg actcaggagg aggaggagat gcagaattcc gacatgactc aggaggagga   1500
ggagatgcag aattccgaca tgactcagga ggaggaggag atttcgagac tggccagaac   1560
accaggttca ctcccgtggg tgtcgttcaa gacggcagcg gaggaggaga tgcagaattc   1620
cgacatgact caggatatga agttggagga ggagatgcag aattccgaca tgactcagga   1680
tatgaagttg gaggaggaga tgcagaattc cgacatgact caggatatga agttggagga   1740
ggagatgcag aattccgaca tgactcagga tatgaagttg gaggaggaga tgcagaattc   1800
cgacatgact caggatatga agttggagga ggagatgcag aattccgaca tgactcagga   1860
tatgaagttg gaggaggaga tgcagaattc cgacatgact caggatatga agttggagga   1920
ggagatgcag aattccgaca tgactcagga tatgaagttg gaggaggaga tgcagaattc   1980
cgacatgact caggatatga agttggagga ggagatgcag aattccgaca tgactcagga   2040
tatgaagttg gaggaggaga tgcagaattc cgacatgact caggatatga agttggagga   2100
ggagatgcag aattccgaca tgactcagga tatgaagttg gaggaggaga tgcagaattc   2160
cgacatgact caggatatga agttggagga ggagatgcag aattccgaca tgactcagga   2220
tatgaagttg gaggaggaga tgcagaattc cgacatgact caggatatga agttggagga   2280
ggagatgcag aattccgaca tgactcagga tatgaagttg gaggaggaga tgcagaattc   2340
cgacatgact caggatatga agttggagga ggagatgcag aattccgaca tgactcagga   2400
```
tatgaagttg gaggaggaga tgcagaattc cgacatgact caggatatga agttggagga 2460
ggagatgcag aattccgaca tgactcagga tatgaagttg gaggaggaga tgcagaattc 2520
cgacatgact caggatatga agttggagga ggagatgcag aattccgaca tgactcagga 2580
tatgaagttg gaggaggaga tgcagaattc cgacatgact caggatatga agttggagga 2640
ggagatgcag aattccgaca tgactcagga tatgaagttg gaggaggaga tgcagaattc 2700
cgacatgact caggatatga agttggagga ggagatgcag aattccgaca tgactcagga 2760
tatgaagttg gaggaggaga tgcagaattc cgacatgact caggatatga agttggagga 2820
ggagatgcag aattccgaca tgactcagga tatgaagttg gaggaggaga tgcagaattc 2880
cgacatgact caggatatga agttggagga ggagatgcag aattccgaca tgactcagga 2940
tatgaagttg gaggaggaac cactcaccag aacgaacccc agcaatgggt cctccctgac 3000
tactcgggca gggattccca caacgttcac ttggctccgg ccgtggctcc aaccttccct 3060
ggagagcagt tgctgttctt cagatccact atgccaggct gctctggata cccgaacatg 3120
aacctcgact gtctcttgcc tcaggagtgg gtgcaacact tctaccagga atctgcccca 3180
gctcaaagcg acgtcgctct gctccgtttc gttaaccccg ataccggtcg cgtgctcttc 3240
gagtgtaagt tgcacaagtc tggttacgtc actgttgccc acacaggcca gcacgacctg 3300
gtcatccctc ccaacggcta cttccgcttc gatagctggg tcaaccagtt ctacacactc 3360
gccccgatgg gaaacggagc cggtcgtcgc agagccttgt aa 3402

<210> SEQ ID NO 96
<211> LENGTH: 4932
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 96
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaacac aaaactacac catgaacttg 240
gcctcgcaga actggaacaa ctacgatcca accgaggaaa tccccgctcc tttgggaact 300
cccgacttcg tgggacgtat ccaaggtgtc ctgacacaga ctacacgtcg cgacggctct 360
actcgcggac acaaggccac tgtgtcgaca ggttccgtcc acttcacccc taagctgggc 420
tctgtgcaat tcagcacaga cacctcaaac gatggaggag gagatgcaga attccgacat 480
gactcaggat atgaagttca tcatcaagga ggaggagatg cagaattccg acatgactca 540
ggatatgaag ttcatcatca aggaggagga gatgcagaat tccgacatga ctcaggatat 600
gaagttcatc atcaaggagg aggagatgca gaattccgac atgactcagg atatgaagtt 660
catcatcaag gaggaggaga tgcagaattc cgacatgact caggatatga agttcatcat 720
caaggaggag gagatgcaga attccgacat gactcaggat atgaagttca tcatcaagga 780
ggaggagatg cagaattccg acatgactca ggatatgaag ttcatcatca aggaggagga 840
gatgcagaat tccgacatga ctcaggatat gaagttcatc atcaaggagg aggagatgca 900
gaattccgac atgactcagg atatgaagtt catcatcaag gaggaggaga tgcagaattc 960
cgacatgact caggatatga agttcatcat caaggaggag gagatgcaga attccgacat 1020

```
gactcaggat atgaagttca tcatcaagga ggaggagatg cagaattccg acatgactca   1080
ggatatgaag ttcatcatca aggaggagga gatgcagaat tccgacatga ctcaggatat   1140
gaagttcatc atcaaggagg aggagatgca gaattccgac atgactcagg atatgaagtt   1200
catcatcaag gaggaggaga tgcagaattc cgacatgact caggatatga agttcatcat   1260
caaggaggag gagatgcaga attccgacat gactcaggat atgaagttca tcatcaagga   1320
ggaggagatg cagaattccg acatgactca ggatatgaag ttcatcatca aggaggagga   1380
gatgcagaat tccgacatga ctcaggatat gaagttcatc atcaaggagg aggagatgca   1440
gaattccgac atgactcagg atatgaagtt catcatcaag gaggaggaga tgcagaattc   1500
cgacatgact caggatatga agttcatcat caaggaggag gagatgcaga attccgacat   1560
gactcaggat atgaagttca tcatcaagga ggaggagatg cagaattccg acatgactca   1620
ggatatgaag ttcatcatca aggaggagga gatgcagaat tccgacatga ctcaggatat   1680
gaagttcatc atcaaggagg aggagatgca gaattccgac atgactcagg atatgaagtt   1740
catcatcaag gaggaggaga tgcagaattc cgacatgact caggatatga agttcatcat   1800
caaggaggag gagatgcaga attccgacat gactcaggat atgaagttca tcatcaagga   1860
ggaggagatg cagaattccg acatgactca ggatatgaag ttcatcatca aggaggagga   1920
gatgcagaat tccgacatga ctcaggatat gaagttcatc atcaaggagg aggagatgca   1980
gaattccgac atgactcagg atatgaagtt catcatcaag gaggaggaga tgcagaattc   2040
cgacatgact caggatatga agttcatcat caaggaggag gagatgcaga attccgacat   2100
gactcaggat atgaagttca tcatcaagga ggaggagatg cagaattccg acatgactca   2160
ggatatgaag ttcatcatca aggaggagga gatgcagaat tccgacatga ctcaggatat   2220
gaagttcatc atcaaggagg aggagatgca gaattccgac atgactcagg atatgaagtt   2280
catcatcaag gaggaggaga tgcagaattc cgacatgact caggatatga agttcatcat   2340
caaggaggag gagatgcaga attccgacat gactcaggat atgaagttca tcatcaagga   2400
ggaggagatg cagaattccg acatgactca ggatatgaag ttcatcatca aggaggagga   2460
gatgcagaat tccgacatga ctcaggatat gaagttcatc atcaaggagg aggagatgca   2520
gaattccgac atgactcagg atatgaagtt catcatcaag gaggaggaga tgcagaattc   2580
cgacatgact caggatatga agttcatcat caaggaggag gattcgagac tggccagaac   2640
accaggttca ctcccgtggg tgtcgttcaa gacggcagca ccggaggagg agatgcagaa   2700
ttccgacatg actcaggata tgaagttgga ggaggagatg cagaattccg acatgactca   2760
ggatatgaag ttggaggagg agatgcagaa ttccgacatg actcaggata tgaagttgga   2820
ggaggagatg cagaattccg acatgactca ggatatgaag ttggaggagg agatgcagaa   2880
ttccgacatg actcaggata tgaagttgga ggaggagatg cagaattccg acatgactca   2940
ggatatgaag ttggaggagg agatgcagaa ttccgacatg actcaggata tgaagttgga   3000
ggaggagatg cagaattccg acatgactca ggatatgaag ttggaggagg agatgcagaa   3060
ttccgacatg actcaggata tgaagttgga ggaggagatg cagaattccg acatgactca   3120
ggatatgaag ttggaggagg agatgcagaa ttccgacatg actcaggata tgaagttgga   3180
ggaggagatg cagaattccg acatgactca ggatatgaag ttggaggagg agatgcagaa   3240
ttccgacatg actcaggata tgaagttgga ggaggagatg cagaattccg acatgactca   3300
ggatatgaag ttggaggagg agatgcagaa ttccgacatg actcaggata tgaagttgga   3360
```

```
ggaggagatg cagaattccg acatgactca ggatatgaag ttggaggagg agatgcagaa   3420
ttccgacatg actcaggata tgaagttgga ggaggagatg cagaattccg acatgactca   3480
ggatatgaag ttggaggagg agatgcagaa ttccgacatg actcaggata tgaagttgga   3540
ggaggagatg cagaattccg acatgactca ggatatgaag ttggaggagg agatgcagaa   3600
ttccgacatg actcaggata tgaagttgga ggaggagatg cagaattccg acatgactca   3660
ggatatgaag ttggaggagg agatgcagaa ttccgacatg actcaggata tgaagttgga   3720
ggaggagatg cagaattccg acatgactca ggatatgaag ttggaggagg agatgcagaa   3780
ttccgacatg actcaggata tgaagttgga ggaggagatg cagaattccg acatgactca   3840
ggatatgaag ttggaggagg agatgcagaa ttccgacatg actcaggata tgaagttgga   3900
ggaggagatg cagaattccg acatgactca ggatatgaag ttggaggagg agatgcagaa   3960
ttccgacatg actcaggata tgaagttgga ggaggagatg cagaattccg acatgactca   4020
ggatatgaag ttggaggagg agatgcagaa ttccgacatg actcaggata tgaagttgga   4080
ggaggagatg cagaattccg acatgactca ggatatgaag ttggaggagg agatgcagaa   4140
ttccgacatg actcaggata tgaagttgga ggaggagatg cagaattccg acatgactca   4200
ggatatgaag ttggaggagg agatgcagaa ttccgacatg actcaggata tgaagttgga   4260
ggaggagatg cagaattccg acatgactca ggatatgaag ttggaggagg agatgcagaa   4320
ttccgacatg actcaggata tgaagttgga ggaggagatg cagaattccg acatgactca   4380
ggatatgaag ttggaggagg agatgcagaa ttccgacatg actcaggata tgaagttgga   4440
ggaggagatg cagaattccg acatgactca ggatatgaag ttggaggagg aactcaccag   4500
aacgaacccc agcaatgggt cctccctgac tactcgggca gggattccca caacgttcac   4560
ttggctccgg ccgtggctcc aaccttccct ggagagcagt tgctgttctt cagatccact   4620
atgccaggct gctctggata cccgaacatg aacctcgact gtctcttgcc tcaggagtgg   4680
gtgcaacact tctaccagga atctgcccca gctcaaagcg acgtcgctct gctccgtttc   4740
gttaaccccg ataccggtcg cgtgctcttc gagtgtaagt tgcacaagtc tggttacgtc   4800
actgttgccc acacaggcca gcacgacctg gtcatccctc ccaacggcta cttccgcttc   4860
gatagctggg tcaaccagtt ctacacactc gccccgatgg gaaacggagc cggtcgtcgc   4920
agagccttgt aa                                                       4932
```

```
<210> SEQ ID NO 97
<211> LENGTH: 1269
<212> TYPE: DNA
<213> ORGANISM: artificial sequence
<220> FEATURE:
<223> OTHER INFORMATION: synthetic nucleotide sequence encoding the
      recombinant P protein

<400> SEQUENCE: 97
atgaagccct tctcggtccc tatcctgaca gttgaggaaa tgaccaactc tagattccca     60
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc gctggaacac aaaactacac catgaacttg    240
gcctcgcaga actggaacaa ctacgatcca accgaggaaa tccccgctcc tttgggaact    300
cccgacttcg tgggacgtat ccaaggtgtc ctgacacaga ctacacgtcg cgacggctct    360
actcgcggac acaaggccac tgtgtcgaca ggttccgtcc acttcacccc taagctgggc    420
```

-continued

```
tctgtgcaat tcagcacaga cacctcagga ggaggagatg cagaattccg acatggagga    480
ggaaacgatt tcgagactgg ccagaacacc aggttcactc ccgtgggtgt cgttcaagac    540
ggcggaggag gagatgcaga attccgacat ggaggaggag atgcagaatt ccgacatgga    600
ggaggagatg cagaattccg acatggagga ggagatgcag aattccgaca tggaggagga    660
gatgcagaat tccgacatgg aggaggagat gcagaattcc gacatggagg aggagatgca    720
gaattccgac atggaggagg agatgcagaa ttccgacatg gaggaggaga tgcagaattc    780
cgacatggag gaggagatgc agaattccga catggaggag gaagcaccac tcaccagaac    840
gaaccccagc aatgggtcct ccctgactac tcgggcaggg attcccacaa cgttcacttg    900
gctccggccg tggctccaac cttccctgga gagcagttgc tgttcttcag atccactatg    960
ccaggctgct ctggataccc gaacatgaac ctcgactgtc tcttgcctca ggagtgggtg   1020
caacacttct accaggaatc tgccccagct caaagcgacg tcgctctgct ccgtttcgtt   1080
aaccccgata ccggtcgcgt gctcttcgag tgtaagttgc acaagtctgg ttacgtcact   1140
gttgcccaca caggccagca cgacctggtc atccctccca acggctactt ccgcttcgat   1200
agctgggtca accagttcta cacactcgcc ccgatgggaa acggagccgg tcgtcgcaga   1260
gccttgtaa                                                           1269
```

<210> SEQ ID NO 98
<211> LENGTH: 2052
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 98

```
atgaagccct tctcggtccc tatcctgaca gttgaggaaa tgaccaactc tagattccca     60
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc gctggaacac aaaactacac catgaacttg    240
gcctcgcaga actggaacaa ctacgatcca accgaggaaa tccccgctcc tttgggaact    300
cccgacttcg tgggacgtat ccaaggtgtc ctgacacaga ctacacgtcg cgacggctct    360
actcgcggac acaaggccac tgtgtcgaca ggttccgtcc acttcacccc taagctgggc    420
tctgtgcaat tcagcacaga cacctcagga ggaggagatg cagaattccg acatgactca    480
ggaggaggag gagatgcaga attccgacat gactcaggag gaggaggaga tgcagaattc    540
cgacatgact caggaggagg aggagatgca gaattccgac atgactcagg aggaggagga    600
gatgcagaat tccgacatga ctcaggagga ggaggagatg cagaattccg acatgactca    660
ggaggaggag gagatgcaga attccgacat gactcaggag gaggaggaga tgcagaattc    720
cgacatgact caggaggagg aggagatgca gaattccgac atgactcagg aggaggagga    780
gatgcagaat tccgacatga ctcaggagga ggaggaaacg atttcgagac tggccagaac    840
accaggttca ctcccgtggg tgtcgttcaa gacggcggag gaggagatgc agaattccga    900
catgactcag gaggaggagg agatgcagaa ttccgacatg actcaggagg aggaggagat    960
gcagaattcc gacatgactc aggaggagga ggagatgcag aattccgaca tgactcagga   1020
ggaggaggag atgcagaatt ccgacatgac tcaggaggag gaggagatgc agaattccga   1080
catgactcag gaggaggagg agatgcagaa ttccgacatg actcaggagg aggaggagat   1140
```

-continued gcagaattcc gacatgactc aggaggagga ggagatgcag aattccgaca tgactcagga 1200
ggaggaggag atgcagaatt ccgacatgac tcaggaggag gaggagatgc agaattccga 1260
catgactcag gaggaggagg agatgcagaa ttccgacatg actcaggagg aggaggagat 1320
gcagaattcc gacatgactc aggaggagga ggagatgcag aattccgaca tgactcagga 1380
ggaggaggag atgcagaatt ccgacatgac tcaggaggag gaggagatgc agaattccga 1440
catgactcag gaggaggagg agatgcagaa ttccgacatg actcaggagg aggaggagat 1500
gcagaattcc gacatgactc aggaggagga ggagatgcag aattccgaca tgactcagga 1560
ggaggaggag atgcagaatt ccgacatgac tcaggaggag gaggaagcac cactcaccag 1620
aacgaacccc agcaatgggt cctccctgac tactcgggca gggattccca caacgttcac 1680
ttggctccgg ccgtggctcc aaccttccct ggagagcagt tgctgttctt cagatccact 1740
atgccaggct gctctggata cccgaacatg aacctcgact gtctcttgcc tcaggagtgg 1800
gtgcaacact tctaccagga atctgcccca gctcaaagcg acgtcgctct gctccgtttc 1860
gttaaccccg ataccggtcg cgtgctcttc gagtgtaagt tgcacaagtc tggttacgtc 1920
actgttgccc acacaggcca gcacgacctg gtcatccctc ccaacggcta cttccgcttc 1980
gatagctggg tcaaccagtt ctacacactc gccccgatgg gaaacggagc cggtcgtcgc 2040
agagccttgt aa 2052

<210> SEQ ID NO 99
<211> LENGTH: 3672
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 99
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaacac aaaactacac catgaacttg 240
gcctcgcaga actggaacaa ctacgatcca accgaggaaa tccccgctcc tttgggaact 300
cccgacttcg tgggacgtat ccaaggtgtc ctgacacaga ctacacgtcg cgacggctct 360
actcgcggac acaaggccac tgtgtcgaca ggttccgtcc acttcacccc taagctgggc 420
tctgtgcaat tcagcacaga cacctcagga ggaggagatg cagaattccg acatgactca 480
ggatatgaag ttggaggagg agatgcagaa ttccgacatg actcaggata tgaagttgga 540
ggaggagatg cagaattccg acatgactca ggatatgaag ttggaggagg agatgcagaa 600
ttccgacatg actcaggata tgaagttgga ggaggagatg cagaattccg acatgactca 660
ggatatgaag ttggaggagg agatgcagaa ttccgacatg actcaggata tgaagttgga 720
ggaggagatg cagaattccg acatgactca ggatatgaag ttggaggagg agatgcagaa 780
ttccgacatg actcaggata tgaagttgga ggaggagatg cagaattccg acatgactca 840
ggatatgaag ttggaggagg agatgcagaa ttccgacatg actcaggata tgaagttgga 900
ggaggagatg cagaattccg acatgactca ggatatgaag ttggaggagg agatgcagaa 960
ttccgacatg actcaggata tgaagttgga ggaggagatg cagaattccg acatgactca 1020
ggatatgaag ttggaggagg agatgcagaa ttccgacatg actcaggata tgaagttgga 1080

-continued ggaggagatg cagaattccg acatgactca ggatatgaag ttggaggagg agatgcagaa 1140
ttccgacatg actcaggata tgaagttgga ggaggagatg cagaattccg acatgactca 1200
ggatatgaag ttggaggagg agatgcagaa ttccgacatg actcaggata tgaagttgga 1260
ggaggagatg cagaattccg acatgactca ggatatgaag ttggaggagg agatgcagaa 1320
ttccgacatg actcaggata tgaagttgga ggaggaaacg atttcgagac tggccagaac 1380
accaggttca ctcccgtggg tgtcgttcaa gacggcggag gaggagatgc agaattccga 1440
catgactcag gatatgaagt tggaggagga gatgcagaat tccgacatga ctcaggatat 1500
gaagttggag gaggagatgc agaattccga catgactcag gatatgaagt tggaggagga 1560
gatgcagaat tccgacatga ctcaggatat gaagttggag gaggagatgc agaattccga 1620
catgactcag gatatgaagt tggaggagga gatgcagaat tccgacatga ctcaggatat 1680
gaagttggag gaggagatgc agaattccga catgactcag gatatgaagt tggaggagga 1740
gatgcagaat tccgacatga ctcaggatat gaagttggag gaggagatgc agaattccga 1800
catgactcag gatatgaagt tggaggagga gatgcagaat tccgacatga ctcaggatat 1860
gaagttggag gaggagatgc agaattccga catgactcag gatatgaagt tggaggagga 1920
gatgcagaat tccgacatga ctcaggatat gaagttggag gaggagatgc agaattccga 1980
catgactcag gatatgaagt tggaggagga gatgcagaat tccgacatga ctcaggatat 2040
gaagttggag gaggagatgc agaattccga catgactcag gatatgaagt tggaggagga 2100
gatgcagaat tccgacatga ctcaggatat gaagttggag gaggagatgc agaattccga 2160
catgactcag gatatgaagt tggaggagga gatgcagaat tccgacatga ctcaggatat 2220
gaagttggag gaggagatgc agaattccga catgactcag gatatgaagt tggaggagga 2280
gatgcagaat tccgacatga ctcaggatat gaagttggag gaggagatgc agaattccga 2340
catgactcag gatatgaagt tggaggagga gatgcagaat tccgacatga ctcaggatat 2400
gaagttggag gaggagatgc agaattccga catgactcag gatatgaagt tggaggagga 2460
gatgcagaat tccgacatga ctcaggatat gaagttggag gaggagatgc agaattccga 2520
catgactcag gatatgaagt tggaggagga gatgcagaat tccgacatga ctcaggatat 2580
gaagttggag gaggagatgc agaattccga catgactcag gatatgaagt tggaggagga 2640
gatgcagaat tccgacatga ctcaggatat gaagttggag gaggagatgc agaattccga 2700
catgactcag gatatgaagt tggaggagga gatgcagaat tccgacatga ctcaggatat 2760
gaagttggag gaggagatgc agaattccga catgactcag gatatgaagt tggaggagga 2820
gatgcagaat tccgacatga ctcaggatat gaagttggag gaggagatgc agaattccga 2880
catgactcag gatatgaagt tggaggagga gatgcagaat tccgacatga ctcaggatat 2940
gaagttggag gaggagatgc agaattccga catgactcag gatatgaagt tggaggagga 3000
gatgcagaat tccgacatga ctcaggatat gaagttggag gaggagatgc agaattccga 3060
catgactcag gatatgaagt tggaggagga gatgcagaat tccgacatga ctcaggatat 3120
gaagttggag gaggagatgc agaattccga catgactcag gatatgaagt tggaggagga 3180
gatgcagaat tccgacatga ctcaggatat gaagttggag gaggaagcac cactcaccag 3240
aacgaacccc agcaatgggt cctccctgac tactcgggca gggattccca caacgttcac 3300
ttggctccgg ccgtggctcc aaccttccct ggagagcagt tgctgttctt cagatccact 3360
atgccaggct gctctggata cccgaacatg aacctcgact gtctcttgcc tcaggagtgg 3420
gtgcaacact tctaccagga atctgcccca gctcaaagcg acgtcgctct gctccgtttc 3480
gttaaccccg ataccggtcg cgtgctcttc gagtgtaagt tgcacaagtc tggttacgtc 3540
actgttgccc acacaggcca gcacgacctg gtcatccctc ccaacggcta cttccgcttc 3600
gatagctggg tcaaccagtt ctacacactc gccccgatgg gaaacggagc cggtcgtcgc 3660
agagccttgt aa 3672

<210> SEQ ID NO 100
<211> LENGTH: 3672
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 100
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaacac aaaactacac catgaacttg 240
gcctcgcaga actggaacaa ctacgatcca accgaggaaa tccccgctcc tttgggaact 300
cccgacttcg tgggacgtat ccaaggtgtc ctgacacaga ctacacgtcg cgacggctct 360
actcgcggac acaaggccac tgtgtcgaca ggttccgtcc acttcacccc taagctgggc 420
tctgtgcaat tcagcacaga cacctcagga ggaggagatg cagaattccg acatgactca 480
ggatatgaag ttcatcatca aggaggagga gatgcagaat tccgacatga ctcaggatat 540
gaagttcatc atcaaggagg aggagatgca gaattccgac atgactcagg atatgaagtt 600
catcatcaag gaggaggaga tgcagaattc cgacatgact caggatatga agttcatcat 660
caaggaggag gagatgcaga attccgacat gactcaggat atgaagttca tcatcaagga 720
ggaggagatg cagaattccg acatgactca ggatatgaag ttcatcatca aggaggagga 780
gatgcagaat tccgacatga ctcaggatat gaagttcatc atcaaggagg aggagatgca 840
gaattccgac atgactcagg atatgaagtt catcatcaag gaggaggaga tgcagaattc 900
cgacatgact caggatatga agttcatcat caaggaggag gagatgcaga attccgacat 960
gactcaggat atgaagttca tcatcaagga ggaggagatg cagaattccg acatgactca 1020
ggatatgaag ttcatcatca aggaggagga gatgcagaat tccgacatga ctcaggatat 1080
gaagttcatc atcaaggagg aggagatgca gaattccgac atgactcagg atatgaagtt 1140
catcatcaag gaggaggaga tgcagaattc cgacatgact caggatatga agttcatcat 1200
caaggaggag gagatgcaga attccgacat gactcaggat atgaagttca tcatcaagga 1260
ggaggagatg cagaattccg acatgactca ggatatgaag ttcatcatca aggaggagga 1320
gatgcagaat tccgacatga ctcaggatat gaagttcatc atcaaggagg aggagatgca 1380
gaattccgac atgactcagg atatgaagtt catcatcaag gaggaggaga tgcagaattc 1440
cgacatgact caggatatga agttcatcat caaggaggag gagatgcaga attccgacat 1500
gactcaggat atgaagttca tcatcaagga ggaggagatg cagaattccg acatgactca 1560
ggatatgaag ttcatcatca aggaggagga gatgcagaat tccgacatga ctcaggatat 1620
gaagttcatc atcaaggagg aggagatgca gaattccgac atgactcagg atatgaagtt 1680
catcatcaag gaggaggaga tgcagaattc cgacatgact caggatatga agttcatcat 1740
caaggaggag gagatgcaga attccgacat gactcaggat atgaagttca tcatcaagga 1800
ggaggagatg cagaattccg acatgactca ggatatgaag ttcatcatca aggaggagga 1860
gatgcagaat tccgacatga ctcaggatat gaagttcatc atcaaggagg aggagatgca 1920
gaattccgac atgactcagg atatgaagtt catcatcaag gaggaggaga tgcagaattc 1980
cgacatgact caggatatga agttcatcat caaggaggag gagatgcaga attccgacat 2040
gactcaggat atgaagttca tcatcaagga ggaggagatg cagaattccg acatgactca 2100
ggatatgaag ttcatcatca aggaggagga gatgcagaat tccgacatga ctcaggatat 2160
gaagttcatc atcaaggagg aggagatgca gaattccgac atgactcagg atatgaagtt 2220
catcatcaag gaggaggaga tgcagaattc cgacatgact caggatatga agttcatcat 2280
caaggaggag gagatgcaga attccgacat gactcaggat atgaagttca tcatcaagga 2340
ggaggagatg cagaattccg acatgactca ggatatgaag ttcatcatca aggaggagga 2400
gatgcagaat tccgacatga ctcaggatat gaagttcatc atcaaggagg aggagatgca 2460
gaattccgac atgactcagg atatgaagtt catcatcaag gaggaggaga tgcagaattc 2520
cgacatgact caggatatga agttcatcat caaggaggag gagatgcaga attccgacat 2580
gactcaggat atgaagttca tcatcaagga ggaggaaacg atttcgagac tggccagaac 2640
accaggttca ctcccgtggg tgtcgttcaa gacggcggag gaggagatgc agaattccga 2700
catgactcag gatatgaagt tcatcatcaa ggaggaggag atgcagaatt ccgacatgac 2760
tcaggatatg aagttcatca tcaaggagga ggagatgcag aattccgaca tgactcagga 2820
tatgaagttc atcatcaagg aggaggagat gcagaattcc gacatgactc aggatatgaa 2880
gttcatcatc aaggaggagg agatgcagaa ttccgacatg actcaggata tgaagttcat 2940
catcaaggag gaggagatgc agaattccga catgactcag gatatgaagt tcatcatcaa 3000
ggaggaggag atgcagaatt ccgacatgac tcaggatatg aagttcatca tcaaggagga 3060
ggagatgcag aattccgaca tgactcagga tatgaagttc atcatcaagg aggaggagat 3120
gcagaattcc gacatgactc aggatatgaa gttcatcatc aaggaggagg agatgcagaa 3180
ttccgacatg actcaggata tgaagttcat catcaaggag gaggaagcac cactcaccag 3240
aacgaacccc agcaatgggt cctccctgac tactcgggca gggattccca caacgttcac 3300
ttggctccgg ccgtggctcc aaccttccct ggagagcagt tgctgttctt cagatccact 3360
atgccaggct gctctggata cccgaacatg aacctcgact gtctcttgcc tcaggagtgg 3420
gtgcaacact tctaccagga atctgcccca gctcaaagcg acgtcgctct gctccgtttc 3480
gttaaccccg ataccggtcg cgtgctcttc gagtgtaagt tgcacaagtc tggttacgtc 3540
actgttgccc acacaggcca gcacgacctg gtcatccctc ccaacggcta cttccgcttc 3600
gatagctggg tcaaccagtt ctacacactc gccccgatgg gaaacggagc cggtcgtcgc 3660
agagccttgt aa 3672

<210> SEQ ID NO 101
<211> LENGTH: 1359
<212> TYPE: DNA
<213> ORGANISM: artificial sequence
<220> FEATURE:
<223> OTHER INFORMATION: synthetic nucleotide sequence encoding the
recombinant P protein

<400> SEQUENCE: 101
atgaagccct tctcggtccc tatcctgaca gttgaggaaa tgaccaactc tagattccca 60
atcccgctgg aaaagctctt caccggaccc tcctctgctt tcgttgtgca gcctcaaaac 120

```
ggtcgttgca ccactgatgg tgtcctgctc ggtaccaccc agctctcacc tgtgaacatc    180
tgtactttcc gcggcgacgt cacacacatc gctggaacac aaaactacac catgaacttg    240
gcctcgcaga actggaacaa ctacgatcca accgaggaaa tccccgctcc tttgggaact    300
cccgacttcg tgggacgtat ccaaggtgtc ctgacacaga ctacacgtcg cgacggctct    360
actcgcggac acaaggccac tgtgtcgaca ggttccgtcc acttcacccc taagctgggc    420
tctgtgcaat tcagcacaga caccggagga ggagatgcag aattccgaca tggaggagga    480
tcaaacgatt tcgagactgg ccagaacacc aggttcactc ccgtgggtgt cgttcaagac    540
ggaggaggag atgcagaatt ccgacatgac tcaggaggag gaggagatgc agaattccga    600
catgactcag gaggaggagg agatgcagaa ttccgacatg actcaggagg aggaggagat    660
gcagaattcc gacatgactc aggaggagga ggagatgcag aattccgaca tgactcagga    720
ggaggaggag atgcagaatt ccgacatgac tcaggaggag gaggagatgc agaattccga    780
catgactcag gaggaggagg agatgcagaa ttccgacatg actcaggagg aggaggagat    840
gcagaattcc gacatgactc aggaggagga ggagatgcag aattccgaca tgactcagga    900
ggaggaggag gcagcaccac tcaccagaac gaaccccagc aatgggtcct ccctgactac    960
tcgggcaggg attcccacaa cgttcacttg gctccggccg tggctccaac cttccctgga   1020
gagcagttgc tgttcttcag atccactatg ccaggctgct ctggataccc gaacatgaac   1080
ctcgactgtc tcttgcctca ggagtgggtg caacacttct accaggaatc tgccccagct   1140
caaagcgacg tcgctctgct ccgtttcgtt aaccccgata ccggtcgcgt gctcttcgag   1200
tgtaagttgc acaagtctgg ttacgtcact gttgcccaca caggccagca cgacctggtc   1260
atccctccca acggctactt ccgcttcgat agctgggtca accagttcta cacactcgcc   1320
ccgatgggaa acggagccgg tcgtcgcaga gccttgtaa                           1359
```

<210> SEQ ID NO 102
<211> LENGTH: 2052
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 102

```
atgaagccct tctcggtccc tatcctgaca gttgaggaaa tgaccaactc tagattccca     60
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc gctggaacac aaaactacac catgaacttg    240
gcctcgcaga actggaacaa ctacgatcca accgaggaaa tccccgctcc tttgggaact    300
cccgacttcg tgggacgtat ccaaggtgtc ctgacacaga ctacacgtcg cgacggctct    360
actcgcggac acaaggccac tgtgtcgaca ggttccgtcc acttcacccc taagctgggc    420
tctgtgcaat tcagcacaga cacctcaaac ggaggaggag atgcagaatt ccgacatgac    480
tcaggatatg aagttcatca tcaaggagga ggagatgcag aattccgaca tgactcagga    540
tatgaagttc atcatcaagg aggaggagat gcagaattcc gacatgactc aggatatgaa    600
gttcatcatc aaggaggagg agatgcagaa ttccgacatg actcaggata tgaagttcat    660
catcaaggag gaggagatgc agaattccga catgactcag gatatgaagt tcatcatcaa    720
ggaggaggag atgcagaatt ccgacatgac tcaggatatg aagttcatca tcaaggagga    780
```

-continued

```
ggagatgcag aattccgaca tgactcagga tatgaagttc atcatcaagg aggaggagat    840
gcagaattcc gacatgactc aggatatgaa gttcatcatc aaggaggagg agatgcagaa    900
ttccgacatg actcaggata tgaagttcat catcaaggag gaggagatgc agaattccga    960
catgactcag gatatgaagt tcatcatcaa ggaggaggag atttcgagac tggccagaac   1020
accaggttca ctcccgtggg tgtcgttcaa gacggcagcg gaggaggaga tgcagaattc   1080
cgacatggag gaggagatgc agaattccga catggaggag gagatgcaga attccgacat   1140
ggaggaggag atgcagaatt ccgacatgga ggaggagatg cagaattccg acatggagga   1200
ggagatgcag aattccgaca tggaggagga gatgcagaat tccgacatgg aggaggagat   1260
gcagaattcc gacatggagg aggagatgca gaattccgac atggaggagg agatgcagaa   1320
ttccgacatg gaggaggaga tgcagaattc cgacatggag gaggagatgc agaattccga   1380
catggaggag gagatgcaga attccgacat ggaggaggag atgcagaatt ccgacatgga   1440
ggaggagatg cagaattccg acatggagga ggagatgcag aattccgaca tggaggagga   1500
gatgcagaat tccgacatgg aggaggagat gcagaattcc gacatggagg aggagatgca   1560
gaattccgac atggaggagg agatgcagaa ttccgacatg gaggaggaac cactcaccag   1620
aacgaacccc agcaatgggt cctccctgac tactcgggca gggattccca caacgttcac   1680
ttggctccgg ccgtggctcc aaccttccct ggagagcagt tgctgttctt cagatccact   1740
atgccaggct gctctggata cccgaacatg aacctcgact gtctcttgcc tcaggagtgg   1800
gtgcaacact tctaccagga atctgcccca gctcaaagcg acgtcgctct gctccgtttc   1860
gttaaccccg ataccggtcg cgtgctcttc gagtgtaagt tgcacaagtc tggttacgtc   1920
actgttgccc acacaggcca gcacgacctg gtcatccctc ccaacggcta cttccgcttc   1980
gatagctggg tcaaccagtt ctacacactc gccccgatgg gaaacggagc cggtcgtcgc   2040
agagccttgt aa                                                       2052
```

```
<210> SEQ ID NO 103
<211> LENGTH: 4032
<212> TYPE: DNA
<213> ORGANISM: artificial sequence
<220> FEATURE:
<223> OTHER INFORMATION: synthetic nucleotide sequence encoding the
      recombinant P protein

<400> SEQUENCE: 103
```

```
atgaagccct tctcggtccc tatcctgaca gttgaggaaa tgaccaactc tagattccca     60
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc gctggaacac aaaactacac catgaacttg    240
gcctcgcaga actggaacaa ctacgatcca accgaggaaa tccccgctcc tttgggaact    300
cccgacttcg tgggacgtat ccaaggtgtc ctgacacaga ctacacgtcg cgacggctct    360
actcgcggac acaaggccac tgtgtcgaca ggttccgtcc acttcacccc taagctgggc    420
tctgtgcaat tcagcacaga cacctcagga ggaggagatg cagaattccg acatgactca    480
ggatatgaag ttggaggagg agatgcagaa ttccgacatg actcaggata tgaagttgga    540
ggaggagatg cagaattccg acatgactca ggatatgaag ttggaggagg agatgcagaa    600
ttccgacatg actcaggata tgaagttgga ggaggagatg cagaattccg acatgactca    660
ggatatgaag ttggaggagg agatgcagaa ttccgacatg actcaggata tgaagttgga    720
```

```
ggaggagatg cagaattccg acatgactca ggatatgaag ttggaggagg agatgcagaa    780
ttccgacatg actcaggata tgaagttgga ggaggagatg cagaattccg acatgactca    840
ggatatgaag ttggaggagg agatgcagaa ttccgacatg actcaggata tgaagttgga    900
ggaggagatg cagaattccg acatgactca ggatatgaag ttggaggagg agatgcagaa    960
ttccgacatg actcaggata tgaagttgga ggaggagatg cagaattccg acatgactca   1020
ggatatgaag ttggaggagg agatgcagaa ttccgacatg actcaggata tgaagttgga   1080
ggaggagatg cagaattccg acatgactca ggatatgaag ttggaggagg agatgcagaa   1140
ttccgacatg actcaggata tgaagttgga ggaggagatg cagaattccg acatgactca   1200
ggatatgaag ttggaggagg agatgcagaa ttccgacatg actcaggata tgaagttgga   1260
ggaggagatg cagaattccg acatgactca ggatatgaag ttggaggagg agatgcagaa   1320
ttccgacatg actcaggata tgaagttgga ggaggaaacg atttcgagac tggccagaac   1380
accaggttca ctcccgtggg tgtcgttcaa gacggcggag gaggagatgc agaattccga   1440
catgactcag gatatgaagt tcatcatcaa ggaggaggag atgcagaatt ccgacatgac   1500
tcaggatatg aagttcatca tcaaggagga ggagatgcag aattccgaca tgactcagga   1560
tatgaagttc atcatcaagg aggaggagat gcagaattcc gacatgactc aggatatgaa   1620
gttcatcatc aaggaggagg agatgcagaa ttccgacatg actcaggata tgaagttcat   1680
catcaaggag gaggagatgc agaattccga catgactcag gatatgaagt tcatcatcaa   1740
ggaggaggag atgcagaatt ccgacatgac tcaggatatg aagttcatca tcaaggagga   1800
ggagatgcag aattccgaca tgactcagga tatgaagttc atcatcaagg aggaggagat   1860
gcagaattcc gacatgactc aggatatgaa gttcatcatc aaggaggagg agatgcagaa   1920
ttccgacatg actcaggata tgaagttcat catcaaggag gaggagatgc agaattccga   1980
catgactcag gatatgaagt tcatcatcaa ggaggaggag atgcagaatt ccgacatgac   2040
tcaggatatg aagttcatca tcaaggagga ggagatgcag aattccgaca tgactcagga   2100
tatgaagttc atcatcaagg aggaggagat gcagaattcc gacatgactc aggatatgaa   2160
gttcatcatc aaggaggagg agatgcagaa ttccgacatg actcaggata tgaagttcat   2220
catcaaggag gaggagatgc agaattccga catgactcag gatatgaagt tcatcatcaa   2280
ggaggaggag atgcagaatt ccgacatgac tcaggatatg aagttcatca tcaaggagga   2340
ggagatgcag aattccgaca tgactcagga tatgaagttc atcatcaagg aggaggagat   2400
gcagaattcc gacatgactc aggatatgaa gttcatcatc aaggaggagg agatgcagaa   2460
ttccgacatg actcaggata tgaagttcat catcaaggag gaggagatgc agaattccga   2520
catgactcag gatatgaagt tcatcatcaa ggaggaggag atgcagaatt ccgacatgac   2580
tcaggatatg aagttcatca tcaaggagga ggagatgcag aattccgaca tgactcagga   2640
tatgaagttc atcatcaagg aggaggagat gcagaattcc gacatgactc aggatatgaa   2700
gttcatcatc aaggaggagg agatgcagaa ttccgacatg actcaggata tgaagttcat   2760
catcaaggag gaggagatgc agaattccga catgactcag gatatgaagt tcatcatcaa   2820
ggaggaggag atgcagaatt ccgacatgac tcaggatatg aagttcatca tcaaggagga   2880
ggagatgcag aattccgaca tgactcagga tatgaagttc atcatcaagg aggaggagat   2940
gcagaattcc gacatgactc aggatatgaa gttcatcatc aaggaggagg agatgcagaa   3000
ttccgacatg actcaggata tgaagttcat catcaaggag gaggagatgc agaattccga   3060
```
catgactcag gatatgaagt tcatcatcaa ggaggaggag atgcagaatt ccgacatgac 3120
tcaggatatg aagttcatca tcaaggagga ggagatgcag aattccgaca tgactcagga 3180
tatgaagttc atcatcaagg aggaggagat gcagaattcc gacatgactc aggatatgaa 3240
gttcatcatc aaggaggagg agatgcagaa ttccgacatg actcaggata tgaagttcat 3300
catcaaggag gaggagatgc agaattccga catgactcag gatatgaagt tcatcatcaa 3360
ggaggaggag atgcagaatt ccgacatgac tcaggatatg aagttcatca tcaaggagga 3420
ggagatgcag aattccgaca tgactcagga tatgaagttc atcatcaagg aggaggagat 3480
gcagaattcc gacatgactc aggatatgaa gttcatcatc aaggaggagg agatgcagaa 3540
ttccgacatg actcaggata tgaagttcat catcaaggag gaggaagcac cactcaccag 3600
aacgaacccc agcaatgggt cctccctgac tactcgggca gggattccca caacgttcac 3660
ttggctccgg ccgtggctcc aaccttccct ggagagcagt tgctgttctt cagatccact 3720
atgccaggct gctctggata cccgaacatg aacctcgact gtctcttgcc tcaggagtgg 3780
gtgcaacact tctaccagga atctgcccca gctcaaagcg acgtcgctct gctccgtttc 3840
gttaaccccg ataccggtcg cgtgctcttc gagtgtaagt tgcacaagtc tggttacgtc 3900
actgttgccc acacaggcca gcacgacctg gtcatccctc ccaacggcta cttccgcttc 3960
gatagctggg tcaaccagtt ctacacactc gccccgatgg gaaacggagc cggtcgtcgc 4020
agagccttgt aa 4032

<210> SEQ ID NO 104
<211> LENGTH: 4032
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 104
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaacac aaaactacac catgaacttg 240
gcctcgcaga actggaacaa ctacgatcca accgaggaaa tccccgctcc tttgggaact 300
cccgacttcg tgggacgtat ccaaggtgtc ctgacacaga ctacacgtcg cgacggctct 360
actcgcggac acaaggccac tgtgtcgaca ggttccgtcc acttcacccc taagctgggc 420
tctgtgcaat tcagcacaga cacctcaaac gatggaggag gagatgcaga attccgacat 480
gactcaggat atgaagttca tcatcaagga ggaggagatg cagaattccg acatgactca 540
ggatatgaag ttcatcatca aggaggagga gatgcagaat tccgacatga ctcaggatat 600
gaagttcatc atcaaggagg aggagatgca gaattccgac atgactcagg atatgaagtt 660
catcatcaag gaggaggaga tgcagaattc cgacatgact caggatatga agttcatcat 720
caaggaggag gagatgcaga attccgacat gactcaggat atgaagttca tcatcaagga 780
ggaggagatg cagaattccg acatgactca ggatatgaag ttcatcatca aggaggagga 840
gatgcagaat tccgacatga ctcaggatat gaagttcatc atcaaggagg aggagatgca 900
gaattccgac atgactcagg atatgaagtt catcatcaag gaggaggaga tgcagaattc 960
cgacatgact caggatatga agttcatcat caaggaggag gagatgcaga attccgacat 1020

-continued

```
gactcaggat atgaagttca tcatcaagga ggaggagatg cagaattccg acatgactca   1080
ggatatgaag ttcatcatca aggaggagga gatgcagaat tccgacatga ctcaggatat   1140
gaagttcatc atcaaggagg aggagatgca gaattccgac atgactcagg atatgaagtt   1200
catcatcaag gaggaggaga tgcagaattc cgacatgact caggatatga agttcatcat   1260
caaggaggag gagatgcaga attccgacat gactcaggat atgaagttca tcatcaagga   1320
ggaggagatg cagaattccg acatgactca ggatatgaag ttcatcatca aggaggagga   1380
gatgcagaat tccgacatga ctcaggatat gaagttcatc atcaaggagg aggagatgca   1440
gaattccgac atgactcagg atatgaagtt catcatcaag gaggaggaga tgcagaattc   1500
cgacatgact caggatatga agttcatcat caaggaggag gagatgcaga attccgacat   1560
gactcaggat atgaagttca tcatcaagga ggaggagatg cagaattccg acatgactca   1620
ggatatgaag ttcatcatca aggaggagga gatgcagaat tccgacatga ctcaggatat   1680
gaagttcatc atcaaggagg aggagatgca gaattccgac atgactcagg atatgaagtt   1740
catcatcaag gaggaggaga tgcagaattc cgacatgact caggatatga agttcatcat   1800
caaggaggag gagatgcaga attccgacat gactcaggat atgaagttca tcatcaagga   1860
ggaggagatg cagaattccg acatgactca ggatatgaag ttcatcatca aggaggagga   1920
gatgcagaat tccgacatga ctcaggatat gaagttcatc atcaaggagg aggagatgca   1980
gaattccgac atgactcagg atatgaagtt catcatcaag gaggaggaga tgcagaattc   2040
cgacatgact caggatatga agttcatcat caaggaggag gagatgcaga attccgacat   2100
gactcaggat atgaagttca tcatcaagga ggaggagatg cagaattccg acatgactca   2160
ggatatgaag ttcatcatca aggaggagga gatgcagaat tccgacatga ctcaggatat   2220
gaagttcatc atcaaggagg aggagatgca gaattccgac atgactcagg atatgaagtt   2280
catcatcaag gaggaggaga tgcagaattc cgacatgact caggatatga agttcatcat   2340
caaggaggag gagatgcaga attccgacat gactcaggat atgaagttca tcatcaagga   2400
ggaggagatg cagaattccg acatgactca ggatatgaag ttcatcatca aggaggagga   2460
gatgcagaat tccgacatga ctcaggatat gaagttcatc atcaaggagg aggagatgca   2520
gaattccgac atgactcagg atatgaagtt catcatcaag gaggaggaga tgcagaattc   2580
cgacatgact caggatatga agttcatcat caaggaggag gattcgagac tggccagaac   2640
accaggttca ctcccgtggg tgtcgttcaa gacggcagca ccggaggagg agatgcagaa   2700
ttccgacatg actcaggata tgaagttgga ggaggagatg cagaattccg acatgactca   2760
ggatatgaag ttggaggagg agatgcagaa ttccgacatg actcaggata tgaagttgga   2820
ggaggagatg cagaattccg acatgactca ggatatgaag ttggaggagg agatgcagaa   2880
ttccgacatg actcaggata tgaagttgga ggaggagatg cagaattccg acatgactca   2940
ggatatgaag ttggaggagg agatgcagaa ttccgacatg actcaggata tgaagttgga   3000
ggaggagatg cagaattccg acatgactca ggatatgaag ttggaggagg agatgcagaa   3060
ttccgacatg actcaggata tgaagttgga ggaggagatg cagaattccg acatgactca   3120
ggatatgaag ttggaggagg agatgcagaa ttccgacatg actcaggata tgaagttgga   3180
ggaggagatg cagaattccg acatgactca ggatatgaag ttggaggagg agatgcagaa   3240
ttccgacatg actcaggata tgaagttgga ggaggagatg cagaattccg acatgactca   3300
ggatatgaag ttggaggagg agatgcagaa ttccgacatg actcaggata tgaagttgga   3360
ggaggagatg cagaattccg acatgactca ggatatgaag ttggaggagg agatgcagaa   3420
```

-continued

```
ttccgacatg actcaggata tgaagttgga ggaggagatg cagaattccg acatgactca   3480
ggatatgaag ttggaggagg agatgcagaa ttccgacatg actcaggata tgaagttgga   3540
ggaggagatg cagaattccg acatgactca ggatatgaag ttggaggagg aactcaccag   3600
aacgaacccc agcaatgggt cctccctgac tactcgggca gggattccca caacgttcac   3660
ttggctccgg ccgtggctcc aaccttccct ggagagcagt tgctgttctt cagatccact   3720
atgccaggct gctctggata cccgaacatg aacctcgact gtctcttgcc tcaggagtgg   3780
gtgcaacact tctaccagga atctgcccca gctcaaagcg acgtcgctct gctccgtttc   3840
gttaaccccg ataccggtcg cgtgctcttc gagtgtaagt tgcacaagtc tggttacgtc   3900
actgttgccc acacaggcca gcacgacctg gtcatccctc ccaacggcta cttccgcttc   3960
gatagctggg tcaaccagtt ctacacactc gccccgatgg gaaacggagc cggtcgtcgc   4020
agagccttgt aa                                                       4032
```

<210> SEQ ID NO 105
<211> LENGTH: 2142
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 105

```
atgaagccct tctcggtccc tatcctgaca gttgaggaaa tgaccaactc tagattccca     60
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc gctggaacac aaaactacac catgaacttg    240
gcctcgcaga actggaacaa ctacgatcca accgaggaaa tccccgctcc tttgggaact    300
cccgacttcg tgggacgtat ccaaggtgtc ctgacacaga ctacacgtcg cgacggctct    360
actcgcggac acaaggccac tgtgtcgaca ggttccgtcc acttcacccc taagctgggc    420
tctgtgcaat tcagcacaga cacctcagga ggaggagatg cagaattccg acatgactca    480
ggatatgaag ttggaggagg agatgcagaa ttccgacatg actcaggata tgaagttgga    540
ggaggagatg cagaattccg acatgactca ggatatgaag ttggaggagg agatgcagaa    600
ttccgacatg actcaggata tgaagttgga ggaggagatg cagaattccg acatgactca    660
ggatatgaag ttggaggagg agatgcagaa ttccgacatg actcaggata tgaagttgga    720
ggaggagatg cagaattccg acatgactca ggatatgaag ttggaggagg agatgcagaa    780
ttccgacatg actcaggata tgaagttgga ggaggagatg cagaattccg acatgactca    840
ggatatgaag ttggaggagg agatgcagaa ttccgacatg actcaggata tgaagttgga    900
ggaggagatg cagaattccg acatgactca ggatatgaag ttggaggagg agatgcagaa    960
ttccgacatg actcaggata tgaagttgga ggaggagatg cagaattccg acatgactca   1020
ggatatgaag ttggaggagg agatgcagaa ttccgacatg actcaggata tgaagttgga   1080
ggaggagatg cagaattccg acatgactca ggatatgaag ttggaggagg agatgcagaa   1140
ttccgacatg actcaggata tgaagttgga ggaggagatg cagaattccg acatgactca   1200
ggatatgaag ttggaggagg agatgcagaa ttccgacatg actcaggata tgaagttgga   1260
ggaggagatg cagaattccg acatgactca ggatatgaag ttggaggagg agatgcagaa   1320
ttccgacatg actcaggata tgaagttgga ggaggaaacg atttcgagac tggccagaac   1380
```

```
accaggttca ctcccgtggg tgtcgttcaa gacggcggag gaggagatgc agaattccga   1440
catggaggag gagatgcaga attccgacat ggaggaggag atgcagaatt ccgacatgga   1500
ggaggagatg cagaattccg acatggagga ggagatgcag aattccgaca tggaggagga   1560
gatgcagaat tccgacatgg aggaggagat gcagaattcc gacatggagg aggagatgca   1620
gaattccgac atggaggagg agatgcagaa ttccgacatg gaggaggaga tgcagaattc   1680
cgacatggag gaggaagcac cactcaccag aacgaacccc agcaatgggt cctccctgac   1740
tactcgggca gggattccca caacgttcac ttggctccgg ccgtggctcc aaccttccct   1800
ggagagcagt tgctgttctt cagatccact atgccaggct gctctggata cccgaacatg   1860
aacctcgact gtctcttgcc tcaggagtgg gtgcaacact tctaccagga atctgcccca   1920
gctcaaagcg acgtcgctct gctccgtttc gttaaccccg ataccggtcg cgtgctcttc   1980
gagtgtaagt tgcacaagtc tggttacgtc actgttgccc acacaggcca gcacgacctg   2040
gtcatccctc ccaacggcta cttccgcttc gatagctggg tcaaccagtt ctacacactc   2100
gccccgatgg gaaacggagc cggtcgtcgc agagccttgt aa                      2142
```

<210> SEQ ID NO 106
<211> LENGTH: 1386
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 106

```
atgaagccct tctcggtccc tatcctgaca gttgaggaaa tgaccaactc tagattccca     60
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc gctggaacac aaaactacac catgaacttg    240
gcctcgcaga actggaacaa ctacgatcca accgaggaaa tccccgctcc tttgggaact    300
cccgacttcg tgggacgtat ccaaggtgtc ctgacacaga ctacacgtcg cgacggctct    360
actcgcggac acaaggccac tgtgtcgaca ggttccgtcc acttcacccc taagctgggc    420
tctgtgcaat tcagcacaga cacctcagga ggaggagatg cagaattccg acatgactca    480
ggaggaggag gagatgcaga attccgacat gactcaggag gaggaggaga tgcagaattc    540
cgacatgact caggaggagg aggagatgca gaattccgac atgactcagg aggaggagga    600
gatgcagaat tccgacatga ctcaggagga ggaggagatg cagaattccg acatgactca    660
ggaggaggag gagatgcaga attccgacat gactcaggag gaggaggaga tgcagaattc    720
cgacatgact caggaggagg aggagatgca gaattccgac atgactcagg aggaggagga    780
gatgcagaat tccgacatga ctcaggagga ggaggaaacg atttcgagac tggccagaac    840
accaggttca ctcccgtggg tgtcgttcaa gacggcggag gaggagatgc agaattccga    900
catgactcag gatatgaagt tcatcatcaa ggaggaggaa gcaccactca ccagaacgaa    960
ccccagcaat gggtcctccc tgactactcg ggcagggatt cccacaacgt tcacttggct   1020
ccggccgtgg ctccaacctt ccctggagag cagttgctgt tcttcagatc cactatgcca   1080
ggctgctctg gatacccgaa catgaacctc gactgtctct tgcctcagga gtgggtgcaa   1140
cacttctacc aggaatctgc cccagctcaa agcgacgtcg ctctgctccg tttcgttaac   1200
cccgataccg gtcgcgtgct cttcgagtgt aagttgcaca agtctggtta cgtcactgtt   1260
```
gcccacacag gccagcacga cctggtcatc cctcccaacg gctacttccg cttcgatagc 1320
tgggtcaacc agttctacac actcgccccg atgggaaacg gagccggtcg tcgcagagcc 1380
ttgtaa 1386

<210> SEQ ID NO 107
<211> LENGTH: 1080
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 107
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaggag gaggagatgc agaattccga 240
catgactcag gatatgaagt tcatcatcaa ggaggaggaa cacaaaacta caccatgaac 300
ttggcctcgc agaactggaa caactacgat ccaaccgagg aaatccccgc tcctttggga 360
actcccgact tcgtgggacg tatccaaggt gtcctgacac agactacacg tcgcgacggc 420
tctactcgcg gacacaaggc cactgtgtcg acaggttccg tccacttcac ccctaagctg 480
ggctctgtgc aattcagcac agacacctca aacgatttcg agactggcca gaacaccagg 540
ttcactcccg tgggtgtcgt tcaagacggc ggaggaggag atgcagaatt ccgacatgac 600
tcaggatatg aagttcatca tcaaggagga ggaagcacca ctcaccagaa cgaaccccag 660
caatgggtcc tccctgacta ctcgggcagg gattcccaca acgttcactt ggctccggcc 720
gtggctccaa ccttccctgg agagcagttg ctgttcttca gatccactat gccaggctgc 780
tctggatacc cgaacatgaa cctcgactgt ctcttgcctc aggagtgggt gcaacacttc 840
taccaggaat ctgccccagc tcaaagcgac gtcgctctgc tccgtttcgt taaccccgat 900
accggtcgcg tgctcttcga gtgtaagttg cacaagtctg gttacgtcac tgttgcccac 960
acaggccagc acgacctggt catccctccc aacggctact tccgcttcga tagctgggtc 1020
aaccagttct acacactcgc cccgatggga aacggagccg gtcgtcgcag agccttgtaa 1080

<210> SEQ ID NO 108
<211> LENGTH: 1692
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 108
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaggag gaggagatgc agaattccga 240
catgactcag gaggaggagg agatgcagaa ttccgacatg actcaggagg aggaggagat 300
gcagaattcc gacatgactc aggaggagga ggagatgcag aattccgaca tgactcagga 360
ggaggaggag atgcagaatt ccgacatgac tcaggaggag gaggagatgc agaattccga 420

```
catgactcag gaggaggagg agatgcagaa ttccgacatg actcaggagg aggaggagat    480
gcagaattcc gacatgactc aggaggagga ggagatgcag aattccgaca tgactcagga    540
ggaggaggag atgcagaatt ccgacatgac tcaggaggag gaggaacaca aaactacacc    600
atgaacttgg cctcgcagaa ctggaacaac tacgatccaa ccgaggaaat ccccgctcct    660
ttgggaactc ccgacttcgt gggacgtatc caaggtgtcc tgacacagac tacacgtcgc    720
gacggctcta ctcgcggaca caaggccact gtgtcgacag gttccgtcca cttcacccct    780
aagctgggct ctgtgcaatt cagcacagac acctcaaacg atttcgagac tggccagaac    840
accaggttca ctcccgtggg tgtcgttcaa gacggcggag gaggagatgc agaattccga    900
catgactcag gaggaggagg agatgcagaa ttccgacatg actcaggagg aggaggagat    960
gcagaattcc gacatgactc aggaggagga ggagatgcag aattccgaca tgactcagga   1020
ggaggaggag atgcagaatt ccgacatgac tcaggaggag gaggagatgc agaattccga   1080
catgactcag gaggaggagg agatgcagaa ttccgacatg actcaggagg aggaggagat   1140
gcagaattcc gacatgactc aggaggagga ggagatgcag aattccgaca tgactcagga   1200
ggaggaggag atgcagaatt ccgacatgac tcaggaggag gaggaagcac cactcaccag   1260
aacgaacccc agcaatgggt cctccctgac tactcgggca gggattccca caacgttcac   1320
ttggctccgg ccgtggctcc aaccttccct ggagagcagt tgctgttctt cagatccact   1380
atgccaggct gctctggata cccgaacatg aacctcgact gtctcttgcc tcaggagtgg   1440
gtgcaacact tctaccagga atctgcccca gctcaaagcg acgtcgctct gctccgtttc   1500
gttaaccccg ataccggtcg cgtgctcttc gagtgtaagt tgcacaagtc tggttacgtc   1560
actgttgccc acacaggcca gcacgacctg gtcatccctc ccaacggcta cttccgcttc   1620
gatagctggg tcaaccagtt ctacacactc gccccgatgg gaaacggagc cggtcgtcgc   1680
agagccttgt aa                                                       1692
```

<210> SEQ ID NO 109
<211> LENGTH: 2052
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 109

```
atgaagccct tctcggtccc tatcctgaca gttgaggaaa tgaccaactc tagattccca     60
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc gctggaggag gaggagatgc agaattccga    240
catggaggag gagatgcaga attccgacat ggaggaggag atgcagaatt ccgacatgga    300
ggaggagatg cagaattccg acatggagga ggagatgcag aattccgaca tggaggagga    360
gatgcagaat tccgacatgg aggaggagat gcagaattcc gacatggagg aggagatgca    420
gaattccgac atggaggagg agatgcagaa ttccgacatg gaggaggaga tgcagaattc    480
cgacatggag gaggagatgc agaattccga catggaggag gagatgcaga attccgacat    540
ggaggaggag atgcagaatt ccgacatgga ggaggagatg cagaattccg acatggagga    600
ggagatgcag aattccgaca tggaggagga gatgcagaat tccgacatgg aggaggagat    660
gcagaattcc gacatggagg aggagatgca gaattccgac atggaggagg agatgcagaa    720
```

-continued

```
ttccgacatg gaggaggaga tgcagaattc cgacatggag gaggaacaca aaactacacc    780
atgaacttgg cctcgcagaa ctggaacaac tacgatccaa ccgaggaaat ccccgctcct    840
ttgggaactc ccgacttcgt gggacgtatc caaggtgtcc tgacacagac tacacgtcgc    900
gacggctcta ctcgcggaca caaggccact gtgtcgacag gttccgtcca cttcacccct    960
aagctgggct ctgtgcaatt cagcacagac acctcaaacg atttcgagac tggccagaac   1020
accaggttca ctcccgtggg tgtcgttcaa gacggcggag gaggagatgc agaattccga   1080
catggaggag gagatgcaga attccgacat ggaggaggag atgcagaatt ccgacatgga   1140
ggaggagatg cagaattccg acatggagga ggagatgcag aattccgaca tggaggagga   1200
gatgcagaat tccgacatgg aggaggagat gcagaattcc gacatggagg aggagatgca   1260
gaattccgac atggaggagg agatgcagaa ttccgacatg gaggaggaga tgcagaattc   1320
cgacatggag gaggagatgc agaattccga catggaggag gagatgcaga attccgacat   1380
ggaggaggag atgcagaatt ccgacatgga ggaggagatg cagaattccg acatggagga   1440
ggagatgcag aattccgaca tggaggagga gatgcagaat tccgacatgg aggaggagat   1500
gcagaattcc gacatggagg aggagatgca gaattccgac atggaggagg agatgcagaa   1560
ttccgacatg gaggaggaga tgcagaattc cgacatggag gaggaagcac cactcaccag   1620
aacgaacccc agcaatgggt cctccctgac tactcgggca gggattccca caacgttcac   1680
ttggctccgg ccgtggctcc aaccttccct ggagagcagt tgctgttctt cagatccact   1740
atgccaggct gctctggata cccgaacatg aacctcgact gtctcttgcc tcaggagtgg   1800
gtgcaacact tctaccagga atctgcccca gctcaaagcg acgtcgctct gctccgtttc   1860
gttaaccccg ataccggtcg cgtgctcttc gagtgtaagt tgcacaagtc tggttacgtc   1920
actgttgccc acacaggcca gcacgacctg gtcatccctc ccaacggcta cttccgcttc   1980
gatagctggg tcaaccagtt ctacacactc gccccgatgg gaaacggagc cggtcgtcgc   2040
agagccttgt aa                                                       2052
```

```
<210> SEQ ID NO 110
<211> LENGTH: 4572
<212> TYPE: DNA
<213> ORGANISM: artificial sequence
<220> FEATURE:
<223> OTHER INFORMATION: synthetic nucleotide sequence encoding the
      recombinant P protein

<400> SEQUENCE: 110
```

```
atgaagccct tctcggtccc tatcctgaca gttgaggaaa tgaccaactc tagattccca     60
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc gctggaggag gaggagatgc agaattccga    240
catgactcag gatatgaagt tggaggagga gatgcagaat tccgacatga ctcaggatat    300
gaagttggag gaggagatgc agaattccga catgactcag gatatgaagt tggaggagga    360
gatgcagaat tccgacatga ctcaggatat gaagttggag gaggagatgc agaattccga    420
catgactcag gatatgaagt tggaggagga gatgcagaat tccgacatga ctcaggatat    480
gaagttggag gaggagatgc agaattccga catgactcag gatatgaagt tggaggagga    540
gatgcagaat tccgacatga ctcaggatat gaagttggag gaggagatgc agaattccga    600
catgactcag gatatgaagt tggaggagga gatgcagaat tccgacatga ctcaggatat    660
```

-continued gaagttggag gaggagatgc agaattccga catgactcag gatatgaagt tggaggagga 720
gatgcagaat tccgacatga ctcaggatat gaagttggag gaggagatgc agaattccga 780
catgactcag gatatgaagt tggaggagga gatgcagaat tccgacatga ctcaggatat 840
gaagttggag gaggagatgc agaattccga catgactcag gatatgaagt tggaggagga 900
gatgcagaat tccgacatga ctcaggatat gaagttggag gaggagatgc agaattccga 960
catgactcag gatatgaagt tggaggagga gatgcagaat tccgacatga ctcaggatat 1020
gaagttggag gaggagatgc agaattccga catgactcag gatatgaagt tggaggagga 1080
gatgcagaat tccgacatga ctcaggatat gaagttggag gaggagatgc agaattccga 1140
catgactcag gatatgaagt tggaggagga gatgcagaat tccgacatga ctcaggatat 1200
gaagttggag gaggagatgc agaattccga catgactcag gatatgaagt tggaggagga 1260
gatgcagaat tccgacatga ctcaggatat gaagttggag gaggagatgc agaattccga 1320
catgactcag gatatgaagt tggaggagga gatgcagaat tccgacatga ctcaggatat 1380
gaagttggag gaggagatgc agaattccga catgactcag gatatgaagt tggaggagga 1440
gatgcagaat tccgacatga ctcaggatat gaagttggag gaggagatgc agaattccga 1500
catgactcag gatatgaagt tggaggagga gatgcagaat tccgacatga ctcaggatat 1560
gaagttggag gaggagatgc agaattccga catgactcag gatatgaagt tggaggagga 1620
gatgcagaat tccgacatga ctcaggatat gaagttggag gaggagatgc agaattccga 1680
catgactcag gatatgaagt tggaggagga gatgcagaat tccgacatga ctcaggatat 1740
gaagttggag gaggagatgc agaattccga catgactcag gatatgaagt tggaggagga 1800
gatgcagaat tccgacatga ctcaggatat gaagttggag gaggagatgc agaattccga 1860
catgactcag gatatgaagt tggaggagga gatgcagaat tccgacatga ctcaggatat 1920
gaagttggag gaggagatgc agaattccga catgactcag gatatgaagt tggaggagga 1980
gatgcagaat tccgacatga ctcaggatat gaagttggag gaggaacaca aaactacacc 2040
atgaacttgg cctcgcagaa ctggaacaac tacgatccaa ccgaggaaat ccccgctcct 2100
ttgggaactc ccgacttcgt gggacgtatc caaggtgtcc tgacacagac tacacgtcgc 2160
gacggctcta ctcgcggaca caaggccact gtgtcgacag gttccgtcca cttcacccct 2220
aagctgggct ctgtgcaatt cagcacagac acctcaaacg atttcgagac tggccagaac 2280
accaggttca ctcccgtggg tgtcgttcaa gacggcggag gaggagatgc agaattccga 2340
catgactcag gatatgaagt tggaggagga gatgcagaat tccgacatga ctcaggatat 2400
gaagttggag gaggagatgc agaattccga catgactcag gatatgaagt tggaggagga 2460
gatgcagaat tccgacatga ctcaggatat gaagttggag gaggagatgc agaattccga 2520
catgactcag gatatgaagt tggaggagga gatgcagaat tccgacatga ctcaggatat 2580
gaagttggag gaggagatgc agaattccga catgactcag gatatgaagt tggaggagga 2640
gatgcagaat tccgacatga ctcaggatat gaagttggag gaggagatgc agaattccga 2700
catgactcag gatatgaagt tggaggagga gatgcagaat tccgacatga ctcaggatat 2760
gaagttggag gaggagatgc agaattccga catgactcag gatatgaagt tggaggagga 2820
gatgcagaat tccgacatga ctcaggatat gaagttggag gaggagatgc agaattccga 2880
catgactcag gatatgaagt tggaggagga gatgcagaat tccgacatga ctcaggatat 2940
gaagttggag gaggagatgc agaattccga catgactcag gatatgaagt tggaggagga 3000
gatgcagaat tccgacatga ctcaggatat gaagttggag gaggagatgc agaattccga 3060
catgactcag gatatgaagt tggaggagga gatgcagaat tccgacatga ctcaggatat 3120
gaagttggag gaggagatgc agaattccga catgactcag gatatgaagt tggaggagga 3180
gatgcagaat tccgacatga ctcaggatat gaagttggag gaggagatgc agaattccga 3240
catgactcag gatatgaagt tggaggagga gatgcagaat tccgacatga ctcaggatat 3300
gaagttggag gaggagatgc agaattccga catgactcag gatatgaagt tggaggagga 3360
gatgcagaat tccgacatga ctcaggatat gaagttggag gaggagatgc agaattccga 3420
catgactcag gatatgaagt tggaggagga gatgcagaat tccgacatga ctcaggatat 3480
gaagttggag gaggagatgc agaattccga catgactcag gatatgaagt tggaggagga 3540
gatgcagaat tccgacatga ctcaggatat gaagttggag gaggagatgc agaattccga 3600
catgactcag gatatgaagt tggaggagga gatgcagaat tccgacatga ctcaggatat 3660
gaagttggag gaggagatgc agaattccga catgactcag gatatgaagt tggaggagga 3720
gatgcagaat tccgacatga ctcaggatat gaagttggag gaggagatgc agaattccga 3780
catgactcag gatatgaagt tggaggagga gatgcagaat tccgacatga ctcaggatat 3840
gaagttggag gaggagatgc agaattccga catgactcag gatatgaagt tggaggagga 3900
gatgcagaat tccgacatga ctcaggatat gaagttggag gaggagatgc agaattccga 3960
catgactcag gatatgaagt tggaggagga gatgcagaat tccgacatga ctcaggatat 4020
gaagttggag gaggagatgc agaattccga catgactcag gatatgaagt tggaggagga 4080
gatgcagaat tccgacatga ctcaggatat gaagttggag gaggaagcac cactcaccag 4140
aacgaacccc agcaatgggt cctccctgac tactcgggca gggattccca caacgttcac 4200
ttggctccgg ccgtggctcc aaccttccct ggagagcagt tgctgttctt cagatccact 4260
atgccaggct gctctggata cccgaacatg aacctcgact gtctcttgcc tcaggagtgg 4320
gtgcaacact tctaccagga atctgcccca gctcaaagcg acgtcgctct gctccgtttc 4380
gttaaccccg ataccggtcg cgtgctcttc gagtgtaagt tgcacaagtc tggttacgtc 4440
actgttgccc acacaggcca gcacgacctg gtcatccctc ccaacggcta cttccgcttc 4500
gatagctggg tcaaccagtt ctacacactc gccccgatgg gaaacggagc cggtcgtcgc 4560
agagccttgt aa 4572

<210> SEQ ID NO 111
<211> LENGTH: 1035
<212> TYPE: DNA
<213> ORGANISM: artificial sequence
<220> FEATURE:
<223> OTHER INFORMATION: synthetic nucleotide sequence encoding the
      recombinant P protein

<400> SEQUENCE: 111
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc ggaggaggag atgcagaatt ccgacatgga 240
ggaggagctg gaacacaaaa ctacaccatg aacttggcct cgcagaactg gaacaactac 300
gatccaaccg aggaaatccc cgctcctttg ggaactcccg acttcgtggg acgtatccaa 360
ggtgtcctga cacagactac acgtcgcgac ggctctactc gcggacacaa ggccactgtg 420
tcgacaggtt ccgtccactt caccccctaag ctgggctctg tgcaattcag cacagacacc 480
tcaaacgatt tcgagactgg ccagaacacc aggttcactc ccgtgggtgt cgttcaagac 540
ggaggaggag atgcagaatt ccgacatgac tcaggaggag gaggaggcag caccactcac 600
cagaacgaac cccagcaatg ggtcctccct gactactcgg gcagggattc ccacaacgtt 660
cacttggctc cggccgtggc tccaaccttc cctggagagc agttgctgtt cttcagatcc 720
actatgccag gctgctctgg atacccgaac atgaacctcg actgtctctt gcctcaggag 780
tgggtgcaac acttctacca ggaatctgcc ccagctcaaa gcgacgtcgc tctgctccgt 840
ttcgttaacc ccgataccgg tcgcgtgctc ttcgagtgta agttgcacaa gtctggttac 900
gtcactgttg cccacacagg ccagcacgac ctggtcatcc ctcccaacgg ctacttccgc 960
ttcgatagct gggtcaacca gttctacaca ctcgccccga tgggaaacgg agccggtcgt 1020
cgcagagcct tgtaa 1035

<210> SEQ ID NO 112
<211> LENGTH: 1188
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 112
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaggag gaggagatgc agaattccga 240
catggaggag gagatgcaga attccgacat ggaggaggag atgcagaatt ccgacatgga 300
ggaggaacac aaaactacac catgaacttg gcctcgcaga actggaacaa ctacgatcca 360
accgaggaaa tccccgctcc tttgggaact cccgacttcg tgggacgtat ccaaggtgtc 420
ctgacacaga ctacacgtcg cgacggctct actcgcggac acaaggccac tgtgtcgaca 480
ggttccgtcc acttcacccc taagctgggc tctgtgcaat tcagcacaga cacctcaaac 540
gatttcgaga ctggccagaa caccaggttc actcccgtgg gtgtcgttca agacggcgga 600
ggaggagatg cagaattccg acatgactca ggatatgaag ttggaggagg agatgcagaa 660
ttccgacatg actcaggata tgaagttgga ggaggagatg cagaattccg acatgactca 720
ggatatgaag ttggaggagg aagcaccact caccagaacg aaccccagca atgggtcctc 780
cctgactact cgggcaggga ttcccacaac gttcacttgg ctccggccgt ggctccaacc 840
ttccctggag agcagttgct gttcttcaga tccactatgc caggctgctc tggatacccg 900
aacatgaacc tcgactgtct cttgcctcag gagtgggtgc aacacttcta ccaggaatct 960
gccccagctc aaagcgacgt cgctctgctc cgtttcgtta accccgatac cggtcgcgtg 1020
ctcttcgagt gtaagttgca caagtctggt tacgtcactg ttgcccacac aggccagcac 1080
gacctggtca tccctcccaa cggctacttc cgcttcgata gctgggtcaa ccagttctac 1140
acactcgccc cgatgggaaa cggagccggt cgtcgcagag ccttgtaa 1188

<210> SEQ ID NO 113
<211> LENGTH: 1872
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 113

```
atgaagccct tctcggtccc tatcctgaca gttgaggaaa tgaccaactc tagattccca     60
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc gctggaggag gagatgcaga attccgacat    240
gactcaggag gaggaggaga tgcagaattc cgacatgact caggaggagg aggagatgca    300
gaattccgac atgactcagg aggaggagga gatgcagaat tccgacatga ctcaggagga    360
ggaggagatg cagaattccg acatgactca ggaggaggag gagatgcaga attccgacat    420
gactcaggag gaggaggaga tgcagaattc cgacatgact caggaggagg aggagatgca    480
gaattccgac atgactcagg aggaggagga gatgcagaat tccgacatga ctcaggagga    540
ggaggagatg cagaattccg acatgactca ggaggaggag gaggaacaca aaactacacc    600
atgaacttgg cctcgcagaa ctggaacaac tacgatccaa ccgaggaaat ccccgctcct    660
ttgggaactc ccgacttcgt gggacgtatc caaggtgtcc tgacacagac tacacgtcgc    720
gacggctcta ctcgcggaca caaggccact gtgtcgacag gttccgtcca cttcacccct    780
aagctgggct ctgtgcaatt cagcacagac acctcaaacg atttcgagac tggccagaac    840
accaggttca ctcccgtggg tgtcgttcaa gacggcggag gaggagatgc agaattccga    900
catgactcag gatatgaagt tcatcatcaa ggaggaggag atgcagaatt ccgacatgac    960
tcaggatatg aagttcatca tcaaggagga ggagatgcag aattccgaca tgactcagga   1020
tatgaagttc atcatcaagg aggaggagat gcagaattcc gacatgactc aggatatgaa   1080
gttcatcatc aaggaggagg agatgcagaa ttccgacatg actcaggata tgaagttcat   1140
catcaaggag gaggagatgc agaattccga catgactcag gatatgaagt tcatcatcaa   1200
ggaggaggag atgcagaatt ccgacatgac tcaggatatg aagttcatca tcaaggagga   1260
ggagatgcag aattccgaca tgactcagga tatgaagttc atcatcaagg aggaggagat   1320
gcagaattcc gacatgactc aggatatgaa gttcatcatc aaggaggagg agatgcagaa   1380
ttccgacatg actcaggata tgaagttcat catcaaggag gaggaagcac cactcaccag   1440
aacgaacccc agcaatgggt cctccctgac tactcgggca gggattccca caacgttcac   1500
ttggctccgg ccgtggctcc aaccttccct ggagagcagt tgctgttctt cagatccact   1560
atgccaggct gctctggata cccgaacatg aacctcgact gtctcttgcc tcaggagtgg   1620
gtgcaacact tctaccagga atctgcccca gctcaaagcg acgtcgctct gctccgtttc   1680
gttaaccccg ataccggtcg cgtgctcttc gagtgtaagt tgcacaagtc tggttacgtc   1740
actgttgccc acacaggcca gcacgacctg gtcatccctc ccaacggcta cttccgcttc   1800
gatagctggg tcaaccagtt ctacacactc gccccgatgg gaaacggagc cggtcgtcgc   1860
agagccttgt aa                                                       1872
```

<210> SEQ ID NO 114
<211> LENGTH: 2592
<212> TYPE: DNA
<213> ORGANISM: artificial sequence
<220> FEATURE:
<223> OTHER INFORMATION: synthetic nucleotide sequence encoding the
recombinant P protein

<400> SEQUENCE: 114

-continued

```
atgaagccct tctcggtccc tatcctgaca gttgaggaaa tgaccaactc tagattccca      60
atcccgctgg aaaagctctt caccggaccc tcctctgctt tcgttgtgca gcctcaaaac     120
ggtcgttgca ccactgatgg tgtcctgctc ggtaccaccc agctctcacc tgtgaacatc     180
tgtactttcc gcggcgacgt cacacacatc gctggaggag gaggagatgc agaattccga     240
catgactcag gatatgaagt tggaggagga gatgcagaat tccgacatga ctcaggatat     300
gaagttggag gaggagatgc agaattccga catgactcag gatatgaagt tggaggagga     360
gatgcagaat tccgacatga ctcaggatat gaagttggag gaggagatgc agaattccga     420
catgactcag gatatgaagt tggaggagga gatgcagaat tccgacatga ctcaggatat     480
gaagttggag gaggagatgc agaattccga catgactcag gatatgaagt tggaggagga     540
gatgcagaat tccgacatga ctcaggatat gaagttggag gaggagatgc agaattccga     600
catgactcag gatatgaagt tggaggagga gatgcagaat tccgacatga ctcaggatat     660
gaagttggag gaggagatgc agaattccga catgactcag gatatgaagt tggaggagga     720
gatgcagaat tccgacatga ctcaggatat gaagttggag gaggagatgc agaattccga     780
catgactcag gatatgaagt tggaggagga gatgcagaat tccgacatga ctcaggatat     840
gaagttggag gaggagatgc agaattccga catgactcag gatatgaagt tggaggagga     900
gatgcagaat tccgacatga ctcaggatat gaagttggag gaggagatgc agaattccga     960
catgactcag gatatgaagt tggaggagga gatgcagaat tccgacatga ctcaggatat    1020
gaagttggag gaggagatgc agaattccga catgactcag gatatgaagt tggaggagga    1080
gatgcagaat tccgacatga ctcaggatat gaagttggag gaggaacaca aaactacacc    1140
atgaacttgg cctcgcagaa ctggaacaac tacgatccaa ccgaggaaat ccccgctcct    1200
ttgggaactc ccgacttcgt gggacgtatc caaggtgtcc tgacacagac tacacgtcgc    1260
gacggctcta ctcgcggaca caaggccact gtgtcgacag gttccgtcca cttcacccct    1320
aagctgggct ctgtgcaatt cagcacagac acctcaaacg atttcgagac tggccagaac    1380
accaggttca ctcccgtggg tgtcgttcaa gacggcagcg gaggaggaga tgcagaattc    1440
cgacatgact caggaggagg aggagatgca gaattccgac atgactcagg aggaggagga    1500
gatgcagaat tccgacatga ctcaggagga ggaggagatg cagaattccg acatgactca    1560
ggaggaggag gagatgcaga attccgacat gactcaggag gaggaggaga tgcagaattc    1620
cgacatgact caggaggagg aggagatgca gaattccgac atgactcagg aggaggagga    1680
gatgcagaat tccgacatga ctcaggagga ggaggagatg cagaattccg acatgactca    1740
ggaggaggag gagatgcaga attccgacat gactcaggag gaggaggaga tgcagaattc    1800
cgacatgact caggaggagg aggagatgca gaattccgac atgactcagg aggaggagga    1860
gatgcagaat tccgacatga ctcaggagga ggaggagatg cagaattccg acatgactca    1920
ggaggaggag gagatgcaga attccgacat gactcaggag gaggaggaga tgcagaattc    1980
cgacatgact caggaggagg aggagatgca gaattccgac atgactcagg aggaggagga    2040
gatgcagaat tccgacatga ctcaggagga ggaggagatg cagaattccg acatgactca    2100
ggaggaggag gagatgcaga attccgacat gactcaggag gaggaggaac cactcaccag    2160
aacgaacccc agcaatgggt cctccctgac tactcgggca gggattccca caacgttcac    2220
ttggctccgg ccgtggctcc aaccttccct ggagagcagt tgctgttctt cagatccact    2280
atgccaggct gctctggata cccgaacatg aacctcgact gtctcttgcc tcaggagtgg    2340
gtgcaacact tctaccagga atctgcccca gctcaaagcg acgtcgctct gctccgtttc    2400
```
gttaaccccg ataccggtcg cgtgctcttc gagtgtaagt tgcacaagtc tggttacgtc 2460
actgttgccc acacaggcca gcacgacctg gtcatccctc ccaacggcta cttccgcttc 2520
gatagctggg tcaaccagtt ctacacactc gccccgatgg gaaacggagc cggtcgtcgc 2580
agagccttgt aa 2592

<210> SEQ ID NO 115
<211> LENGTH: 3942
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 115
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaacac aaggaggagg agatgcagaa 240
ttccgacatg actcaggata tgaagttgga ggaggagatg cagaattccg acatgactca 300
ggatatgaag ttggaggagg agatgcagaa ttccgacatg actcaggata tgaagttgga 360
ggaggagatg cagaattccg acatgactca ggatatgaag ttggaggagg agatgcagaa 420
ttccgacatg actcaggata tgaagttgga ggaggagatg cagaattccg acatgactca 480
ggatatgaag ttggaggagg agatgcagaa ttccgacatg actcaggata tgaagttgga 540
ggaggagatg cagaattccg acatgactca ggatatgaag ttggaggagg agatgcagaa 600
ttccgacatg actcaggata tgaagttgga ggaggagatg cagaattccg acatgactca 660
ggatatgaag ttggaggagg agatgcagaa ttccgacatg actcaggata tgaagttgga 720
ggaggagatg cagaattccg acatgactca ggatatgaag ttggaggagg agatgcagaa 780
ttccgacatg actcaggata tgaagttgga ggaggagatg cagaattccg acatgactca 840
ggatatgaag ttggaggagg agatgcagaa ttccgacatg actcaggata tgaagttgga 900
ggaggagatg cagaattccg acatgactca ggatatgaag ttggaggagg agatgcagaa 960
ttccgacatg actcaggata tgaagttgga ggaggagatg cagaattccg acatgactca 1020
ggatatgaag ttggaggagg agatgcagaa ttccgacatg actcaggata tgaagttgga 1080
ggaggagatg cagaattccg acatgactca ggatatgaag ttggaggagg agatgcagaa 1140
ttccgacatg actcaggata tgaagttgga ggaggagatg cagaattccg acatgactca 1200
ggatatgaag ttggaggagg agatgcagaa ttccgacatg actcaggata tgaagttgga 1260
ggaggagatg cagaattccg acatgactca ggatatgaag ttggaggagg agatgcagaa 1320
ttccgacatg actcaggata tgaagttgga ggaggagatg cagaattccg acatgactca 1380
ggatatgaag ttggaggagg agatgcagaa ttccgacatg actcaggata tgaagttgga 1440
ggaggagatg cagaattccg acatgactca ggatatgaag ttggaggagg agatgcagaa 1500
ttccgacatg actcaggata tgaagttgga ggaggagatg cagaattccg acatgactca 1560
ggatatgaag ttggaggagg aaactacacc atgaacttgg cctcgcagaa ctggaacaac 1620
tacgatccaa ccgaggaaat ccccgctcct ttgggaactc ccgacttcgt gggacgtatc 1680
caaggtgtcc tgacacagac tacacgtcgc gacggctcta ctcgcggaca caaggccact 1740
gtgtcgacag gttccgtcca cttcacccct aagctgggct ctgtgcaatt cagcacagac 1800

-continued

```
acctcaaacg atttcgagac tggccagaac accaggttca ctcccgtggg tgtcgttcaa   1860
gacggcagca ccggaggagg agatgcagaa ttccgacatg actcaggata tgaagttcat   1920
catcaaggag gaggagatgc agaattccga catgactcag gatatgaagt tcatcatcaa   1980
ggaggaggag atgcagaatt ccgacatgac tcaggatatg aagttcatca tcaaggagga   2040
ggagatgcag aattccgaca tgactcagga tatgaagttc atcatcaagg aggaggagat   2100
gcagaattcc gacatgactc aggatatgaa gttcatcatc aaggaggagg agatgcagaa   2160
ttccgacatg actcaggata tgaagttcat catcaaggag gaggagatgc agaattccga   2220
catgactcag gatatgaagt tcatcatcaa ggaggaggag atgcagaatt ccgacatgac   2280
tcaggatatg aagttcatca tcaaggagga ggagatgcag aattccgaca tgactcagga   2340
tatgaagttc atcatcaagg aggaggagat gcagaattcc gacatgactc aggatatgaa   2400
gttcatcatc aaggaggagg agatgcagaa ttccgacatg actcaggata tgaagttcat   2460
catcaaggag gaggagatgc agaattccga catgactcag gatatgaagt tcatcatcaa   2520
ggaggaggag atgcagaatt ccgacatgac tcaggatatg aagttcatca tcaaggagga   2580
ggagatgcag aattccgaca tgactcagga tatgaagttc atcatcaagg aggaggagat   2640
gcagaattcc gacatgactc aggatatgaa gttcatcatc aaggaggagg agatgcagaa   2700
ttccgacatg actcaggata tgaagttcat catcaaggag gaggagatgc agaattccga   2760
catgactcag gatatgaagt tcatcatcaa ggaggaggag atgcagaatt ccgacatgac   2820
tcaggatatg aagttcatca tcaaggagga ggagatgcag aattccgaca tgactcagga   2880
tatgaagttc atcatcaagg aggaggagat gcagaattcc gacatgactc aggatatgaa   2940
gttcatcatc aaggaggagg agatgcagaa ttccgacatg actcaggata tgaagttcat   3000
catcaaggag gaggagatgc agaattccga catgactcag gatatgaagt tcatcatcaa   3060
ggaggaggag atgcagaatt ccgacatgac tcaggatatg aagttcatca tcaaggagga   3120
ggagatgcag aattccgaca tgactcagga tatgaagttc atcatcaagg aggaggagat   3180
gcagaattcc gacatgactc aggatatgaa gttcatcatc aaggaggagg agatgcagaa   3240
ttccgacatg actcaggata tgaagttcat catcaaggag gaggagatgc agaattccga   3300
catgactcag gatatgaagt tcatcatcaa ggaggaggag atgcagaatt ccgacatgac   3360
tcaggatatg aagttcatca tcaaggagga ggagatgcag aattccgaca tgactcagga   3420
tatgaagttc atcatcaagg aggaggagat gcagaattcc gacatgactc aggatatgaa   3480
gttcatcatc aaggaggagg aactcaccag aacgaacccc agcaatgggt cctccctgac   3540
tactcgggca gggattccca caacgttcac ttggctccgg ccgtggctcc aaccttccct   3600
ggagagcagt tgctgttctt cagatccact atgccaggct gctctggata cccgaacatg   3660
aacctcgact gtctcttgcc tcaggagtgg gtgcaacact tctaccagga atctgcccca   3720
gctcaaagcg acgtcgctct gctccgtttc gttaaccccg ataccggtcg cgtgctcttc   3780
gagtgtaagt tgcacaagtc tggttacgtc actgttgccc acacaggcca gcacgacctg   3840
gtcatccctc ccaacggcta cttccgcttc gatagctggg tcaaccagtt ctacacactc   3900
gccccgatgg gaaacggagc cggtcgtcgc agagccttgt aa                      3942
```

<210> SEQ ID NO 116
<211> LENGTH: 4212
<212> TYPE: DNA
<213> ORGANISM: artificial sequence
<220> FEATURE:

<223> OTHER INFORMATION: synthetic nucleotide sequence encoding the
      recombinant P protein

<400> SEQUENCE: 116
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaacag gaggaggaga tgcagaattc 240
cgacatgact caggatatga agttcatcat caaggaggag gagatgcaga attccgacat 300
gactcaggat atgaagttca tcatcaagga ggaggagatg cagaattccg acatgactca 360
ggatatgaag ttcatcatca aggaggagga gatgcagaat tccgacatga ctcaggatat 420
gaagttcatc atcaaggagg aggagatgca gaattccgac atgactcagg atatgaagtt 480
catcatcaag gaggaggaga tgcagaattc cgacatgact caggatatga agttcatcat 540
caaggaggag gagatgcaga attccgacat gactcaggat atgaagttca tcatcaagga 600
ggaggagatg cagaattccg acatgactca ggatatgaag ttcatcatca aggaggagga 660
gatgcagaat tccgacatga ctcaggatat gaagttcatc atcaaggagg aggagatgca 720
gaattccgac atgactcagg atatgaagtt catcatcaag gaggaggaga tgcagaattc 780
cgacatgact caggatatga agttcatcat caaggaggag gagatgcaga attccgacat 840
gactcaggat atgaagttca tcatcaagga ggaggagatg cagaattccg acatgactca 900
ggatatgaag ttcatcatca aggaggagga gatgcagaat tccgacatga ctcaggatat 960
gaagttcatc atcaaggagg aggagatgca gaattccgac atgactcagg atatgaagtt 1020
catcatcaag gaggaggaga tgcagaattc cgacatgact caggatatga agttcatcat 1080
caaggaggag gagatgcaga attccgacat gactcaggat atgaagttca tcatcaagga 1140
ggaggagatg cagaattccg acatgactca ggatatgaag ttcatcatca aggaggagga 1200
gatgcagaat tccgacatga ctcaggatat gaagttcatc atcaaggagg aggagatgca 1260
gaattccgac atgactcagg atatgaagtt catcatcaag gaggaggaga tgcagaattc 1320
cgacatgact caggatatga agttcatcat caaggaggag gagatgcaga attccgacat 1380
gactcaggat atgaagttca tcatcaagga ggaggagatg cagaattccg acatgactca 1440
ggatatgaag ttcatcatca aggaggagga gatgcagaat tccgacatga ctcaggatat 1500
gaagttcatc atcaaggagg aggagatgca gaattccgac atgactcagg atatgaagtt 1560
catcatcaag gaggaggaga tgcagaattc cgacatgact caggatatga agttcatcat 1620
caaggaggag gagatgcaga attccgacat gactcaggat atgaagttca tcatcaagga 1680
ggaggagatg cagaattccg acatgactca ggatatgaag ttcatcatca aggaggagga 1740
gatgcagaat tccgacatga ctcaggatat gaagttcatc atcaaggagg aggagatgca 1800
gaattccgac atgactcagg atatgaagtt catcatcaag gaggaggaga tgcagaattc 1860
cgacatgact caggatatga agttcatcat caaggaggag gagatgcaga attccgacat 1920
gactcaggat atgaagttca tcatcaagga ggaggagatg cagaattccg acatgactca 1980
ggatatgaag ttcatcatca aggaggagga gatgcagaat tccgacatga ctcaggatat 2040
gaagttcatc atcaaggagg aggagatgca gaattccgac atgactcagg atatgaagtt 2100
catcatcaag gaggaggaga tgcagaattc cgacatgact caggatatga agttcatcat 2160
caaggaggag gagatgcaga attccgacat gactcaggat atgaagttca tcatcaagga 2220
ggaggagatg cagaattccg acatgactca ggatatgaag ttcatcatca aggaggagga 2280
gatgcagaat tccgacatga ctcaggatat gaagttcatc atcaaggagg aggagatgca 2340
gaattccgac atgactcagg atatgaagtt catcatcaag gaggaggaca aaactacacc 2400
atgaacttgg cctcgcagaa ctggaacaac tacgatccaa ccgaggaaat ccccgctcct 2460
ttgggaactc ccgacttcgt gggacgtatc caaggtgtcc tgacacagac tacacgtcgc 2520
gacggctcta ctcgcggaca caaggccact gtgtcgacag gttccgtcca cttcacccct 2580
aagctgggct ctgtgcaatt cagcacagac acctcaaacg atttcgagac tggccagaac 2640
accaggttca ctcccgtggg tgtcgttcaa gacggcggag gaggagatgc agaattccga 2700
catggaggag gagatgcaga attccgacat ggaggaggag atgcagaatt ccgacatgga 2760
ggaggagatg cagaattccg acatggagga ggagatgcag aattccgaca tggaggagga 2820
gatgcagaat tccgacatgg aggaggagat gcagaattcc gacatggagg aggagatgca 2880
gaattccgac atggaggagg agatgcagaa ttccgacatg gaggaggaga tgcagaattc 2940
cgacatggag gaggagatgc agaattccga catggaggag gagatgcaga attccgacat 3000
ggaggaggag atgcagaatt ccgacatgga ggaggagatg cagaattccg acatggagga 3060
ggagatgcag aattccgaca tggaggagga gatgcagaat tccgacatgg aggaggagat 3120
gcagaattcc gacatggagg aggagatgca gaattccgac atggaggagg agatgcagaa 3180
ttccgacatg gaggaggaga tgcagaattc cgacatggag gaggagatgc agaattccga 3240
catggaggag gagatgcaga attccgacat ggaggaggag atgcagaatt ccgacatgga 3300
ggaggagatg cagaattccg acatggagga ggagatgcag aattccgaca tggaggagga 3360
gatgcagaat tccgacatgg aggaggagat gcagaattcc gacatggagg aggagatgca 3420
gaattccgac atggaggagg agatgcagaa ttccgacatg gaggaggaga tgcagaattc 3480
cgacatggag gaggagatgc agaattccga catggaggag gagatgcaga attccgacat 3540
ggaggaggag atgcagaatt ccgacatgga ggaggagatg cagaattccg acatggagga 3600
ggagatgcag aattccgaca tggaggagga gatgcagaat tccgacatgg aggaggagat 3660
gcagaattcc gacatggagg aggagatgca gaattccgac atggaggagg agatgcagaa 3720
ttccgacatg gaggaggaga tgcagaattc cgacatggag gaggaagcac cactcaccag 3780
aacgaacccc agcaatgggt cctccctgac tactcgggca gggattccca caacgttcac 3840
ttggctccgg ccgtggctcc aaccttccct ggagagcagt tgctgttctt cagatccact 3900
atgccaggct gctctggata cccgaacatg aacctcgact gtctcttgcc tcaggagtgg 3960
gtgcaacact tctaccagga atctgcccca gctcaaagcg acgtcgctct gctccgtttc 4020
gttaaccccg ataccggtcg cgtgctcttc gagtgtaagt tgcacaagtc tggttacgtc 4080
actgttgccc acacaggcca gcacgacctg gtcatccctc ccaacggcta cttccgcttc 4140
gatagctggg tcaaccagtt ctacacactc gccccgatgg gaaacggagc cggtcgtcgc 4200
agagccttgt aa 4212

<210> SEQ ID NO 117
<211> LENGTH: 1269
<212> TYPE: DNA
<213> ORGANISM: artificial sequence
<220> FEATURE:
<223> OTHER INFORMATION: synthetic nucleotide sequence encoding the
      recombinant P protein

<400> SEQUENCE: 117

-continued atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaggag gaggagatgc agaattccga 240
catggaggag gaacacaaaa ctacaccatg aacttggcct cgcagaactg gaacaactac 300
gatccaaccg aggaaatccc cgctcctttg ggaactcccg acttcgtggg acgtatccaa 360
ggtgtcctga cacagactac acgtcgcgac ggctctactc gcggacacaa ggccactgtg 420
tcgacaggtt ccgtccactt caccccctaag ctgggctctg tgcaattcag cacagacacc 480
tcaaacgatt tcgagactgg ccagaacacc aggttcactc ccgtgggtgt cgttcaagac 540
ggcggaggag gagatgcaga attccgacat ggaggaggag atgcagaatt ccgacatgga 600
ggaggagatg cagaattccg acatggagga ggagatgcag aattccgaca tggaggagga 660
gatgcagaat tccgacatgg aggaggagat gcagaattcc gacatggagg aggagatgca 720
gaattccgac atggaggagg agatgcagaa ttccgacatg gaggaggaga tgcagaattc 780
cgacatggag gaggagatgc agaattccga catggaggag gaagcaccac tcaccagaac 840
gaaccccagc aatgggtcct ccctgactac tcgggcaggg attcccacaa cgttcacttg 900
gctccggccg tggctccaac cttccctgga gagcagttgc tgttcttcag atccactatg 960
ccaggctgct ctggataccc gaacatgaac ctcgactgtc tcttgcctca ggagtgggtg 1020
caacacttct accaggaatc tgccccagct caaagcgacg tcgctctgct ccgtttcgtt 1080
aaccccgata ccggtcgcgt gctcttcgag tgtaagttgc acaagtctgg ttacgtcact 1140
gttgcccaca caggccagca cgacctggtc atccctccca acggctactt ccgcttcgat 1200
agctgggtca accagttcta cacactcgcc ccgatgggaa acggagccgg tcgtcgcaga 1260
gccttgtaa 1269

<210> SEQ ID NO 118
<211> LENGTH: 2052
<212> TYPE: DNA
<213> ORGANISM: artificial sequence
<220> FEATURE:
<223> OTHER INFORMATION: synthetic nucleotide sequence encoding the
      recombinant P protein

<400> SEQUENCE: 118
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaggag gaggagatgc agaattccga 240
catgactcag gaggaggagg agatgcagaa ttccgacatg actcaggagg aggaggagat 300
gcagaattcc gacatgactc aggaggagga ggagatgcag aattccgaca tgactcagga 360
ggaggaggag atgcagaatt ccgacatgac tcaggaggag gaggagatgc agaattccga 420
catgactcag gaggaggagg agatgcagaa ttccgacatg actcaggagg aggaggagat 480
gcagaattcc gacatgactc aggaggagga ggagatgcag aattccgaca tgactcagga 540
ggaggaggag atgcagaatt ccgacatgac tcaggaggag gaggaacaca aaactacacc 600
atgaacttgg cctcgcagaa ctggaacaac tacgatccaa ccgaggaaat ccccgctcct 660
ttgggaactc ccgacttcgt gggacgtatc caaggtgtcc tgacacagac tacacgtcgc 720

```
gacggctcta ctcgcggaca caaggccact gtgtcgacag gttccgtcca cttcacccct    780
aagctgggct ctgtgcaatt cagcacagac acctcaaacg atttcgagac tggccagaac    840
accaggttca ctcccgtggg tgtcgttcaa gacggcggag gaggagatgc agaattccga    900
catgactcag gaggaggagg agatgcagaa ttccgacatg actcaggagg aggaggagat    960
gcagaattcc gacatgactc aggaggagga ggagatgcag aattccgaca tgactcagga   1020
ggaggaggag atgcagaatt ccgacatgac tcaggaggag gaggagatgc agaattccga   1080
catgactcag gaggaggagg agatgcagaa ttccgacatg actcaggagg aggaggagat   1140
gcagaattcc gacatgactc aggaggagga ggagatgcag aattccgaca tgactcagga   1200
ggaggaggag atgcagaatt ccgacatgac tcaggaggag gaggagatgc agaattccga   1260
catgactcag gaggaggagg agatgcagaa ttccgacatg actcaggagg aggaggagat   1320
gcagaattcc gacatgactc aggaggagga ggagatgcag aattccgaca tgactcagga   1380
ggaggaggag atgcagaatt ccgacatgac tcaggaggag gaggagatgc agaattccga   1440
catgactcag gaggaggagg agatgcagaa ttccgacatg actcaggagg aggaggagat   1500
gcagaattcc gacatgactc aggaggagga ggagatgcag aattccgaca tgactcagga   1560
ggaggaggag atgcagaatt ccgacatgac tcaggaggag gaggaagcac cactcaccag   1620
aacgaacccc agcaatgggt cctccctgac tactcgggca gggattccca caacgttcac   1680
ttggctccgg ccgtggctcc aaccttccct ggagagcagt tgctgttctt cagatccact   1740
atgccaggct gctctggata cccgaacatg aacctcgact gtctcttgcc tcaggagtgg   1800
gtgcaacact tctaccagga atctgcccca gctcaaagcg acgtcgctct gctccgtttc   1860
gttaaccccg ataccggtcg cgtgctcttc gagtgtaagt tgcacaagtc tggttacgtc   1920
actgttgccc acacaggcca gcacgacctg gtcatccctc ccaacggcta cttccgcttc   1980
gatagctggg tcaaccagtt ctacacactc gccccgatgg gaaacggagc cggtcgtcgc   2040
agagccttgt aa                                                       2052
```

<210> SEQ ID NO 119
<211> LENGTH: 3672
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 119

```
atgaagccct tctcggtccc tatcctgaca gttgaggaaa tgaccaactc tagattccca     60
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc gctggaggag gaggagatgc agaattccga    240
catgactcag gatatgaagt tggaggagga gatgcagaat tccgacatga ctcaggatat    300
gaagttggag gaggagatgc agaattccga catgactcag gatatgaagt tggaggagga    360
gatgcagaat tccgacatga ctcaggatat gaagttggag gaggagatgc agaattccga    420
catgactcag gatatgaagt tggaggagga gatgcagaat tccgacatga ctcaggatat    480
gaagttggag gaggagatgc agaattccga catgactcag gatatgaagt tggaggagga    540
gatgcagaat tccgacatga ctcaggatat gaagttggag gaggagatgc agaattccga    600
catgactcag gatatgaagt tggaggagga gatgcagaat tccgacatga ctcaggatat    660
```

-continued

```
gaagttggag gaggagatgc agaattccga catgactcag gatatgaagt tggaggagga    720
gatgcagaat tccgacatga ctcaggatat gaagttggag gaggagatgc agaattccga    780
catgactcag gatatgaagt tggaggagga gatgcagaat tccgacatga ctcaggatat    840
gaagttggag gaggagatgc agaattccga catgactcag gatatgaagt tggaggagga    900
gatgcagaat tccgacatga ctcaggatat gaagttggag gaggagatgc agaattccga    960
catgactcag gatatgaagt tggaggagga gatgcagaat tccgacatga ctcaggatat   1020
gaagttggag gaggagatgc agaattccga catgactcag gatatgaagt tggaggagga   1080
gatgcagaat tccgacatga ctcaggatat gaagttggag gaggaacaca aaactacacc   1140
atgaacttgg cctcgcagaa ctggaacaac tacgatccaa ccgaggaaat ccccgctcct   1200
ttgggaactc ccgacttcgt gggacgtatc caaggtgtcc tgacacagac tacacgtcgc   1260
gacggctcta ctcgcggaca caaggccact gtgtcgacag gttccgtcca cttcacccct   1320
aagctgggct ctgtgcaatt cagcacagac acctcaaacg atttcgagac tggccagaac   1380
accaggttca ctcccgtggg tgtcgttcaa gacggcggag gaggagatgc agaattccga   1440
catgactcag gatatgaagt tggaggagga gatgcagaat tccgacatga ctcaggatat   1500
gaagttggag gaggagatgc agaattccga catgactcag gatatgaagt tggaggagga   1560
gatgcagaat tccgacatga ctcaggatat gaagttggag gaggagatgc agaattccga   1620
catgactcag gatatgaagt tggaggagga gatgcagaat tccgacatga ctcaggatat   1680
gaagttggag gaggagatgc agaattccga catgactcag gatatgaagt tggaggagga   1740
gatgcagaat tccgacatga ctcaggatat gaagttggag gaggagatgc agaattccga   1800
catgactcag gatatgaagt tggaggagga gatgcagaat tccgacatga ctcaggatat   1860
gaagttggag gaggagatgc agaattccga catgactcag gatatgaagt tggaggagga   1920
gatgcagaat tccgacatga ctcaggatat gaagttggag gaggagatgc agaattccga   1980
catgactcag gatatgaagt tggaggagga gatgcagaat tccgacatga ctcaggatat   2040
gaagttggag gaggagatgc agaattccga catgactcag gatatgaagt tggaggagga   2100
gatgcagaat tccgacatga ctcaggatat gaagttggag gaggagatgc agaattccga   2160
catgactcag gatatgaagt tggaggagga gatgcagaat tccgacatga ctcaggatat   2220
gaagttggag gaggagatgc agaattccga catgactcag gatatgaagt tggaggagga   2280
gatgcagaat tccgacatga ctcaggatat gaagttggag gaggagatgc agaattccga   2340
catgactcag gatatgaagt tggaggagga gatgcagaat tccgacatga ctcaggatat   2400
gaagttggag gaggagatgc agaattccga catgactcag gatatgaagt tggaggagga   2460
gatgcagaat tccgacatga ctcaggatat gaagttggag gaggagatgc agaattccga   2520
catgactcag gatatgaagt tggaggagga gatgcagaat tccgacatga ctcaggatat   2580
gaagttggag gaggagatgc agaattccga catgactcag gatatgaagt tggaggagga   2640
gatgcagaat tccgacatga ctcaggatat gaagttggag gaggagatgc agaattccga   2700
catgactcag gatatgaagt tggaggagga gatgcagaat tccgacatga ctcaggatat   2760
gaagttggag gaggagatgc agaattccga catgactcag gatatgaagt tggaggagga   2820
gatgcagaat tccgacatga ctcaggatat gaagttggag gaggagatgc agaattccga   2880
catgactcag gatatgaagt tggaggagga gatgcagaat tccgacatga ctcaggatat   2940
gaagttggag gaggagatgc agaattccga catgactcag gatatgaagt tggaggagga   3000
gatgcagaat tccgacatga ctcaggatat gaagttggag gaggagatgc agaattccga   3060
```
catgactcag gatatgaagt tggaggagga gatgcagaat tccgacatga ctcaggatat 3120
gaagttggag gaggagatgc agaattccga catgactcag gatatgaagt tggaggagga 3180
gatgcagaat tccgacatga ctcaggatat gaagttggag gaggaagcac cactcaccag 3240
aacgaacccc agcaatgggt cctccctgac tactcgggca gggattccca caacgttcac 3300
ttggctccgg ccgtggctcc aaccttccct ggagagcagt tgctgttctt cagatccact 3360
atgccaggct gctctggata cccgaacatg aacctcgact gtctcttgcc tcaggagtgg 3420
gtgcaacact tctaccagga atctgcccca gctcaaagcg acgtcgctct gctccgtttc 3480
gttaaccccg ataccggtcg cgtgctcttc gagtgtaagt tgcacaagtc tggttacgtc 3540
actgttgccc acacaggcca gcacgacctg gtcatccctc ccaacggcta cttccgcttc 3600
gatagctggg tcaaccagtt ctacacactc gccccgatgg gaaacggagc cggtcgtcgc 3660
agagccttgt aa 3672

<210> SEQ ID NO 120
<211> LENGTH: 3672
<212> TYPE: DNA
<213> ORGANISM: artificial sequence
<220> FEATURE:
<223> OTHER INFORMATION: synthetic nucleotide sequence encoding the
recombinant P protein

<400> SEQUENCE: 120
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaggag gaggagatgc agaattccga 240
catgactcag gatatgaagt tcatcatcaa ggaggaggag atgcagaatt ccgacatgac 300
tcaggatatg aagttcatca tcaaggagga ggagatgcag aattccgaca tgactcagga 360
tatgaagttc atcatcaagg aggaggagat gcagaattcc gacatgactc aggatatgaa 420
gttcatcatc aaggaggagg agatgcagaa ttccgacatg actcaggata tgaagttcat 480
catcaaggag gaggagatgc agaattccga catgactcag gatatgaagt tcatcatcaa 540
ggaggaggag atgcagaatt ccgacatgac tcaggatatg aagttcatca tcaaggagga 600
ggagatgcag aattccgaca tgactcagga tatgaagttc atcatcaagg aggaggagat 660
gcagaattcc gacatgactc aggatatgaa gttcatcatc aaggaggagg agatgcagaa 720
ttccgacatg actcaggata tgaagttcat catcaaggag gaggagatgc agaattccga 780
catgactcag gatatgaagt tcatcatcaa ggaggaggag atgcagaatt ccgacatgac 840
tcaggatatg aagttcatca tcaaggagga ggagatgcag aattccgaca tgactcagga 900
tatgaagttc atcatcaagg aggaggagat gcagaattcc gacatgactc aggatatgaa 960
gttcatcatc aaggaggagg agatgcagaa ttccgacatg actcaggata tgaagttcat 1020
catcaaggag gaggagatgc agaattccga catgactcag gatatgaagt tcatcatcaa 1080
ggaggaggag atgcagaatt ccgacatgac tcaggatatg aagttcatca tcaaggagga 1140
ggagatgcag aattccgaca tgactcagga tatgaagttc atcatcaagg aggaggagat 1200
gcagaattcc gacatgactc aggatatgaa gttcatcatc aaggaggagg agatgcagaa 1260
ttccgacatg actcaggata tgaagttcat catcaaggag gaggagatgc agaattccga 1320
catgactcag gatatgaagt tcatcatcaa ggaggaggag atgcagaatt ccgacatgac 1380

-continued tcaggatatg aagttcatca tcaaggagga ggagatgcag aattccgaca tgactcagga 1440
tatgaagttc atcatcaagg aggaggagat gcagaattcc gacatgactc aggatatgaa 1500
gttcatcatc aaggaggagg agatgcagaa ttccgacatg actcaggata tgaagttcat 1560
catcaaggag gaggagatgc agaattccga catgactcag gatatgaagt tcatcatcaa 1620
ggaggaggag atgcagaatt ccgacatgac tcaggatatg aagttcatca tcaaggagga 1680
ggagatgcag aattccgaca tgactcagga tatgaagttc atcatcaagg aggaggagat 1740
gcagaattcc gacatgactc aggatatgaa gttcatcatc aaggaggagg agatgcagaa 1800
ttccgacatg actcaggata tgaagttcat catcaaggag gaggagatgc agaattccga 1860
catgactcag gatatgaagt tcatcatcaa ggaggaggag atgcagaatt ccgacatgac 1920
tcaggatatg aagttcatca tcaaggagga ggagatgcag aattccgaca tgactcagga 1980
tatgaagttc atcatcaagg aggaggagat gcagaattcc gacatgactc aggatatgaa 2040
gttcatcatc aaggaggagg agatgcagaa ttccgacatg actcaggata tgaagttcat 2100
catcaaggag gaggagatgc agaattccga catgactcag gatatgaagt tcatcatcaa 2160
ggaggaggag atgcagaatt ccgacatgac tcaggatatg aagttcatca tcaaggagga 2220
ggagatgcag aattccgaca tgactcagga tatgaagttc atcatcaagg aggaggagat 2280
gcagaattcc gacatgactc aggatatgaa gttcatcatc aaggaggagg agatgcagaa 2340
ttccgacatg actcaggata tgaagttcat catcaaggag gaggaacaca aaactacacc 2400
atgaacttgg cctcgcagaa ctggaacaac tacgatccaa ccgaggaaat ccccgctcct 2460
ttgggaactc ccgacttcgt gggacgtatc caaggtgtcc tgacacagac tacacgtcgc 2520
gacggctcta ctcgcggaca caaggccact gtgtcgacag gttccgtcca cttcacccct 2580
aagctgggct ctgtgcaatt cagcacagac acctcaaacg atttcgagac tggccagaac 2640
accaggttca ctcccgtggg tgtcgttcaa gacggcggag gaggagatgc agaattccga 2700
catgactcag gatatgaagt tcatcatcaa ggaggaggag atgcagaatt ccgacatgac 2760
tcaggatatg aagttcatca tcaaggagga ggagatgcag aattccgaca tgactcagga 2820
tatgaagttc atcatcaagg aggaggagat gcagaattcc gacatgactc aggatatgaa 2880
gttcatcatc aaggaggagg agatgcagaa ttccgacatg actcaggata tgaagttcat 2940
catcaaggag gaggagatgc agaattccga catgactcag gatatgaagt tcatcatcaa 3000
ggaggaggag atgcagaatt ccgacatgac tcaggatatg aagttcatca tcaaggagga 3060
ggagatgcag aattccgaca tgactcagga tatgaagttc atcatcaagg aggaggagat 3120
gcagaattcc gacatgactc aggatatgaa gttcatcatc aaggaggagg agatgcagaa 3180
ttccgacatg actcaggata tgaagttcat catcaaggag gaggaagcac cactcaccag 3240
aacgaacccc agcaatgggt cctccctgac tactcgggca gggattccca caacgttcac 3300
ttggctccgg ccgtggctcc aaccttccct ggagagcagt tgctgttctt cagatccact 3360
atgccaggct gctctggata cccgaacatg aacctcgact gtctcttgcc tcaggagtgg 3420
gtgcaacact tctaccagga atctgcccca gctcaaagcg acgtcgctct gctccgtttc 3480
gttaaccccg ataccggtcg cgtgctcttc gagtgtaagt tgcacaagtc tggttacgtc 3540
actgttgccc acacaggcca gcacgacctg gtcatccctc ccaacggcta cttccgcttc 3600
gatagctggg tcaaccagtt ctacacactc gccccgatgg gaaacggagc cggtcgtcgc 3660
agagccttgt aa 3672

<210> SEQ ID NO 121
<211> LENGTH: 1359
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 121
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc ggaggaggag atgcagaatt ccgacatgga 240
ggaggagctg gaacacaaaa ctacaccatg aacttggcct cgcagaactg gaacaactac 300
gatccaaccg aggaaatccc cgctcctttg ggaactcccg acttcgtggg acgtatccaa 360
ggtgtcctga cacagactac acgtcgcgac ggctctactc gcggacacaa ggccactgtg 420
tcgacaggtt ccgtccactt cacccctaag ctgggctctg tgcaattcag cacagacacc 480
tcaaacgatt tcgagactgg ccagaacacc aggttcactc ccgtgggtgt cgttcaagac 540
ggaggaggag atgcagaatt ccgacatgac tcaggaggag gaggagatgc agaattccga 600
catgactcag gaggaggagg agatgcagaa ttccgacatg actcaggagg aggaggagat 660
gcagaattcc gacatgactc aggaggagga ggagatgcag aattccgaca tgactcagga 720
ggaggaggag atgcagaatt ccgacatgac tcaggaggag gaggagatgc agaattccga 780
catgactcag gaggaggagg agatgcagaa ttccgacatg actcaggagg aggaggagat 840
gcagaattcc gacatgactc aggaggagga ggagatgcag aattccgaca tgactcagga 900
ggaggaggag gcagcaccac tcaccagaac gaaccccagc aatgggtcct ccctgactac 960
tcgggcaggg attcccacaa cgttcacttg gctccggccg tggctccaac cttccctgga 1020
gagcagttgc tgttcttcag atccactatg ccaggctgct ctggataccc gaacatgaac 1080
ctcgactgtc tcttgcctca ggagtgggtg caacacttct accaggaatc tgccccagct 1140
caaagcgacg tcgctctgct ccgtttcgtt aaccccgata ccggtcgcgt gctcttcgag 1200
tgtaagttgc acaagtctgg ttacgtcact gttgcccaca caggccagca cgacctggtc 1260
atccctccca acggctactt ccgcttcgat agctgggtca accagttcta cacactcgcc 1320
ccgatgggaa acggagccgg tcgtcgcaga gccttgtaa 1359

<210> SEQ ID NO 122
<211> LENGTH: 1503
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 122
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaggag gaggagatgc agaattccga 240
catggaggag gagatgcaga attccgacat ggaggaggag atgcagaatt ccgacatgga 300
ggaggaacac aaaactacac catgaacttg gcctcgcaga actggaacaa ctacgatcca 360

```
accgaggaaa tccccgctcc tttgggaact cccgacttcg tgggacgtat ccaaggtgtc    420
ctgacacaga ctacacgtcg cgacggctct actcgcggac acaaggccac tgtgtcgaca    480
ggttccgtcc acttcacccc taagctgggc tctgtgcaat tcagcacaga cacctcaaac    540
gatttcgaga ctggccagaa caccaggttc actcccgtgg gtgtcgttca agacggcgga    600
ggaggagatg cagaattccg acatgactca ggatatgaag ttggaggagg agatgcagaa    660
ttccgacatg actcaggata tgaagttgga ggaggagatg cagaattccg acatgactca    720
ggatatgaag ttggaggagg agatgcagaa ttccgacatg actcaggata tgaagttgga    780
ggaggagatg cagaattccg acatgactca ggatatgaag ttggaggagg agatgcagaa    840
ttccgacatg actcaggata tgaagttgga ggaggagatg cagaattccg acatgactca    900
ggatatgaag ttggaggagg agatgcagaa ttccgacatg actcaggata tgaagttgga    960
ggaggagatg cagaattccg acatgactca ggatatgaag ttggaggagg agatgcagaa   1020
ttccgacatg actcaggata tgaagttgga ggaggaagca ccactcacca gaacgaaccc   1080
cagcaatggg tcctccctga ctactcgggc agggattccc acaacgttca cttggctccg   1140
gccgtggctc caaccttccc tggagagcag ttgctgttct tcagatccac tatgccaggc   1200
tgctctggat acccgaacat gaacctcgac tgtctcttgc ctcaggagtg ggtgcaacac   1260
ttctaccagg aatctgcccc agctcaaagc gacgtcgctc tgctccgttt cgttaacccc   1320
gataccggtc gcgtgctctt cgagtgtaag ttgcacaagt ctggttacgt cactgttgcc   1380
cacacaggcc agcacgacct ggtcatccct cccaacggct acttccgctt cgatagctgg   1440
gtcaaccagt tctacacact cgccccgatg ggaaacggag ccggtcgtcg cagagccttg   1500
taa                                                                 1503
```

```
<210> SEQ ID NO 123
<211> LENGTH: 1476
<212> TYPE: DNA
<213> ORGANISM: artificial sequence
<220> FEATURE:
<223> OTHER INFORMATION: synthetic nucleotide sequence encoding the
      recombinant P protein

<400> SEQUENCE: 123
```

```
atgaagccct tctcggtccc tatcctgaca gttgaggaaa tgaccaactc tagattccca     60
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc gctggaggag gaggagatgc agaattccga    240
catgactcag gatatgaagt tggaggagga gatgcagaat tccgacatga ctcaggatat    300
gaagttggag gaggagatgc agaattccga catgactcag gatatgaagt tggaggagga    360
gatgcagaat tccgacatga ctcaggatat gaagttggag gaggagatgc agaattccga    420
catgactcag gatatgaagt tggaggagga gatgcagaat tccgacatga ctcaggatat    480
gaagttggag gaggagatgc agaattccga catgactcag gatatgaagt tggaggagga    540
gatgcagaat tccgacatga ctcaggatat gaagttggag gaggagatgc agaattccga    600
catgactcag gatatgaagt tggaggagga gatgcagaat tccgacatga ctcaggatat    660
gaagttggag gaggaacaca aaactacacc atgaacttgg cctcgcagaa ctggaacaac    720
tacgatccaa ccgaggaaat ccccgctcct ttgggaactc ccgacttcgt gggacgtatc    780
caaggtgtcc tgacacagac tacacgtcgc gacggctcta ctcgcggaca caaggccact    840
```

```
gtgtcgacag gttccgtcca cttcacccct aagctgggct ctgtgcaatt cagcacagac     900
acctcaaacg atttcgagac tggccagaac accaggttca ctcccgtggg tgtcgttcaa     960
gacggcagcg gaggaggaga tgcagaattc cgacatgact caggatatga agttcatcat    1020
caaggaggag gaaccactca ccagaacgaa ccccagcaat gggtcctccc tgactactcg    1080
ggcagggatt cccacaacgt tcacttggct ccggccgtgg ctccaacctt ccctggagag    1140
cagttgctgt tcttcagatc cactatgcca ggctgctctg gatacccgaa catgaacctc    1200
gactgtctct tgcctcagga gtgggtgcaa cacttctacc aggaatctgc cccagctcaa    1260
agcgacgtcg ctctgctccg tttcgttaac cccgataccg gtcgcgtgct cttcgagtgt    1320
aagttgcaca agtctggtta cgtcactgtt gcccacacag gccagcacga cctggtcatc    1380
cctcccaacg gctacttccg cttcgatagc tgggtcaacc agttctacac actcgccccg    1440
atgggaaacg gagccggtcg tcgcagagcc ttgtaa                              1476

<210> SEQ ID NO 124
<211> LENGTH: 3852
<212> TYPE: DNA
<213> ORGANISM: artificial sequence
<220> FEATURE:
<223> OTHER INFORMATION: synthetic nucleotide sequence encoding the
      recombinant P protein

<400> SEQUENCE: 124
atgaagccct tctcggtccc tatcctgaca gttgaggaaa tgaccaactc tagattccca      60
atcccgctgg aaaagctctt caccggaccc tcctctgctt tcgttgtgca gcctcaaaac     120
ggtcgttgca ccactgatgg tgtcctgctc ggtaccaccc agctctcacc tgtgaacatc     180
tgtactttcc gcggcgacgt cacacacatc gctggaggag gagatgcaga attccgacat     240
gactcaggag gaggaggaga tgcagaattc cgacatgact caggaggagg aggagatgca     300
gaattccgac atgactcagg aggaggagga gatgcagaat tccgacatga ctcaggagga     360
ggaggagatg cagaattccg acatgactca ggaggaggag gagatgcaga attccgacat     420
gactcaggag gaggaggaga tgcagaattc cgacatgact caggaggagg aggagatgca     480
gaattccgac atgactcagg aggaggagga gatgcagaat tccgacatga ctcaggagga     540
ggaggagatg cagaattccg acatgactca ggaggaggag gagatgcaga attccgacat     600
gactcaggag gaggaggaga tgcagaattc cgacatgact caggaggagg aggagatgca     660
gaattccgac atgactcagg aggaggagga gatgcagaat tccgacatga ctcaggagga     720
ggaggagatg cagaattccg acatgactca ggaggaggag gagatgcaga attccgacat     780
gactcaggag gaggaggaga tgcagaattc cgacatgact caggaggagg aggagatgca     840
gaattccgac atgactcagg aggaggagga gatgcagaat tccgacatga ctcaggagga     900
ggaggagatg cagaattccg acatgactca ggaggaggag gaggaacaca aaactacacc     960
atgaacttgg cctcgcagaa ctggaacaac tacgatccaa ccgaggaaat ccccgctcct    1020
ttgggaactc ccgacttcgt gggacgtatc caaggtgtcc tgacacagac tacacgtcgc    1080
gacggctcta ctcgcggaca caaggccact gtgtcgacag gttccgtcca cttcacccct    1140
aagctgggct ctgtgcaatt cagcacagac acctcaaacg atttcgagac tggccagaac    1200
accaggttca ctcccgtggg tgtcgttcaa gacggcggag gaggagatgc agaattccga    1260
catgactcag gatatgaagt tcatcatcaa ggaggaggag atgcagaatt ccgacatgac    1320
tcaggatatg aagttcatca tcaaggagga ggagatgcag aattccgaca tgactcagga    1380
```

```
tatgaagttc atcatcaagg aggaggagat gcagaattcc gacatgactc aggatatgaa   1440
gttcatcatc aaggaggagg agatgcagaa ttccgacatg actcaggata tgaagttcat   1500
catcaaggag gaggagatgc agaattccga catgactcag gatatgaagt tcatcatcaa   1560
ggaggaggag atgcagaatt ccgacatgac tcaggatatg aagttcatca tcaaggagga   1620
ggagatgcag aattccgaca tgactcagga tatgaagttc atcatcaagg aggaggagat   1680
gcagaattcc gacatgactc aggatatgaa gttcatcatc aaggaggagg agatgcagaa   1740
ttccgacatg actcaggata tgaagttcat catcaaggag gaggagatgc agaattccga   1800
catgactcag gatatgaagt tcatcatcaa ggaggaggag atgcagaatt ccgacatgac   1860
tcaggatatg aagttcatca tcaaggagga ggagatgcag aattccgaca tgactcagga   1920
tatgaagttc atcatcaagg aggaggagat gcagaattcc gacatgactc aggatatgaa   1980
gttcatcatc aaggaggagg agatgcagaa ttccgacatg actcaggata tgaagttcat   2040
catcaaggag gaggagatgc agaattccga catgactcag gatatgaagt tcatcatcaa   2100
ggaggaggag atgcagaatt ccgacatgac tcaggatatg aagttcatca tcaaggagga   2160
ggagatgcag aattccgaca tgactcagga tatgaagttc atcatcaagg aggaggagat   2220
gcagaattcc gacatgactc aggatatgaa gttcatcatc aaggaggagg agatgcagaa   2280
ttccgacatg actcaggata tgaagttcat catcaaggag gaggagatgc agaattccga   2340
catgactcag gatatgaagt tcatcatcaa ggaggaggag atgcagaatt ccgacatgac   2400
tcaggatatg aagttcatca tcaaggagga ggagatgcag aattccgaca tgactcagga   2460
tatgaagttc atcatcaagg aggaggagat gcagaattcc gacatgactc aggatatgaa   2520
gttcatcatc aaggaggagg agatgcagaa ttccgacatg actcaggata tgaagttcat   2580
catcaaggag gaggagatgc agaattccga catgactcag gatatgaagt tcatcatcaa   2640
ggaggaggag atgcagaatt ccgacatgac tcaggatatg aagttcatca tcaaggagga   2700
ggagatgcag aattccgaca tgactcagga tatgaagttc atcatcaagg aggaggagat   2760
gcagaattcc gacatgactc aggatatgaa gttcatcatc aaggaggagg agatgcagaa   2820
ttccgacatg actcaggata tgaagttcat catcaaggag gaggagatgc agaattccga   2880
catgactcag gatatgaagt tcatcatcaa ggaggaggag atgcagaatt ccgacatgac   2940
tcaggatatg aagttcatca tcaaggagga ggagatgcag aattccgaca tgactcagga   3000
tatgaagttc atcatcaagg aggaggagat gcagaattcc gacatgactc aggatatgaa   3060
gttcatcatc aaggaggagg agatgcagaa ttccgacatg actcaggata tgaagttcat   3120
catcaaggag gaggagatgc agaattccga catgactcag gatatgaagt tcatcatcaa   3180
ggaggaggag atgcagaatt ccgacatgac tcaggatatg aagttcatca tcaaggagga   3240
ggagatgcag aattccgaca tgactcagga tatgaagttc atcatcaagg aggaggagat   3300
gcagaattcc gacatgactc aggatatgaa gttcatcatc aaggaggagg agatgcagaa   3360
ttccgacatg actcaggata tgaagttcat catcaaggag gaggaagcac cactcaccag   3420
aacgaacccc agcaatgggt cctccctgac tactcgggca gggattccca caacgttcac   3480
ttggctccgg ccgtggctcc aaccttccct ggagagcagt tgctgttctt cagatccact   3540
atgccaggct gctctggata cccgaacatg aacctcgact gtctcttgcc tcaggagtgg   3600
gtgcaacact tctaccagga atctgcccca gctcaaagcg acgtcgctct gctccgtttc   3660
gttaaccccg ataccggtcg cgtgctcttc gagtgtaagt tgcacaagtc tggttacgtc   3720
```

```
actgttgccc acacaggcca gcacgacctg gtcatccctc ccaacggcta cttccgcttc   3780
gatagctggg tcaaccagtt ctacacactc gccccgatgg gaaacggagc cggtcgtcgc   3840
agagccttgt aa                                                        3852
```

<210> SEQ ID NO 125
<211> LENGTH: 3312
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 125

```
atgaagccct tctcggtccc tatcctgaca gttgaggaaa tgaccaactc tagattccca     60
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc gctggaacac aaggaggagg agatgcagaa    240
ttccgacatg actcaggagg aggaggagat gcagaattcc gacatgactc aggaggagga    300
ggagatgcag aattccgaca tgactcagga ggaggaggag atgcagaatt ccgacatgac    360
tcaggaggag gaggagatgc agaattccga catgactcag gaggaggagg agatgcagaa    420
ttccgacatg actcaggagg aggaggagat gcagaattcc gacatgactc aggaggagga    480
ggagatgcag aattccgaca tgactcagga ggaggaggag atgcagaatt ccgacatgac    540
tcaggaggag gaggagatgc agaattccga catgactcag gaggaggagg agatgcagaa    600
ttccgacatg actcaggagg aggaggagat gcagaattcc gacatgactc aggaggagga    660
ggagatgcag aattccgaca tgactcagga ggaggaggag atgcagaatt ccgacatgac    720
tcaggaggag gaggagatgc agaattccga catgactcag gaggaggagg agatgcagaa    780
ttccgacatg actcaggagg aggaggagat gcagaattcc gacatgactc aggaggagga    840
ggagatgcag aattccgaca tgactcagga ggaggaggag atgcagaatt ccgacatgac    900
tcaggaggag gaggagatgc agaattccga catgactcag gaggaggagg agatgcagaa    960
ttccgacatg actcaggagg aggaggagat gcagaattcc gacatgactc aggaggagga   1020
ggagatgcag aattccgaca tgactcagga ggaggaggag atgcagaatt ccgacatgac   1080
tcaggaggag gaggagatgc agaattccga catgactcag gaggaggagg agatgcagaa   1140
ttccgacatg actcaggagg aggaggagat gcagaattcc gacatgactc aggaggagga   1200
ggagatgcag aattccgaca tgactcagga ggaggaggag atgcagaatt ccgacatgac   1260
tcaggaggag gaggagatgc agaattccga catgactcag gaggaggagg agatgcagaa   1320
ttccgacatg actcaggagg aggaggagat gcagaattcc gacatgactc aggaggagga   1380
ggagatgcag aattccgaca tgactcagga ggaggaggag atgcagaatt ccgacatgac   1440
tcaggaggag gaggagatgc agaattccga catgactcag gaggaggagg agatgcagaa   1500
ttccgacatg actcaggagg aggaggagat gcagaattcc gacatgactc aggaggagga   1560
ggagatgcag aattccgaca tgactcagga ggaggaggag atgcagaatt ccgacatgac   1620
tcaggaggag gaggagatgc agaattccga catgactcag gaggaggagg aaactacacc   1680
atgaacttgg cctcgcagaa ctggaacaac tacgatccaa ccgaggaaat ccccgctcct   1740
ttgggaactc ccgacttcgt gggacgtatc caaggtgtcc tgacacagac tacacgtcgc   1800
gacggctcta ctcgcggaca caaggccact gtgtcgacag gttccgtcca cttcacccct   1860
```

-continued

```
aagctgggct ctgtgcaatt cagcacagac acctcaaacg atttcgagac tggccagaac   1920
accaggttca ctcccgtggg tgtcgttcaa gacggcagca ccggaggagg agatgcagaa   1980
ttccgacatg actcaggata tgaagttgga ggaggagatg cagaattccg acatgactca   2040
ggatatgaag ttggaggagg agatgcagaa ttccgacatg actcaggata tgaagttgga   2100
ggaggagatg cagaattccg acatgactca ggatatgaag ttggaggagg agatgcagaa   2160
ttccgacatg actcaggata tgaagttgga ggaggagatg cagaattccg acatgactca   2220
ggatatgaag ttggaggagg agatgcagaa ttccgacatg actcaggata tgaagttgga   2280
ggaggagatg cagaattccg acatgactca ggatatgaag ttggaggagg agatgcagaa   2340
ttccgacatg actcaggata tgaagttgga ggaggagatg cagaattccg acatgactca   2400
ggatatgaag ttggaggagg agatgcagaa ttccgacatg actcaggata tgaagttgga   2460
ggaggagatg cagaattccg acatgactca ggatatgaag ttggaggagg agatgcagaa   2520
ttccgacatg actcaggata tgaagttgga ggaggagatg cagaattccg acatgactca   2580
ggatatgaag ttggaggagg agatgcagaa ttccgacatg actcaggata tgaagttgga   2640
ggaggagatg cagaattccg acatgactca ggatatgaag ttggaggagg agatgcagaa   2700
ttccgacatg actcaggata tgaagttgga ggaggagatg cagaattccg acatgactca   2760
ggatatgaag ttggaggagg agatgcagaa ttccgacatg actcaggata tgaagttgga   2820
ggaggagatg cagaattccg acatgactca ggatatgaag ttggaggagg aactcaccag   2880
aacgaacccc agcaatgggt cctccctgac tactcgggca gggattccca caacgttcac   2940
ttggctccgg ccgtggctcc aaccttccct ggagagcagt tgctgttctt cagatccact   3000
atgccaggct gctctggata cccgaacatg aacctcgact gtctcttgcc tcaggagtgg   3060
gtgcaacact tctaccagga atctgcccca gctcaaagcg acgtcgctct gctccgtttc   3120
gttaaccccg ataccggtcg cgtgctcttc gagtgtaagt tgcacaagtc tggttacgtc   3180
actgttgccc acacaggcca gcacgacctg gtcatccctc ccaacggcta cttccgcttc   3240
gatagctggg tcaaccagtt ctacacactc gccccgatgg gaaacggagc cggtcgtcgc   3300
agagccttgt aa                                                      3312
```

<210> SEQ ID NO 126
<211> LENGTH: 2997
<212> TYPE: DNA
<213> ORGANISM: artificial sequence
<220> FEATURE:
<223> OTHER INFORMATION: synthetic nucleotide sequence encoding the
      recombinant P protein

<400> SEQUENCE: 126

```
atgaagccct tctcggtccc tatcctgaca gttgaggaaa tgaccaactc tagattccca     60
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc gctggaacag gaggaggaga tgcagaattc    240
cgacatgact caggatatga agttcatcat caaggaggag gagatgcaga attccgacat    300
gactcaggat atgaagttca tcatcaagga ggaggagatg cagaattccg acatgactca    360
ggatatgaag ttcatcatca aggaggagga gatgcagaat tccgacatga ctcaggatat    420
gaagttcatc atcaaggagg aggagatgca gaattccgac atgactcagg atatgaagtt    480
catcatcaag gaggaggaga tgcagaattc cgacatgact caggatatga agttcatcat    540
```

-continued

```
caaggaggag gagatgcaga attccgacat gactcaggat atgaagttca tcatcaagga    600
ggaggagatg cagaattccg acatgactca ggatatgaag ttcatcatca aggaggagga    660
gatgcagaat tccgacatga ctcaggatat gaagttcatc atcaaggagg aggagatgca    720
gaattccgac atgactcagg atatgaagtt catcatcaag gaggaggaga tgcagaattc    780
cgacatgact caggatatga agttcatcat caaggaggag gagatgcaga attccgacat    840
gactcaggat atgaagttca tcatcaagga ggaggagatg cagaattccg acatgactca    900
ggatatgaag ttcatcatca aggaggagga gatgcagaat tccgacatga ctcaggatat    960
gaagttcatc atcaaggagg aggagatgca gaattccgac atgactcagg atatgaagtt   1020
catcatcaag gaggaggaga tgcagaattc cgacatgact caggatatga agttcatcat   1080
caaggaggag gagatgcaga attccgacat gactcaggat atgaagttca tcatcaagga   1140
ggaggagatg cagaattccg acatgactca ggatatgaag ttcatcatca aggaggagga   1200
gatgcagaat tccgacatga ctcaggatat gaagttcatc atcaaggagg aggagatgca   1260
gaattccgac atgactcagg atatgaagtt catcatcaag gaggaggaga tgcagaattc   1320
cgacatgact caggatatga agttcatcat caaggaggag gagatgcaga attccgacat   1380
gactcaggat atgaagttca tcatcaagga ggaggagatg cagaattccg acatgactca   1440
ggatatgaag ttcatcatca aggaggagga gatgcagaat tccgacatga ctcaggatat   1500
gaagttcatc atcaaggagg aggagatgca gaattccgac atgactcagg atatgaagtt   1560
catcatcaag gaggaggaga tgcagaattc cgacatgact caggatatga agttcatcat   1620
caaggaggag gagatgcaga attccgacat gactcaggat atgaagttca tcatcaagga   1680
ggaggagatg cagaattccg acatgactca ggatatgaag ttcatcatca aggaggagga   1740
gatgcagaat tccgacatga ctcaggatat gaagttcatc atcaaggagg aggagatgca   1800
gaattccgac atgactcagg atatgaagtt catcatcaag gaggaggaca aaactacacc   1860
atgaacttgg cctcgcagaa ctggaacaac tacgatccaa ccgaggaaat ccccgctcct   1920
ttgggaactc ccgacttcgt gggacgtatc caaggtgtcc tgacacagac tacacgtcgc   1980
gacggctcta ctcgcggaca caaggccact gtgtcgacag gttccgtcca cttcacccct   2040
aagctgggct ctgtgcaatt cagcacagac acctcaaacg atttcgagac tggccagaac   2100
accaggttca ctcccgtggg tgtcgttcaa gacggcggag gaggagatgc agaattccga   2160
catggaggag gagatgcaga attccgacat ggaggaggag atgcagaatt ccgacatgga   2220
ggaggagatg cagaattccg acatggagga ggagatgcag aattccgaca tggaggagga   2280
gatgcagaat tccgacatgg aggaggagat gcagaattcc gacatggagg aggagatgca   2340
gaattccgac atggaggagg agatgcagaa ttccgacatg gaggaggaga tgcagaattc   2400
cgacatggag gaggagatgc agaattccga catggaggag gagatgcaga attccgacat   2460
ggaggaggag atgcagaatt ccgacatgga ggaggagatg cagaattccg acatggagga   2520
ggagatgcag aattccgaca tggaggagga agcaccactc accagaacga accccagcaa   2580
tgggtcctcc ctgactactc gggcagggat tcccacaacg ttcacttggc tccggccgtg   2640
gctccaacct tccctggaga gcagttgctg ttcttcagat ccactatgcc aggctgctct   2700
ggatacccga acatgaacct cgactgtctc ttgcctcagg agtgggtgca acacttctac   2760
caggaatctg ccccagctca aagcgacgtc gctctgctcc gtttcgttaa ccccgatacc   2820
ggtcgcgtgc tcttcgagtg taagttgcac aagtctggtt acgtcactgt tgcccacaca   2880
ggccagcacg acctggtcat ccctcccaac ggctacttcc gcttcgatag ctgggtcaac   2940
```
cagttctaca cactcgcccc gatgggaaac ggagccggtc gtcgcagagc cttgtaa 2997

<210> SEQ ID NO 127
<211> LENGTH: 2268
<212> TYPE: DNA
<213> ORGANISM: artificial sequence
<220> FEATURE:
<223> OTHER INFORMATION: synthetic nucleotide sequence encoding the
recombinant P protein

<400> SEQUENCE: 127
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc ggaggaggag atgcagaatt ccgacatgga 240
ggaggagctg gaacacaaaa ctacaccatg aacttggcct cgcagaactg gaacaactac 300
gatccaaccg aggaaatccc cgctcctttg ggaactcccg acttcgtggg acgtatccaa 360
ggtgtcctga cacagactac acgtcgcgac ggctctactc gcggacacaa ggccactgtg 420
tcgacaggtt ccgtccactt cacccctaag ctgggctctg tgcaattcag cacagacacc 480
ggaggaggag atgcagaatt ccgacatgac tcaggaggag gaggagatgc agaattccga 540
catgactcag gaggaggagg agatgcagaa ttccgacatg actcaggagg aggaggagat 600
gcagaattcc gacatgactc aggaggagga ggagatgcag aattccgaca tgactcagga 660
ggaggaggag atgcagaatt ccgacatgac tcaggaggag gaggagatgc agaattccga 720
catgactcag gaggaggagg agatgcagaa ttccgacatg actcaggagg aggaggagat 780
gcagaattcc gacatgactc aggaggagga ggagatgcag aattccgaca tgactcagga 840
ggaggaggat caaacgattt cgagactggc cagaacacca ggttcactcc cgtgggtgtc 900
gttcaagacg gaggaggaga tgcagaattc cgacatgact caggatatga agttggagga 960
ggagatgcag aattccgaca tgactcagga tatgaagttg gaggaggaga tgcagaattc 1020
cgacatgact caggatatga agttggagga ggagatgcag aattccgaca tgactcagga 1080
tatgaagttg gaggaggaga tgcagaattc cgacatgact caggatatga agttggagga 1140
ggagatgcag aattccgaca tgactcagga tatgaagttg gaggaggaga tgcagaattc 1200
cgacatgact caggatatga agttggagga ggagatgcag aattccgaca tgactcagga 1260
tatgaagttg gaggaggaga tgcagaattc cgacatgact caggatatga agttggagga 1320
ggagatgcag aattccgaca tgactcagga tatgaagttg gaggaggaga tgcagaattc 1380
cgacatgact caggatatga agttggagga ggagatgcag aattccgaca tgactcagga 1440
tatgaagttg gaggaggaga tgcagaattc cgacatgact caggatatga agttggagga 1500
ggagatgcag aattccgaca tgactcagga tatgaagttg gaggaggaga tgcagaattc 1560
cgacatgact caggatatga agttggagga ggagatgcag aattccgaca tgactcagga 1620
tatgaagttg gaggaggaga tgcagaattc cgacatgact caggatatga agttggagga 1680
ggagatgcag aattccgaca tgactcagga tatgaagttg gaggaggaga tgcagaattc 1740
cgacatgact caggatatga agttggagga ggagatgcag aattccgaca tgactcagga 1800
tatgaagttg gaggaggagg cagcaccact caccagaacg aaccccagca atgggtcctc 1860
cctgactact cgggcaggga ttcccacaac gttcacttgg ctccggccgt ggctccaacc 1920
ttccctggag agcagttgct gttcttcaga tccactatgc caggctgctc tggataccccg 1980

-continued

```
aacatgaacc tcgactgtct cttgcctcag gagtgggtgc aacacttcta ccaggaatct   2040
gccccagctc aaagcgacgt cgctctgctc cgtttcgtta accccgatac cggtcgcgtg   2100
ctcttcgagt gtaagttgca caagtctggt tacgtcactg ttgcccacac aggccagcac   2160
gacctggtca tccctcccaa cggctacttc cgcttcgata gctgggtcaa ccagttctac   2220
acactcgccc cgatgggaaa cggagccggt cgtcgcagag ccttgtaa                2268
```

```
<210> SEQ ID NO 128
<211> LENGTH: 3861
<212> TYPE: DNA
<213> ORGANISM: artificial sequence
<220> FEATURE:
<223> OTHER INFORMATION: synthetic nucleotide sequence encoding the
      recombinant P protein

<400> SEQUENCE: 128
atgaagccct tctcggtccc tatcctgaca gttgaggaaa tgaccaactc tagattccca     60
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc gctggaggag gagatgcaga attccgacat    240
gactcaggat atgaagttca tcatcaagga ggaggagatg cagaattccg acatgactca    300
ggatatgaag ttcatcatca aggaggagga gatgcagaat tccgacatga ctcaggatat    360
gaagttcatc atcaaggagg aggagatgca gaattccgac atgactcagg atatgaagtt    420
catcatcaag gaggaggaga tgcagaattc cgacatgact caggatatga agttcatcat    480
caaggaggag gagatgcaga attccgacat gactcaggat atgaagttca tcatcaagga    540
ggaggagatg cagaattccg acatgactca ggatatgaag ttcatcatca aggaggagga    600
gatgcagaat tccgacatga ctcaggatat gaagttcatc atcaaggagg aggagatgca    660
gaattccgac atgactcagg atatgaagtt catcatcaag gaggaggaga tgcagaattc    720
cgacatgact caggatatga agttcatcat caaggaggag gaggaacaca aaactacacc    780
atgaacttgg cctcgcagaa ctggaacaac tacgatccaa ccgaggaaat ccccgctcct    840
ttgggaactc ccgacttcgt gggacgtatc caaggtgtcc tgacacagac tacacgtcgc    900
gacggctcta ctcgcggaca caaggccact gtgtcgacag gttccgtcca cttcacccct    960
aagctgggct ctgtgcaatt cagcacagac acctcaggag gaggagatgc agaattccga   1020
catgactcag gatatgaagt tggaggagga gatgcagaat tccgacatga ctcaggatat   1080
gaagttggag gaggagatgc agaattccga catgactcag gatatgaagt tggaggagga   1140
gatgcagaat tccgacatga ctcaggatat gaagttggag gaggagatgc agaattccga   1200
catgactcag gatatgaagt tggaggagga gatgcagaat tccgacatga ctcaggatat   1260
gaagttggag gaggagatgc agaattccga catgactcag gatatgaagt tggaggagga   1320
gatgcagaat tccgacatga ctcaggatat gaagttggag gaggagatgc agaattccga   1380
catgactcag gatatgaagt tggaggagga gatgcagaat tccgacatga ctcaggatat   1440
gaagttggag gaggagatgc agaattccga catgactcag gatatgaagt tggaggagga   1500
gatgcagaat tccgacatga ctcaggatat gaagttggag gaggagatgc agaattccga   1560
catgactcag gatatgaagt tggaggagga gatgcagaat tccgacatga ctcaggatat   1620
gaagttggag gaggagatgc agaattccga catgactcag gatatgaagt tggaggagga   1680
gatgcagaat tccgacatga ctcaggatat gaagttggag gaggagatgc agaattccga   1740
```

```
catgactcag gatatgaagt tggaggagga gatgcagaat tccgacatga ctcaggatat   1800
gaagttggag gaggagatgc agaattccga catgactcag gatatgaagt tggaggagga   1860
gatgcagaat tccgacatga ctcaggatat gaagttggag gaggaaacga tttcgagact   1920
ggccagaaca ccaggttcac tcccgtgggt gtcgttcaag acggcggagg aggagatgca   1980
gaattccgac atgactcagg aggaggagga gatgcagaat tccgacatga ctcaggagga   2040
ggaggagatg cagaattccg acatgactca ggaggaggag gagatgcaga attccgacat   2100
gactcaggag gaggaggaga tgcagaattc cgacatgact caggaggagg aggagatgca   2160
gaattccgac atgactcagg aggaggagga gatgcagaat tccgacatga ctcaggagga   2220
ggaggagatg cagaattccg acatgactca ggaggaggag gagatgcaga attccgacat   2280
gactcaggag gaggaggaga tgcagaattc cgacatgact caggaggagg aggagatgca   2340
gaattccgac atgactcagg aggaggagga gatgcagaat tccgacatga ctcaggagga   2400
ggaggagatg cagaattccg acatgactca ggaggaggag gagatgcaga attccgacat   2460
gactcaggag gaggaggaga tgcagaattc cgacatgact caggaggagg aggagatgca   2520
gaattccgac atgactcagg aggaggagga gatgcagaat tccgacatga ctcaggagga   2580
ggaggagatg cagaattccg acatgactca ggaggaggag gagatgcaga attccgacat   2640
gactcaggag gaggaggaga tgcagaattc cgacatgact caggaggagg aggagatgca   2700
gaattccgac atgactcagg aggaggagga gatgcagaat tccgacatga ctcaggagga   2760
ggaggagatg cagaattccg acatgactca ggaggaggag gagatgcaga attccgacat   2820
gactcaggag gaggaggaga tgcagaattc cgacatgact caggaggagg aggagatgca   2880
gaattccgac atgactcagg aggaggagga gatgcagaat tccgacatga ctcaggagga   2940
ggaggagatg cagaattccg acatgactca ggaggaggag gagatgcaga attccgacat   3000
gactcaggag gaggaggaga tgcagaattc cgacatgact caggaggagg aggagatgca   3060
gaattccgac atgactcagg aggaggagga gatgcagaat tccgacatga ctcaggagga   3120
ggaggagatg cagaattccg acatgactca ggaggaggag gagatgcaga attccgacat   3180
gactcaggag gaggaggaga tgcagaattc cgacatgact caggaggagg aggagatgca   3240
gaattccgac atgactcagg aggaggagga gatgcagaat tccgacatga ctcaggagga   3300
ggaggagatg cagaattccg acatgactca ggaggaggag gagatgcaga attccgacat   3360
gactcaggag gaggaggaga tgcagaattc cgacatgact caggaggagg aggaagcacc   3420
actcaccaga acgaacccca gcaatgggtc ctccctgact actcgggcag ggattcccac   3480
aacgttcact tggctccggc cgtggctcca accttccctg gagagcagtt gctgttcttc   3540
agatccacta tgccaggctg ctctggatac ccgaacatga acctcgactg tctcttgcct   3600
caggagtggg tgcaacactt ctaccaggaa tctgccccag ctcaaagcga cgtcgctctg   3660
ctccgtttcg ttaaccccga taccggtcgc gtgctcttcg agtgtaagtt gcacaagtct   3720
ggttacgtca ctgttgccca cacaggccag cacgacctgg tcatccctcc caacggctac   3780
ttccgcttcg atagctgggt caaccagttc tacacactcg ccccgatggg aaacggagcc   3840
ggtcgtcgca gagccttgta a                                             3861
```

<210> SEQ ID NO 129
<211> LENGTH: 1656
<212> TYPE: DNA
<213> ORGANISM: artificial sequence
<220> FEATURE:

<223> OTHER INFORMATION: synthetic nucleotide sequence encoding the
      recombinant P protein

<400> SEQUENCE: 129
atgaagccct tctcggtccc tatcctgaca gttgaggaaa tgaccaactc tagattccca     60
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc gctggaggag gaggagatgc agaattccga    240
catggaggag gaacacaaaa ctacaccatg aacttggcct cgcagaactg gaacaactac    300
gatccaaccg aggaaatccc cgctcctttg ggaactcccg acttcgtggg acgtatccaa    360
ggtgtcctga cacagactac acgtcgcgac ggctctactc gcggacacaa ggccactgtg    420
tcgacaggtt ccgtccactt cacccctaag ctgggctctg tgcaattcag cacagacacc    480
tcaaacggag gaggagatgc agaattccga catgactcag gaggaggagg agatgcagaa    540
ttccgacatg actcaggagg aggaggagat gcagaattcc gacatgactc aggaggagga    600
ggagatttcg agactggcca gaacaccagg ttcactcccg tgggtgtcgt tcaagacggc    660
agcggaggag gagatgcaga attccgacat gactcaggat atgaagttca tcatcaagga    720
ggaggagatg cagaattccg acatgactca ggatatgaag ttcatcatca aggaggagga    780
gatgcagaat tccgacatga ctcaggatat gaagttcatc atcaaggagg aggagatgca    840
gaattccgac atgactcagg atatgaagtt catcatcaag gaggaggaga tgcagaattc    900
cgacatgact caggatatga agttcatcat caaggaggag gagatgcaga attccgacat    960
gactcaggat atgaagttca tcatcaagga ggaggagatg cagaattccg acatgactca   1020
ggatatgaag ttcatcatca aggaggagga gatgcagaat tccgacatga ctcaggatat   1080
gaagttcatc atcaaggagg aggagatgca gaattccgac atgactcagg atatgaagtt   1140
catcatcaag gaggaggaga tgcagaattc cgacatgact caggatatga agttcatcat   1200
caaggaggag gaaccactca ccagaacgaa ccccagcaat gggtcctccc tgactactcg   1260
ggcagggatt cccacaacgt tcacttggct ccggccgtgg ctccaacctt ccctggagag   1320
cagttgctgt tcttcagatc cactatgcca ggctgctctg gatacccgaa catgaacctc   1380
gactgtctct tgcctcagga gtgggtgcaa cacttctacc aggaatctgc cccagctcaa   1440
agcgacgtcg ctctgctccg tttcgttaac cccgataccg gtcgcgtgct cttcgagtgt   1500
aagttgcaca agtctggtta cgtcactgtt gcccacacag gccagcacga cctggtcatc   1560
cctcccaacg gctacttccg cttcgatagc tgggtcaacc agttctacac actcgccccg   1620
atgggaaacg gagccggtcg tcgcagagcc ttgtaa                             1656

<210> SEQ ID NO 130
<211> LENGTH: 3681
<212> TYPE: DNA
<213> ORGANISM: artificial sequence
<220> FEATURE:
<223> OTHER INFORMATION: synthetic nucleotide sequence encoding the
      recombinant P protein

<400> SEQUENCE: 130
atgaagccct tctcggtccc tatcctgaca gttgaggaaa tgaccaactc tagattccca     60
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc gctggaacac aaggaggagg agatgcagaa    240

-continued

```
ttccgacatg gaggaggaga tgcagaattc cgacatggag gaggagatgc agaattccga    300
catggaggag gagatgcaga attccgacat ggaggaggag atgcagaatt ccgacatgga    360
ggaggagatg cagaattccg acatggagga ggagatgcag aattccgaca tggaggagga    420
gatgcagaat tccgacatgg aggaggagat gcagaattcc gacatggagg aggagatgca    480
gaattccgac atggaggagg aaactacacc atgaacttgg cctcgcagaa ctggaacaac    540
tacgatccaa ccgaggaaat ccccgctcct ttgggaactc ccgacttcgt gggacgtatc    600
caaggtgtcc tgacacagac tacacgtcgc gacggctcta ctcgcggaca caaggccact    660
gtgtcgacag gttccgtcca cttcacccct aagctgggct ctgtgcaatt cagcacagac    720
acctcaggag gaggagatgc agaattccga catgactcag gatatgaagt tggaggagga    780
gatgcagaat tccgacatga ctcaggatat gaagttggag gaggagatgc agaattccga    840
catgactcag gatatgaagt tggaggagga gatgcagaat tccgacatga ctcaggatat    900
gaagttggag gaggagatgc agaattccga catgactcag gatatgaagt tggaggagga    960
gatgcagaat tccgacatga ctcaggatat gaagttggag gaggagatgc agaattccga   1020
catgactcag gatatgaagt tggaggagga gatgcagaat tccgacatga ctcaggatat   1080
gaagttggag gaggagatgc agaattccga catgactcag gatatgaagt tggaggagga   1140
gatgcagaat tccgacatga ctcaggatat gaagttggag gaggagatgc agaattccga   1200
catgactcag gatatgaagt tggaggagga gatgcagaat tccgacatga ctcaggatat   1260
gaagttggag gaggagatgc agaattccga catgactcag gatatgaagt tggaggagga   1320
gatgcagaat tccgacatga ctcaggatat gaagttggag gaggagatgc agaattccga   1380
catgactcag gatatgaagt tggaggagga gatgcagaat tccgacatga ctcaggatat   1440
gaagttggag gaggagatgc agaattccga catgactcag gatatgaagt tggaggagga   1500
gatgcagaat tccgacatga ctcaggatat gaagttggag gaggagatgc agaattccga   1560
catgactcag gatatgaagt tggaggagga gatgcagaat tccgacatga ctcaggatat   1620
gaagttggag gaggagatgc agaattccga catgactcag gatatgaagt tggaggagga   1680
gatgcagaat tccgacatga ctcaggatat gaagttggag gaggagatgc agaattccga   1740
catgactcag gatatgaagt tggaggagga gatgcagaat tccgacatga ctcaggatat   1800
gaagttggag gaggagatgc agaattccga catgactcag gatatgaagt tggaggagga   1860
gatgcagaat tccgacatga ctcaggatat gaagttggag gaggagatgc agaattccga   1920
catgactcag gatatgaagt tggaggagga gatgcagaat tccgacatga ctcaggatat   1980
gaagttggag gaggagatgc agaattccga catgactcag gatatgaagt tggaggagga   2040
gatgcagaat tccgacatga ctcaggatat gaagttggag gaggaaacga tttcgagact   2100
ggccagaaca ccaggttcac tcccgtgggt gtcgttcaag acggcagcac cggaggagga   2160
gatgcagaat tccgacatga ctcaggatat gaagttcatc atcaaggagg aggagatgca   2220
gaattccgac atgactcagg atatgaagtt catcatcaag gaggaggaga tgcagaattc   2280
cgacatgact caggatatga agttcatcat caaggaggag gagatgcaga attccgacat   2340
gactcaggat atgaagttca tcatcaagga ggaggagatg cagaattccg acatgactca   2400
ggatatgaag ttcatcatca aggaggagga gatgcagaat tccgacatga ctcaggatat   2460
gaagttcatc atcaaggagg aggagatgca gaattccgac atgactcagg atatgaagtt   2520
catcatcaag gaggaggaga tgcagaattc cgacatgact caggatatga agttcatcat   2580
```
caaggaggag gagatgcaga attccgacat gactcaggat atgaagttca tcatcaagga 2640
ggaggagatg cagaattccg acatgactca ggatatgaag ttcatcatca aggaggagga 2700
gatgcagaat tccgacatga ctcaggatat gaagttcatc atcaaggagg aggagatgca 2760
gaattccgac atgactcagg atatgaagtt catcatcaag gaggaggaga tgcagaattc 2820
cgacatgact caggatatga agttcatcat caaggaggag gagatgcaga attccgacat 2880
gactcaggat atgaagttca tcatcaagga ggaggagatg cagaattccg acatgactca 2940
ggatatgaag ttcatcatca aggaggagga gatgcagaat tccgacatga ctcaggatat 3000
gaagttcatc atcaaggagg aggagatgca gaattccgac atgactcagg atatgaagtt 3060
catcatcaag gaggaggaga tgcagaattc cgacatgact caggatatga agttcatcat 3120
caaggaggag gagatgcaga attccgacat gactcaggat atgaagttca tcatcaagga 3180
ggaggagatg cagaattccg acatgactca ggatatgaag ttcatcatca aggaggagga 3240
actcaccaga acgaacccca gcaatgggtc ctccctgact actcgggcag ggattcccac 3300
aacgttcact tggctccggc cgtggctcca accttccctg gagagcagtt gctgttcttc 3360
agatccacta tgccaggctg ctctggatac ccgaacatga acctcgactg tctcttgcct 3420
caggagtggg tgcaacactt ctaccaggaa tctgccccag ctcaaagcga cgtcgctctg 3480
ctccgtttcg ttaaccccga taccggtcgc gtgctcttcg agtgtaagtt gcacaagtct 3540
ggttacgtca ctgttgccca cacaggccag cacgacctgg tcatccctcc caacggctac 3600
ttccgcttcg atagctgggt caaccagttc tacacactcg ccccgatggg aaacggagcc 3660
ggtcgtcgca gagccttgta a 3681

<210> SEQ ID NO 131
<211> LENGTH: 1791
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 131
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaacag gaggaggaga tgcagaattc 240
cgacatggag gaggagatgc agaattccga catggaggag gagatgcaga attccgacat 300
ggaggaggag atgcagaatt ccgacatgga ggaggagatg cagaattccg acatggagga 360
ggagatgcag aattccgaca tggaggagga gatgcagaat tccgacatgg aggaggagat 420
gcagaattcc gacatggagg aggagatgca gaattccgac atggaggagg agatgcagaa 480
ttccgacatg gaggaggaca aaactacacc atgaacttgg cctcgcagaa ctggaacaac 540
tacgatccaa ccgaggaaat ccccgctcct ttgggaactc ccgacttcgt gggacgtatc 600
caaggtgtcc tgacacagac tacacgtcgc gacggctcta ctcgcggaca caaggccact 660
gtgtcgacag gttccgtcca cttcacccct aagctgggct ctgtgcaatt cagcacagac 720
acctcaaacg atggaggagg agatgcagaa ttccgacatg gaggaggaga tgcagaattc 780
cgacatggag gaggagatgc agaattccga catggaggag gagatgcaga attccgacat 840
ggaggaggag atgcagaatt ccgacatgga ggaggagatg cagaattccg acatggagga 900

```
ggagatgcag aattccgaca tggaggagga gatgcagaat tccgacatgg aggaggagat    960
gcagaattcc gacatggagg aggagatgca gaattccgac atggaggagg attcgagact   1020
ggccagaaca ccaggttcac tcccgtgggt gtcgttcaag acggcggagg aggagatgca   1080
gaattccgac atggaggagg agatgcagaa ttccgacatg gaggaggaga tgcagaattc   1140
cgacatggag gaggagatgc agaattccga catggaggag gagatgcaga attccgacat   1200
ggaggaggag atgcagaatt ccgacatgga ggaggagatg cagaattccg acatggagga   1260
ggagatgcag aattccgaca tggaggagga gatgcagaat tccgacatgg aggaggagat   1320
gcagaattcc gacatggagg aggaagcacc actcaccaga acgaacccca gcaatgggtc   1380
ctccctgact actcgggcag ggattcccac aacgttcact tggctccggc cgtggctcca   1440
accttccctg gagagcagtt gctgttcttc agatccacta tgccaggctg ctctggatac   1500
ccgaacatga acctcgactg tctcttgcct caggagtggg tgcaacactt ctaccaggaa   1560
tctgccccag ctcaaagcga cgtcgctctg ctccgtttcg ttaaccccga taccggtcgc   1620
gtgctcttcg agtgtaagtt gcacaagtct ggttacgtca ctgttgccca cacaggccag   1680
cacgacctgg tcatccctcc caacggctac ttccgcttcg atagctgggt caaccagttc   1740
tacacactcg ccccgatggg aaacggagcc ggtcgtcgca gagccttgta a            1791
```

```
<210> SEQ ID NO 132
<211> LENGTH: 1062
<212> TYPE: DNA
<213> ORGANISM: artificial sequence
<220> FEATURE:
<223> OTHER INFORMATION: synthetic nucleotide sequence encoding the
      recombinant P protein

<400> SEQUENCE: 132
atgaagccct tctcggtccc tatcctgaca gttgaggaaa tgaccaactc tagattccca     60
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc gctggaggag gaggagatgc agaattccga    240
catggaggag gaacacaaaa ctacaccatg aacttggcct cgcagaactg gaacaactac    300
gatccaaccg aggaaatccc cgctcctttg ggaactcccg acttcgtggg acgtatccaa    360
ggtgtcctga cacagactac acgtcgcgac ggctctactc gcggacacaa ggccactgtg    420
tcgacaggtt ccgtccactt caccccctaag ctgggctctg tgcaattcag cacagacacc    480
tcaggaggag gagatgcaga attccgacat ggaggaggaa acgatttcga gactggccag    540
aacaccaggt tcactcccgt gggtgtcgtt caagacggcg gaggaggaga tgcagaattc    600
cgacatggag gaggaagcac cactcaccag aacgaacccc agcaatgggt cctccctgac    660
tactcgggca gggattccca caacgttcac ttggctccgg ccgtggctcc aaccttccct    720
ggagagcagt tgctgttctt cagatccact atgccaggct gctctggata cccgaacatg    780
aacctcgact gtctcttgcc tcaggagtgg gtgcaacact tctaccagga atctgcccca    840
gctcaaagcg acgtcgctct gctccgtttc gttaaccccg ataccggtcg cgtgctcttc    900
gagtgtaagt tgcacaagtc tggttacgtc actgttgccc acacaggcca gcacgacctg    960
gtcatccctc ccaacggcta cttccgcttc gatagctggg tcaaccagtt ctacacactc   1020
gccccgatgg gaaacggagc cggtcgtcgc agagccttgt aa                      1062

<210> SEQ ID NO 133
```

<211> LENGTH: 1224
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 133
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaggag gaggagatgc agaattccga 240
catggaggag gagatgcaga attccgacat ggaggaggag atgcagaatt ccgacatgga 300
ggaggaacac aaaactacac catgaacttg gcctcgcaga actggaacaa ctacgatcca 360
accgaggaaa tccccgctcc tttgggaact cccgacttcg tgggacgtat ccaaggtgtc 420
ctgacacaga ctacacgtcg cgacggctct actcgcggac acaaggccac tgtgtcgaca 480
ggttccgtcc acttcacccc taagctgggc tctgtgcaat tcagcacaga cacctcagga 540
ggaggagatg cagaattccg acatggagga ggagatgcag aattccgaca tggaggagga 600
gatgcagaat tccgacatgg aggaggaaac gatttcgaga ctggccagaa caccaggttc 660
actcccgtgg gtgtcgttca agacggcgga ggaggagatg cagaattccg acatggagga 720
ggagatgcag aattccgaca tggaggagga gatgcagaat tccgacatgg aggaggaagc 780
accactcacc agaacgaacc ccagcaatgg gtcctccctg actactcggg cagggattcc 840
cacaacgttc acttggctcc ggccgtggct ccaaccttcc ctggagagca gttgctgttc 900
ttcagatcca ctatgccagg ctgctctgga tacccgaaca tgaacctcga ctgtctcttg 960
cctcaggagt gggtgcaaca cttctaccag gaatctgccc cagctcaaag cgacgtcgct 1020
ctgctccgtt tcgttaaccc cgataccggt cgcgtgctct tcgagtgtaa gttgcacaag 1080
tctggttacg tcactgttgc ccacacaggc cagcacgacc tggtcatccc tcccaacggc 1140
tacttccgct tcgatagctg ggtcaaccag ttctacacac tcgccccgat gggaaacgga 1200
gccggtcgtc gcagagcctt gtaa 1224

<210> SEQ ID NO 134
<211> LENGTH: 1791
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 134
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaggag gaggagatgc agaattccga 240
catggaggag gagatgcaga attccgacat ggaggaggag atgcagaatt ccgacatgga 300
ggaggagatg cagaattccg acatggagga ggagatgcag aattccgaca tggaggagga 360
gatgcagaat tccgacatgg aggaggagat gcagaattcc gacatggagg aggagatgca 420
gaattccgac atggaggagg agatgcagaa ttccgacatg gaggaggaga tgcagaattc 480
cgacatggag gaggaacaca aaactacacc atgaacttgg cctcgcagaa ctggaacaac 540

```
tacgatccaa ccgaggaaat ccccgctcct ttgggaactc ccgacttcgt gggacgtatc    600
caaggtgtcc tgacacagac tacacgtcgc gacggctcta ctcgcggaca caaggccact    660
gtgtcgacag gttccgtcca cttcacccct aagctgggct ctgtgcaatt cagcacagac    720
acctcaggag gaggagatgc agaattccga catggaggag gagatgcaga attccgacat    780
ggaggaggag atgcagaatt ccgacatgga ggaggagatg cagaattccg acatggagga    840
ggagatgcag aattccgaca tggaggagga gatgcagaat tccgacatgg aggaggagat    900
gcagaattcc gacatggagg aggagatgca gaattccgac atggaggagg agatgcagaa    960
ttccgacatg gaggaggaga tgcagaattc cgacatggag gaggaaacga tttcgagact   1020
ggccagaaca ccaggttcac tcccgtgggt gtcgttcaag acggcggagg aggagatgca   1080
gaattccgac atggaggagg agatgcagaa ttccgacatg gaggaggaga tgcagaattc   1140
cgacatggag gaggagatgc agaattccga catggaggag gagatgcaga attccgacat   1200
ggaggaggag atgcagaatt ccgacatgga ggaggagatg cagaattccg acatggagga   1260
ggagatgcag aattccgaca tggaggagga gatgcagaat tccgacatgg aggaggagat   1320
gcagaattcc gacatggagg aggaagcacc actcaccaga acgaacccca gcaatgggtc   1380
ctccctgact actcgggcag ggattcccac aacgttcact tggctccggc cgtggctcca   1440
accttccctg gagagcagtt gctgttcttc agatccacta tgccaggctg ctctggatac   1500
ccgaacatga acctcgactg tctcttgcct caggagtggg tgcaacactt ctaccaggaa   1560
tctgccccag ctcaaagcga cgtcgctctg ctccgtttcg ttaaccccga taccggtcgc   1620
gtgctcttcg agtgtaagtt gcacaagtct ggttacgtca ctgttgccca cacaggccag   1680
cacgacctgg tcatccctcc caacggctac ttccgcttcg atagctgggt caaccagttc   1740
tacacactcg ccccgatggg aaacggagcc ggtcgtcgca gagccttgta a            1791
```

```
<210> SEQ ID NO 135
<211> LENGTH: 4221
<212> TYPE: DNA
<213> ORGANISM: artificial sequence
<220> FEATURE:
<223> OTHER INFORMATION: synthetic nucleotide sequence encoding the
      recombinant P protein

<400> SEQUENCE: 135
```

```
atgaagccct tctcggtccc tatcctgaca gttgaggaaa tgaccaactc tagattccca     60
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc gctggaggag gaggagatgc agaattccga    240
catggaggag gagatgcaga attccgacat ggaggaggag atgcagaatt ccgacatgga    300
ggaggagatg cagaattccg acatggagga ggagatgcag aattccgaca tggaggagga    360
gatgcagaat tccgacatgg aggaggagat gcagaattcc gacatggagg aggagatgca    420
gaattccgac atggaggagg agatgcagaa ttccgacatg gaggaggaga tgcagaattc    480
cgacatggag gaggagatgc agaattccga catggaggag gagatgcaga attccgacat    540
ggaggaggag atgcagaatt ccgacatgga ggaggagatg cagaattccg acatggagga    600
ggagatgcag aattccgaca tggaggagga gatgcagaat tccgacatgg aggaggagat    660
gcagaattcc gacatggagg aggagatgca gaattccgac atggaggagg agatgcagaa    720
ttccgacatg gaggaggaga tgcagaattc cgacatggag gaggagatgc agaattccga    780
```

-continued

```
catggaggag gagatgcaga attccgacat ggaggaggag atgcagaatt ccgacatgga    840
ggaggagatg cagaattccg acatggagga ggagatgcag aattccgaca tggaggagga    900
gatgcagaat tccgacatgg aggaggagat gcagaattcc gacatggagg aggagatgca    960
gaattccgac atggaggagg agatgcagaa ttccgacatg gaggaggaga tgcagaattc   1020
cgacatggag gaggagatgc agaattccga catggaggag gagatgcaga attccgacat   1080
ggaggaggag atgcagaatt ccgacatgga ggaggagatg cagaattccg acatggagga   1140
ggagatgcag aattccgaca tggaggagga gatgcagaat tccgacatgg aggaggagat   1200
gcagaattcc gacatggagg aggagatgca gaattccgac atggaggagg agatgcagaa   1260
ttccgacatg gaggaggaga tgcagaattc cgacatggag gaggaacaca aaactacacc   1320
atgaacttgg cctcgcagaa ctggaacaac tacgatccaa ccgaggaaat ccccgctcct   1380
ttgggaactc ccgacttcgt gggacgtatc caaggtgtcc tgacacagac tacacgtcgc   1440
gacggctcta ctcgcggaca caaggccact gtgtcgacag gttccgtcca cttcacccct   1500
aagctgggct ctgtgcaatt cagcacagac acctcaggag gaggagatgc agaattccga   1560
catggaggag gagatgcaga attccgacat ggaggaggag atgcagaatt ccgacatgga   1620
ggaggagatg cagaattccg acatggagga ggagatgcag aattccgaca tggaggagga   1680
gatgcagaat tccgacatgg aggaggagat gcagaattcc gacatggagg aggagatgca   1740
gaattccgac atggaggagg agatgcagaa ttccgacatg gaggaggaga tgcagaattc   1800
cgacatggag gaggagatgc agaattccga catggaggag gagatgcaga attccgacat   1860
ggaggaggag atgcagaatt ccgacatgga ggaggagatg cagaattccg acatggagga   1920
ggagatgcag aattccgaca tggaggagga gatgcagaat tccgacatgg aggaggagat   1980
gcagaattcc gacatggagg aggagatgca gaattccgac atggaggagg agatgcagaa   2040
ttccgacatg gaggaggaga tgcagaattc cgacatggag gaggagatgc agaattccga   2100
catggaggag gagatgcaga attccgacat ggaggaggag atgcagaatt ccgacatgga   2160
ggaggagatg cagaattccg acatggagga ggagatgcag aattccgaca tggaggagga   2220
gatgcagaat tccgacatgg aggaggagat gcagaattcc gacatggagg aggagatgca   2280
gaattccgac atggaggagg agatgcagaa ttccgacatg gaggaggaga tgcagaattc   2340
cgacatggag gaggagatgc agaattccga catggaggag gagatgcaga attccgacat   2400
ggaggaggag atgcagaatt ccgacatgga ggaggagatg cagaattccg acatggagga   2460
ggagatgcag aattccgaca tggaggagga gatgcagaat tccgacatgg aggaggagat   2520
gcagaattcc gacatggagg aggagatgca gaattccgac atggaggagg agatgcagaa   2580
ttccgacatg gaggaggaga tgcagaattc cgacatggag gaggaaacga tttcgagact   2640
ggccagaaca ccaggttcac tcccgtgggt gtcgttcaag acggcggagg aggagatgca   2700
gaattccgac atggaggagg agatgcagaa ttccgacatg gaggaggaga tgcagaattc   2760
cgacatggag gaggagatgc agaattccga catggaggag gagatgcaga attccgacat   2820
ggaggaggag atgcagaatt ccgacatgga ggaggagatg cagaattccg acatggagga   2880
ggagatgcag aattccgaca tggaggagga gatgcagaat tccgacatgg aggaggagat   2940
gcagaattcc gacatggagg aggagatgca gaattccgac atggaggagg agatgcagaa   3000
ttccgacatg gaggaggaga tgcagaattc cgacatggag gaggagatgc agaattccga   3060
catggaggag gagatgcaga attccgacat ggaggaggag atgcagaatt ccgacatgga   3120
```

```
ggaggagatg cagaattccg acatggagga ggagatgcag aattccgaca tggaggagga   3180
gatgcagaat tccgacatgg aggaggagat gcagaattcc gacatggagg aggagatgca   3240
gaattccgac atggaggagg agatgcagaa ttccgacatg gaggaggaga tgcagaattc   3300
cgacatggag gaggagatgc agaattccga catggaggag gagatgcaga attccgacat   3360
ggaggaggag atgcagaatt ccgacatgga ggaggagatg cagaattccg acatggagga   3420
ggagatgcag aattccgaca tggaggagga gatgcagaat tccgacatgg aggaggagat   3480
gcagaattcc gacatggagg aggagatgca gaattccgac atggaggagg agatgcagaa   3540
ttccgacatg gaggaggaga tgcagaattc cgacatggag gaggagatgc agaattccga   3600
catggaggag gagatgcaga attccgacat ggaggaggag atgcagaatt ccgacatgga   3660
ggaggagatg cagaattccg acatggagga ggagatgcag aattccgaca tggaggagga   3720
gatgcagaat tccgacatgg aggaggagat gcagaattcc gacatggagg aggaagcacc   3780
actcaccaga acgaacccca gcaatgggtc ctccctgact actcgggcag ggattcccac   3840
aacgttcact tggctccggc cgtggctcca accttccctg gagagcagtt gctgttcttc   3900
agatccacta tgccaggctg ctctggatac ccgaacatga acctcgactg tctcttgcct   3960
caggagtggg tgcaacactt ctaccaggaa tctgccccag ctcaaagcga cgtcgctctg   4020
ctccgtttcg ttaaccccga taccggtcgc gtgctcttcg agtgtaagtt gcacaagtct   4080
ggttacgtca ctgttgccca cacaggccag cacgacctgg tcatccctcc caacggctac   4140
ttccgcttcg atagctgggt caaccagttc tacacactcg ccccgatggg aaacggagcc   4200
ggtcgtcgca gagccttgta a                                             4221
```

```
<210> SEQ ID NO 136
<211> LENGTH: 1134
<212> TYPE: DNA
<213> ORGANISM: artificial sequence
<220> FEATURE:
<223> OTHER INFORMATION: synthetic nucleotide sequence encoding the
      recombinant P protein

<400> SEQUENCE: 136
atgaagccct tctcggtccc tatcctgaca gttgaggaaa tgaccaactc tagattccca     60
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc gctggaacac aaaactacac catgaacttg    240
gcctcgcaga actggaacaa ctacgatcca accgaggaaa tccccgctcc tttgggaact    300
cccgacttcg tgggacgtat ccaaggtgtc ctgacacaga ctacacgtcg cgacggctct    360
actcgcggac acaaggccac tgtgtcgaca ggttccgtcc acttcacccc taagctgggc    420
tctgtgcaat tcagcacaga cacctcagat gcagaattcc gacatgatgc agaattccga    480
catgatgcag aattccgaca tgatgcagaa ttccgacatg atgcagaatt ccgacatgat    540
gcagaattcc gacatgatgc agaattccga catgatgcag aattccgaca tgatgcagaa    600
ttccgacatg atgcagaatt ccgacataac gatttcgaga ctggccagaa caccaggttc    660
actcccgtgg gtgtcgttca agacggcagc accactcacc agaacgaacc ccagcaatgg    720
gtcctccctg actactcggg cagggattcc cacaacgttc acttggctcc ggccgtggct    780
ccaaccttcc ctggagagca gttgctgttc ttcagatcca ctatgccagg ctgctctgga    840
tacccgaaca tgaacctcga ctgtctcttg cctcaggagt gggtgcaaca cttctaccag    900
```
gaatctgccc cagctcaaag cgacgtcgct ctgctccgtt tcgttaaccc cgataccggt 960
cgcgtgctct tcgagtgtaa gttgcacaag tctggttacg tcactgttgc ccacacaggc 1020
cagcacgacc tggtcatccc tcccaacggc tacttccgct tcgatagctg ggtcaaccag 1080
ttctacacac tcgccccgat gggaaacgga gccggtcgtc gcagagcctt gtaa 1134

<210> SEQ ID NO 137
<211> LENGTH: 1167
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 137
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaacac aaaactacac catgaacttg 240
gcctcgcaga actggaacaa ctacgatcca accgaggaaa tccccgctcc tttgggaact 300
cccgacttcg tgggacgtat ccaaggtgtc ctgacacaga ctacacgtcg cgacggctct 360
actcgcggac acaaggccac tgtgtcgaca ggttccgtcc acttcacccc taagctgggc 420
tctgtgcaat tcagcacaga cacctcagga gatgcagaat tccgacatgg agatgcagaa 480
ttccgacatg gagatgcaga attccgacat ggagatgcag aattccgaca tggagatgca 540
gaattccgac atggagatgc agaattccga catggagatg cagaattccg acatggagat 600
gcagaattcc gacatggaga tgcagaattc cgacatggag atgcagaatt ccgacatgga 660
aacgatttcg agactggcca gaacaccagg ttcactcccg tgggtgtcgt tcaagacggc 720
agcaccactc accagaacga accccagcaa tgggtcctcc ctgactactc gggcagggat 780
tcccacaacg ttcacttggc tccggccgtg gctccaacct tccctggaga gcagttgctg 840
ttcttcagat ccactatgcc aggctgctct ggatacccga acatgaacct cgactgtctc 900
ttgcctcagg agtgggtgca acacttctac caggaatctg ccccagctca aagcgacgtc 960
gctctgctcc gtttcgttaa ccccgatacc ggtcgcgtgc tcttcgagtg taagttgcac 1020
aagtctggtt acgtcactgt tgcccacaca ggccagcacg acctggtcat ccctcccaac 1080
ggctacttcc gcttcgatag ctgggtcaac cagttctaca cactcgcccc gatgggaaac 1140
ggagccggtc gtcgcagagc cttgtaa 1167

<210> SEQ ID NO 138
<211> LENGTH: 1299
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 138
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaacac aaaactacac catgaacttg 240
gcctcgcaga actggaacaa ctacgatcca accgaggaaa tccccgctcc tttgggaact 300

```
cccgacttcg tgggacgtat ccaaggtgtc ctgacacaga ctacacgtcg cgacggctct    360
actcgcggac acaaggccac tgtgtcgaca ggttccgtcc acttcacccc taagctgggc    420
tctgtgcaat tcagcacaga cacctcagga ggaggaggag gagatgcaga attccgacat    480
ggaggaggag gaggagatgc agaattccga catggaggag gaggaggaga tgcagaattc    540
cgacatggag gaggaggagg agatgcagaa ttccgacatg gaggaggagg aggagatgca    600
gaattccgac atggaggagg aggaggagat gcagaattcc gacatggagg aggaggagga    660
gatgcagaat tccgacatgg aggaggagga ggagatgcag aattccgaca tggaggagga    720
ggaggagatg cagaattccg acatggagga ggaggaggag atgcagaatt ccgacatgga    780
ggaggaggag gaaacgattt cgagactggc cagaacacca ggttcactcc cgtgggtgtc    840
gttcaagacg gcagcaccac tcaccagaac gaaccccagc aatgggtcct ccctgactac    900
tcgggcaggg attcccacaa cgttcacttg gctccggccg tggctccaac cttccctgga    960
gagcagttgc tgttcttcag atccactatg ccaggctgct ctggataccc gaacatgaac   1020
ctcgactgtc tcttgcctca ggagtgggtg caacacttct accaggaatc tgccccagct   1080
caaagcgacg tcgctctgct ccgtttcgtt aaccccgata ccggtcgcgt gctcttcgag   1140
tgtaagttgc acaagtctgg ttacgtcact gttgcccaca caggccagca cgacctggtc   1200
atccctccca acggctactt ccgcttcgat agctgggtca accagttcta cacactcgcc   1260
ccgatgggaa acggagccgg tcgtcgcaga gccttgtaa                          1299
```

```
<210> SEQ ID NO 139
<211> LENGTH: 1464
<212> TYPE: DNA
<213> ORGANISM: artificial sequence
<220> FEATURE:
<223> OTHER INFORMATION: synthetic nucleotide sequence encoding the
      recombinant P protein

<400> SEQUENCE: 139
atgaagccct tctcggtccc tatcctgaca gttgaggaaa tgaccaactc tagattccca     60
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc gctggaacac aaaactacac catgaacttg    240
gcctcgcaga actggaacaa ctacgatcca accgaggaaa tccccgctcc tttgggaact    300
cccgacttcg tgggacgtat ccaaggtgtc ctgacacaga ctacacgtcg cgacggctct    360
actcgcggac acaaggccac tgtgtcgaca ggttccgtcc acttcacccc taagctgggc    420
tctgtgcaat tcagcacaga cacctcagga ggaggaggag gaggaggagg aggaggagat    480
gcagaattcc gacatggagg aggaggagga ggaggaggag gaggagatgc agaattccga    540
catggaggag gaggaggagg aggaggagga ggagatgcag aattccgaca tggaggagga    600
ggaggaggag gaggaggagg agatgcagaa ttccgacatg gaggaggagg aggaggagga    660
ggaggaggag atgcagaatt ccgacatgga ggaggaggag gaggaggagg aggaggagat    720
gcagaattcc gacatggagg aggaggagga ggaggaggag gaggagatgc agaattccga    780
catggaggag gaggaggagg aggaggagga ggagatgcag aattccgaca tggaggagga    840
ggaggaggag gaggaggagg agatgcagaa ttccgacatg gaggaggagg aggaggagga    900
ggaggaggag atgcagaatt ccgacatgga ggaggaggag gaggaggagg aggaggaaac    960
gatttcgaga ctggccagaa caccaggttc actcccgtgg gtgtcgttca agacggcagc   1020
```

```
accactcacc agaacgaacc ccagcaatgg gtcctccctg actactcggg cagggattcc   1080
cacaacgttc acttggctcc ggccgtggct ccaaccttcc ctggagagca gttgctgttc   1140
ttcagatcca ctatgccagg ctgctctgga tacccgaaca tgaacctcga ctgtctcttg   1200
cctcaggagt gggtgcaaca cttctaccag gaatctgccc cagctcaaag cgacgtcgct   1260
ctgctccgtt tcgttaaccc cgataccggt cgcgtgctct tcgagtgtaa gttgcacaag   1320
tctggttacg tcactgttgc ccacacaggc cagcacgacc tggtcatccc tcccaacggc   1380
tacttccgct tcgatagctg ggtcaaccag ttctacacac tcgccccgat gggaaacgga   1440
gccggtcgtc gcagagcctt gtaa                                          1464
```

<210> SEQ ID NO 140
<211> LENGTH: 1233
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 140

```
atgaagccct tctcggtccc tatcctgaca gttgaggaaa tgaccaactc tagattccca     60
atcccgctgg aaaagctctt caccggaccc tcctctgctt tcgttgtgca gcctcaaaac    120
ggtcgttgca ccactgatgg tgtcctgctc ggtaccaccc agctctcacc tgtgaacatc    180
tgtactttcc gcggcgacgt cacacacatc gctggaacac aaaactacac catgaacttg    240
gcctcgcaga actggaacaa ctacgatcca accgaggaaa tccccgctcc tttgggaact    300
cccgacttcg tgggacgtat ccaaggtgtc ctgacacaga ctacacgtcg cgacggctct    360
actcgcggac acaaggccac tgtgtcgaca ggttccgtcc acttcacccc taagctgggc    420
tctgtgcaat tcagcacaga cacctcaggc ggcggcgatg cagaattccg acatggcggc    480
ggcgatgcag aattccgaca tggcggcggc gatgcagaat tccgacatgg cggcggcgat    540
gcagaattcc gacatggcgg cggcgatgca gaattccgac atggcggcgg cgatgcagaa    600
ttccgacatg gcggcggcga tgcagaattc cgacatggcg gcggcgatgc agaattccga    660
catggcggcg gcgatgcaga attccgacat ggcggcggcg atgcagaatt ccgacatggc    720
ggcggcaacg atttcgagac tggccagaac accaggttca ctcccgtggg tgtcgttcaa    780
gacggcagca ccactcacca gaacgaaccc cagcaatggg tcctccctga ctactcgggc    840
agggattccc acaacgttca cttggctccg gccgtggctc caaccttccc tggagagcag    900
ttgctgttct tcagatccac tatgccaggc tgctctggat acccgaacat gaacctcgac    960
tgtctcttgc ctcaggagtg ggtgcaacac ttctaccagg aatctgcccc agctcaaagc   1020
gacgtcgctc tgctccgttt cgttaacccc gataccggtc gcgtgctctt cgagtgtaag   1080
ttgcacaagt ctggttacgt cactgttgcc cacacaggcc agcacgacct ggtcatccct   1140
cccaacggct acttccgctt cgatagctgg gtcaaccagt tctacacact cgccccgatg   1200
ggaaacggag ccggtcgtcg cagagccttg taa                                1233
```

<210> SEQ ID NO 141
<211> LENGTH: 1062
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 141
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggtaccaccc agctctcacc tgtgaacatc 180
tgtactttcc gcggcgacgt cacacacatc gctggaacac aaaactacac catgaacttg 240
gcctcgcaga actggaacaa ctacgatcca accgaggaaa tccccgctcc tttgggaact 300
cccgacttcg tgggacgtat ccaaggtgtc ctgacacaga ctacacgtcg cgacggctct 360
actcgcggac acaaggccac tgtgtcgaca ggttccgtcc acttcacccc taagctgggc 420
tctgtgcaat tcagcacaga caccggagga ggagatgcag aattccgaca tggaggagga 480
tcaggaggag gagatgcaga attccgacat ggaggaggaa acggaggagg agatgcagaa 540
ttccgacatg gaggaggaga tttcgagact ggccagaaca ccaggttcac tcccgtgggt 600
gtcgttcaag acggcagcac cactcaccag aacgaacccc agcaatgggt cctccctgac 660
tactcgggca gggattccca caacgttcac ttggctccgg ccgtggctcc aaccttccct 720
ggagagcagt tgctgttctt cagatccact atgccaggct gctctggata cccgaacatg 780
aacctcgact gtctcttgcc tcaggagtgg gtgcaacact tctaccagga atctgcccca 840
gctcaaagcg acgtcgctct gctccgtttc gttaaccccg ataccggtcg cgtgctcttc 900
gagtgtaagt tgcacaagtc tggttacgtc actgttgccc acacaggcca gcacgacctg 960
gtcatccctc ccaacggcta cttccgcttc gatagctggg tcaaccagtt ctacacactc 1020
gccccgatgg gaaacggagc cggtcgtcgc agagccttgt aa 1062

<210> SEQ ID NO 142
<211> LENGTH: 1098
<212> TYPE: DNA
<213> ORGANISM: artificial sequence
<220> FEATURE:
<223> OTHER INFORMATION: synthetic nucleotide sequence encoding the recombinant P protein

<400> SEQUENCE: 142
atgaagccct tctcggtccc tatcctgaca gttgaggaaa tgaccaactc tagattccca 60
atcccgctgg aaaagctctt caccggaccc tcctctgctt tcgttgtgca gcctcaaaac 120
ggtcgttgca ccactgatgg tgtcctgctc ggcacaaccc agctctcacc tgtgaacatc 180
tgtactttcc gcggcgacgt cacacacatc ggaggaggag atgcagaatt ccgacatgga 240
ggaggagctg gaggaggaga tgcagaattc cgacatggag gaggaggaac acaaaactac 300
accatgaact tggcctcgca gaactggaac aactacgatc caaccgagga aatccccgct 360
cctttgggaa ctcccgactt cgtgggacgt atccaaggtg tcctgacaca gactacacgt 420
cgcgacggct ctactcgcgg acacaaggcc actgtgtcga caggttccgt ccacttcacc 480
cctaagctgg gctctgtgca attcagcaca gacacctcag gaggaggaga tgcagaattc 540
cgacatggag gaggaaacgg aggaggagat gcagaattcc gacatggagg aggagatttc 600
gagactggcc agaacaccag gttcactccc gtgggtgtcg ttcaagacgg cagcaccact 660
caccagaacg aaccccagca atgggtcctc cctgactact cgggcaggga ttcccacaac 720
gttcacttgg ctcccgccgt ggctccaacc ttccctggag agcagttgct gttcttcaga 780
tccactatgc caggctgctc tggatacccg aacatgaacc tcgactgtct cttgcctcag 840
gagtgggtgc aacacttcta ccaggaatct gccccagctc aaagcgacgt cgctctgctc 900
cgtttcgtta accccgatac cggtcgcgtg ctcttcgagt gtaagttgca caagtctggt 960
tacgtcactg ttgcccacac aggccagcac gacctggtca tccctcccaa cggctacttc 1020
cgcttcgata gctgggtcaa ccagttctac acactcgccc cgatgggaaa cggagccggt 1080
cgtcgcagag ccttgtaa 1098

<210> SEQ ID NO 143
<211> LENGTH: 518
<212> TYPE: DNA
<213> ORGANISM: artificial sequence
<220> FEATURE:
<223> OTHER INFORMATION: synthetic sequence of the synthetic gene fragment

<400> SEQUENCE: 143
ggtaccaccc agctctcacc tgtgaacatc tgtactttcc gcggcgacgt cacacacatc 60
gctggaggag gaggagatgc agaattccga catggaggag gagatgcaga attccgacat 120
ggaggaggag atgcagaatt ccgacatgga ggaggagatg cagaattccg acatggagga 180
ggagatgcag aattccgaca tggaggagga gatgcagaat tccgacatgg aggaggagat 240
gcagaattcc gacatggagg aggagatgca gaattccgac atggaggagg agatgcagaa 300
ttccgacatg gaggaggaga tgcagaattc cgacatggag gaggaacaca aaactacacc 360
atgaacttgg cctcgcagaa ctggaacaac tacgatccaa ccgaggaaat ccccgctcct 420
ttgggaactc ccgacttcgt gggacgtatc caaggtgtcc tgacacagac tacacgtcgc 480
gacggctcta ctcgcggaca caaggccact gtgtcgac 518

<210> SEQ ID NO 144
<211> LENGTH: 248
<212> TYPE: DNA
<213> ORGANISM: artificial sequence
<220> FEATURE:
<223> OTHER INFORMATION: synthetic sequence of the synthetic gene fragment

<400> SEQUENCE: 144
gtcgacaggt tccgtccact tcacccctaa gctgggctct gtgcaattca gcacagacac 60
ctcaggagga ggagatgcag aattccgaca tggaggagga aacgatttcg agactggcca 120
gaacaccagg ttcactcccg tgggtgtcgt tcaagacggc agcaccactc accagaacga 180
accccagcaa tgggtcctcc ctgactactc gggcagggat tcccacaacg ttcacttggc 240
tccggccg 248

<210> SEQ ID NO 145
<211> LENGTH: 491
<212> TYPE: DNA
<213> ORGANISM: artificial sequence
<220> FEATURE:
<223> OTHER INFORMATION: synthetic sequence of the synthetic gene fragment

<400> SEQUENCE: 145
gtcgacaggt tccgtccact tcacccctaa gctgggctct gtgcaattca gcacagacac 60
ctcaggagga ggagatgcag aattccgaca tggaggagga gatgcagaat tccgacatgg 120
aggaggagat gcagaattcc gacatggagg aggagatgca gaattccgac atggaggagg 180
agatgcagaa ttccgacatg gaggaggaga tgcagaattc cgacatggag gaggagatgc 240
agaattccga catggaggag gagatgcaga attccgacat ggaggaggag atgcagaatt 300
ccgacatgga ggaggagatg cagaattccg acatggagga ggaaacgatt tcgagactgg 360
ccagaacacc aggttcactc ccgtgggtgt cgttcaagac ggcagcacca ctcaccagaa 420
cgaaccccag caatgggtcc tccctgacta ctcgggcagg gattcccaca acgttcactt 480
ggctccggcc g 491

<210> SEQ ID NO 146
<211> LENGTH: 761
<212> TYPE: DNA
<213> ORGANISM: artificial sequence
<220> FEATURE:
<223> OTHER INFORMATION: synthetic sequence of the synthetic gene fragment

<400> SEQUENCE: 146
gtcgacaggt tccgtccact tcacccctaa gctgggctct gtgcaattca gcacagacac 60
ctcaaacgat ttcgagactg gccagaacac caggttcact cccgtgggtg tcgttcaaga 120
cggcggagga ggagatgcag aattccgaca tggaggagga gatgcagaat tccgacatgg 180
aggaggagat gcagaattcc gacatggagg aggagatgca gaattccgac atggaggagg 240
agatgcagaa ttccgacatg gaggaggaga tgcagaattc cgacatggag gaggagatgc 300
agaattccga catggaggag gagatgcaga attccgacat ggaggaggag atgcagaatt 360
ccgacatgga ggaggagatg cagaattccg acatggagga ggagatgcag aattccgaca 420
tggaggagga gatgcagaat tccgacatgg aggaggagat gcagaattcc gacatggagg 480
aggagatgca gaattccgac atggaggagg agatgcagaa ttccgacatg gaggaggaga 540
tgcagaattc cgacatggag gaggagatgc agaattccga catggaggag gagatgcaga 600
attccgacat ggaggaggag atgcagaatt ccgacatgga ggaggagatg cagaattccg 660
acatggagga ggaagcacca ctcaccagaa cgaaccccag caatgggtcc tccctgacta 720
ctcgggcagg gattcccaca acgttcactt ggctccggcc g 761

<210> SEQ ID NO 147
<211> LENGTH: 446
<212> TYPE: DNA
<213> ORGANISM: artificial sequence
<220> FEATURE:
<223> OTHER INFORMATION: synthetic sequence of the synthetic gene fragment

<400> SEQUENCE: 147
gtcgacaggt tccgtccact tcacccctaa gctgggctct gtgcaattca gcacagacac 60
ctcaggagga ggagatgcag aattccgaca tgactcagga tatgaagttg gaggaggaga 120
tgcagaattc cgacatgact caggatatga agttggagga ggagatgcag aattccgaca 180
tgactcagga tatgaagttg gaggaggaaa cgatttcgag actggccaga acaccaggtt 240
cactcccgtg ggtgtcgttc aagacggcgg aggaggagat gcagaattcc gacatggagg 300
aggagatgca gaattccgac atggaggagg agatgcagaa ttccgacatg gaggaggaag 360
caccactcac cagaacgaac cccagcaatg ggtcctccct gactactcgg gcagggattc 420
ccacaacgtt cacttggctc cggccg 446

<210> SEQ ID NO 148
<211> LENGTH: 1273
<212> TYPE: DNA
<213> ORGANISM: artificial sequence
<220> FEATURE:
<223> OTHER INFORMATION: synthetic sequence of the synthetic gene fragment

<400> SEQUENCE: 148
ggtaccaccc agctctcacc tgtgaacatc tgtactttcc gcggcgacgt cacacacatc 60
gctggaggag gaggagatgc agaattccga catgactcag gatatgaagt tcatcatcaa 120
ggaggaggag atgcagaatt ccgacatgac tcaggatatg aagttcatca tcaaggagga 180
ggagatgcag aattccgaca tgactcagga tatgaagttc atcatcaagg aggaggagat 240
gcagaattcc gacatgactc aggatatgaa gttcatcatc aaggaggagg agatgcagaa 300
ttccgacatg actcaggata tgaagttcat catcaaggag gaggagatgc agaattccga 360
catgactcag gatatgaagt tcatcatcaa ggaggaggag atgcagaatt ccgacatgac 420
tcaggatatg aagttcatca tcaaggagga ggagatgcag aattccgaca tgactcagga 480
tatgaagttc atcatcaagg aggaggagat gcagaattcc gacatgactc aggatatgaa 540
gttcatcatc aaggaggagg agatgcagaa ttccgacatg actcaggata tgaagttcat 600
catcaaggag gaggaacaca aaactacacc atgaacttgg cctcgcagaa ctggaacaac 660
tacgatccaa ccgaggaaat ccccgctcct ttgggaactc ccgacttcgt gggacgtatc 720
caaggtgtcc tgacacagac tacacgtcgc gacggctcta ctcgcggaca caaggccact 780
gtgtcgacag gttccgtcca cttcacccct aagctgggct ctgtgcaatt cagcacagac 840
acctcaggag gaggagatgc agaattccga catggaggag gagatgcaga attccgacat 900
ggaggaggag atgcagaatt ccgacatgga ggaggagatg cagaattccg acatggagga 960
ggagatgcag aattccgaca tggaggagga gatgcagaat tccgacatgg aggaggagat 1020
gcagaattcc gacatggagg aggagatgca gaattccgac atggaggagg agatgcagaa 1080
ttccgacatg gaggaggaga tgcagaattc cgacatggag gaggaaacga tttcgagact 1140
ggccagaaca ccaggttcac tcccgtgggt gtcgttcaag acggcagcac cactcaccag 1200
aacgaacccc agcaatgggt cctccctgac tactcgggca gggattccca caacgttcac 1260
ttggctccgg ccg 1273

<210> SEQ ID NO 149
<211> LENGTH: 760
<212> TYPE: DNA
<213> ORGANISM: artificial sequence
<220> FEATURE:
<223> OTHER INFORMATION: synthetic sequence of the synthetic gene
fragment

<400> SEQUENCE: 149
ggtaccaccc agctctcacc tgtgaacatc tgtactttcc gcggcgacgt cacacacatc 60
gctggaggag gaggagatgc agaattccga catggaggag gaacacaaaa ctacaccatg 120
aacttggcct cgcagaactg gaacaactac gatccaaccg aggaaatccc cgctcctttg 180
ggaactcccg acttcgtggg acgtatccaa ggtgtcctga cacagactac acgtcgcgac 240
ggctctactc gcggacacaa ggccactgtg tcgacaggtt ccgtccactt cacccctaag 300
ctgggctctg tgcaattcag cacagacacc tcaaacgatt tcgagactgg ccagaacacc 360
aggttcactc ccgtgggtgt cgttcaagac ggcggaggag gagatgcaga attccgacat 420
ggaggaggag atgcagaatt ccgacatgga ggaggagatg cagaattccg acatggagga 480
ggagatgcag aattccgaca tggaggagga gatgcagaat tccgacatgg aggaggagat 540
gcagaattcc gacatggagg aggagatgca gaattccgac atggaggagg agatgcagaa 600
ttccgacatg gaggaggaga tgcagaattc cgacatggag gaggagatgc agaattccga 660
catggaggag gaagcaccac tcaccagaac gaaccccagc aatgggtcct ccctgactac 720
tcgggcaggg attcccacaa cgttcacttg gctccggccg 760

<210> SEQ ID NO 150
<211> LENGTH: 553
<212> TYPE: DNA
<213> ORGANISM: artificial sequence
<220> FEATURE:
<223> OTHER INFORMATION: synthetic sequence of the synthetic gene fragment

<400> SEQUENCE: 150
ggtaccaccc agctctcacc tgtgaacatc tgtactttcc gcggcgacgt cacacacatc 60
gctggaggag gaggagatgc agaattccga catggaggag gaacacaaaa ctacaccatg 120
aacttggcct cgcagaactg gaacaactac gatccaaccg aggaaatccc cgctcctttg 180
ggaactcccg acttcgtggg acgtatccaa ggtgtcctga cacagactac acgtcgcgac 240
ggctctactc gcggacacaa ggccactgtg tcgacaggtt ccgtccactt cacccctaag 300
ctgggctctg tgcaattcag cacagacacc tcaggaggag gagatgcaga attccgacat 360
ggaggaggaa acgatttcga gactggccag aacaccaggt tcactcccgt gggtgtcgtt 420
caagacggcg gaggaggaga tgcagaattc cgacatggag gaggaagcac cactcaccag 480
aacgaacccc agcaatgggt cctccctgac tactcgggca gggattccca caacgttcac 540
ttggctccgg ccg 553

<210> SEQ ID NO 151
<211> LENGTH: 715
<212> TYPE: DNA
<213> ORGANISM: artificial sequence
<220> FEATURE:
<223> OTHER INFORMATION: synthetic sequence of the synthetic gene fragment

<400> SEQUENCE: 151
ggtaccaccc agctctcacc tgtgaacatc tgtactttcc gcggcgacgt cacacacatc 60
gctggaggag gaggagatgc agaattccga catggaggag gagatgcaga attccgacat 120
ggaggaggag atgcagaatt ccgacatgga ggaggaacac aaaactacac catgaacttg 180
gcctcgcaga actggaacaa ctacgatcca accgaggaaa tccccgctcc tttgggaact 240
cccgacttcg tgggacgtat ccaaggtgtc ctgacacaga ctacacgtcg cgacggctct 300
actcgcggac acaaggccac tgtgtcgaca ggttccgtcc acttcacccc taagctgggc 360
tctgtgcaat tcagcacaga cacctcagga ggaggagatg cagaattccg acatggagga 420
ggagatgcag aattccgaca tggaggagga gatgcagaat tccgacatgg aggaggaaac 480
gatttcgaga ctggccagaa caccaggttc actcccgtgg gtgtcgttca agacggcgga 540
ggaggagatg cagaattccg acatggagga ggagatgcag aattccgaca tggaggagga 600
gatgcagaat tccgacatgg aggaggaagc accactcacc agaacgaacc ccagcaatgg 660
gtcctccctg actactcggg cagggattcc cacaacgttc acttggctcc ggccg 715

<210> SEQ ID NO 152
<211> LENGTH: 1282
<212> TYPE: DNA
<213> ORGANISM: artificial sequence
<220> FEATURE:
<223> OTHER INFORMATION: synthetic sequence of the synthetic gene -continued

```
      fragment

<400> SEQUENCE: 152
ggtaccaccc agctctcacc tgtgaacatc tgtactttcc gcggcgacgt cacacacatc     60
gctggaggag gaggagatgc agaattccga catggaggag gagatgcaga attccgacat    120
ggaggaggag atgcagaatt ccgacatgga ggaggagatg cagaattccg acatggagga    180
ggagatgcag aattccgaca tggaggagga gatgcagaat tccgacatgg aggaggagat    240
gcagaattcc gacatggagg aggagatgca gaattccgac atggaggagg agatgcagaa    300
ttccgacatg gaggaggaga tgcagaattc cgacatggag gaggaacaca aaactacacc    360
atgaacttgg cctcgcagaa ctggaacaac tacgatccaa ccgaggaaat ccccgctcct    420
ttgggaactc ccgacttcgt gggacgtatc caaggtgtcc tgacacagac tacacgtcgc    480
gacggctcta ctcgcggaca caaggccact gtgtcgacag gttccgtcca cttcacccct    540
aagctgggct ctgtgcaatt cagcacagac acctcaggag gaggagatgc agaattccga    600
catggaggag gagatgcaga attccgacat ggaggaggag atgcagaatt ccgacatgga    660
ggaggagatg cagaattccg acatggagga ggagatgcag aattccgaca tggaggagga    720
gatgcagaat tccgacatgg aggaggagat gcagaattcc gacatggagg aggagatgca    780
gaattccgac atggaggagg agatgcagaa ttccgacatg gaggaggaga tgcagaattc    840
cgacatggag gaggaaacga tttcgagact ggccagaaca ccaggttcac tcccgtgggt    900
gtcgttcaag acggcggagg aggagatgca gaattccgac atggaggagg agatgcagaa    960
ttccgacatg gaggaggaga tgcagaattc cgacatggag gaggagatgc agaattccga   1020
catggaggag gagatgcaga attccgacat ggaggaggag atgcagaatt ccgacatgga   1080
ggaggagatg cagaattccg acatggagga ggagatgcag aattccgaca tggaggagga   1140
gatgcagaat tccgacatgg aggaggagat gcagaattcc gacatggagg aggaagcacc   1200
actcaccaga acgaacccca gcaatgggtc ctccctgact actcgggcag ggattcccac   1260
aacgttcact tggctccggc cg                                            1282

<210> SEQ ID NO 153
<211> LENGTH: 27
<212> TYPE: DNA
<213> ORGANISM: artificial sequence
<220> FEATURE:
<223> OTHER INFORMATION: synthetic sequence for CpG adjuvant

<400> SEQUENCE: 153
tgtcgtcgtc gtttgtcgtt tgtcgtt                                        27
```